(12) United States Patent
Guindon et al.

(10) Patent No.: US 11,453,695 B2
(45) Date of Patent: Sep. 27, 2022

(54) NUCLEOSIDE ANALOGUES AND METHODS OF USE THEREOF

(71) Applicant: LCB PHARMA INC., Montréal (CA)

(72) Inventors: Yvan Guindon, Montréal (CA);
Philippe Mochirian, Montréal (CA);
Mona Nemer, Ottawa (CA); Michel Prévost, Montréal (CA)

(73) Assignee: LCB Pharma Inc., Montreal (CA)

( * ) Notice: Subject to any disclaimer, the term of this patent is extended or adjusted under 35 U.S.C. 154(b) by 665 days.

(21) Appl. No.: 16/333,833

(22) PCT Filed: Sep. 18, 2017

(86) PCT No.: PCT/CA2017/051096
§ 371 (c)(1),
(2) Date: Mar. 15, 2019

(87) PCT Pub. No.: WO2018/049535
PCT Pub. Date: Mar. 22, 2018

(65) Prior Publication Data
US 2019/0322693 A1    Oct. 24, 2019

Related U.S. Application Data

(60) Provisional application No. 62/395,401, filed on Sep. 16, 2016, provisional application No. 62/395,411, filed on Sep. 16, 2016, provisional application No. 62/395,430, filed on Sep. 16, 2016.

(51) Int. Cl.

| | |
|---|---|
| *C07H 19/10* | (2006.01) |
| *C07H 19/20* | (2006.01) |
| *C07H 19/23* | (2006.01) |
| *A61P 31/12* | (2006.01) |
| *A61P 35/00* | (2006.01) |
| *A61P 9/00* | (2006.01) |

(52) U.S. Cl.
CPC .............. *C07H 19/10* (2013.01); *A61P 9/00* (2018.01); *A61P 31/12* (2018.01); *A61P 35/00* (2018.01); *C07H 19/20* (2013.01); *C07H 19/23* (2013.01)

(58) Field of Classification Search
CPC ........ C07H 19/10; C07H 19/20; C07H 19/23; A61P 9/00; A61P 31/12; A61P 35/00
See application file for complete search history.

(56) References Cited

U.S. PATENT DOCUMENTS

| | | | |
|---|---|---|---|
| 8,361,988 B2 * | 1/2013 | Guindon ................ | A61P 31/20 514/45 |
| 8,846,636 B2 * | 9/2014 | Guindon ................ | A61P 31/16 514/45 |
| 2019/0389897 A1 * | 12/2019 | Guindon ................ | C07H 19/23 |

FOREIGN PATENT DOCUMENTS

| | | |
|---|---|---|
| CA | 2712073 | 7/2008 |
| CA | 2755235 | 9/2009 |
| CA | 2819700 | 11/2010 |
| WO | 2011143593 A1 | 11/2011 |

OTHER PUBLICATIONS

Dostie, S., et al., "Diastereoselective Synthesis of C2'-Fluorinated Nucleoside Analogues Using an Acyclic Approach", J. Org. Chem., 2016, 81(22), pp. 10769-10790.

Tambutet, G., et al. "Dual-Face Nucleoside Scaffold Featuring a Stereogenic All-Carbon Quaternary Center. Intramolecular Silicon Tethered Group-Transfer Reaction", Org. Lett., 2014, 16(21), pp. 5698-5701.

Vande Voorde, J. et al., "The cytostatic activity of NUC-3073, a phosphoramidate prodrug of 5-fluoro-2'-deoxyuridine, is independent of activation by thymidine kinase and insensitive to degradation by phosphorolytic enzymes", Biochem. Pharmacol., 2011, 82(5), pp. 441-452.

International Search Report and Written Opinion cited in PCT/CA2017/051096 dated Dec. 8, 2017, 17 pages.

(Continued)

*Primary Examiner* — Layla D Berry
(74) *Attorney, Agent, or Firm* — Rothwell, Figg, Ernst & Manbeck, P.C.

(57) ABSTRACT

The compounds are nucleoside and nucleotide analogues that can be used as anticancer or antiviral agents. The compounds include tetrahydrofuranyl or tetrahydrothienyl moieties with quaternary stereogenic all-carbon center at the 3' position and bear a phosphoryl group at either one of, or both of positions C5' and/or C3'; have a quaternary stereogenic all-carbon center at one of the 3' position, 2' position, or no quaternary stereogenic center at all, and bear a β-blocked lipoate derivative attached through an amide bond to the primary amine of the nucleobase; or have a quaternary stereogenic all-carbon center at the 2' position and bear a phosphorylated prodrug at the C5'-position and a β-blocked lipoate derivative attached through an amide bond to the primary amine of the nucleobase

18 Claims, 5 Drawing Sheets

(56) References Cited

OTHER PUBLICATIONS

Basavapathruni et al, "Conformational Adaptation Drives Potent, Selective and Durable Inhibition of the Human Protein Methyltransferase DOT1L", Chem. Biol. Drug Des. 2012, 80 (6), 971-980.

Giovannetti et al., "Transcription Analysis of Human Equilibrative Nucleoside Transporter-1 Predicts Survival in Pancreas Cancer Patients Treated with Gemcitabine", Cancer Res. 2006, 66 (7), 3928-35.

Sofia et al., "Discovery of a β-D-2'-Deoxy-2'-α-fluoro-2'-β-C-methyluridine Nucleotide Prodrug (PSI-7977) for the Treatment of Hepatitis C Virus", J. Med. Chem. 2010, 53 (19), 7202-18.

Naghavi, M., et al., Global Burden of Disease Cancer 2013, JAMA Oncology 2015, 1 (4), 505-527.

Wilhelm et al., "Discovery and development of sorafenib: a multikinase inhibitor for treating cancer", Nat. Rev. Drug Discov. 2006, 5 (10), 835-44.

Lönnberg et al. "Mechanisms for the Acid-catalyzed Hydrolysis of Some Alkyl Aldofuranosides with trans-1,2-Configuration", Acta Chem. Scand. A, 1977, 31, 306-312.

Stuart et al., "A strategically designed small molecule attacks alpha-ketoglutarate dehydrogenase in tumor cells through a redox process", Cancer Metab 2014, 2 (1), 4, 1-15.

Zachar et al., "Non-redox-active lipoate derivates disrupt cancer cell mitochondrial metabolism and are potent anticancer agents in vivo", J. Mol. Med. 2011, 89 (11), 1137-48.

DeBerardinis et al., "The Biology of Cancer: Metabolic Reprogramming Fuels Cell Growth and Proliferation Cell Metab." 2008, 7 (1), 11-20.

Bartlett et al., "Mitochondrial ß-oxidation", Eur. J. Biochem. 2004, 271 (3), 462-169.

Abeysuriya et al., "Control of a wetting transition by substrate surface chemistry: The interplay of long- and short-range forces" Phys Rev B, May 1987, 35 (13), 6771-6778.

Hjeresen et al., "Ontogeny of Seizure Incidence, Latency, and Seventy in Genetically Epilepsy Prone Rats", Dev. Psychobiol. 1987, 20 (3), 355-63.

Cahilly-Snyder et al., "Molecular Analysis and Chromosomal Mapping of Amplified Genes Isolated from a Transformed Mouse 3T3 Cell Line", Somatic Cell and Molecular Genetics, 1987, 13 (3), 235-44.

Neelarapu et al., "Design, Synthesis, Docking, and Biological Evaluation of Novel Diazide-Containing Isoxazole- and Pyrazole-Based Histone Deacetylase Probes", J. Med. Chem. 2011, 54 (13), 4350-64.

\* cited by examiner

Lipoate moities:

Lipoic acid

Dihydrolipoate 8-thioacetate dihydrolipoate

CPI-613

β-oxidation:

A)

B)

C)

D)

E)

NUCLEOSIDE ANALOGUES AND METHODS OF USE THEREOF

CROSS REFERENCE TO RELATED APPLICATIONS

This application is a 35 U.S.C. 371 National Phase Entry Application from PCT/CA2017/051096, filed Sep. 18, 2017, which claims benefit, under 35 U.S.C. § 119(e), of U.S. provisional application Ser. No. 62/395,401 filed on Sep. 16, 2016, U.S. provisional application Ser. No. 62/395,411 filed on Sep. 16, 2016, and U.S. provisional application Ser. No. 62/395,430 filed on Sep. 16, 2016. All documents above are incorporated herein in their entirety by reference.

FIELD OF THE INVENTION

The present invention relates to nucleoside analogues useful as antitumor and/or antiviral agents.

BACKGROUND OF THE INVENTION

Nucleosides and nucleotides are part of the molecules of life. They are the constitutive units of RNA and DNA. They are also required for numerous functions in the cells. They are involved, for instance, in phosphate transfer reactions (ATP), methylation of the histone (SAM) or as coenzymes.[1] The nucleosides are transported by human equilibrative nucleoside transporters (hENTs) and human concentrative nucleoside transporters (hCNTs) in the cells.[2]

Nucleotide analogues are also an important class of pharmaceutical agents. They are utilized notably as antitumor or antiviral agents.[3]

The medical needs for new antiviral therapies are due to lack of efficacy of existing treatment, such as Hepatitis B infection (HBV); the occurrence of resistance to existing one, such as Ganciclovir resistant Human Cytomegalovirus infection (HCM); and the emergence of novel virus pandemic, including bioterrorism. HCMV infection is for instance a main source of morbidity and mortality in stem cell transplant and solid organ transplant patients.

Cancer is the second leading cause of mortality worldwide accounting for over 8 million deaths a year.[4] Despite remarkable progress over the past two decades, the prognosis of many cancers remain grim and treatment options limited. This is especially the case for gastrointestinal (GI) tumors. For example, hepatocellular carcinoma (HCC), the most common hepatic malignancy, has a poor five-year survival rate (Table 1); depending on the stage of the disease, treatment is limited to resection and administration of a tyrosine kinase inhibitor (e.g. Sorafenib)[5] of vascular growth factor receptors (VEGFRs). Similarly, pancreatic cancer has become the third leading cause of cancer related deaths in North America and is expected to become the second by 2030.[4] Tumor resection and the current standard combination treatment with Gemcitabine, a nucleoside analogue, and Folfirinox (fluorouracil, leucovorin, irinotecan and oxaliplatin) achieve a dismal five-year survival rate of 5-7%. Gemcitabine (Gem), a 2'-difluoro-cytidine analogue displays cytotoxic activity through incorporation in DNA and RNA and inhibition of various nucleic acid synthesis enzymes. Unfortunately, in many cases, solid tumors develop resistance, greatly limiting Gem clinical usefulness. Several tyrosine kinase inhibitors have been tested in combination with Gem, such as Erlotinib (EGFR), Cetuximab (antibody to EGFR) or Sorafenib (VEGFR), but the clinical outcome was not improved. Other older drugs are also still used such as doxorubicin, etoposide (topoisomerase II inhibitor) and cisplatin, but their efficacy is limited and several are poorly tolerated by patients. Today, pancreatic and other GI tumor cells are essentially resistant to conventional therapies and the treatment of these cancers is an unmet medical need.[6]

Deamination of adenine or cytosine-based nucleosides or nucleotides is a metabolic pathway causing significant reduction of the half-life time of these molecules in vivo. It has been reported that linking the primary amine of those nucleobases to lipids or lipoates delay this process.[7] The activity of Gemcitabine having an octanoic amide attached to the nucleobase shows 100 μM $EC_{50}$ in cancer pancreatic cancer cells.

The metabolism of cancer cells is different from the normal cells. It is altered to respond to their needs for biosynthetic intermediates necessitated to maintain cell division.

Interfering with the metabolism of cancer cells has become a recognized viable target to improve the treatment of certain forms of cancer.[9]

One of the characteristics of cancer cell metabolism is its preference for the aerobic glycolytic mechanism as opposed to the mitochondrial oxidation of pyruvate (the Warburg Effect). The truncated TCA cycle leads to the cytosolic export of citrate for use in lipid synthesis. The cancer cells thus rely disproportionally on glutamine, which enters the TCA cycle transformed notably by α-ketoglutamate dehydrogenase (KGDH) complex. The transition to this pathway requires shutting down of pyruvate dehydrogenase complex (PDH) by an overexpression of the pyruvate dehydrogenase kinase (PDK) that renders the PDH complex inactive. Lipoic acid is a catalytic cofactor for both PDH and KGDH enzymes.

Lipids and lipoates are normally metabolized through β-oxidation pathways (FIG. 2).[10]

Nucleoside analogues having an all-carbon quaternary stereogenic center at C3' have been reported.[11]

SUMMARY OF THE INVENTION

The present invention relates to:

1. A compound of formula:

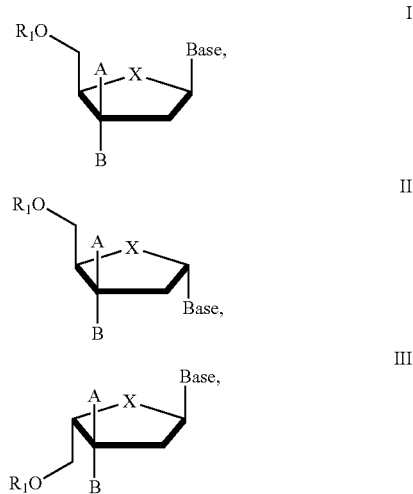

IV
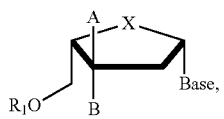

V
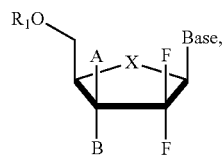

VI
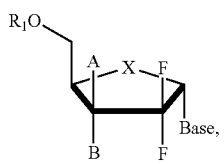

VII
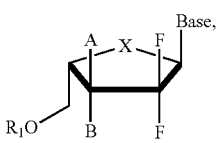

VIII
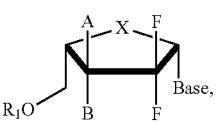

IX
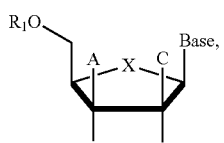

X
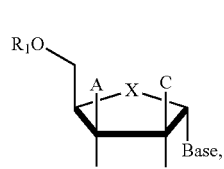

XI
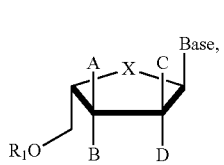

XII
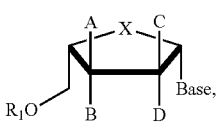

XIII
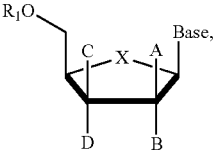

XIV
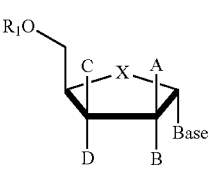

XV
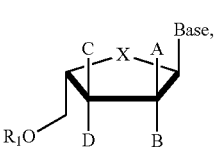

XVI
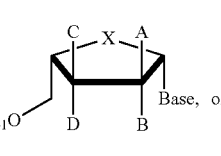

XVII
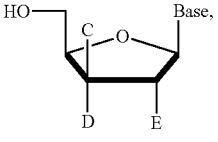

wherein:

A and B are $C_1$-$C_6$ alkyl, mono- to per-halo alkyl or —$(CH_2)_n$M, with the proviso that:
- A is different from B,
- when one of A and B is methyl, the other is not —$CF_3$, and
- when one of A and B is $C_2$-$C_6$ alkyl, the other is not $C_2$-$C_6$ fluoroalkyl;

n is 1 to 3;

M is —$OR_2$, —$SR_2$, —CN, —C(O)$OR_3$, —OC(O)$R_4$,

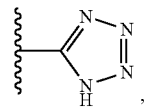

or —$NHR_{15}$;

$R_1$ is —H, —$C_1$-$C_6$ alkyl, alkylaryl, or a phosphoryl group of formula (XX):

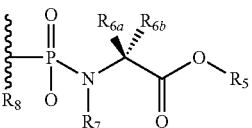

(XX)

$R_2$ is H, $C_1$-$C_6$-alkyl, aryl-$C_1$-$C_6$ alkyl, or a phosphoryl group of formula (XX), each of the alkyl and aryl moieties being optionally substituted with one or more groups selected from halo, —CN, —C(O)OH, —C(O)$R_3$, —$N_3$, —$C_1$-$C_6$ alkyl, —C(O)$OR_4$, —$CF_3$, —$C_1$-$C_6$ alkyl-$N_3$, —$SiF_5$, and —$NHR_{15}$;

$R_3$ is H, $C_1$-$C_6$ alkyl, or aryl-$C_1$-$C_6$ alkyl, each of the alkyl and aryl moieties being optionally substituted with one or more groups selected from halo, —CN, —C(O)OH, —C(O)$OR_4$, —$N_3$, —$C_1$-$C_6$ alkyl-C(O)$OR_4$, —$CF_3$, —$C_1$-$C_6$alkyl-$N_3$, and —$SiF_5$;

R₄ is C₁-C₆ alkyl, aryl, or aryl-C₁-C₆ alkyl, each of the alkyl and aryl moieties being optionally substituted with one or more groups selected from halo, —CN, —C(O)OH, —N₃, CF₃, —C₁-C₆ alkyl-N₃, —SiF₅, and —NHR₁₅;

R₅ is H, C₁-C₆ alkyl, or arylalkyl;

R₆ₐ is H, methyl, isopropyl, n-propyl, or —CH₂—CH₂—SMe;

R₆ᵦ is H or methyl;

R₇ is H or methyl;

R₈ is H, C₁-C₆ alkyl, or aryl, the aryl being optionally substituted with one group selected from C₁-C₆ alkyl and halo;

R₁₅ is H, C₁-C₆ alkyl, —SO₂-aryl or aryl, each of the aryl moieties being optionally substituted with one or more C₁-C₆ alkyl or halo;

X is O or S;

C and D are independently —H, —OH, halo, azido, —CN, —NHR₂, or —CF₃;

E is H or OH;

Base is:

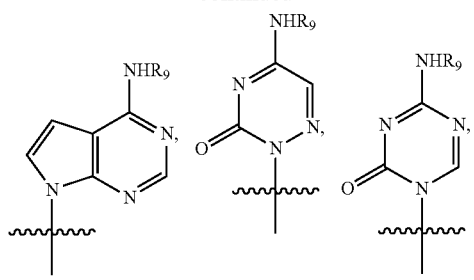

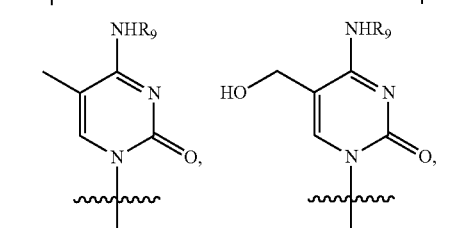

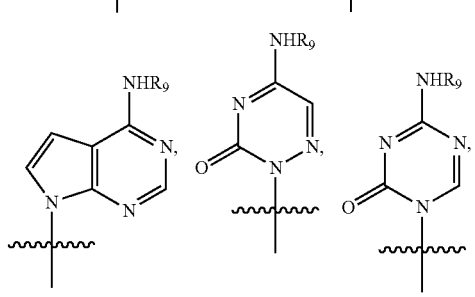

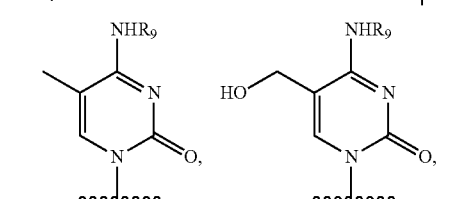

-continued

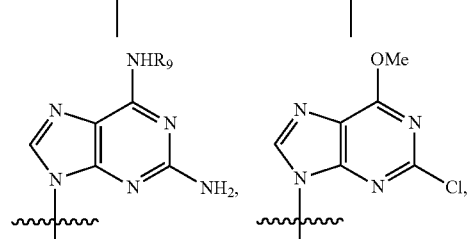

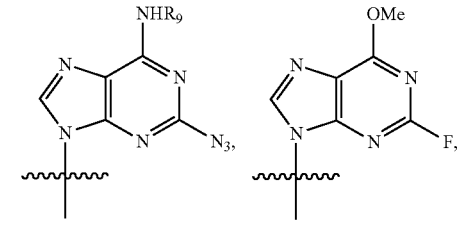

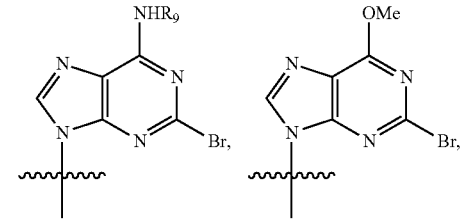

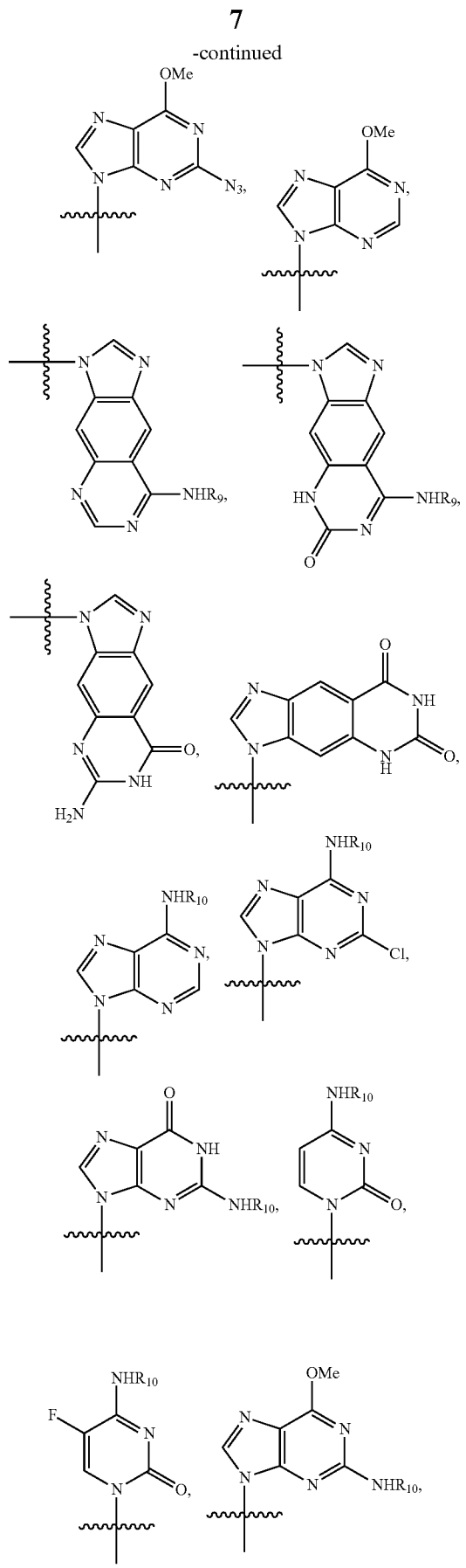
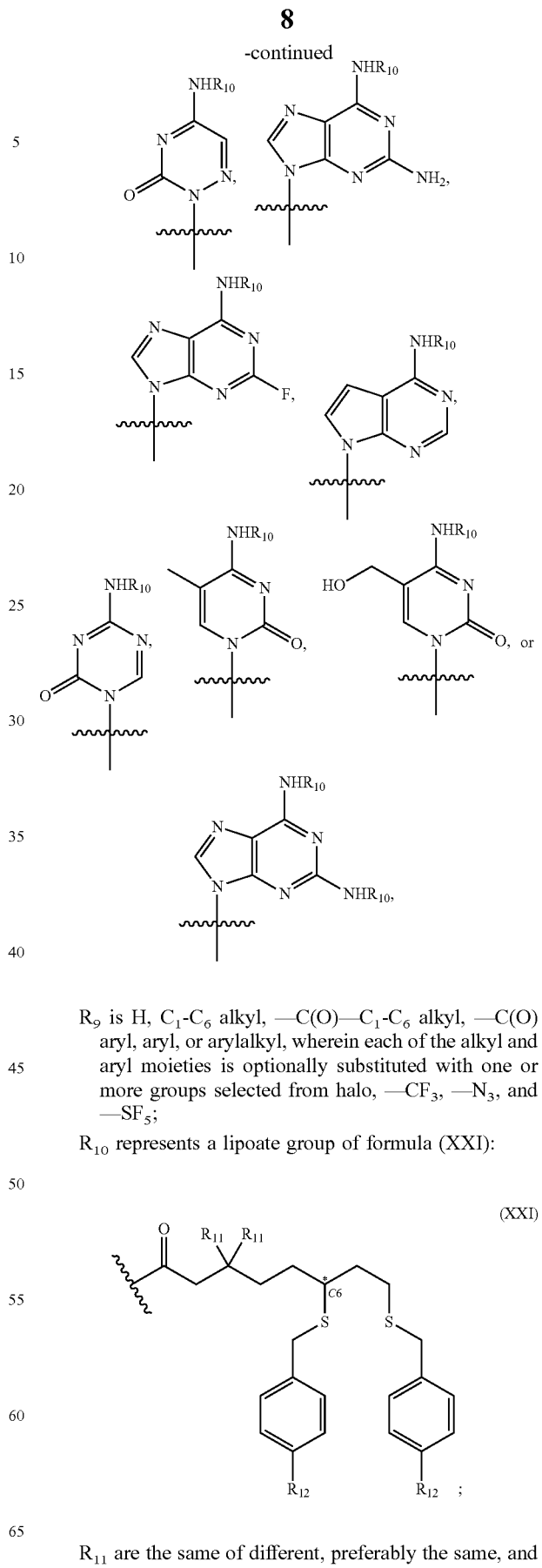
$R_9$ is H, $C_1$-$C_6$ alkyl, —C(O)—$C_1$-$C_6$ alkyl, —C(O) aryl, aryl, or arylalkyl, wherein each of the alkyl and aryl moieties is optionally substituted with one or more groups selected from halo, —$CF_3$, —$N_3$, and —$SF_5$;
$R_{10}$ represents a lipoate group of formula (XXI):
$R_{11}$ are the same of different, preferably the same, and represents F or methyl; and $R_{12}$ are the same of different, preferably the same, and represents F or —$CF_3$; and
* denotes the R, S, or R/S configuration,
with the proviso that the compound comprises:
one or two phosphoryl groups of formula (XX), the compound being free of a lipoate group of formula (XXI),
one lipoate group of formula (XXI), the compound being free of a phosphoryl group of formula (XX), or
one lipoate group of formula (XXI) and only one phosphoryl group of formula (XX), said phosphoryl group being in $R_1$, and
with the further proviso that when the compound is of formula XIII to XVII, the compound comprises one lipoate group of formula (XXI),
or a pharmaceutically acceptable salt thereof.
2. The compound of item 1, wherein n is 1.
3. The compound of item 1 or 2, wherein each of the alkyl and aryl moieties in $R_3$ is optionally substituted with one or more groups selected from halo (preferably F), —$N_3$, —$CF_3$, —$C_1$-$C_6$ alkyl-$N_3$, or —$SiF_5$.
4. The compound of any one of items 1 to 3, wherein each of the alkyl and aryl moieties in $R_3$ is optionally substituted with one or more groups selected from halo (preferably) or —$CF_3$.
5. The compound of any one of items 1 to 4, wherein $R_3$ is H or arylalkyl.
6. The compound of any one of items 1 to 5, wherein $R_3$ is H, benzyl, or

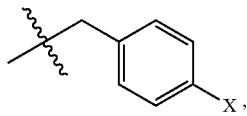

wherein X is F or —$CF_3$.
7. The compound of any one of items 1 to 6, wherein, in $R_4$, each of the alkyl and aryl moieties being optionally substituted with one or more groups selected from halo, —$N_3$, —$CF_3$, —$C_1$-$C_6$ alkyl-$N_3$, or —$SiF_5$.
8. The compound of any one of items 1 to 7, wherein $R_5$ is $C_1$-$C_6$ alkyl, preferably iso-propyl.
9. The compound of any one of items 1 to 8, wherein one of $R_{6a}$ and $R_{6b}$ is H and the other of $R_{6a}$ and $R_{6b}$ is methyl.
10. The compound of any one of items 1 to 9, wherein $R_{6a}$ is methyl and $R_{6b}$ is H.
11. The compound of any one of items 1 to 10, wherein $R_7$ is H.
12. The compound of any one of items 1 to 11, wherein $R_8$ is aryl, preferably phenyl.
13. The compound of any one of items 1 to 12, wherein the phosphoryl groups of formula (XX) is:

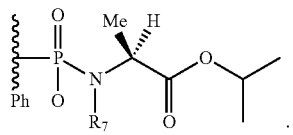

14. The compound of any one of items 1 to 13, wherein X is O.

15. The compound of any one of items 1 to 14, wherein one of A and B is $C_1$-$C_6$ alkyl, preferably methyl.
16. The compound of any one of items 1 to 15, wherein one of A and B is —$(CH_2)_n$M.
17. The compound of any one of items 1 to 16, wherein one of A and B is $C_1$-$C_6$ alkyl, preferably methyl, and the other of A and B is —$(CH_2)_n$M.
18. The compound of any one of items 1 to 17, wherein A is $C_1$-$C_6$ alkyl, preferably methyl, and B is —$(CH_2)_n$M.
19. The compound of any one of items 1 to 18, wherein M is —$OR_2$, —$OC(O)R_4$, —CN,

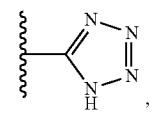

or —$NHR_{15}$, preferably —$OR_2$, —$OC(O)R_4$, —CN, or

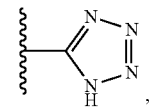

more preferably, —$OR_2$—$OC(O)R_4$, or —CN, even more preferably —$OR_2$ or —$OC(O)R_4$, and most preferably —$OR_2$.
20. The compound of any one of items 1 to 19, wherein $R_2$ is H, $C_1$-$C_6$-alkyl, aryl-$C_1$-$C_6$ alkyl, or a phosphoryl group of formula (XX), preferably H, aryl-$C_1$-$C_6$ alkyl, or a phosphoryl group of formula (XX), more preferably H or a phosphoryl group of formula (XX), each of the alkyl and aryl moieties being optionally substituted with one or more groups selected from halo (preferably F), —CN, —C(O)OH, —C(O)$R_3$, —$N_3$, —$C_1$-$C_6$ alkyl, —C(O)O$R_4$, —$CF_3$, —$C_1$-$C_6$alkyl-$N_3$, —$SiF_5$, and —$NHR_{15}$.
21. The compound of any one of items 1 to 20, wherein each of the alkyl and aryl moieties in $R_2$ is optionally substituted with one or more groups selected from halo (preferably F), —C(O)$R_3$, —$N_3$, —$C_1$-$C_6$ alkyl, —$CF_3$, or —$SiF_5$.
22. The compound of any one of items 1 to 21, wherein each of the alkyl and aryl moieties in $R_2$ is optionally substituted with one or more groups selected from halo (preferably F), —$N_3$, -or —$CF_3$.
23. The compound of any one of items 1 to 22, wherein the alkyl in $R_2$ is methyl, preferably unsubstituted.
24. The compound of any one of items 1 to 23, wherein the aryl-$C_1$-$C_6$ alkyl in $R_2$ is benzyl unsubstituted or substituted, preferably with fluor, preferably in para position.
25. The compound of any one of items 1 to 24, wherein $R_2$ is H, methyl, benzyl, para-fluoro benzyl, para-$CF_3$ benzyl, or a phosphoryl group of formula (XX), preferably H, methyl, benzyl, or a phosphoryl group of formula (XX), and more preferably H or a phosphoryl group of formula (XX).
26. The compound of any one of items 1 to 25, wherein C and D are independently —H, —OH, halo, —CN, —$NHR_2$, or —$CF_3$, preferably —H, —OH, halo, —CN or —$NHR_2$, and more preferably —H, —OH, or halo.

27. The compound of any one of items 1 to 26, wherein one of C and D is H and the other of C and D is halo or OH, preferably halo or alternatively preferably OH.
28. The compound of any one of items 1 to 27, wherein the halo in C or D is F.
29. The compound of any one of items 1 to 28, wherein E is H.
30. The compound of any one of items 1 to 28, wherein E is OH.
31. The compound of any one of items 1 to 30, wherein, in $R_9$, each of alkyl moiety is unsubstituted and wherein each of the aryl moieties is optionally substituted with one or more groups selected from halo, —$CF_3$, —$N_3$, and —$SF_5$, preferably halo, —$CF_3$ or —$SF_5$, more preferably —$CF_3$ or —$SF_5$ or more preferably halo, the substituent being preferably located in para position.
32. The compound of any one of items 1 to 31, wherein the halo in $R_9$ is F.
33. The compound of any one of items 1 to 32, wherein $R_9$ is H, $C_1$-$C_6$ alkyl, —C(O)—$C_1$-$C_6$ alkyl, aryl substituted with halo, or arylalkyl, preferably H, $C_1$-$C_6$ alkyl, —C(O)—$C_1$-$C_6$ alkyl, aryl, or arylalkyl, more preferably H, $C_1$-$C_6$ alkyl, —C(O)—$C_1$-$C_6$ alkyl, or arylalkyl, yet more preferably H, C(O)—$C_1$-$C_6$ alkyl, or arylalkyl, and most preferably H.
34. The compound of any one of items 1 to 33, wherein the —C(O)—$C_1$-$C_6$ alkyl in $R_9$ is —C(O)-propyl.
35. The compound of any one of items 1 to 34, wherein the aryl in $R_9$ is substituted with halo, preferably F.
36. The compound of any one of items 1 to 35, wherein the aryl in $R_9$ is phenyl substituted with halo, preferably F, more preferably parafluorophenyl.
37. The compound of any one of items 1 to 36, wherein the arylalkyl in $R_9$ is benzyl, preferably unsubstituted.
38. The compound of any one of items 1 to 37, wherein both $R_{11}$ are the same.
39. The compound of any one of items 1 to 38, wherein both $R_{11}$ are methyl.
40. The compound of any one of items 1 to 39, wherein both $R_{12}$ are the same.
41. The compound of any one of items 1 to 40, wherein both $R_{12}$ are F.
42. The compound of any one of items 1 to 41, wherein both $R_{12}$ are —$CF_3$.
43. The compound of any one of items 1 to 42, wherein * denotes the R/S configuration.
44. The compound of any one of items 1 to 43, wherein the lipoate group of formula (XXI) is:

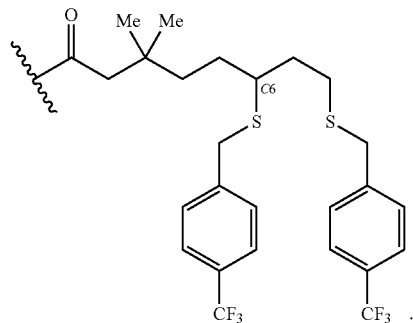 [SMILES: *C(=O)CC(C)(C)CCC(CCSCc1ccc(C(F)(F)F)cc1)SCc1ccc(C(F)(F)F)cc1]

45. The compound of any one of items 1 to 42, wherein * denotes the R or R/S configuration.

46. The compound of any one of items 1 to 42, wherein * denotes the R configuration.
47. The compound of any one of items 1 to 46, wherein $R_{15}$ is H, —$SO_2$-aryl or aryl, preferably H, each of the aryl moieties being optionally substituted with one or more $C_1$-$C_6$ alkyl (preferably methyl) or halo (preferably F).
48. The compound of any one of items 1 to 47, wherein $R_{15}$ is H, p-methylphenyl or p-fluorophenyl.
49. The compound of any one of items 1 to 48, comprising one or two phosphoryl groups of formula (XX), and being free of a lipoate group of formula (XXI).
50. The compound of item 49, being of formula I, V, VI, IX, or X, preferably I, V, or IX, more preferably V or IX, most preferably IX.
51. The compound of item 49 or 50, wherein C is halo or OH, preferably halo, and D is H.
52. The compound of any one of items 49 to 51, wherein Base is:

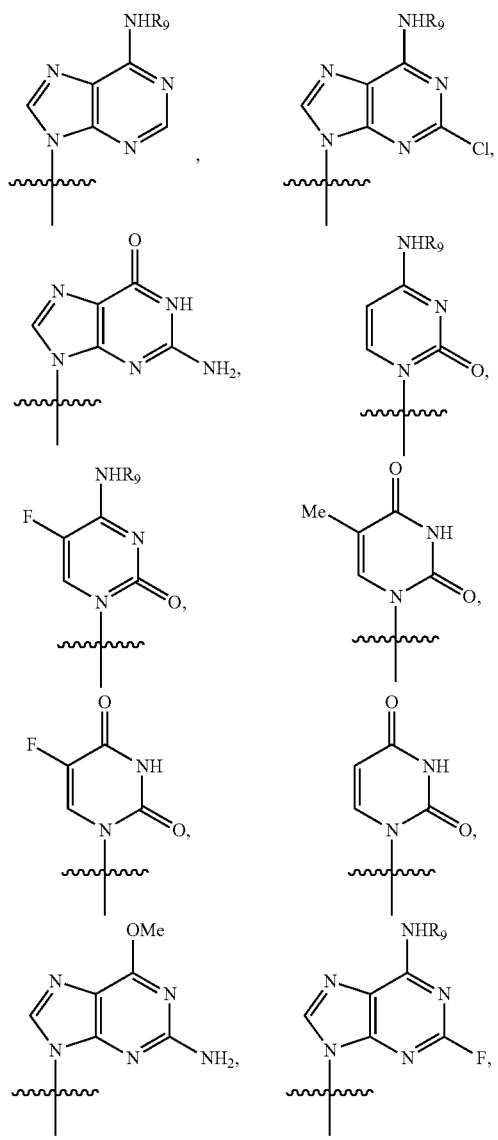

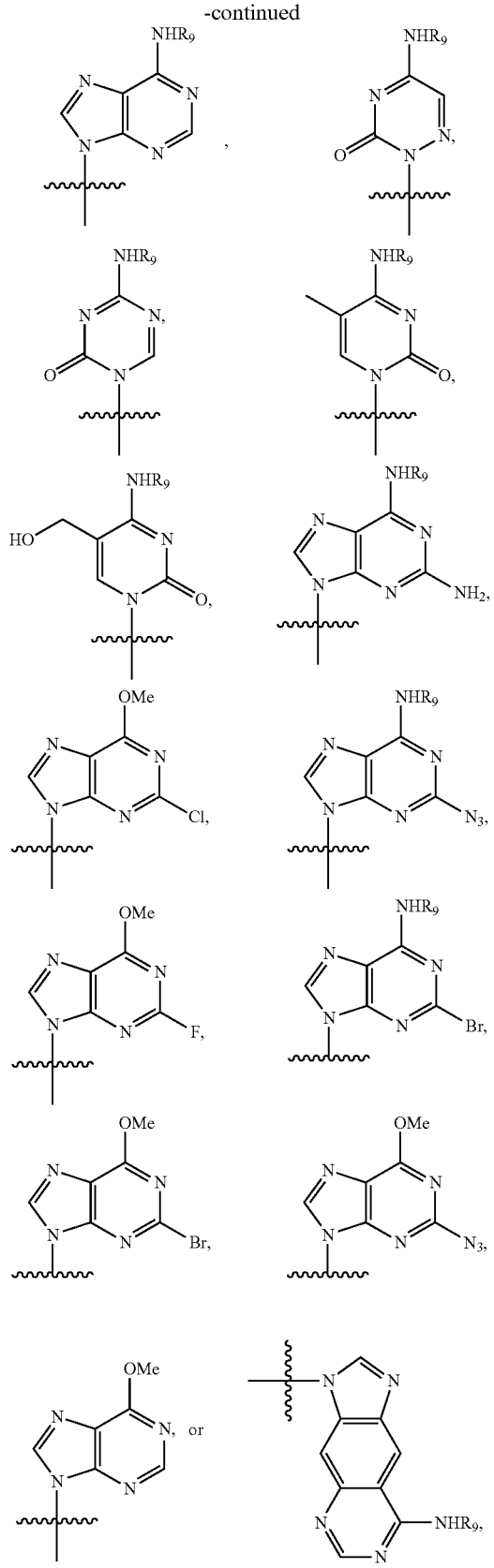
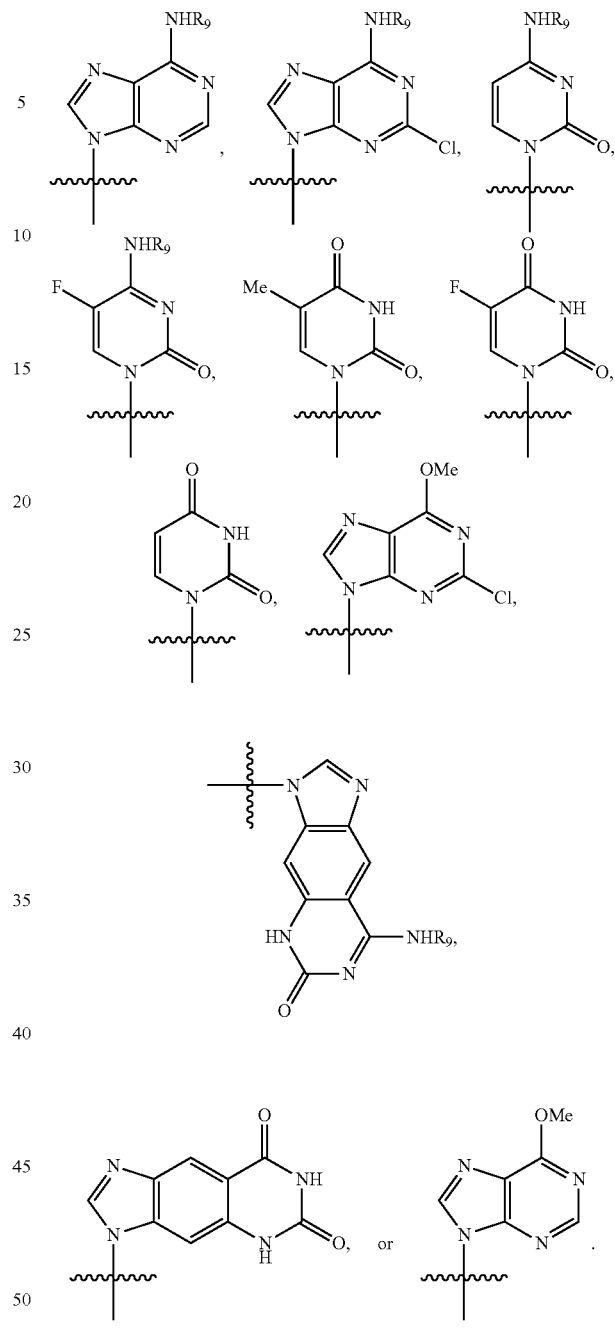

53. The compound of any one of items 49 to 52, wherein Base is:

54. The compound of any one of items 49 to 53, comprising only one phosphoryl group of formula (XX).

55. The compound of item 54, being of formula V, VI, IX, or X, preferably of formula VI, IX, or X, more preferably of formula IX.

56. The compound of item 54 or 55, wherein one of A and B is —(CH$_2$)$_n$M, M is OR$_2$, and R$_2$ is a phosphoryl group of formula (XX).

57. The compound of item 56, being of formula V, VI, IX, or X, preferably of formula IX or X, more preferably X.

58. The compound of item 56 or 57, wherein R$_1$ is H.

59. The compound of any one of items 56 to 58, wherein Base is:

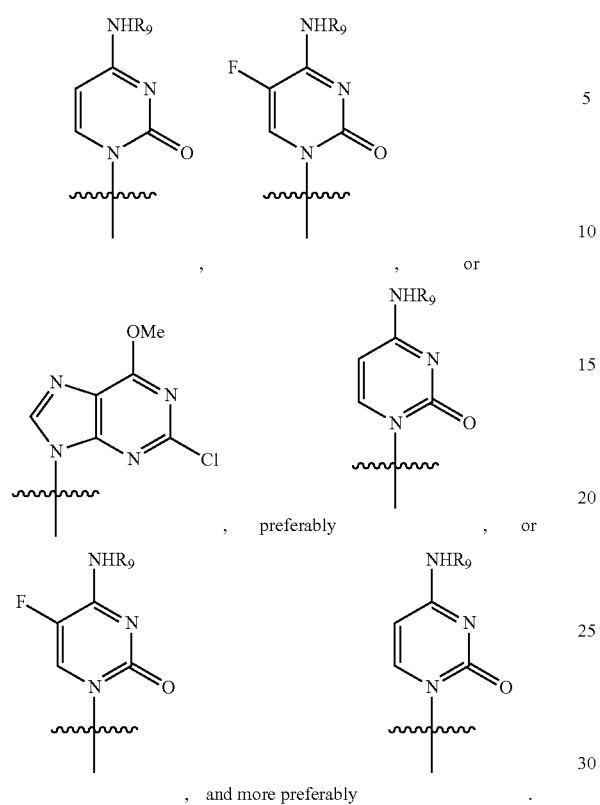
, 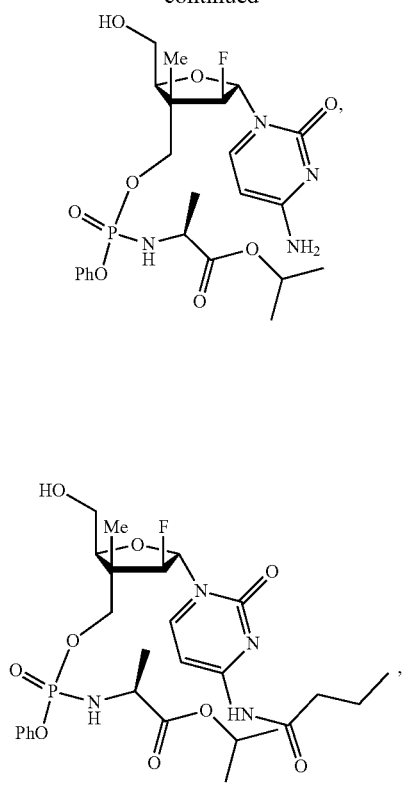
, preferably
, or
, and more preferably .
60. The compound of any one of items 56 to 59 being:
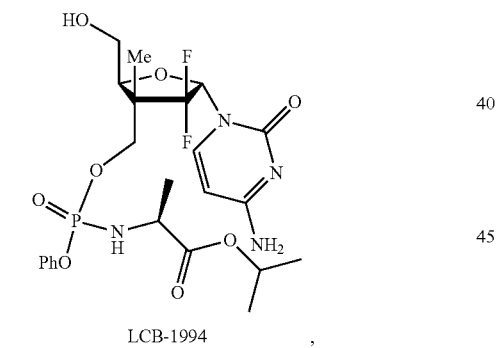
LCB-1994 ,
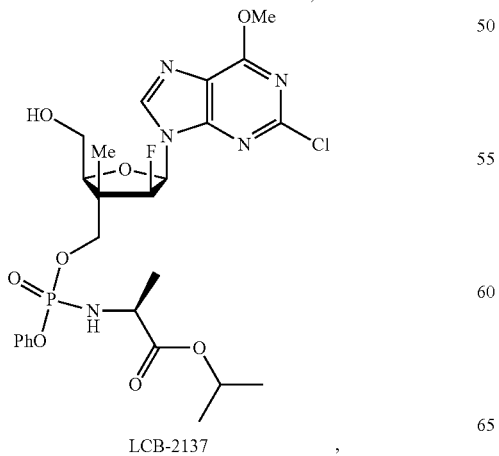
LCB-2137 ,
-continued
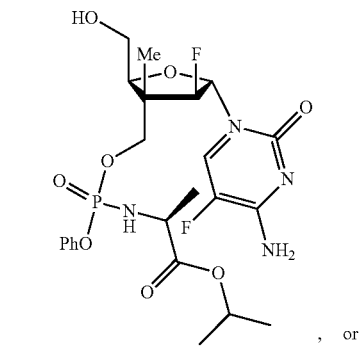
,
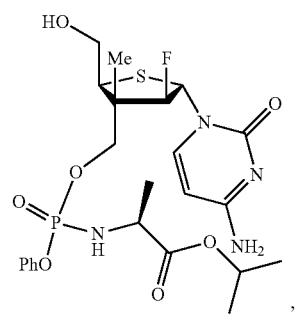
, or
or a pharmaceutically acceptable salt thereof.

61. The compound of any one of items 56 to 60 being:
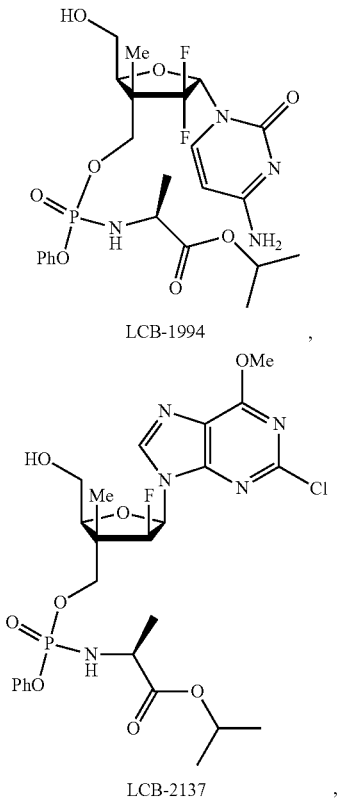
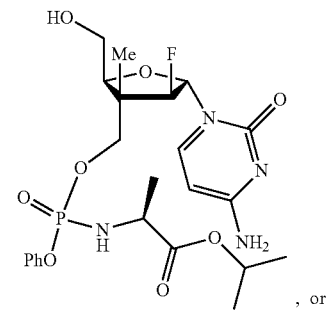
,
or a pharmaceutically acceptable salt thereof.
62. The compound of any one of items 56 to 61 being:
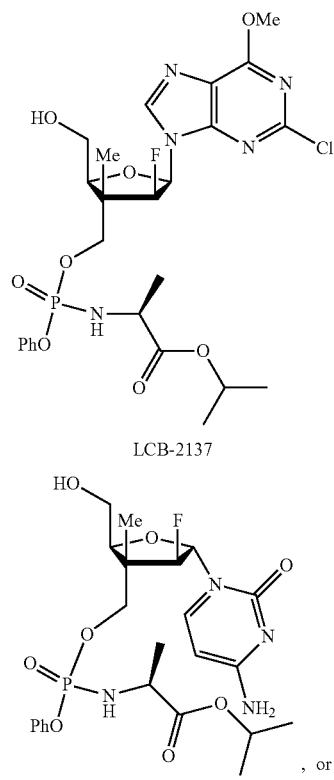
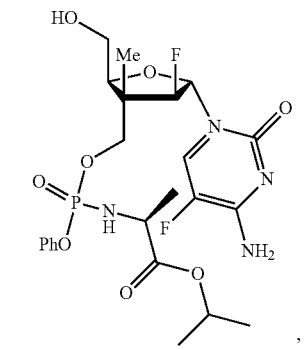
or a pharmaceutically acceptable salt thereof.
63. The compound of any one of items 56 to 62 being:
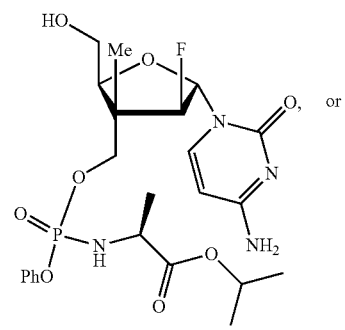

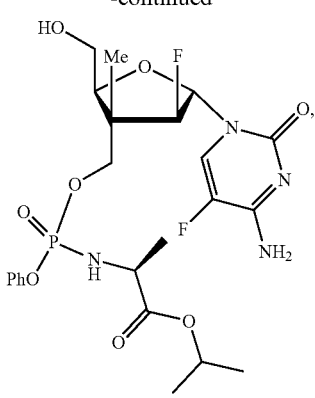
or a pharmaceutically acceptable salt thereof.
64. The compound of any one of items 54 or 55, wherein $R_1$ is a phosphoryl group.
65. The compound of item 64, being of formula V, VI, IX, or X, preferably of formula V or IX, more preferably IX.
66. The compound of any one of items 64 or 65, wherein Base is:
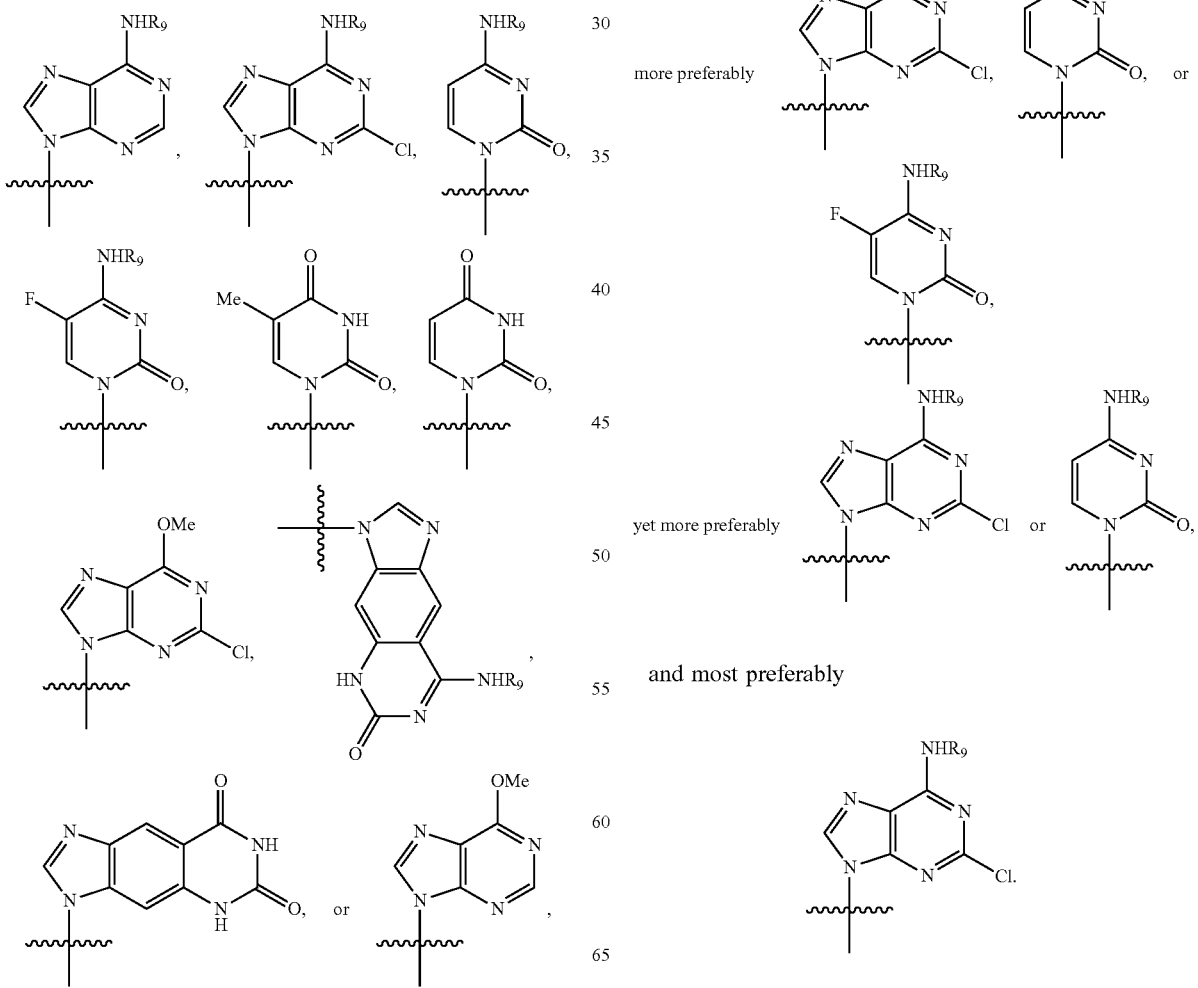
preferably
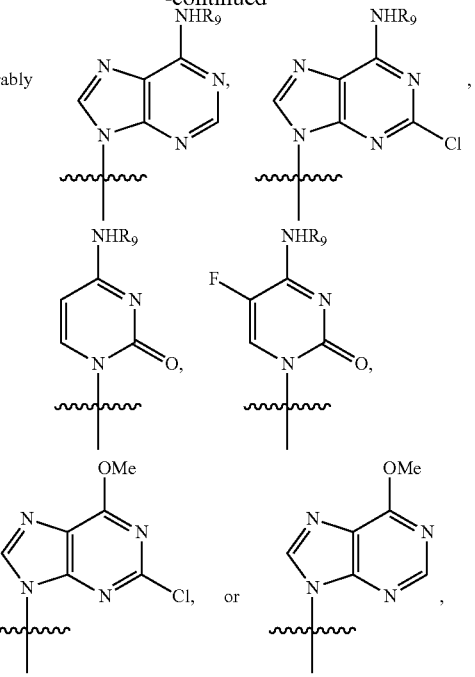
more preferably
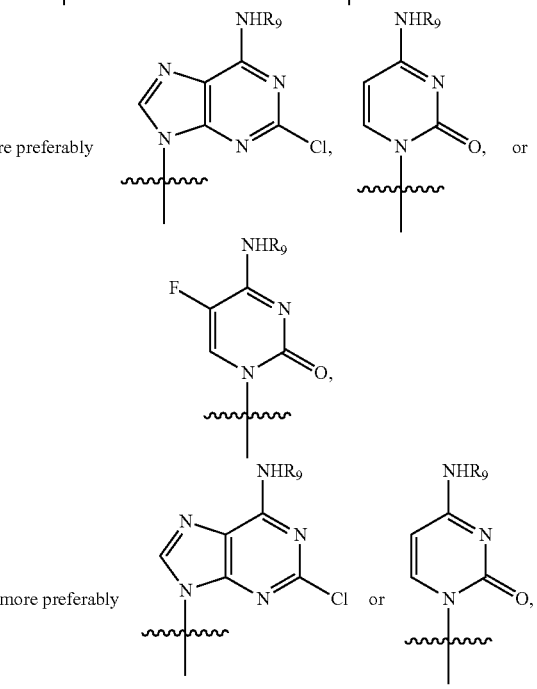
yet more preferably
and most preferably 67. The compound of any one of items 64 to 66, being:
LCB-1992
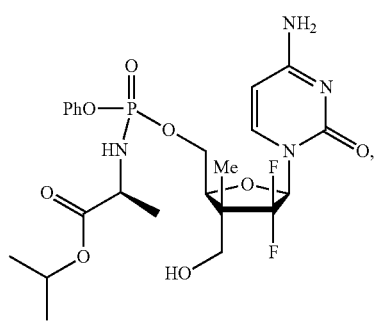
LCB-1998
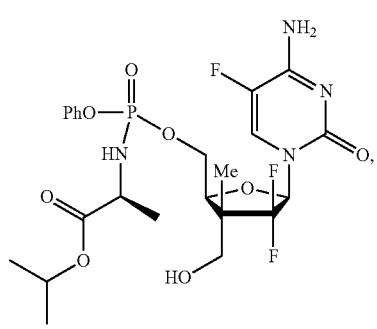
LCB-2000
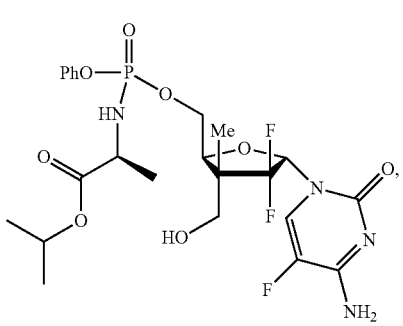
LCB-2001
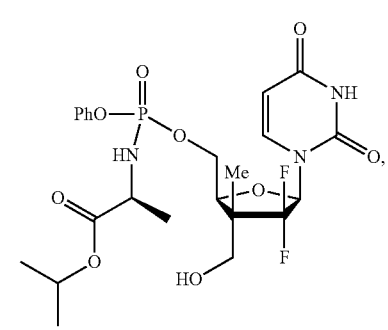
LCB-2018
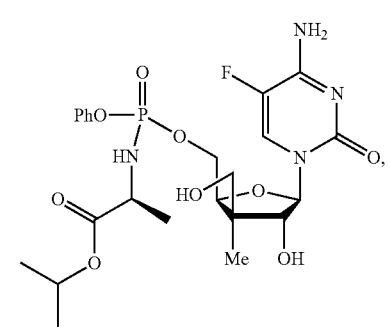
LCB-2027
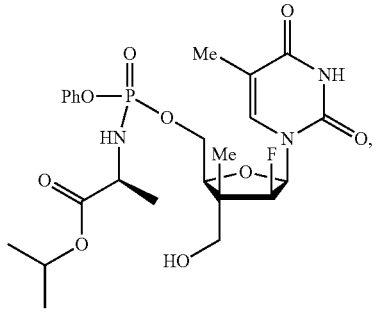
LCB-2028
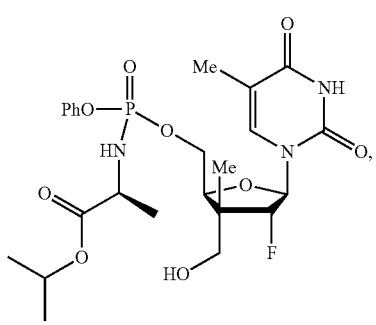
LCB-2034
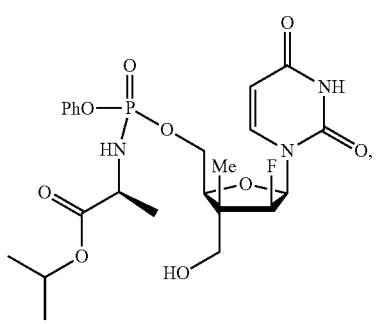
LCB-2093
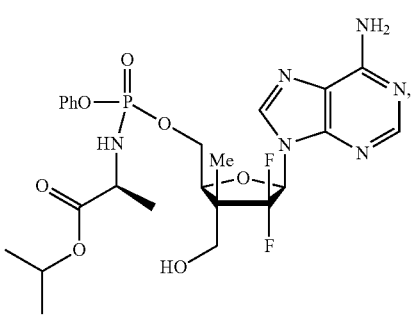
LCB-2106
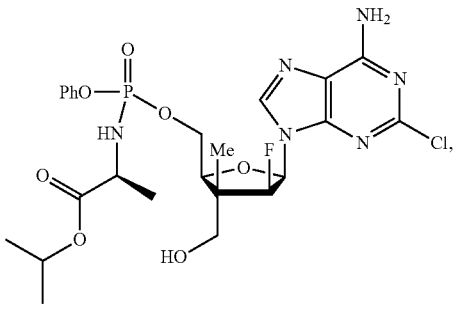

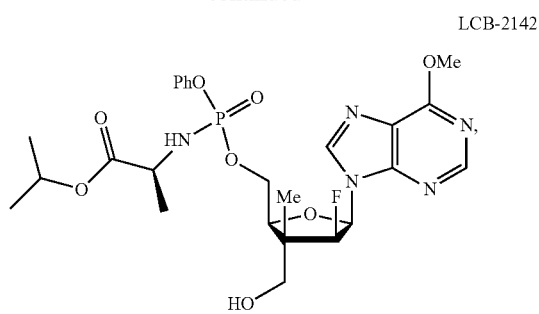
LCB-2142
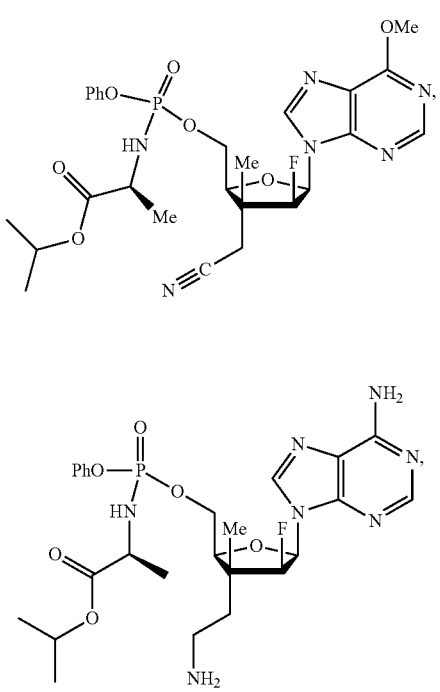
LCB-2146
LCB-2147
LCB-2168
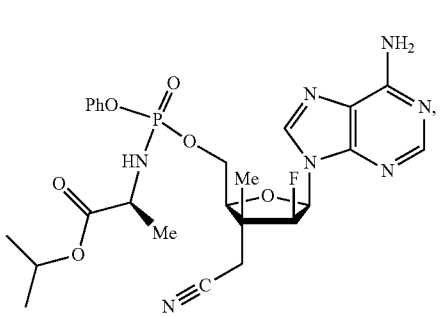
LCB-2172
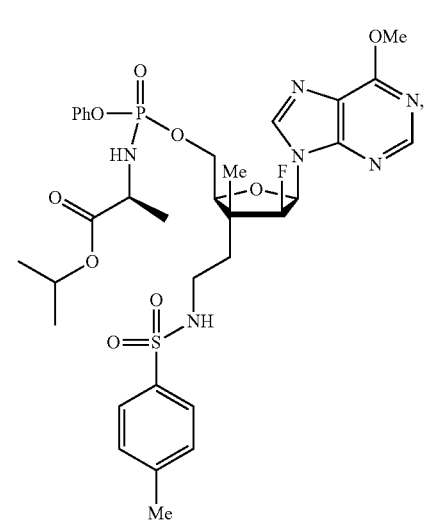
LCB-2173
LCB-2174
LCB-2175
LCB-2176

LCB-2187
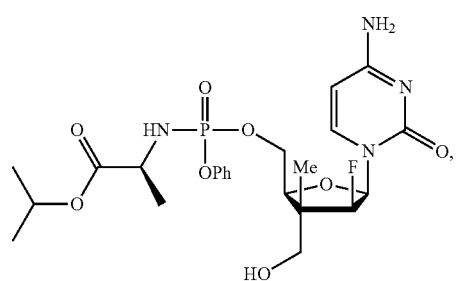
LCB-2189
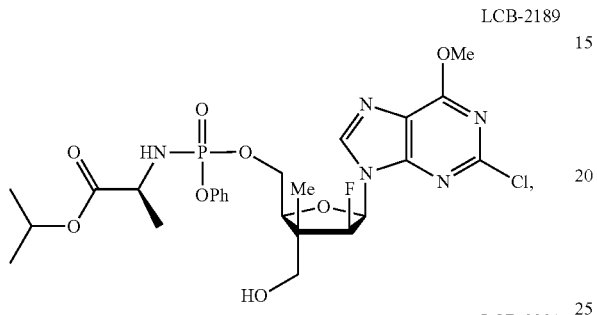
LCB-2201
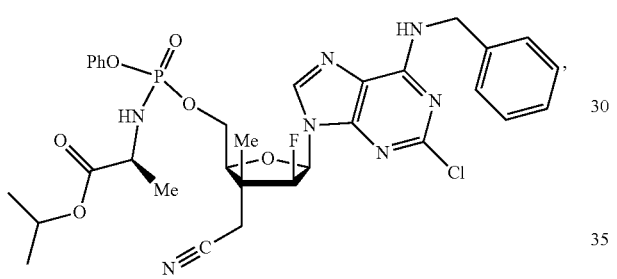
LCB-2220
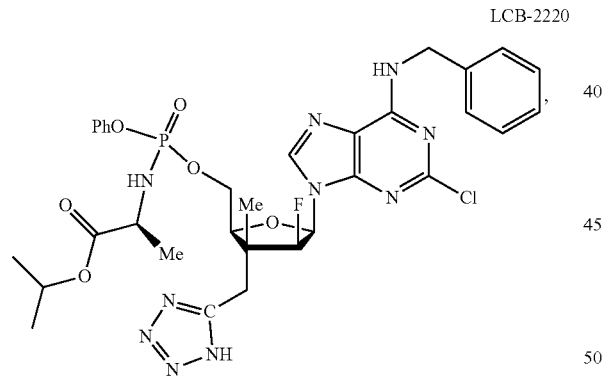
LCB-2229
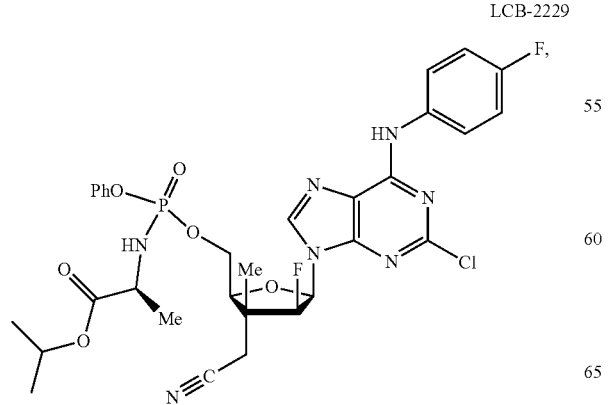
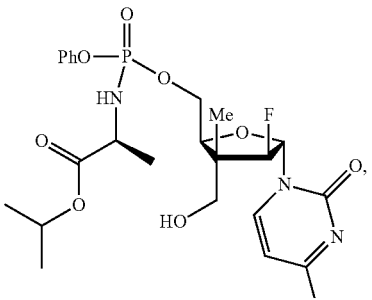
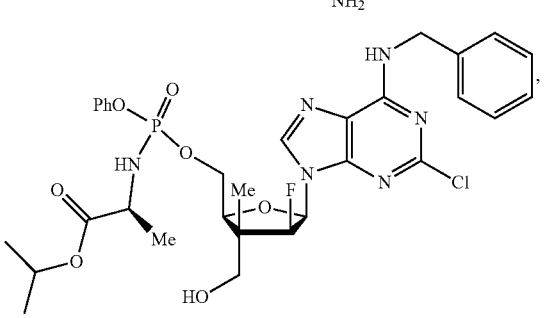
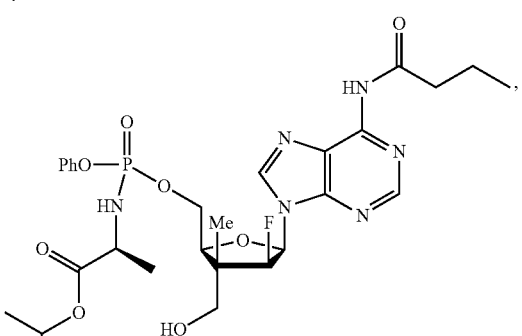
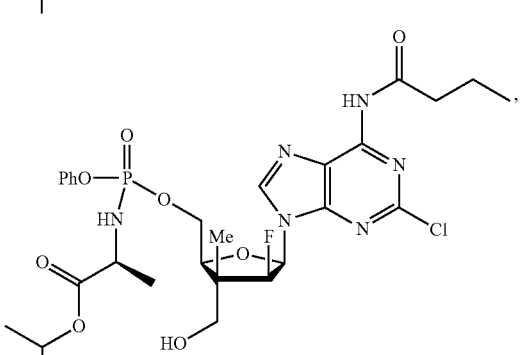
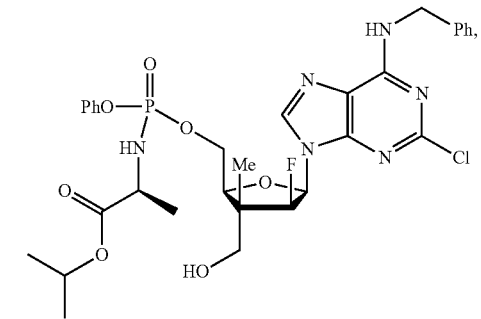

27
-continued
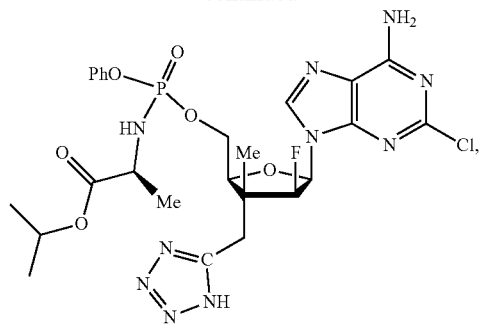
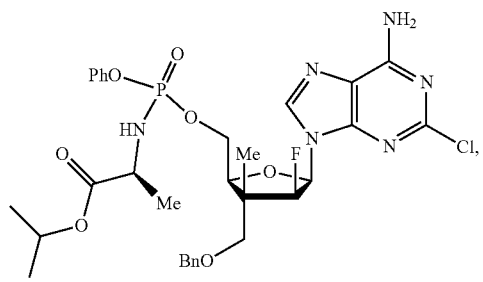
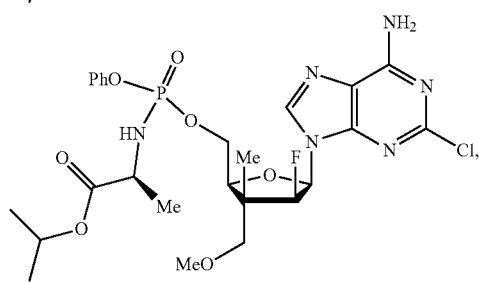
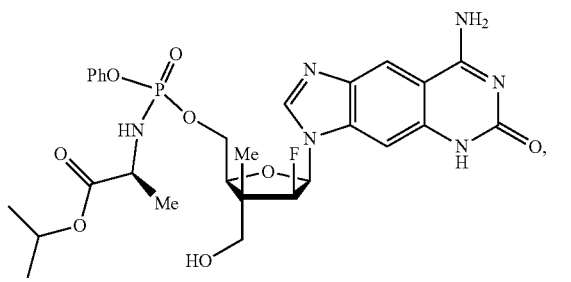
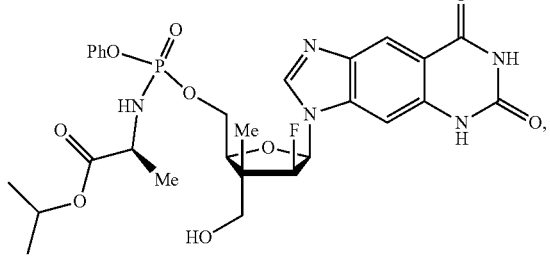
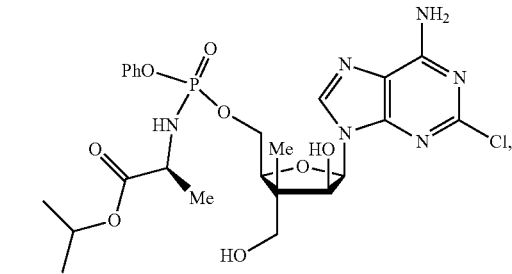
28
-continued
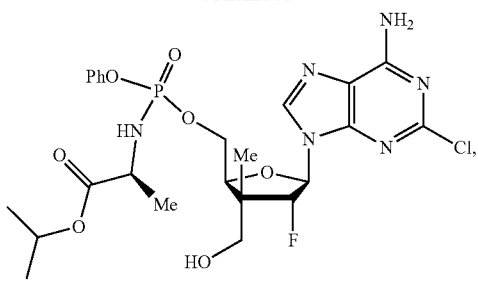
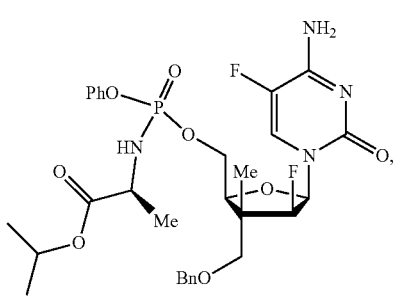
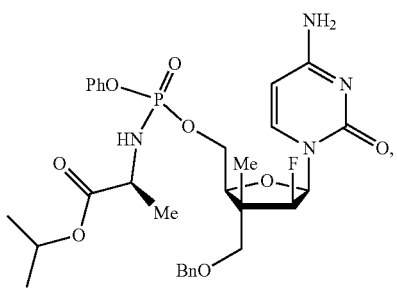
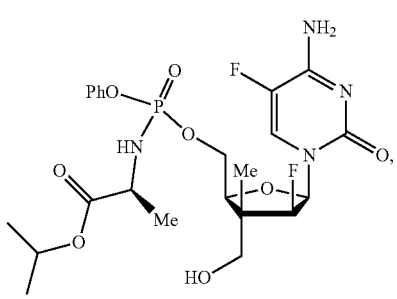
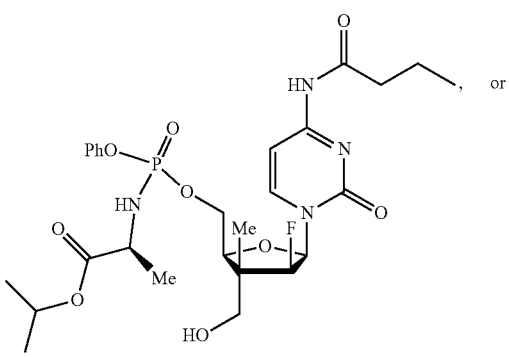

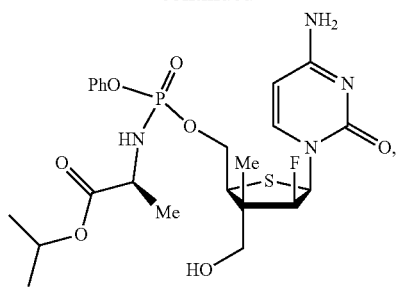
or a pharmaceutically acceptable salt thereof.
68. The compound of any one of items 64 to 67, being:
LCB-1992
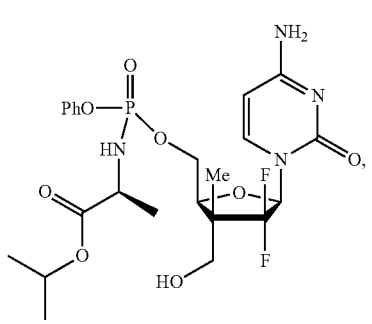
LCB-1998
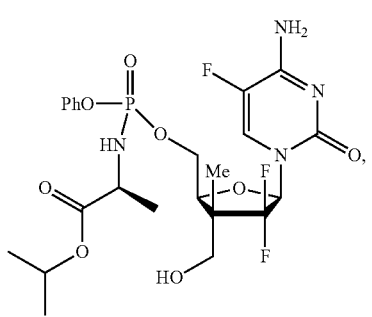
LCB-2000
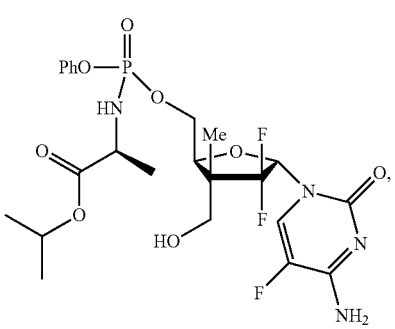
LCB-2001
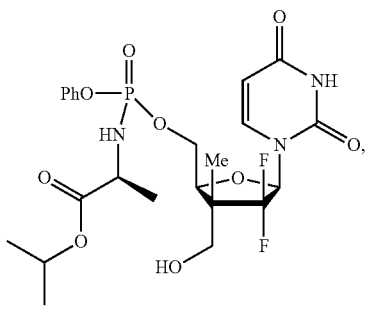
LCB-2018
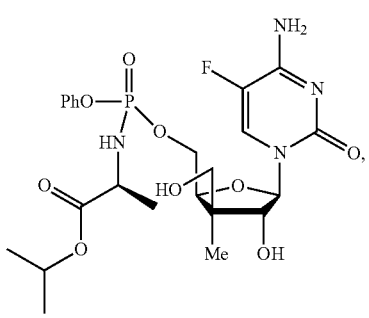
LCB-2027
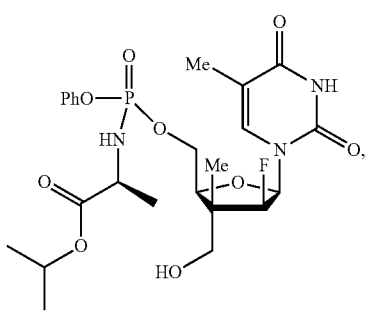
LCB-2028
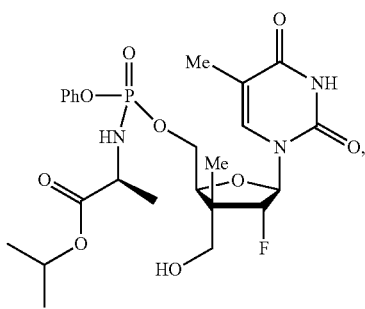
LCB-2034

LCB-2093
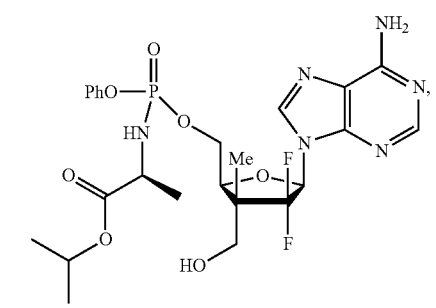
LCB-2106
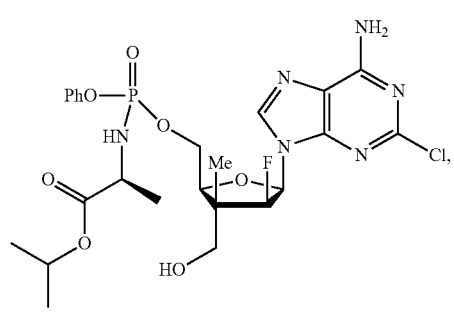
LCB-2142
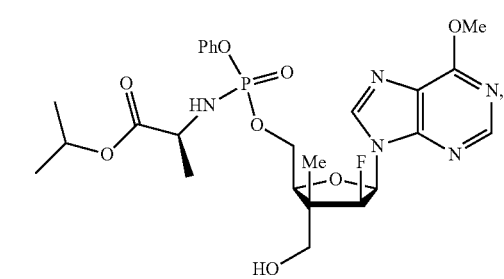
LCB-2146
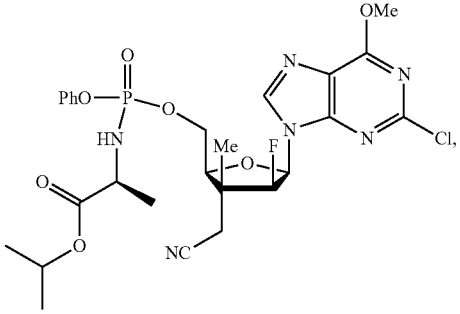
LCB-2147
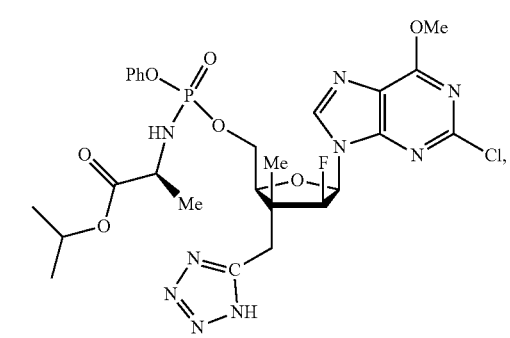
LCB-2168
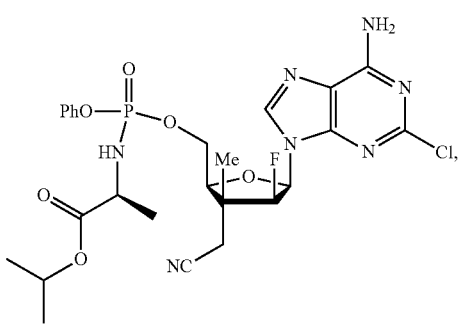
LCB-2172
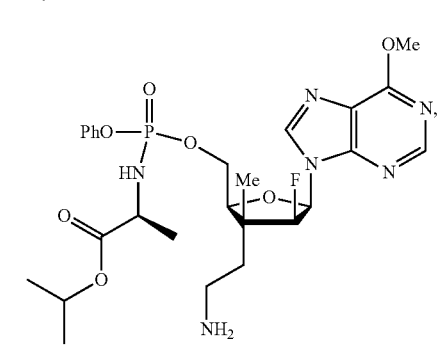
LCB-2173
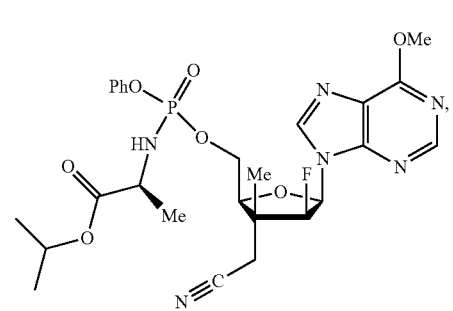
LCB-2174
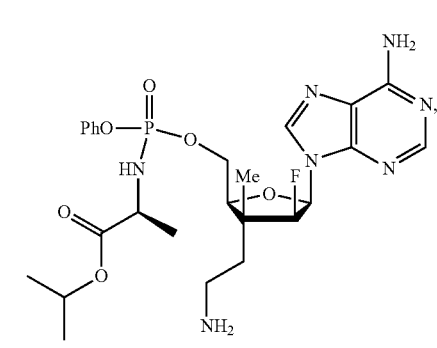
LCB-2175
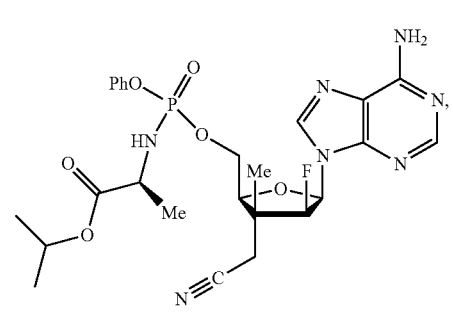

LCB-2176
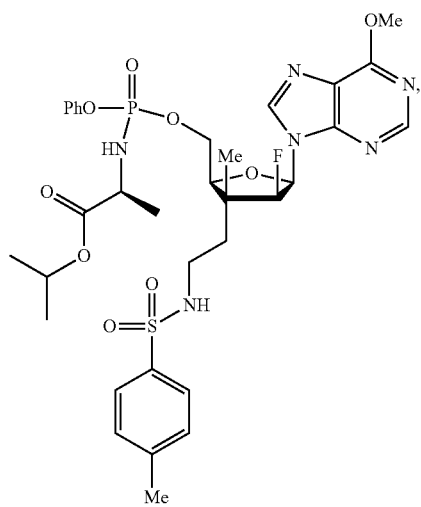
LCB-2187
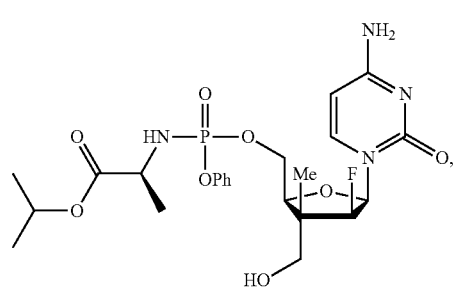
LCB-2189
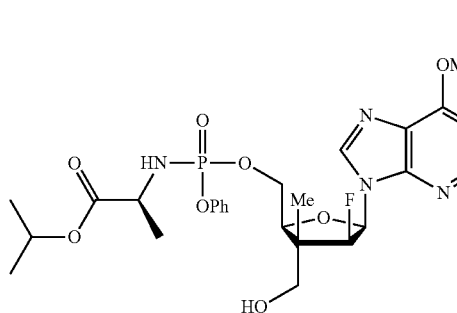
LCB-2201
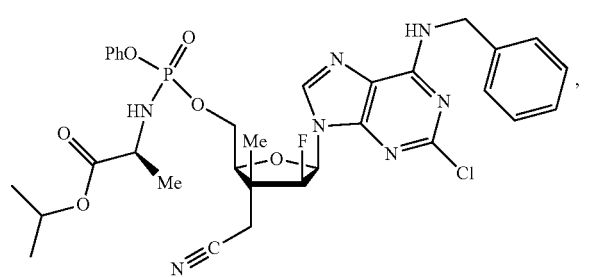
LCB-2220
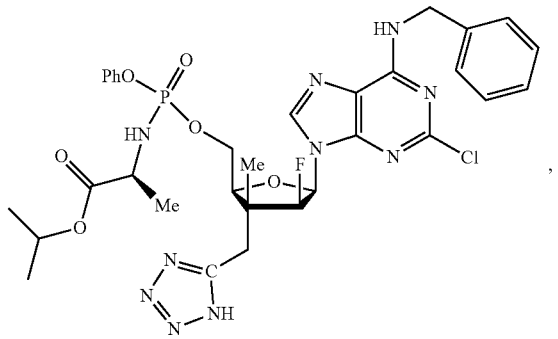
LCB-2229
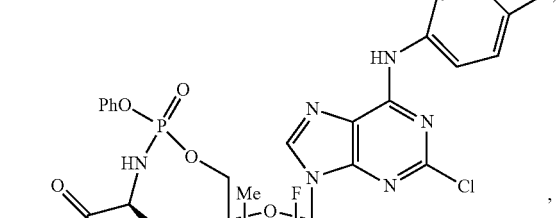
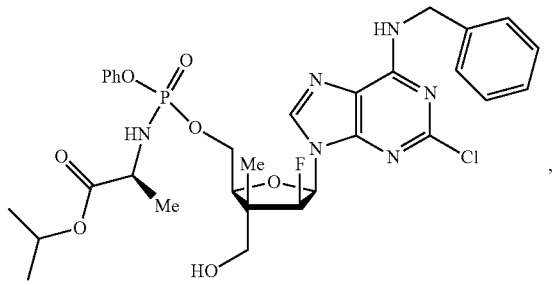
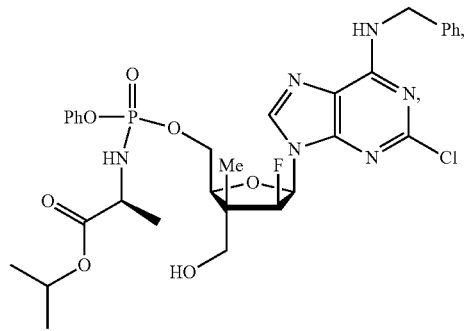

-continued
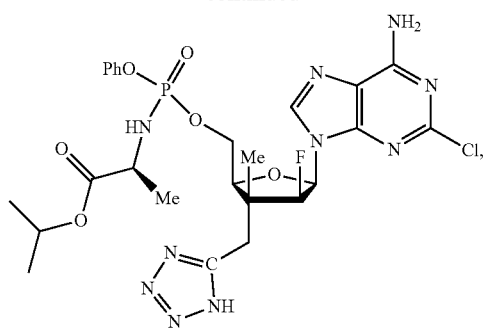
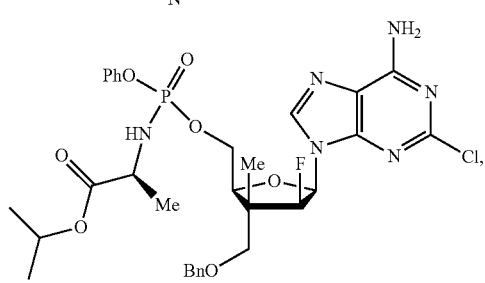
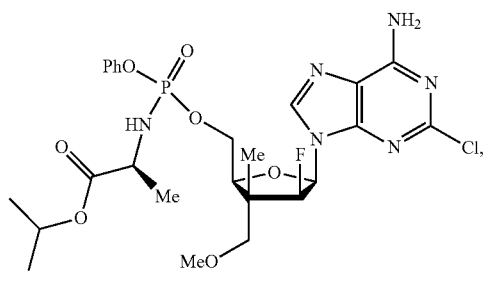
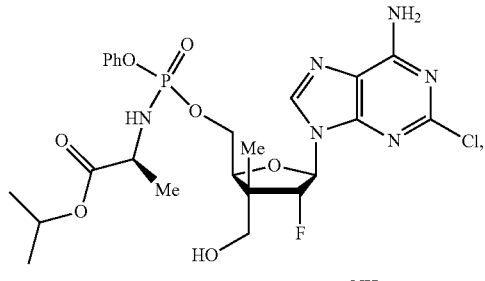
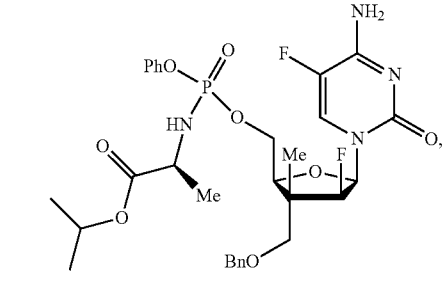
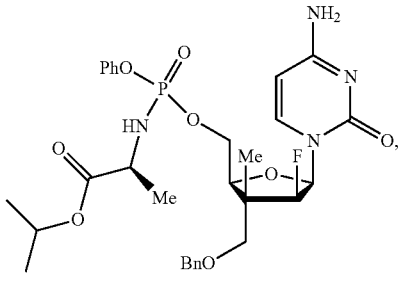
-continued
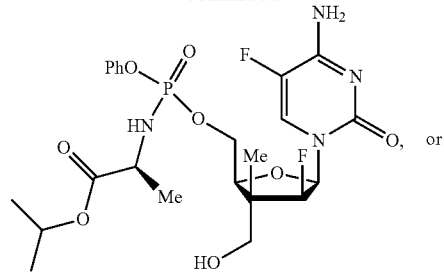, or
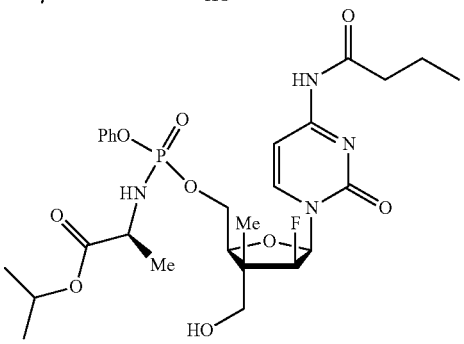,
or a pharmaceutically acceptable salt thereof.
69. The compound of any one of items 64 to 68, being:
LCB-2027
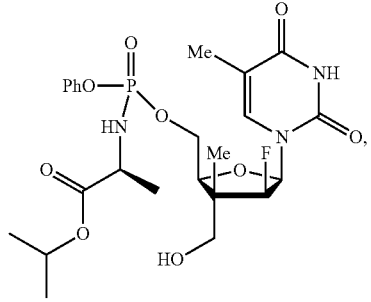,
LCB-2028
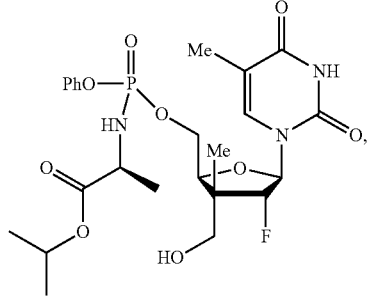,
LCB-2034
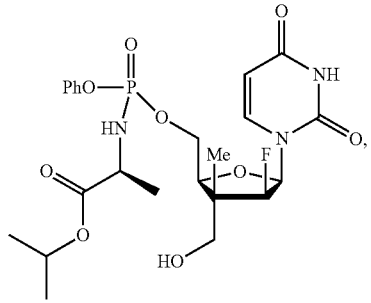, -continued
LCB-2106
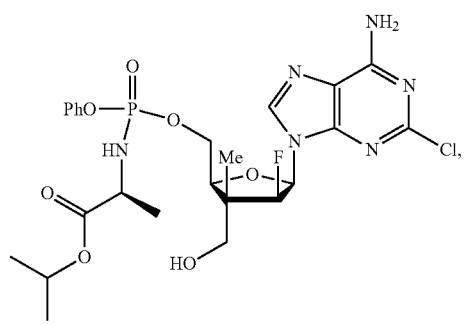
LCB-2142
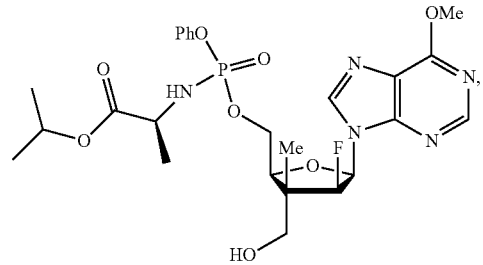
LCB-2146
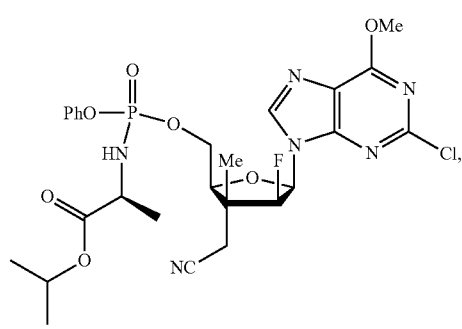
LCB-2147
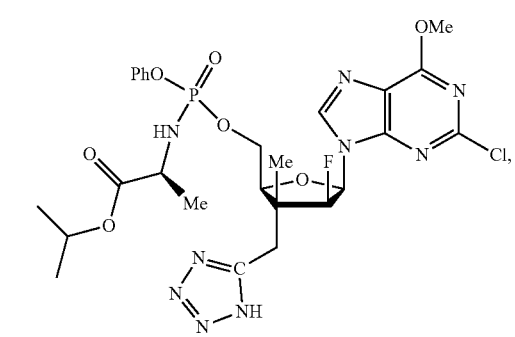
LCB-2168
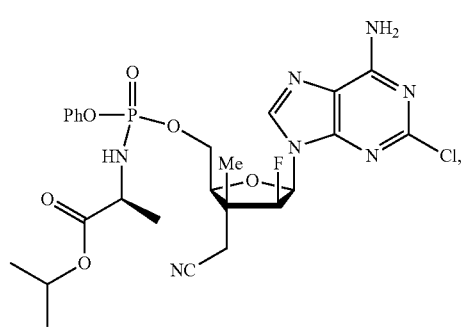
-continued
LCB-2173
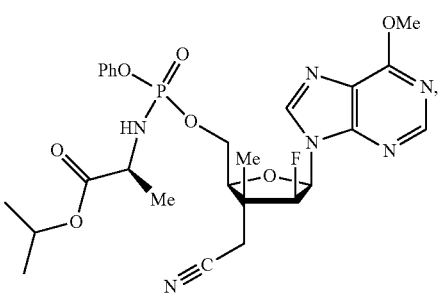
LCB-2174
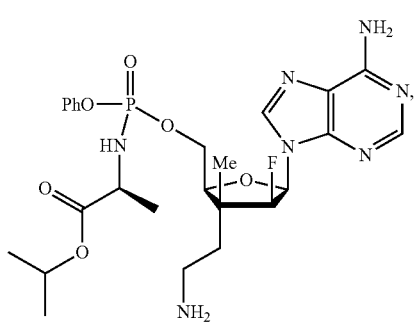
LCB-2175
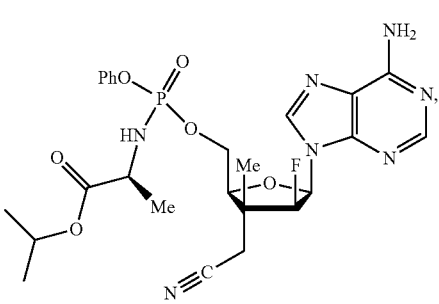
LCB-2187
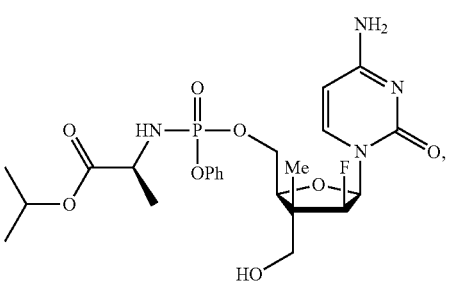
LCB-2189
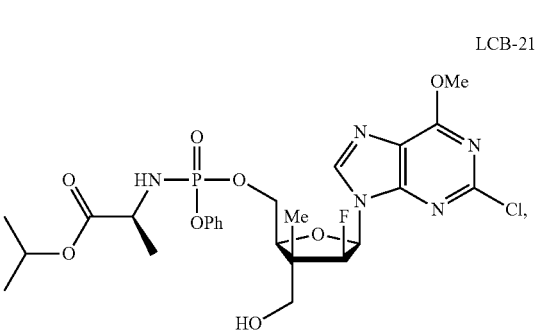

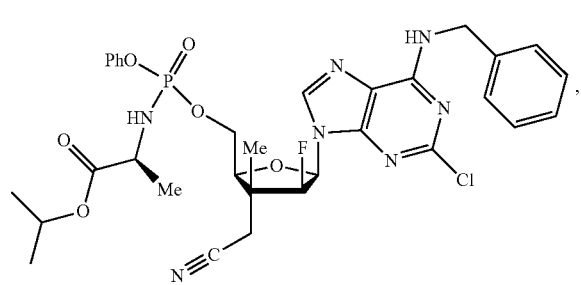
LCB-2201
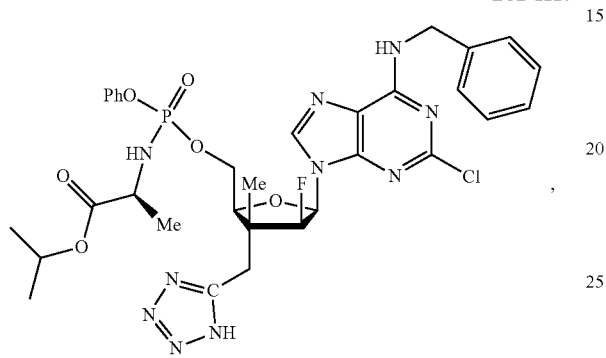
LCB-2220
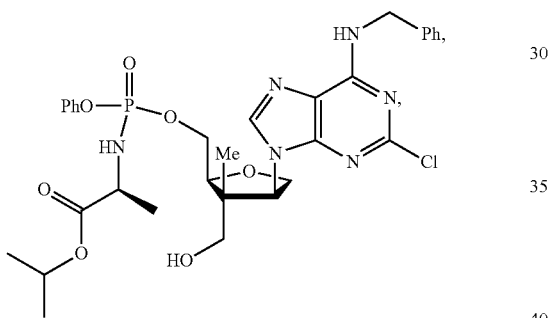
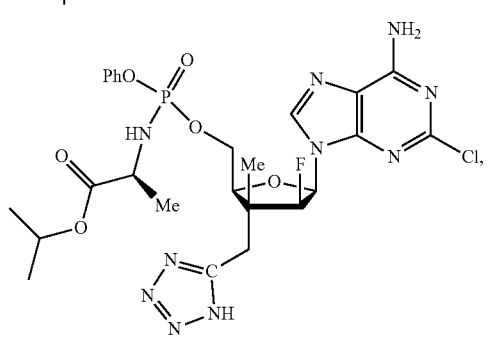
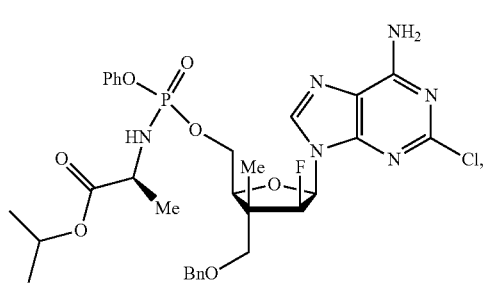
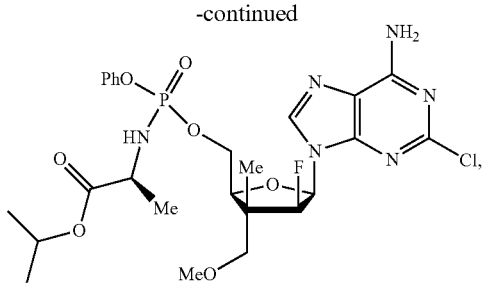
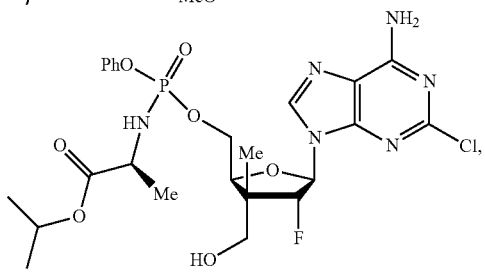
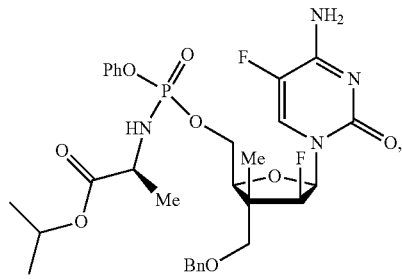
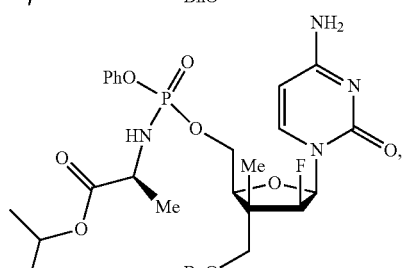
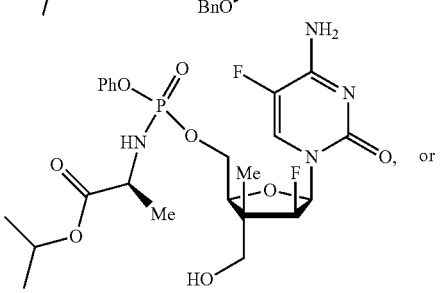
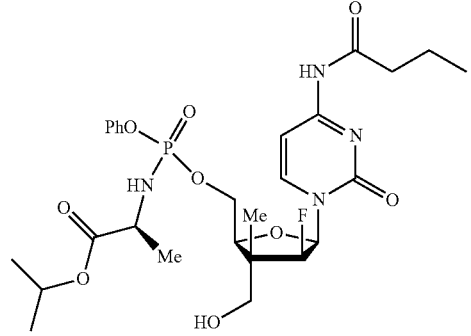
or a pharmaceutically acceptable salt thereof.

70. The compound of any one of items 64 to 69, being:
LCB-2027
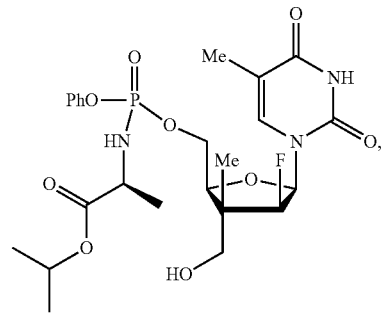
LCB-2034
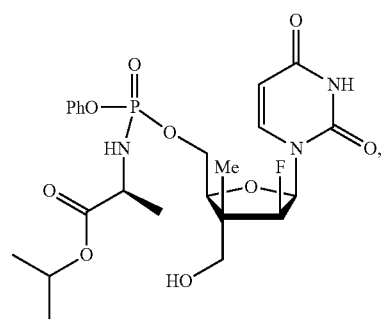
LCB-2106
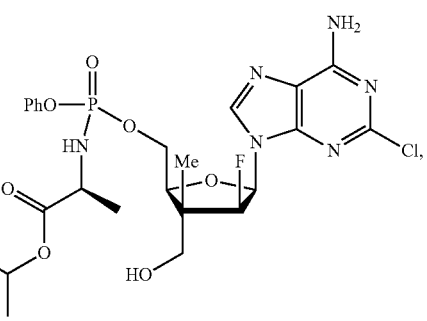
LCB-2168
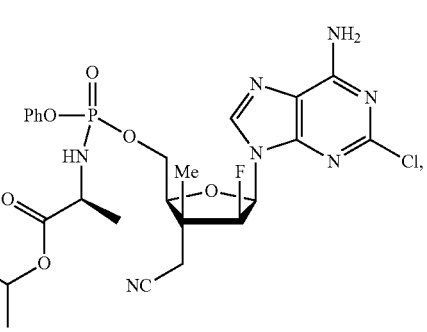
-continued
LCB-2174
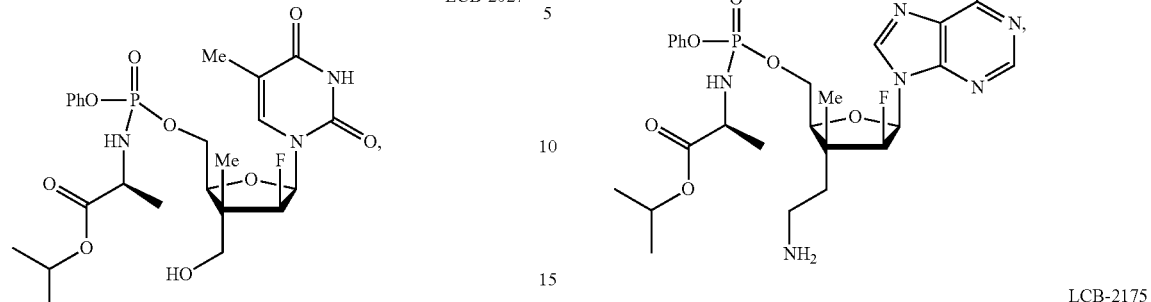
LCB-2175
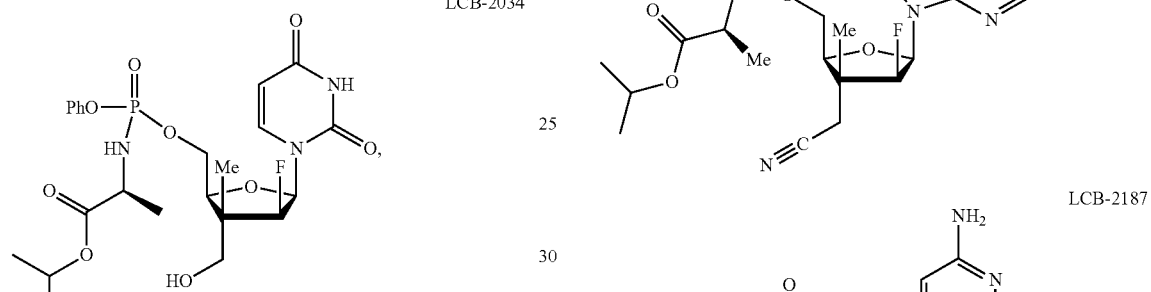
LCB-2187
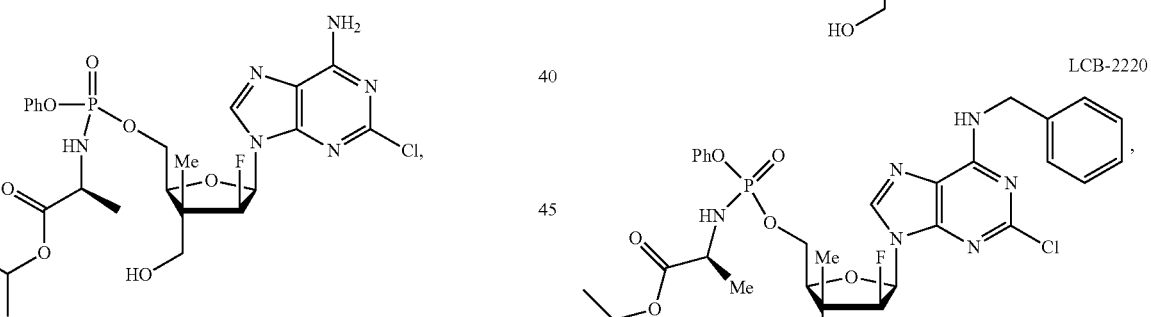
LCB-2220
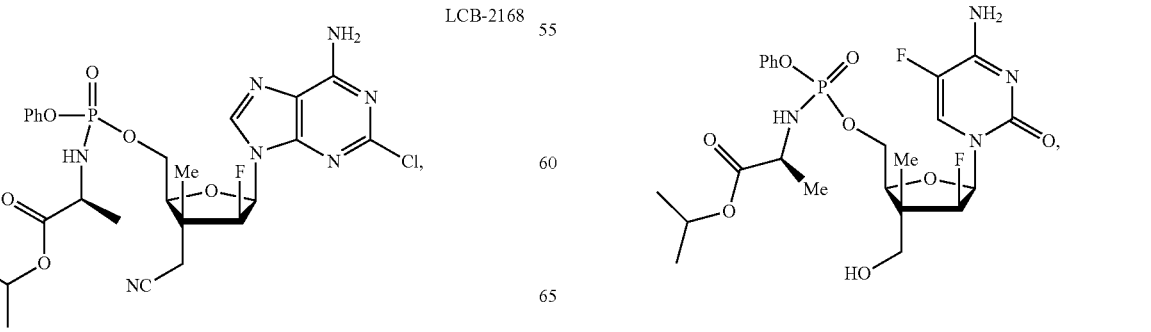

-continued

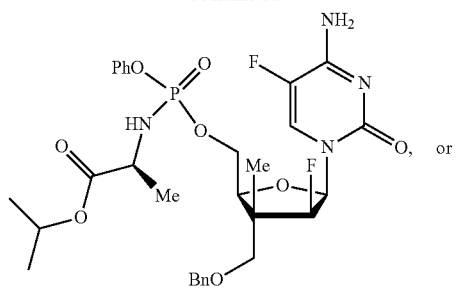

or

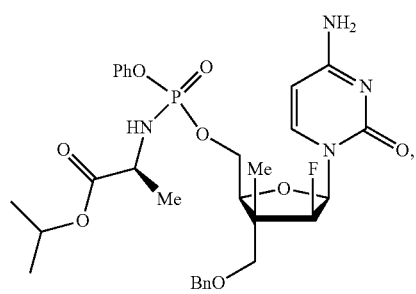

or a pharmaceutically acceptable salt thereof.

71. The compound of any one of items 64 to 70, being:

LCB-2187

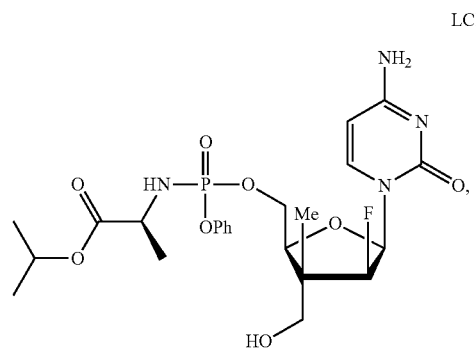

LCB-2220

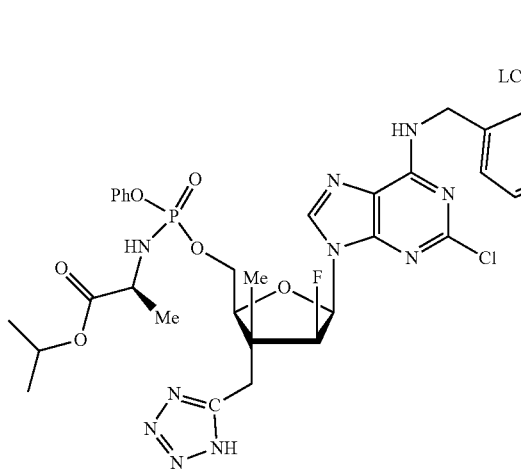

-continued

or

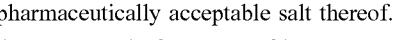

or a pharmaceutically acceptable salt thereof.

72. The compound of any one of items 64 to 71, being:

LCB-2187

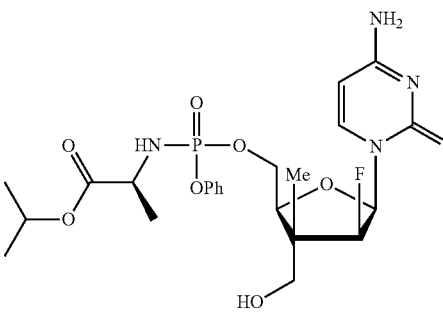

or a pharmaceutically acceptable salt thereof.

73. The compound of any one of items 1 to 53, comprising two phosphoryl groups of formula (XX), $R_1$ representing one said phosphoryl groups and one of A and B being —$(CH_2)_n$M, M being $OR_2$, and $R_2$ representing another of said phosphoryl group of formula (XX).

74. The compound of item 73, being of formula V, VI, IX, or X, preferably of formula V or IX, more preferably IX.

75. The compound of item 73 or 74, wherein Base is:
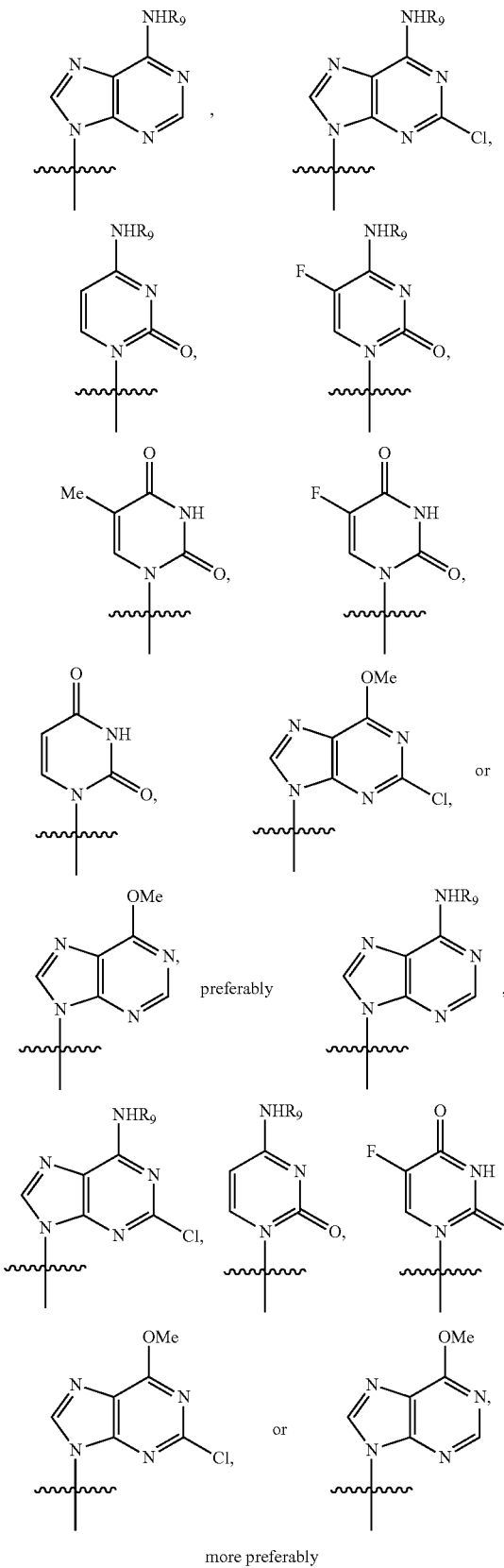
preferably
more preferably
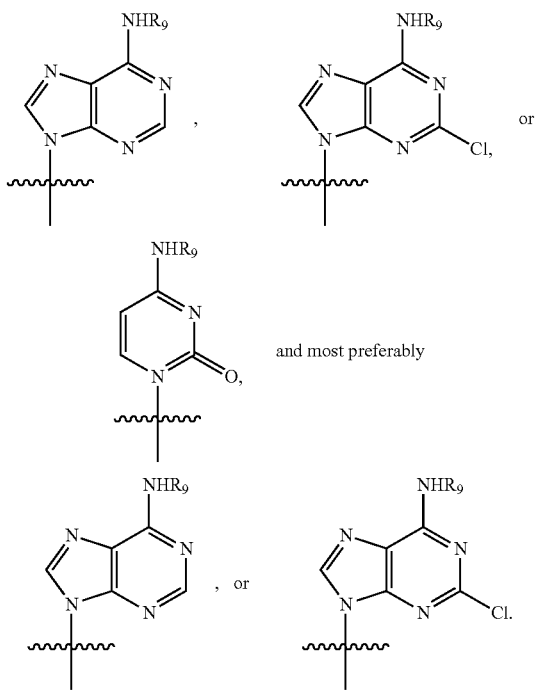
and most preferably
76. The compound of any one of items 73 to 75 being:
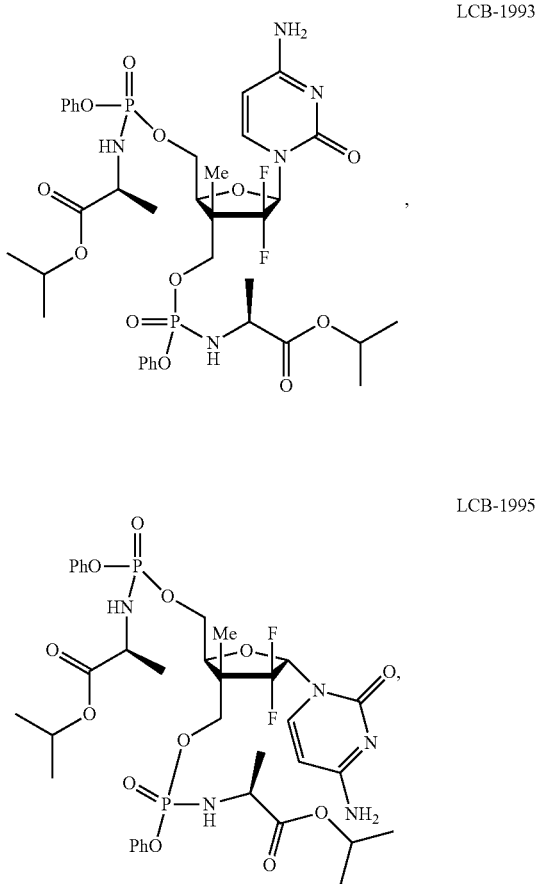
LCB-1993
LCB-1995

LCB-1996
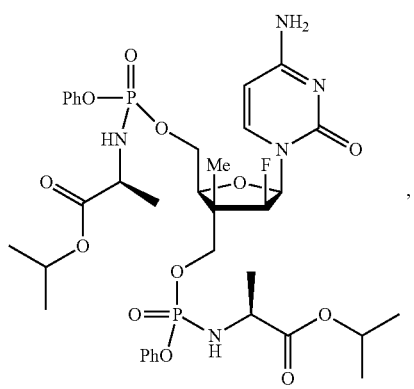
LCB-1997
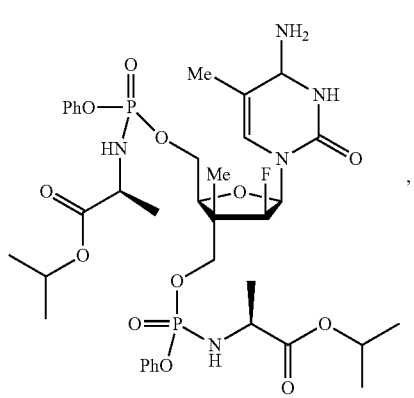
LCB-1999
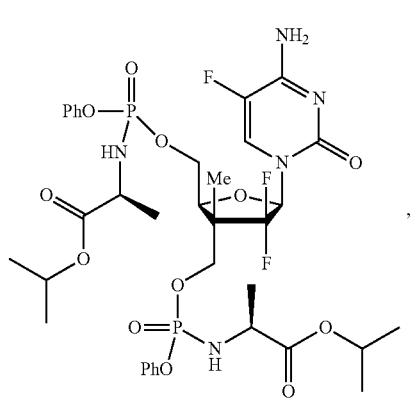
LCB-2002
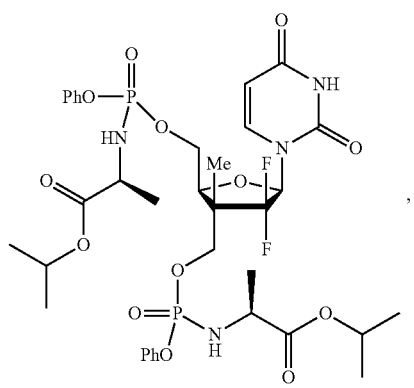
LCB-2009
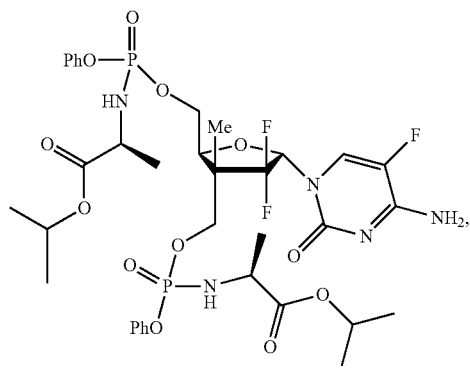
LCB-2015
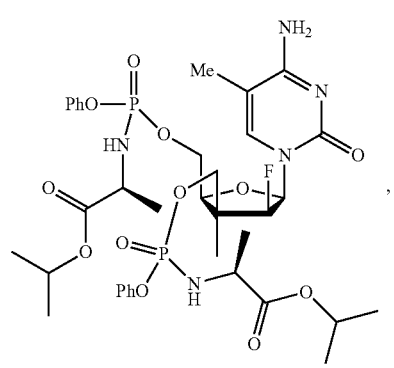
LCB-2016
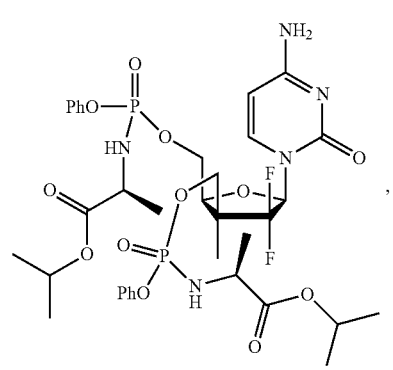
LCB-2017
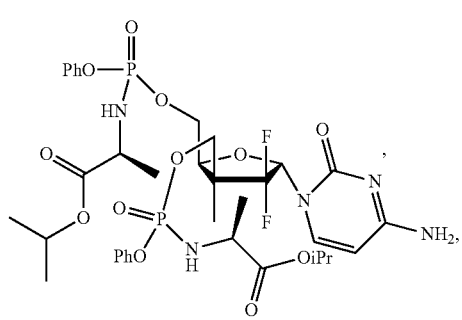

LCB-2029
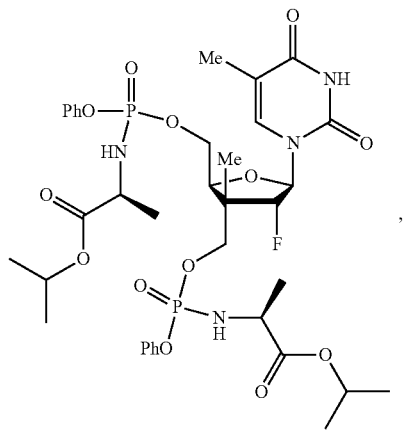
LCB-2035
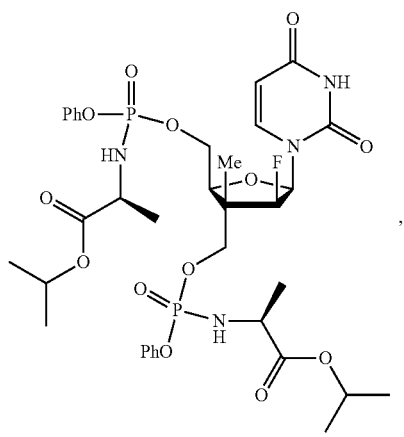
LCB-2036
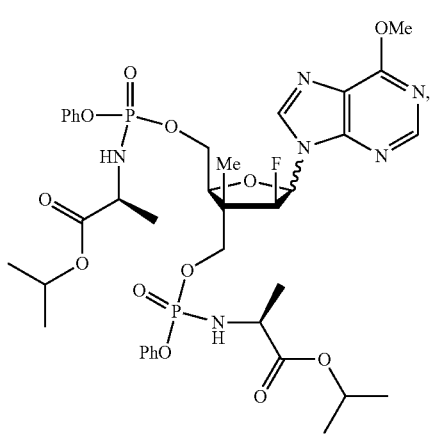
LCB-2045
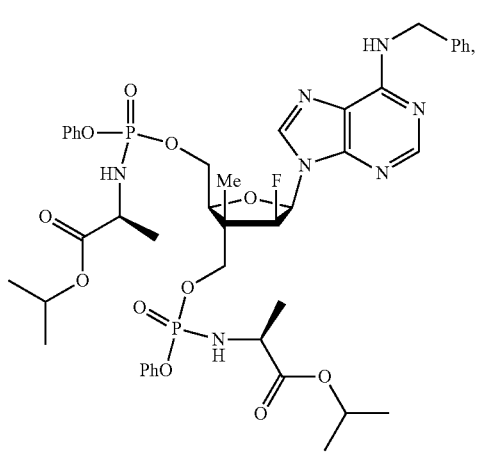
LCB-2076
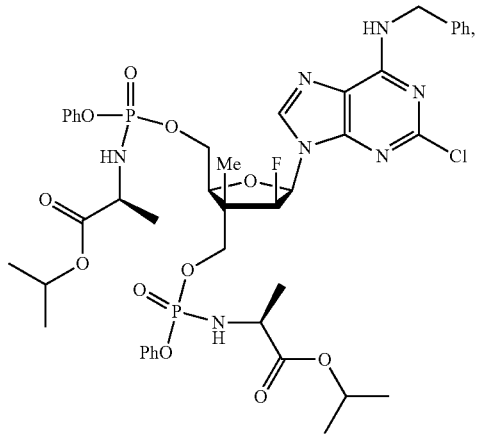
LCB-2079
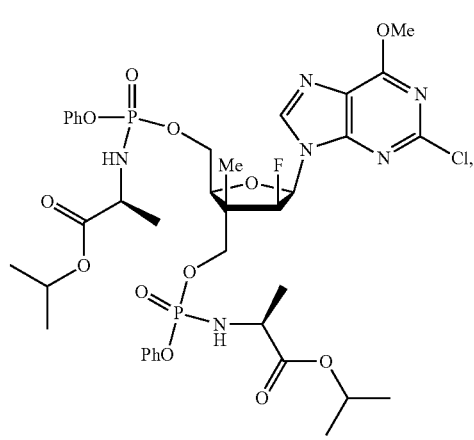

-continued
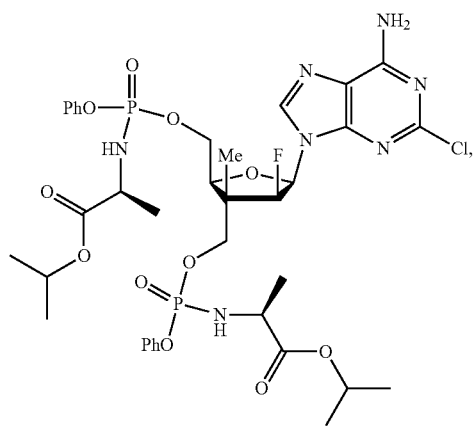
LCB-2080
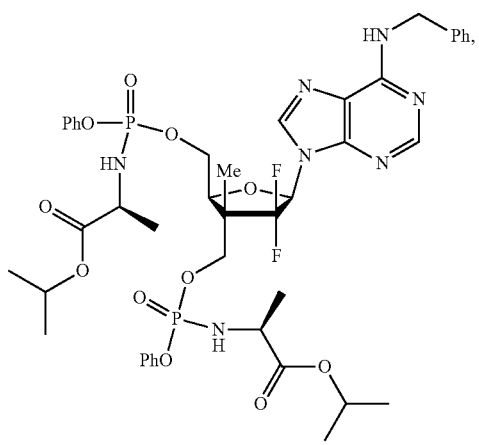
LCB-2095
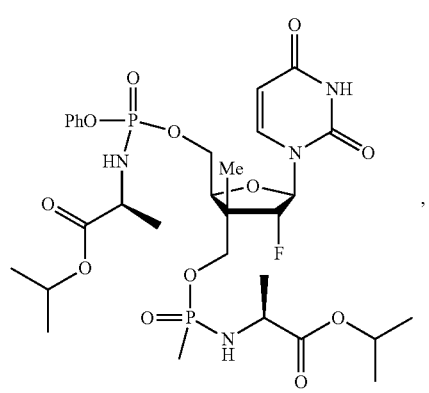
LCB-2088
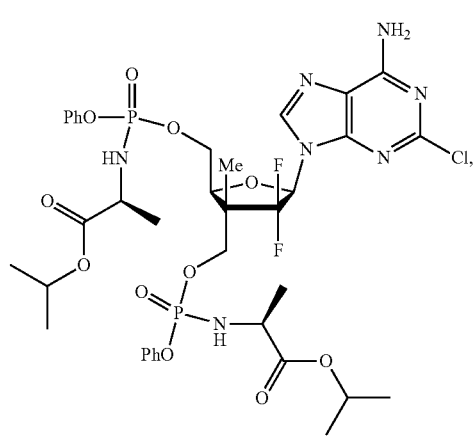
LCB-2105
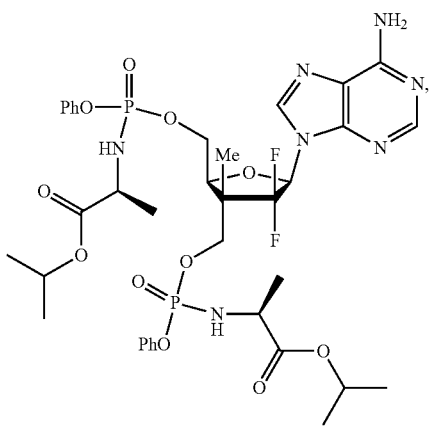
LCB-2092
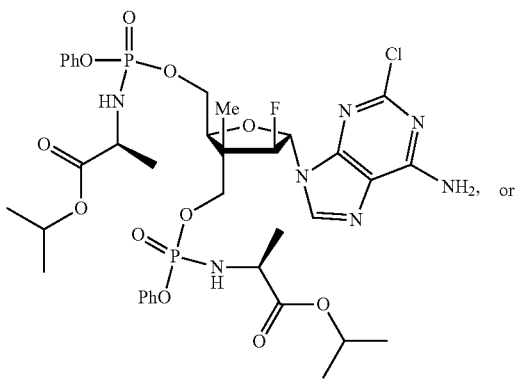
LCB-2127, or

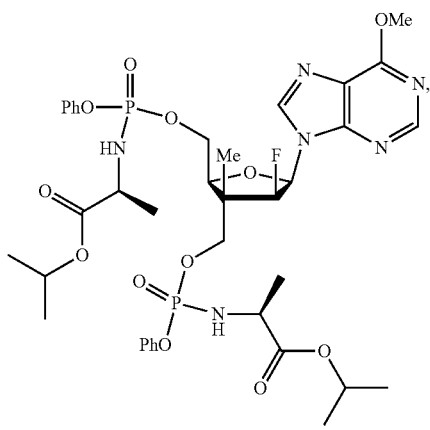
LCB-2143
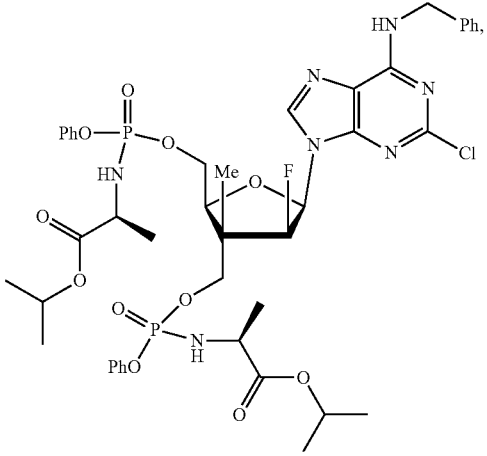
LCB-2076
or a pharmaceutically acceptable salt thereof.
77. The compound of any one of items 73 to 76 being:
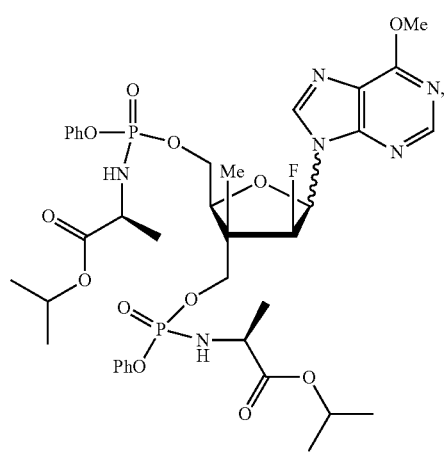
LCB-2036
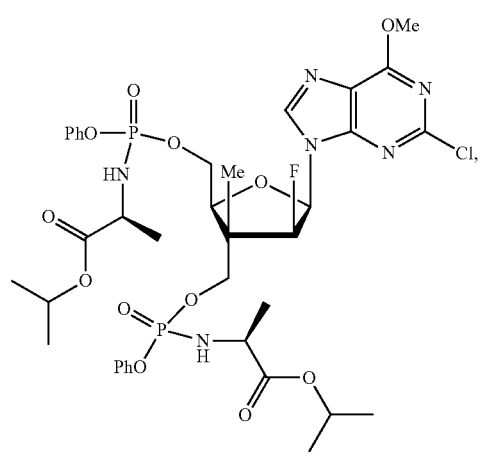
LCB-2079
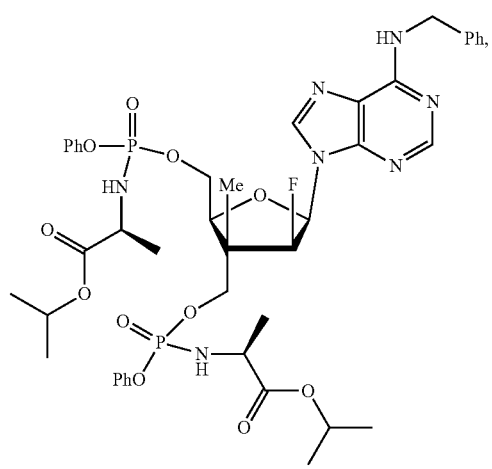
LCB-2045
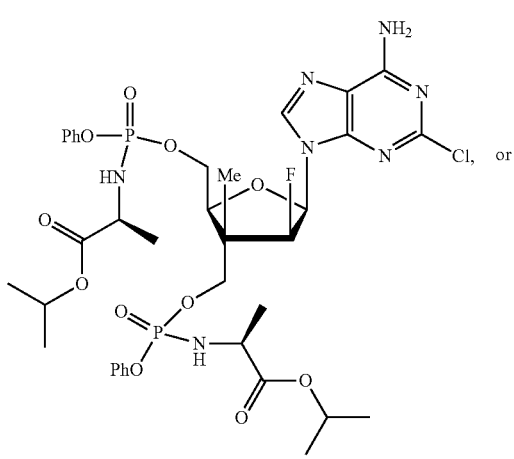
LCB-2080

-continued

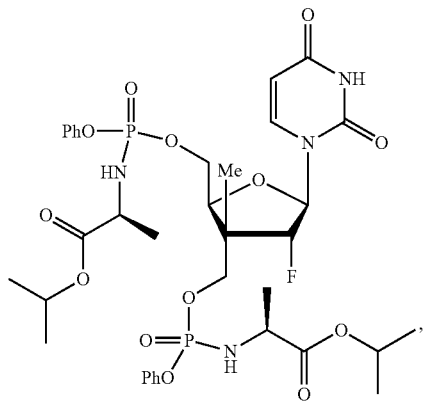
LCB-2088 or a pharmaceutically acceptable salt thereof.

78. The compound of any one of items 1 to 48, comprising one lipoate group of formula (XXI), said compound either being free of a phosphoryl group of formula (XX) or comprising a phosphoryl group of formula (XX) in $R_1$.
79. The compound of item 78, being of formula I, II, V, VI, IX, X, XIII, XIV, or XVII, preferably I, V, IX, XIII, or XVII, more preferably V, XIII, or XVII or alternatively I, IX, or XVII, and more preferably of formula XIII or XVII.
80. The compound of item 78 or 79, wherein C is H and D is halo or OH, preferably OH.
81. The compound of any one of items 78 to 80, wherein Base is:

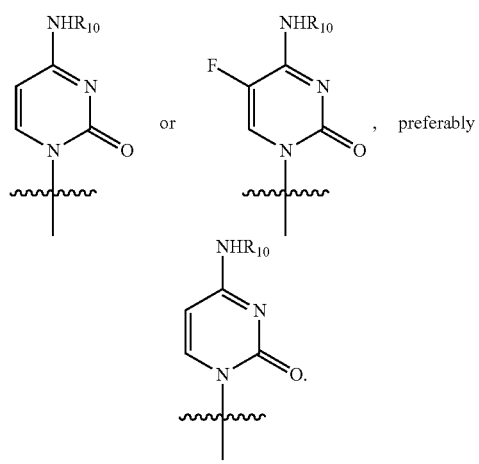

, preferably

82. The compound of any one of items 78 to 81, being free of phosphoryl group.
83. The compound of any one of items 78 to 82, wherein $R_1$ is H.
84. The compound of any one of items 78 to 83, being of formula I, V, IX, XIII, or XVII.
85. The compound of any one of items 78 to 84, being of formula I, IX, or XVII, preferably IX or XVII.
86. The compound of any one of items 78 to 84, being of formula V or XVII, preferably of formula XVII, or alternatively of formula V.

87. The compound of any one of items 78 to 86, being:

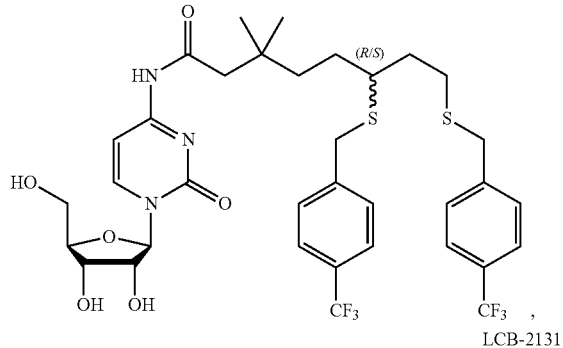
LCB-2125

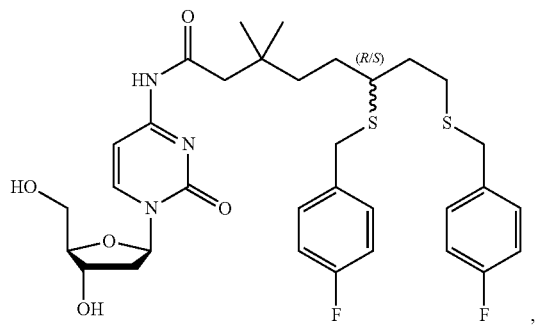
LCB-2131

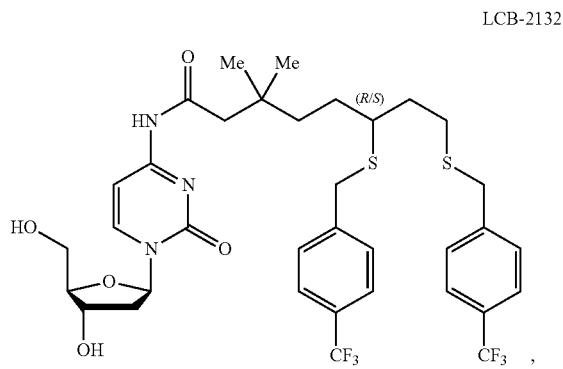
LCB-2132

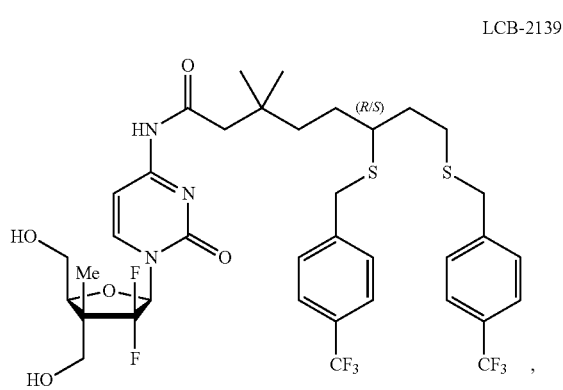
LCB-2139

-continued
LCB-2140
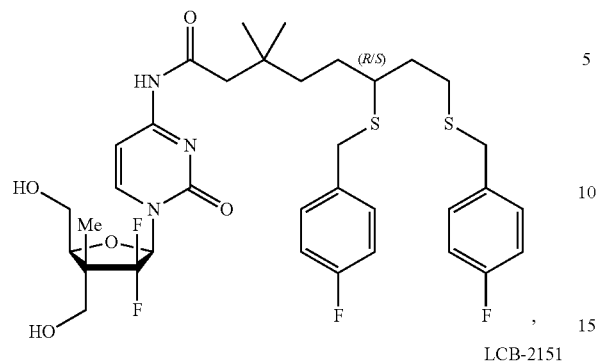
LCB-2151
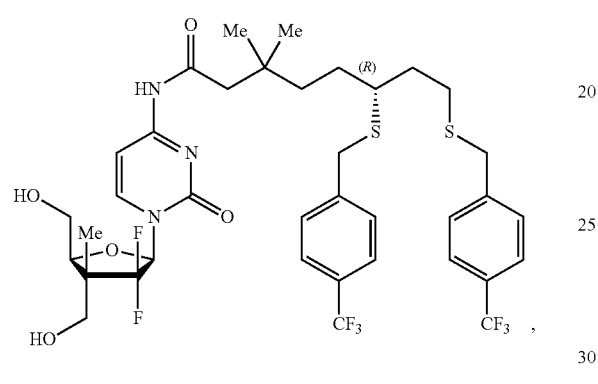
LCB-2216
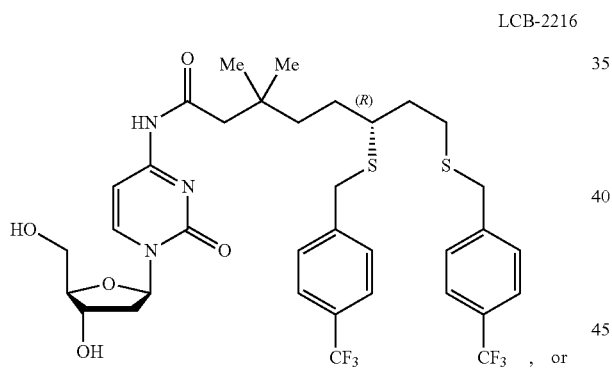
LCB-2227
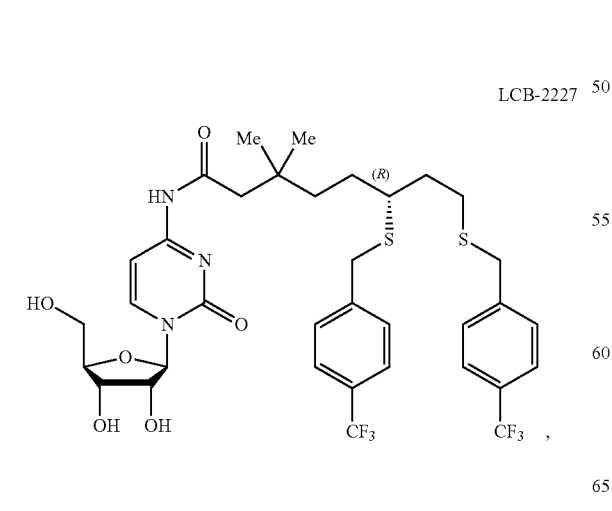
or a pharmaceutically acceptable salt thereof.
88. The compound of any one of items 78 to 87 being:
LCB-2125
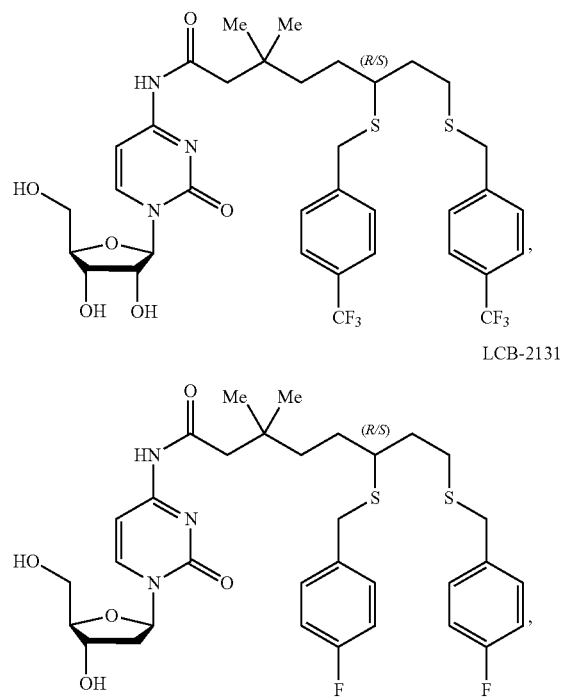
LCB-2131
LCB-2132
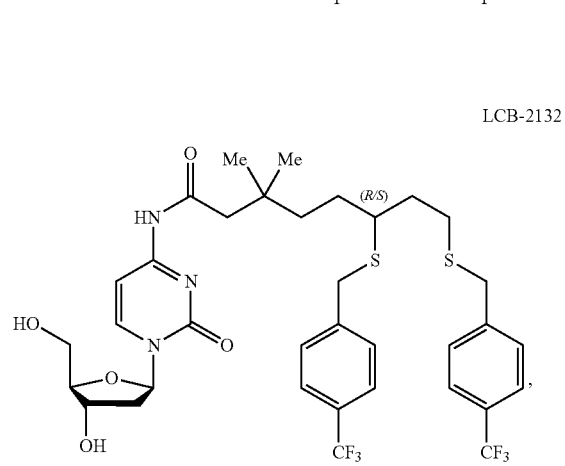
LCB-2140
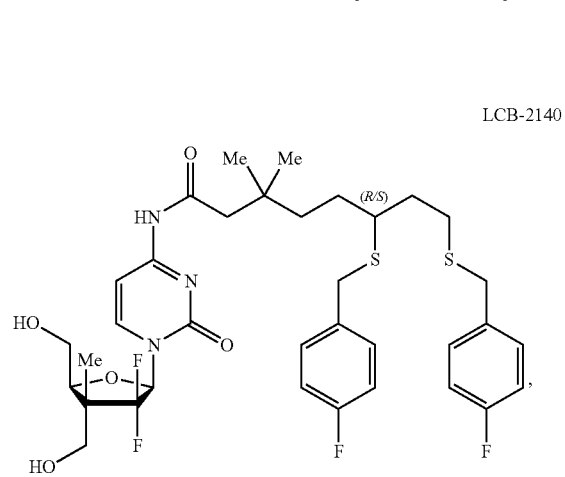

-continued

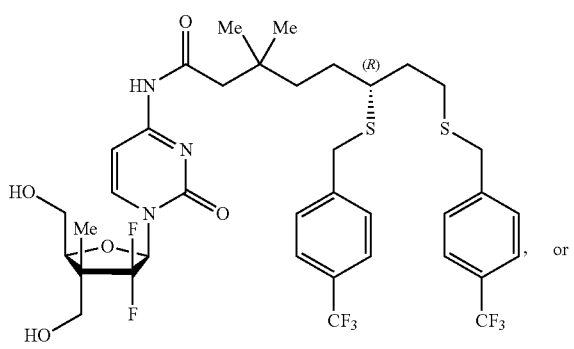
LCB-2151

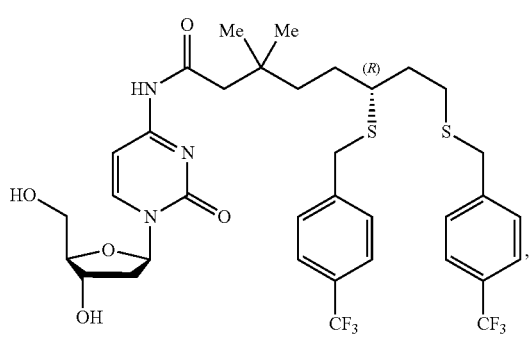
LCB-2216 or a pharmaceutically acceptable salt thereof.

89. The compound of any one of items 78 to 88 being:

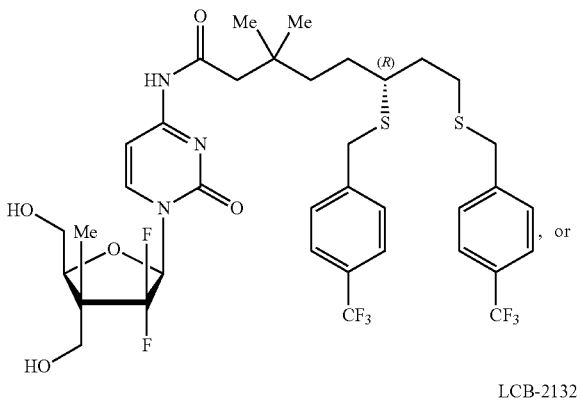
LCB-2151

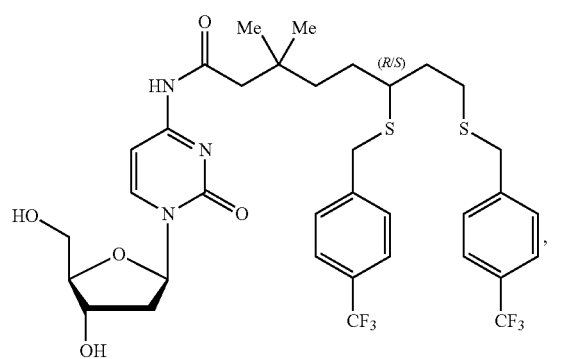
LCB-2132 or a pharmaceutically acceptable salt thereof.

90. The compound of any one of items 78 to 81, comprising said phosphoryl group in $R_1$.

91. The compound of item 90, being of formula I, V, IX, XIII, or XVII, preferably I, V, IX, or XIII.

92. The compound of item 90 or 91, being of formula I, IX, or XIII, preferably IX or XIII.

93. The compound of item 90 or 91, being of formula V or XIII, preferably XIII.

94. The compound of any one of items 90 to 93, being:

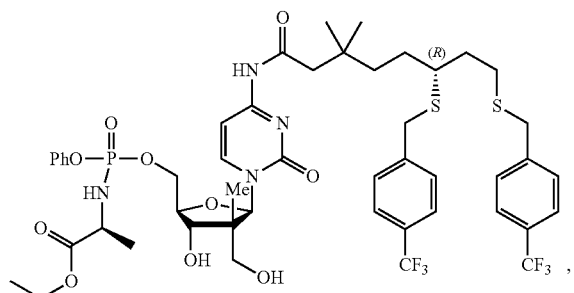

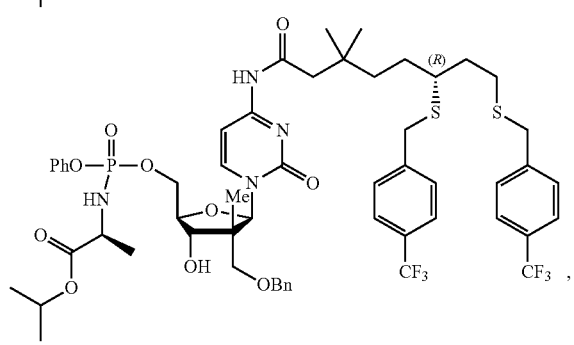

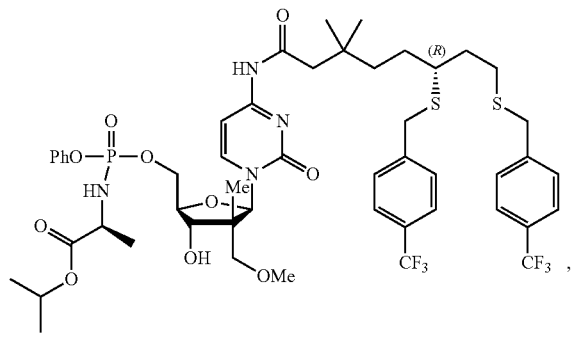

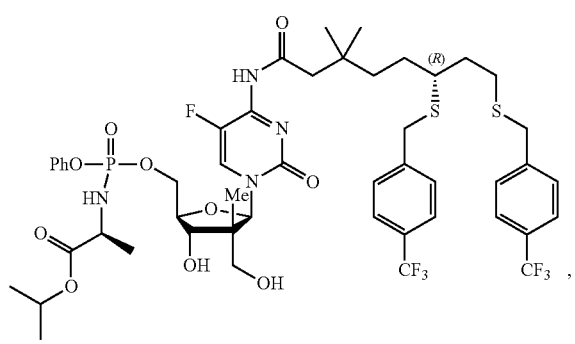

-continued

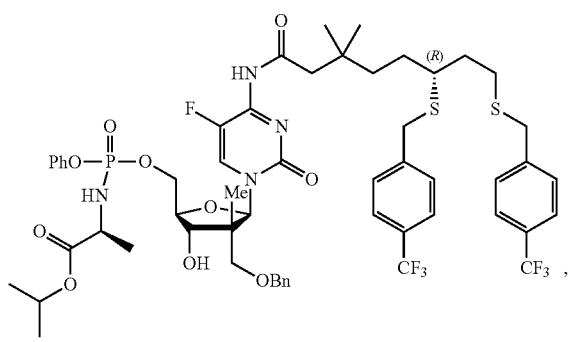

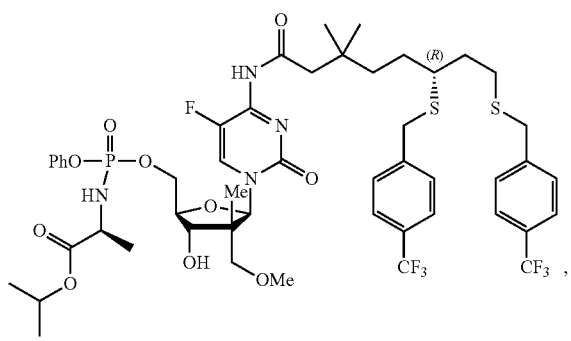

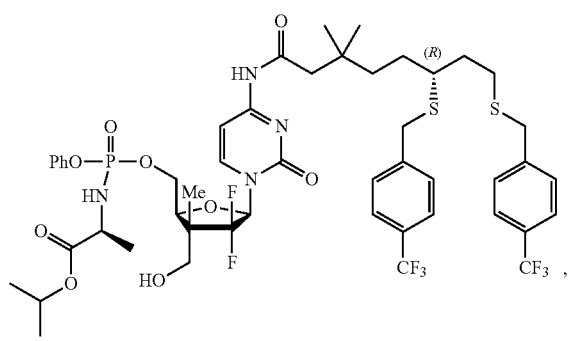

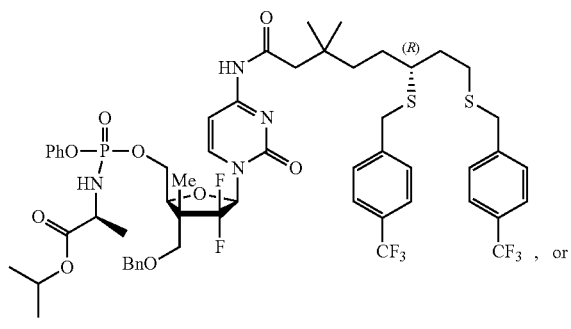

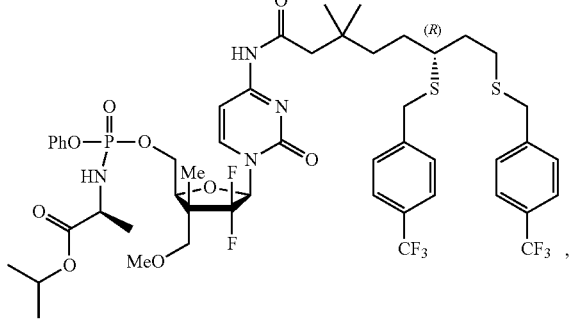

or a pharmaceutically acceptable salt thereof.

95. The compound of any one of items 90 to 94, being:

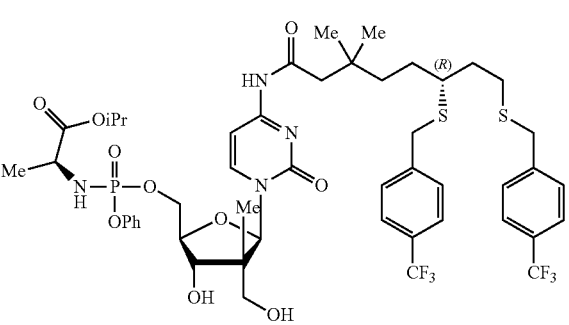

LCB2179 or a pharmaceutically acceptable salt thereof.
96. A pharmaceutical composition comprising the compound of any one items 1 to 95 and a pharmaceutical carrier, excipients or diluents.
97. A pharmaceutical composition comprising the compound of any one items 49 to 77 and a pharmaceutical carrier, excipients or diluents.
98. A pharmaceutical composition comprising the compound of any one items 82 to 89 and a pharmaceutical carrier, excipients or diluents.
99. A pharmaceutical composition comprising the compound of any one items 90 to 95 and a pharmaceutical carrier, excipients or diluents.
100. Use of the compound of any one items 1 to 95 or the pharmaceutical composition of any one items 96 to 99 for treating cancer in a subject in need thereof.
101. A method of treating cancer in a subject in need thereof, the method comprising administering the compound of any one items 1 to 95 or the pharmaceutical composition of any one items 96 to 99 to the subject.
102. Use of the compound of any one items 1 to 95 or the pharmaceutical composition of any one items 96 to 99 for inhibiting tumor growth in a subject in need thereof.
103. A method of inhibiting tumor growth in a subject in need thereof, the method comprising administering the compound of any one items 1 to 95 or the pharmaceutical composition of any one items 96 to 99 to the subject.
104. Use of the compound of any one items 1 to 95 for in vitro inhibition of tumor cell growth.
105. A method of inhibiting tumor cell growth in vitro, the method comprising contacting the compound of any one items 1 to 95 with the tumor cell.
106. The use or method of any one of items 100 to 105, wherein the cancer is breast cancer, lung cancer, liver cancer, pancreas cancer, or colon cancer, preferably liver cancer or pancreas cancer.
107. The use or method of any one of items 100 to 106, wherein the compound is a compound as defined in any one of items 49 to 77.
108. The use or method of any one of items 100 to 106, wherein the compound is a compound as defined in any one of items 82 to 89.
109. The use or method of any one of items 100 to 106, wherein the compound is a compound as defined in any one of items 90 to 95.
110. Use of the compound of any one items 49 to 77 and 90 to 95 or the pharmaceutical composition of item 97 or 99 for providing antiviral treatment in a subject in need thereof.

111. A method of providing antiviral treatment in a subject in need thereof, the method comprising administering the compound of any one items 49 to 77 and 90 to 95 or the pharmaceutical composition of item 97 or 99 to the subject.

112. Use of the compound of any one items 49 to 77 and 90 to 95 or the pharmaceutical composition of item 97 or 99 for inhibiting viral replication in a subject in need thereof.

113. A method of inhibiting viral replication in a subject in need thereof, the method comprising administering the compound of any one items 49 to 77 and 90 to 95 or the pharmaceutical composition of item 97 or 99 to the subject.

114. Use of the compound of any one items 49 to 77 and 90 to 95 for in vitro inhibition of viral replication.

115. A method of inhibiting viral replication in vitro, the method comprising contacting the compound of any one items 49 to 77 and 90 to 95 to cells infected with a virus.

116. The use or method of any one of items 110 to 115, wherein the virus is HCMV, HBV, RSV, Influenza, $AH_1N_1$, HSV-1, HSV-2, or Zika virus.

117. The use or method of any one of items 110 to 116, wherein the virus is HCMV or HBV.

118. The use or method of any one of items 110 to 117, wherein the virus is HCMV.

119. The use or method of any one of items 110 to 118, wherein the compound is a compound as defined in any one of items 49 to 77.

120. The use or method of any one of items 110 to 118, wherein the compound is a compound as defined in any one of items 90 to 95.

DETAILED DESCRIPTION OF THE INVENTION

The invention relates to antitumor/anticancer agents and/or antiviral agents. In fact, the present invention relates to novel nucleoside analogues that can be used as anticancer or antiviral agents. These compounds are nucleoside and/or nucleotide prodrugs.

In particular, the invention relates to nucleoside analogues comprising a tetrahydrofuranyl, or tetrahydrothienyl moiety, which:

Group A: has a quaternary stereogenic all-carbon center at the C3' position and bear a phosphoryl group at either or both positions C5' and C3';

Group B: bear a β-blocked lipoate derivative attached through an amide bond to the primary amine of the nucleobase); or Group C: bear a phosphorylated prodrug at the C5' position and a β-blocked lipoate derivative attached through an amide bond to the primary amine of the nucleobase.

Figure 3:
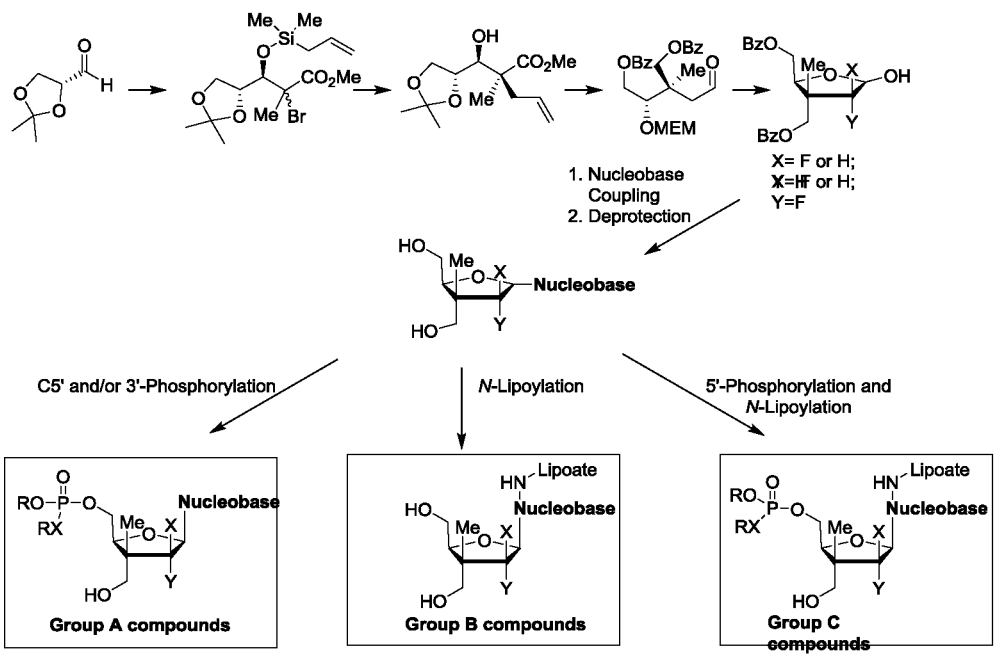
FIG. 3 shows the general synthetic procedure for the production of the compounds of the invention.
Figure 3:
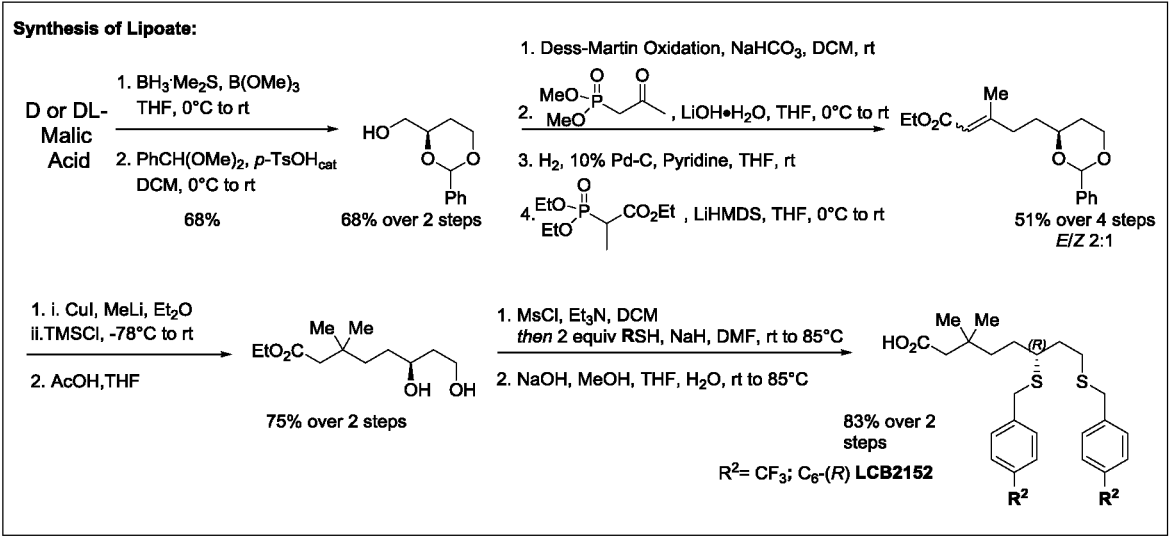

These groups of compounds are shown in FIG. 3.

The compounds of the invention are in the formula:

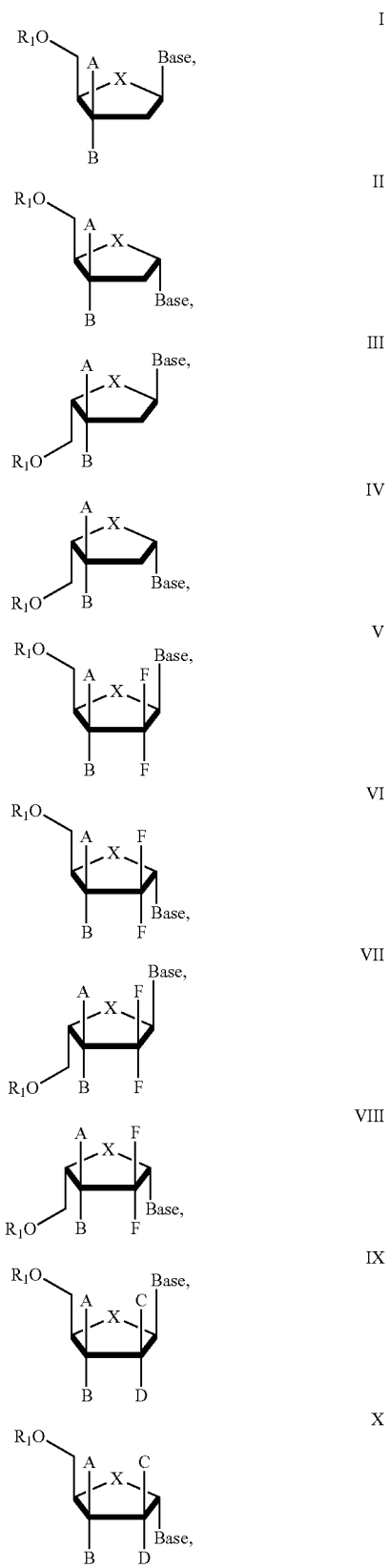

-continued (XI)
(XII)
(XIII)
(XIV)
(XV)
(XVI)
(XVII)

wherein:

A and B are $C_1$-$C_6$ alkyl, mono- to per-halo alkyl or —$(CH_2)_nM$, with the proviso that:
  A is different from B,
  when one of A and B is methyl, the other is not —$CF_3$, and
  when one of A and B is $C_2$-$C_6$ alkyl, the other is not $C_2$-$C_6$ fluoroalkyl;
n is 1 to 3;
M is —$OR_2$, —$SR_2$, —CN, —$C(O)OR_3$, —$OC(O)R_4$ or —$NHR_{15}$;
$R_1$ is —H, —$C_1$-$C_6$ alkyl, alkylaryl, or a phosphoryl group of formula (XX):

(XX)

$R_2$ is H, $C_1$-$C_6$-alkyl, aryl-$C_1$-$C_6$ alkyl, or a phosphoryl group of formula (XX), each of the alkyl and aryl moieties being optionally substituted with one or more groups selected from halo, —CN, —C(O)OH, —C(O)$R_3$, —$N_3$, —$C_1$-$C_6$ alkyl, —C(O)O$R_4$, —$CF_3$, —$C_1$-$C_6$ alkyl-$N_3$, —$SiF_5$, and —$NHR_{15}$;

$R_3$ is H, $C_1$-$C_6$ alkyl, or aryl-$C_1$-$C_6$ alkyl, each of the alkyl and aryl moieties being optionally substituted with one or more groups selected from halo, —CN, —C(O)OH, —C(O)O$R_4$, —$N_3$, —$C_1$-$C_6$ alkyl-C(O)O$R_4$, —$CF_3$, —$C_1$-$C_6$alkyl-$N_3$, and —$SiF_5$;

$R_4$ is $C_1$-$C_6$ alkyl, aryl, or aryl-$C_1$-$C_6$ alkyl, each of the alkyl and aryl moieties being optionally substituted with one or more groups selected from halo, —CN, —C(O)OH, —$N_3$, $CF_3$, —$C_1$-$C_6$ alkyl-$N_3$, —$SiF_5$, and —$NHR_{15}$;

$R_5$ is H, $C_1$-$C_6$ alkyl, or arylalkyl;

$R_{6a}$ is H, methyl, isopropyl, n-propyl, or —$CH_2$—$CH_2$—SMe;

$R_{6b}$ is H or methyl;

$R_7$ is H or methyl;

$R_8$ is H, $C_1$-$C_6$ alkyl, or aryl, the aryl being optionally substituted with one group selected from $C_1$-$C_6$ alkyl and halo;

$R_{15}$ is H, $C_1$-$C_6$ alkyl, —$SO_2$-alkylaryl, or arylalkyl;

X is O or S;

C and D are independently —H, —OH, halo, azido, —CN, —$NHR_2$, or —$CF_3$;

E is H or OH;

Base is:

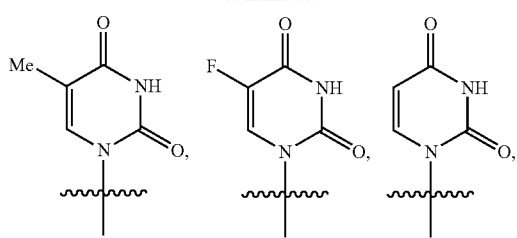
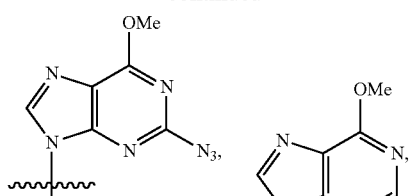
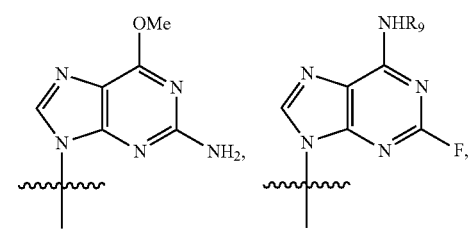
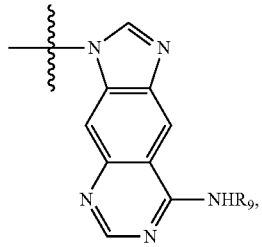
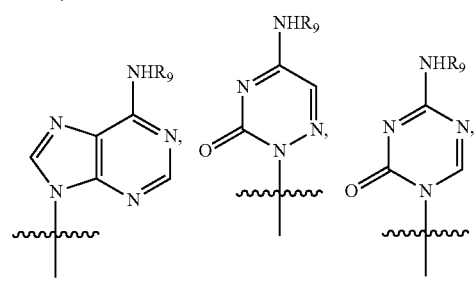
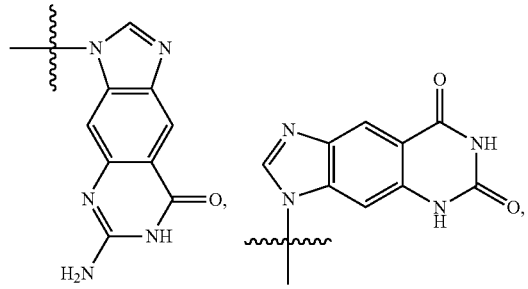
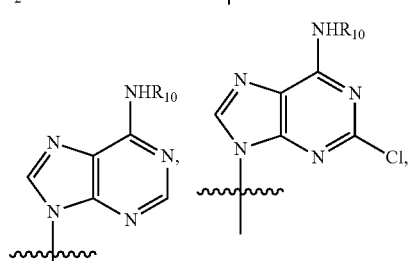
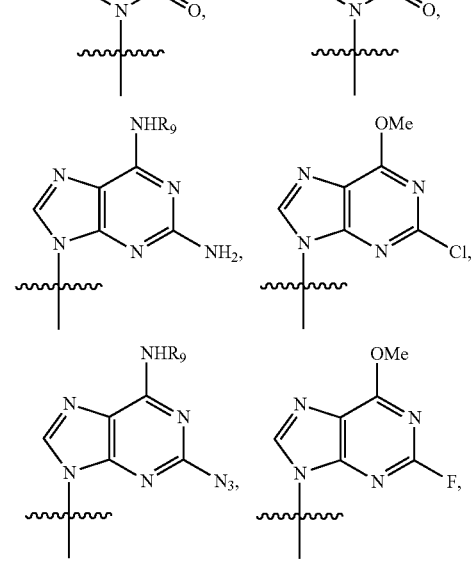
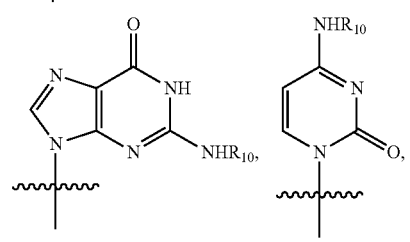
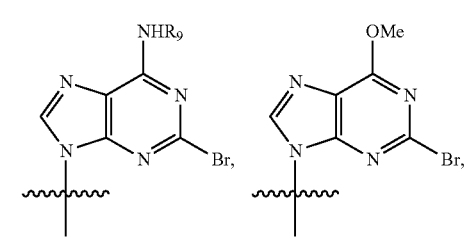
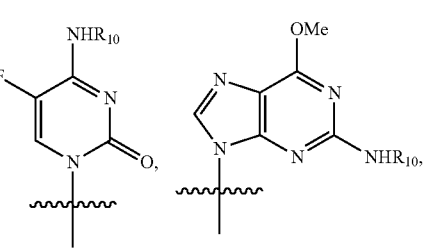

-continued

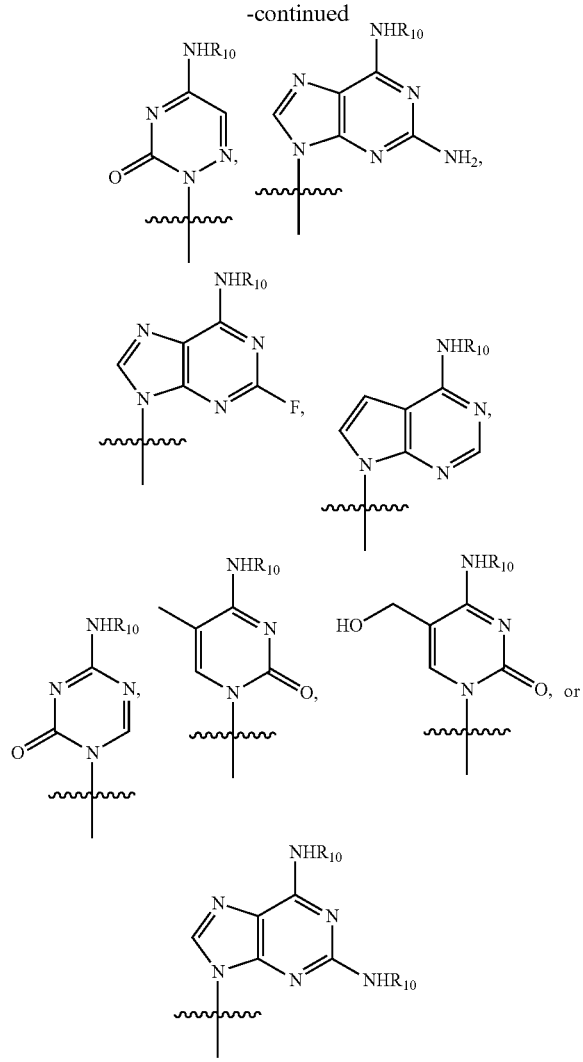

R$_9$ is H, —C(O)—C$_1$-C$_6$ alkyl, —C(O)aryl, aryl, or arylalkyl, wherein each of the alkyl and aryl moieties is optionally substituted with one or more groups selected from halo, —CF$_3$, —N$_3$, and —SF$_5$;

R$_{10}$ represents a lipoate group of formula (XXI):

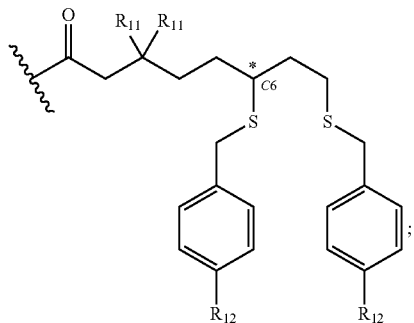

(XXI)

R$_{11}$ are the same of different, preferably the same, and represents F or methyl; and R$_{12}$ are the same of different, preferably the same, and represents F or —CF$_3$; and

* denotes the R, S, or R/S configuration, or a pharmaceutically acceptable salt thereof.

The above general chemical formula is further qualified by two provisos:

The first proviso is that the compound comprises:

one or two phosphoryl groups of formula (XX), the compound being free of a lipoate group of formula (XXI)—(molecules respecting this criterion fall within Group A described above), one lipoate group of formula (XXI), the compound being free of a phosphoryl group of formula (XX)—(molecules respecting this criterion fall within Group B described above), or one lipoate group of formula (XXI) and only one phosphoryl group of formula (XX), said phosphoryl group being in R$_1$—(molecules respecting this criterion fall within Group C described above).

Of note, the phosphoryl groups of formula (XX) can only be found in the definitions of R$_1$ and R$_2$ in the above general chemical formula. Hence, the first part of the above proviso corresponds to embodiments in which R$_1$ and/or R$_2$ represent the phosphoryl groups of formula (XX).

In the second part of this proviso, there is no phosphoryl group of formula (XX). In other words, neither R$_1$, nor R$_2$ can represent a phosphoryl groups of formula (XX).

In the third part of this proviso, there is only one phosphoryl group of formula (XX) and it is in R$_1$. In other words, R$_2$ cannot represent a phosphoryl groups of formula (XX).

Of note, in the above general chemical formula, only R$_{10}$ represents the lipoate group of formula (XXI) and R$_{10}$ is only present in certain Bases. Therefore, when the compound of the invention comprises a lipoate group of formula (XXI), as in the second and third parts of the above proviso, the Base is necessarily one of the Bases comprising a R$_{10}$ group: that is:

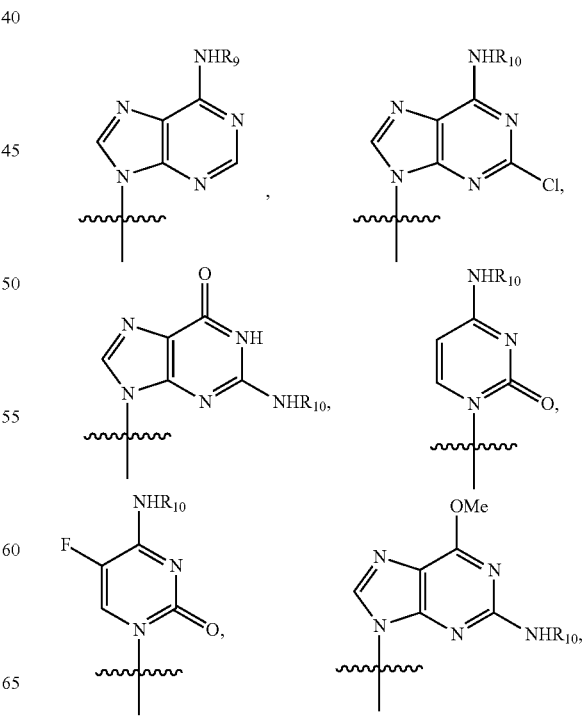

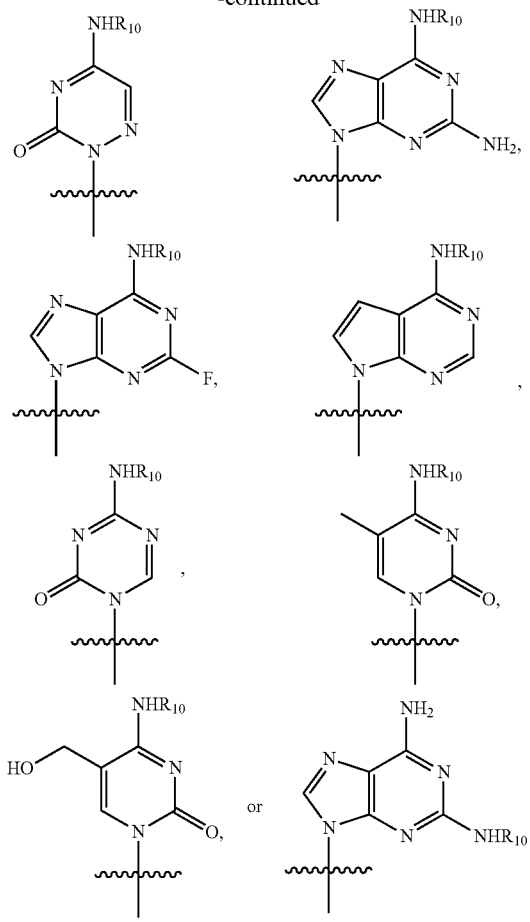
wherein R₁₀ is as defined above.
In contrast, when the compound of the invention is free from a lipoate group of formula (XXI), the Base cannot be R₁₀. Therefore, when the compound of the invention is free from a lipoate group of formula (XXI), as in the first part of the above proviso, the Base is necessarily one of the Bases free from a R₁₀ group: that is:
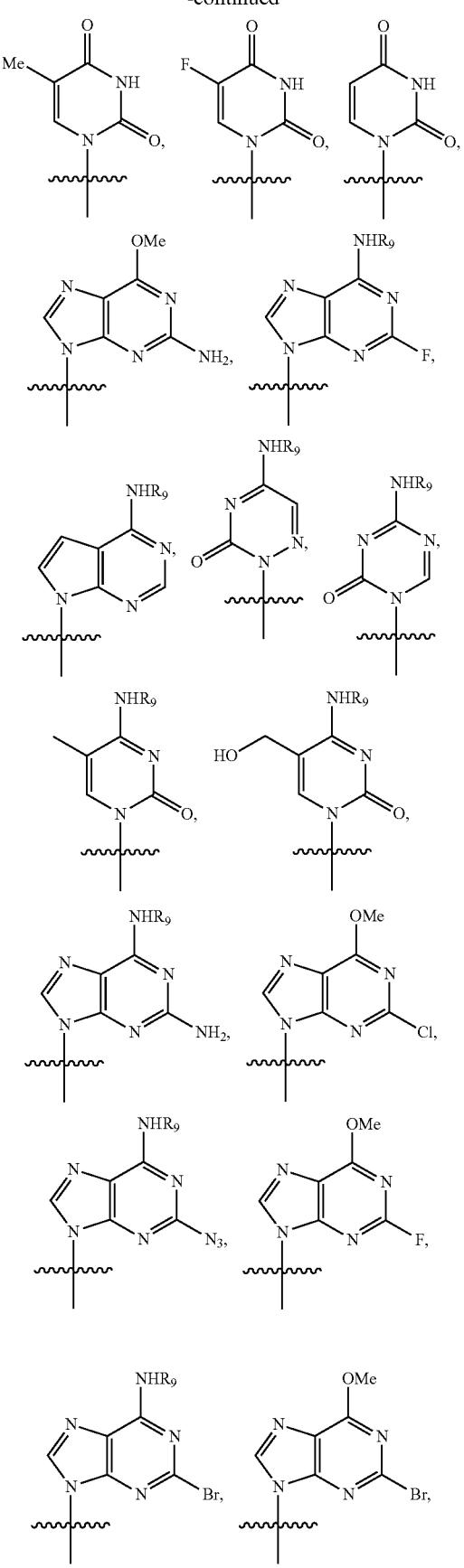

-continued

[Structures shown with OMe-substituted purines, imidazole-fused quinazoline derivatives with NHR9 substituents, and related heterocycles]

wherein R9 is as defined above.

In embodiments, in R9, each of alkyl or aryl moieties, preferably each of aryl moieties only, is optionally substituted with one or more groups selected from halo, —CF3, —N3, and —SF5, preferably halo, —CF3 or —SF5, more preferably —CF3 or —SF5 or more preferably halo, the substituent being preferably located in para position.

In embodiments, the halo in R9 is F.

In preferred embodiments, R9 is H, C1-C6 alkyl, —C(O)—C1-C6 alkyl, aryl substituted with halo, or arylalkyl, preferably H, C1-C6 alkyl, —C(O)—C1-C6 alkyl, aryl, or arylalkyl, more preferably H, C1-C6 alkyl, —C(O)—C1-C6 alkyl, or arylalkyl, yet more preferably H, C(O)—C1-C6 alkyl, or arylalkyl, and most preferably H.

Preferably, the —C(O)—C1-C6 alkyl in R9 is —C(O)-propyl; the aryl in R9 is substituted with halo, preferably F; the aryl in R9 is phenyl substituted with halo, preferably F, more preferably parafluorophenyl; and/or the arylalkyl in R9 is benzyl, preferably unsubstituted.

The second proviso is that, when the compound is of formula XIII to XVII, it comprises one lipoate group of formula (XXI). In other words, this means that, when a lipoate groups is absent, the nucleoside analogues (which are thus of Group A) can only be of formulas I to XII. In contrast, when a lipoate groups is present, the nucleoside analogues (which are thus of Groups B and C) can have any of formulas I to XVII. Of note:

nucleoside analogues of formulas XIII to XVI have a quaternary stereogenic all-carbon center at C-2', nucleoside analogues of formulas I to XII have a quaternary stereogenic all-carbon center at C-3', and nucleoside analogues of formula XVII have a ribose or deoxy ribose unit.

Of note, in the definition of A and B above, neither A, nor B can be H and A is different from B. This ensures that any carbon atom bearing both A and B is a quaternary stereogenic all-carbon center.

As shown above, the phosphoryl group, which is found in compounds of Groups A and C, is of formula XX:

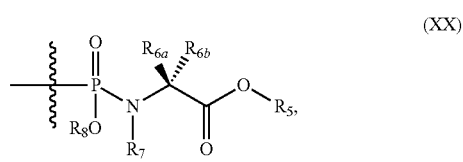

(XX)

wherein $R_5$, $R_{6a}$, $R_{6b}$, $R_7$, and $R_8$ are as defined above. In embodiments, $R_5$ is $C_1$-$C_6$ alkyl, preferably iso-propyl. In embodiments, one of $R_{6a}$ and $R_{6b}$ is H and the other of $R_{6a}$ and $R_{6b}$ is methyl. In preferred embodiments, $R_{6a}$ is methyl and $R_{6b}$ is H. In embodiments, $R_7$ is H. In embodiments, $R_8$ is aryl, preferably phenyl.

In preferred embodiments, the phosphoryl groups of formula (XX) is:

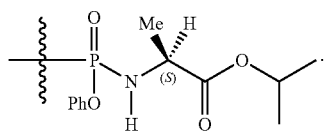

Octanoic acid disubstituted by a difluorinated or dimethyl at C-3 and having para-substituted (F or —CF3) thiobenzyl at C-7 (R, S, or R/S) and C-8 were prepared and coined "β-blocked lipoate derivative" or "lipoate group". These groups, which are found (in $R_{10}$) in compounds of groups B and C, are of formula XXI:

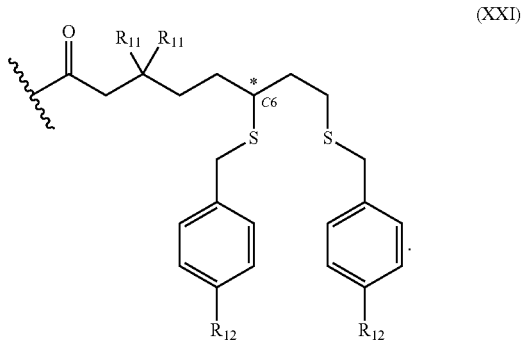

(XXI)

These were attached through an amide bond to the —$N_{H2}$ functionality of nucleobase (e.g. cytosine, adenine, guanine or derivatives thereof) leading to nucleoside analogues. In embodiments, both $R_{11}$ are the same, preferably both $R_{11}$ are methyl. In embodiments, both $R_{12}$ are the same. In preferred embodiments, both $R_{12}$ are F. In alternative preferred embodiments, both $R_{12}$ are —$CF_3$. In embodiments, * denotes the R or R/S configuration. In preferred embodiments, * denotes the R configuration. In alternative preferred embodiments, * denotes the R/S configuration.

In embodiments, the lipoates group of formula (XXI) is:

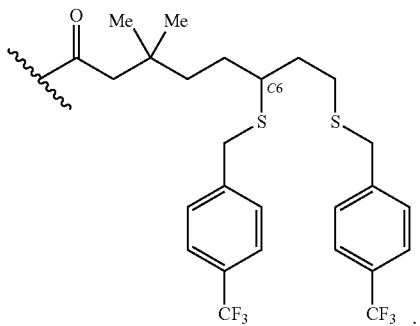 [SMILES: *C(=O)CC(C)(C)CCC(CCSCc1ccc(C(F)(F)F)cc1)SCc1ccc(C(F)(F)F)cc1]

In embodiments, one of A and B is $C_1$-$C_6$ alkyl, preferably methyl. In embodiments, one of A and B is —$(CH_2)_n M$. In preferred embodiments, one of A and B is $C_1$-$C_6$ alkyl, preferably methyl, and the other of A and B is —$(CH_2)_n M$. In most preferred embodiments, A is $C_1$-$C_6$ alkyl, preferably methyl, and B is —$(CH_2)_n M$.

In embodiments, M is —$OR_2$, —$OC(O)R_4$, —CN,

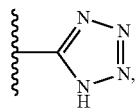

or —$NHR_{15}$, preferably —$OR_2$, —$OC(O)R_4$, —CN, or

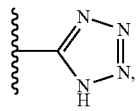

more preferably, —$OR_2$—$OC(O)R_4$, or —CN, even more preferably —$OR_2$ or —$OC(O)R_4$, and most preferably —$OR_2$.

In embodiments, $R_2$ is H, $C_1$-$C_6$-alkyl, aryl-$C_1$-$C_6$ alkyl, or a phosphoryl group of formula (XX), preferably H, aryl-$C_1$-$C_6$ alkyl, or a phosphoryl group of formula (XX), more preferably H or a phosphoryl group of formula (XX), each of the alkyl and aryl moieties being optionally substituted with one or more groups selected from halo (preferably F), —CN, —C(O)OH, —C(O)$R_3$, —$N_3$, —$C_1$-$C_6$ alkyl, —C(O)$OR_4$, —$CF_3$, —$C_1$-$C_6$ alkyl-$N_3$, —$SiF_5$, and —$NHR_{15}$.

In embodiments, each of the alkyl and aryl moieties in $R_2$ is optionally substituted with one or more groups selected from halo (preferably F), —C(O)$R_3$, —$N_3$, —$C_1$-$C_6$ alkyl, —$CF_3$, or —$SiF_5$. In preferred embodiments, each of the alkyl and aryl moieties in $R_2$ is optionally substituted with one or more groups selected from halo (preferably F), —$N_3$, -or —$CF_3$.

In embodiments, the alkyl in $R_2$ is methyl, preferably unsubstituted. In embodiments, the aryl-$C_1$-$C_6$ alkyl in $R_2$ is benzyl unsubstituted or substituted, preferably with fluor, preferably in para position.

In preferred embodiments, $R_2$ is H, methyl, benzyl, para-fluoro benzyl, para-$CF_3$ benzyl, or a phosphoryl group of formula (XX), preferably H, methyl, benzyl, or a phosphoryl group of formula (XX), and more preferably H or a phosphoryl group of formula (XX).

In embodiments, $R_{15}$ is H, —$SO_2$-aryl or aryl, and preferably H. In such embodiments, each of the aryl moieties is optionally substituted with one or more $C_1$-$C_6$ alkyl (preferably methyl) or halo (preferably F). In embodiments, the aryl moieties is phenyl. In preferred embodiments, the aryl moieties are substituted with $C_1$-$C_6$ alkyl (preferably methyl) or halo (preferably F). In most preferred embodiments, $R_{15}$ is H, p-methylphenyl or p-fluorophenyl. Such embodiments are particularly relevant when one or A and B is —$(CH_2)_n M$ and M is —$NHR_{15}$ In embodiments, C and D are independently —H, —OH, halo, —CN, —$NHR_2$, or —$CF_3$, preferably —H, —OH, halo, —CN or —$NHR_2$, and more preferably —H, —OH, or halo. In preferred embodiments, one of C and D is H and the other of C and D is halo or OH, preferably halo or alternatively preferably OH. In embodiments, the halo in C or D is F.

In embodiments, E is H. In alternative embodiments, E is OH.

In embodiments, n is 1.

In embodiments, each of the alkyl and aryl moieties in R3 is optionally substituted with one or more groups selected from halo, —$N_3$, —$CF_3$, —$C_1$-$C_6$ alkyl-$N_3$, or —$SiF_5$.

In embodiments, each of the alkyl and aryl moieties being optionally substituted with one or more groups selected from halo, —$N_3$, —$CF_3$, —$C_1$-$C_6$ alkyl-$N_3$, or —$SiF_5$.

In embodiments, X is O.

Compounds of Group A

In embodiments, the compound of the invention, as described above, comprises one or two phosphoryl groups of formula (XX), and is free of a lipoate group of formula (XXI). These are compounds of Group A as defined above.

In embodiments, these compounds are of formula I, II V, VI, IX, or X, preferably I, V, or IX, more preferably V or IX, most preferably IX.

In embodiments, C is halo or OH, preferably halo, and D is H.

In embodiments, Base is:

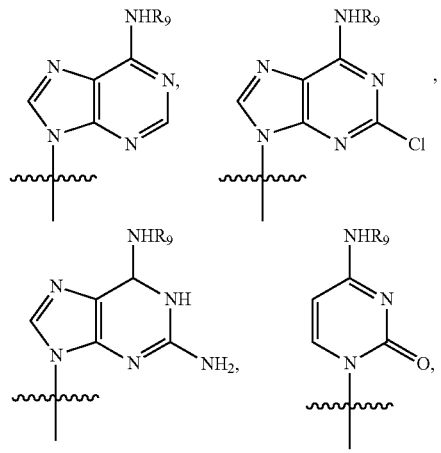

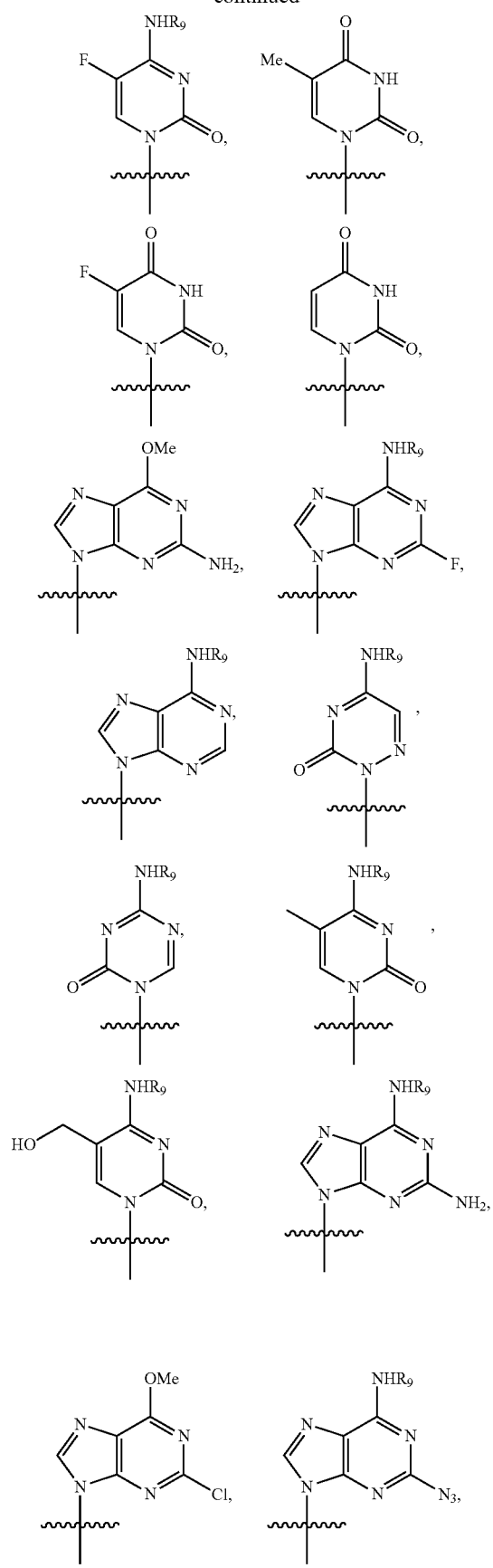
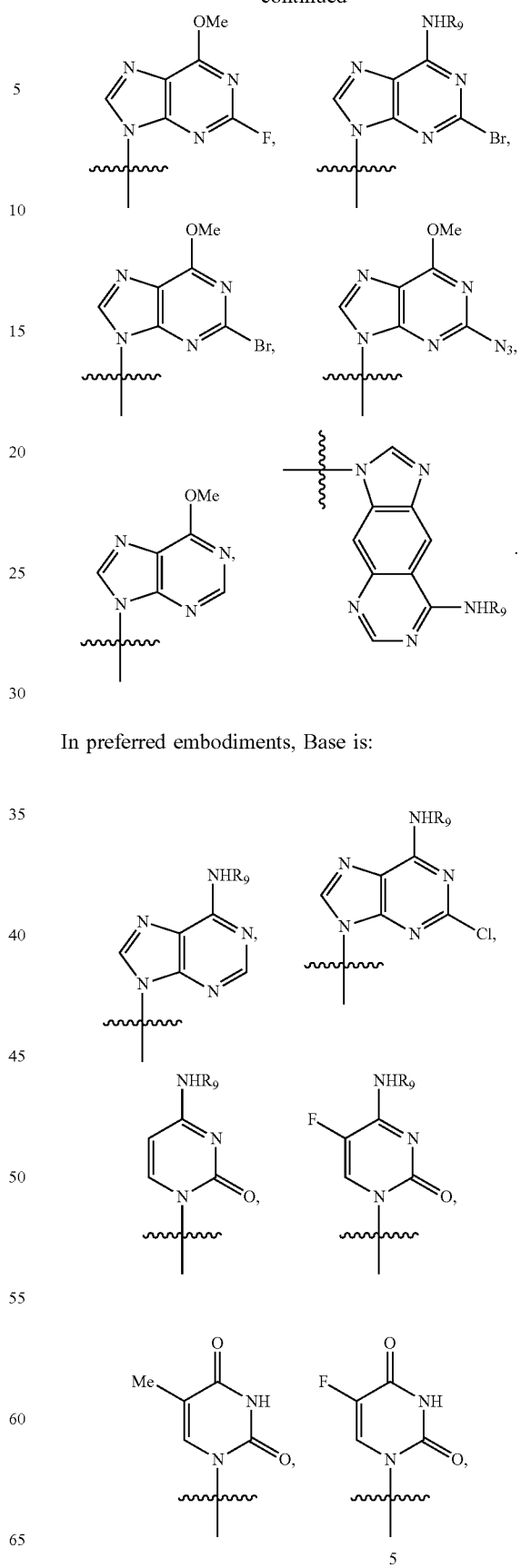
In preferred embodiments, Base is:
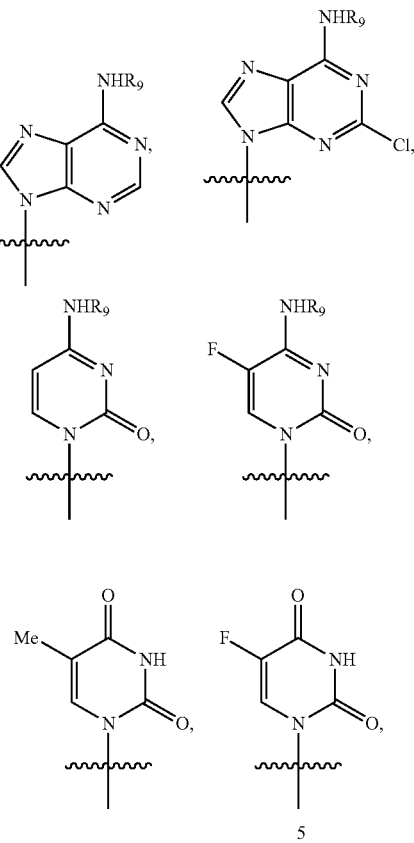

-continued

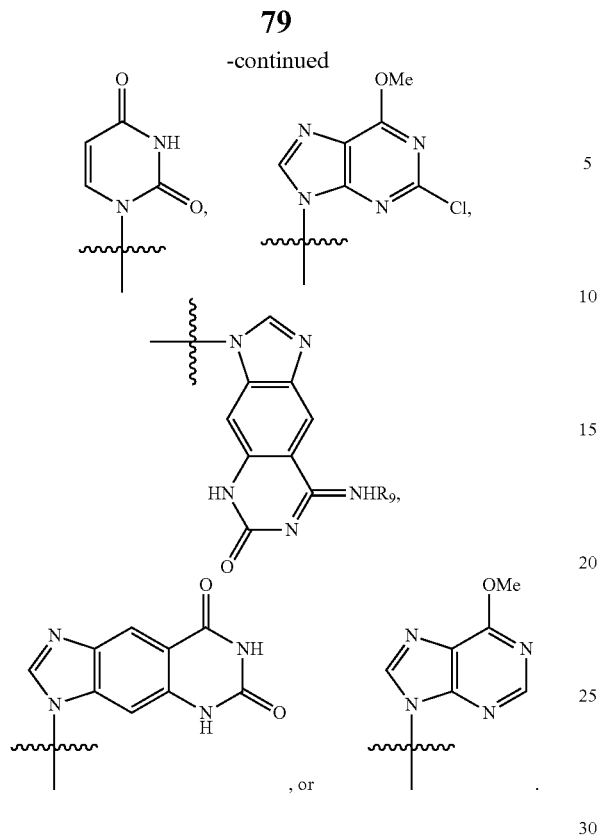

, or

Compounds of Group A—with Only One Phosphoryl Group

In embodiments, the compound of the invention is a compound of Group A as described above, further characterized by the fact that it comprises only one phosphoryl group of formula (XX).

In embodiments, these compounds are of formula V, VI, IX, or X, preferably of formula VI, IX, or X, more preferably of formula IX.

Compounds of Group A—with its Only Phosphoryl Group in $R_2$

In embodiments, the compound of the invention is a compound of Group A with only one phosphoryl group as described above, wherein one of A and B is —$(CH_2)_n$M, M is $OR_2$, and $R_2$ is said only one phosphoryl group of formula (XX). In other words, the only phosphoryl group in this compound is in $R_2$, i.e. at position C-3'.

In embodiments, these compounds are of formula V, VI, IX, or X, preferably of formula IX or X, more preferably X.

In these embodiments, $R_1$ cannot represents a phosphoryl group. Thus, it rather represents the other groups defined for $R_1$ in the above general chemical formula. In preferred embodiments, $R_1$ is H.

In embodiments, Base is:

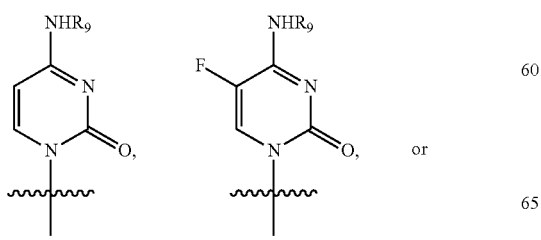

-continued

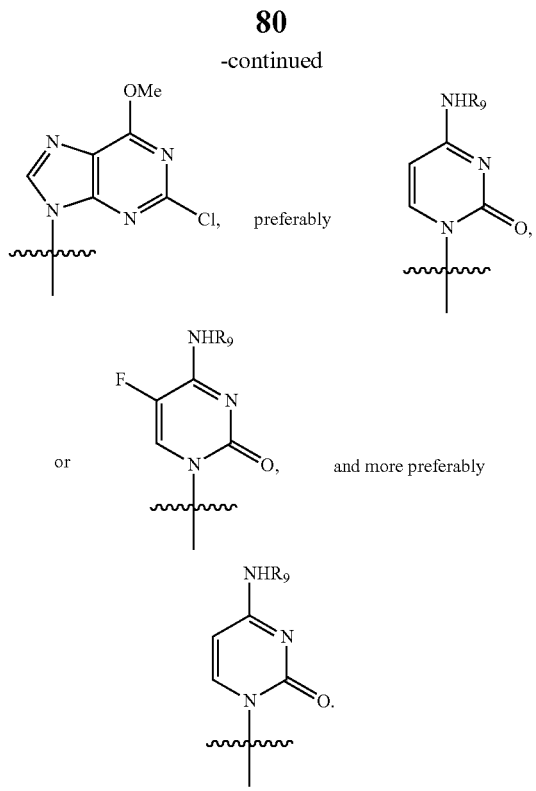

In embodiments, the compound is:

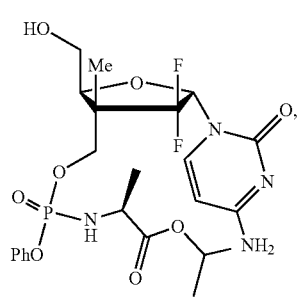

LCB-1994

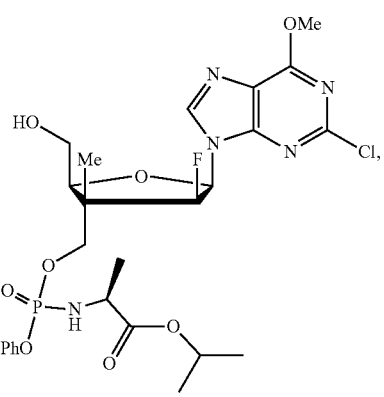

LCB-2137

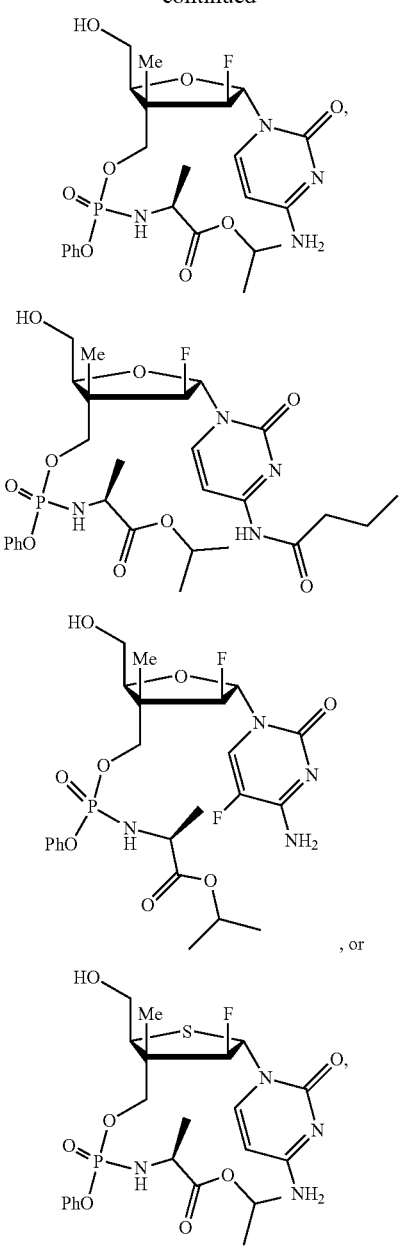
or a pharmaceutically acceptable salt thereof.
In preferred embodiments, the compound is:
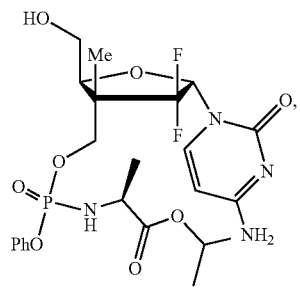
LCB-1994
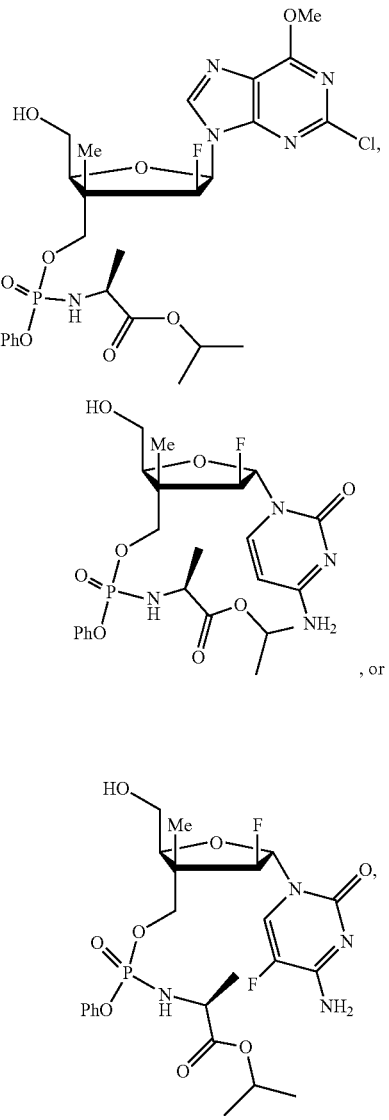
or a pharmaceutically acceptable salt thereof.
In more preferred embodiments, the compound is:
LCB-2137

83

-continued

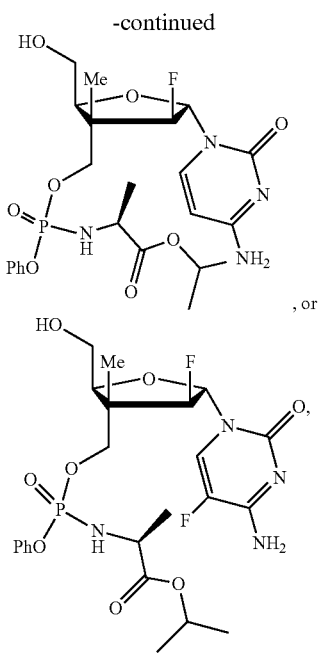

, or or a pharmaceutically acceptable salt thereof.
In most preferred embodiments, the compound is:

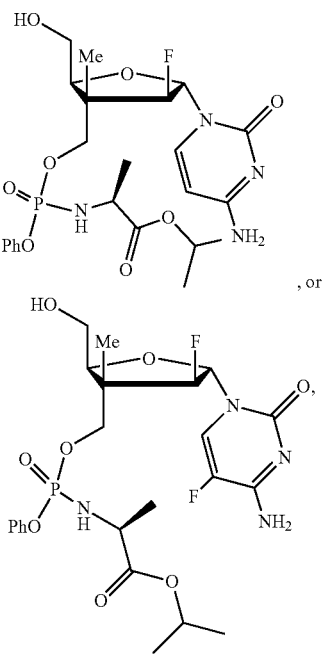

, or or a pharmaceutically acceptable salt thereof.
Compounds of Group A—with its Only Phosphoryl Group in R₁

In embodiments, the compound of the invention is a compound of Group A with only one phosphoryl group as described above, wherein $R_1$ is said only one phosphoryl group. In other words, the only phosphoryl group in this compound is in $R_1$, i.e. at position C-5'.

Therefore, in these embodiments, $R_2$ cannot represents a phosphoryl group. Thus, it rather represents the other groups defined for $R_2$ above, including those provided in the above

84 general chemical formula and those preferred in specific embodiments in the previous sections.

In embodiments, these compounds are of formula V, VI, IX, or X, preferably of formula V or IX, more preferably IX.

In embodiments, Base is:

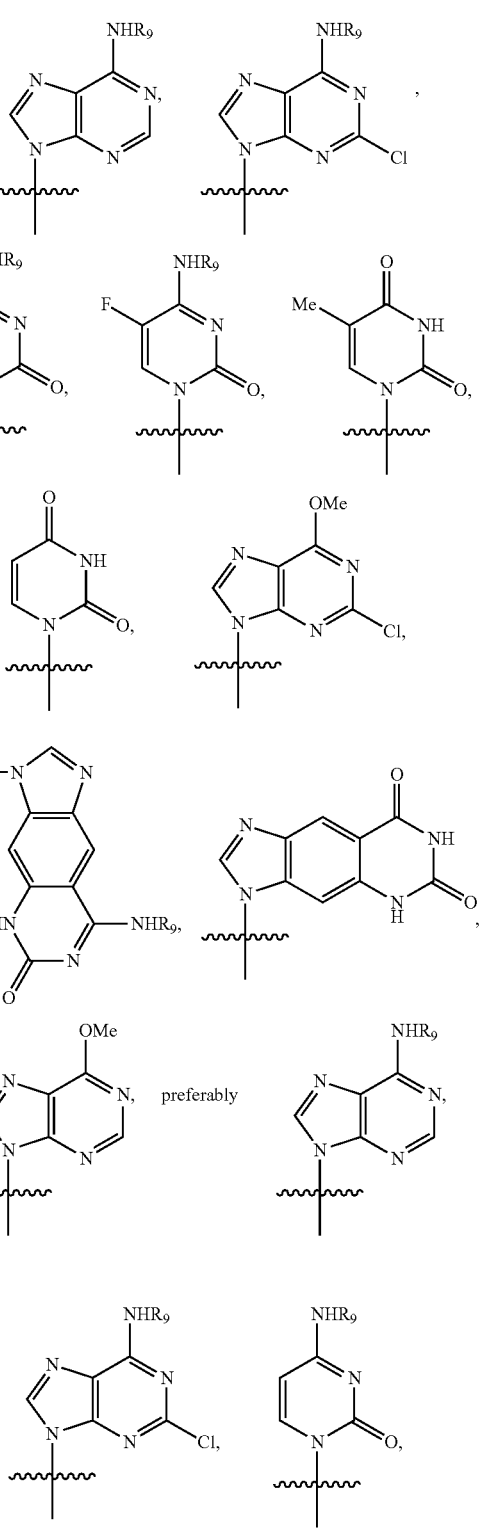

preferably

-continued
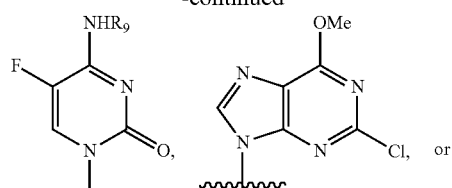
or
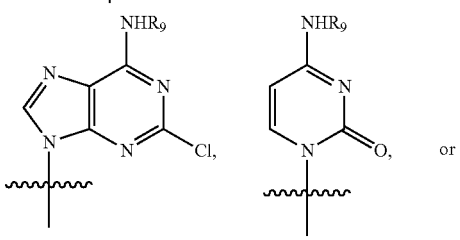
more preferably
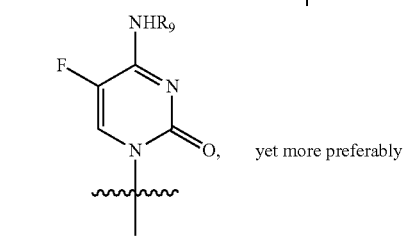
or
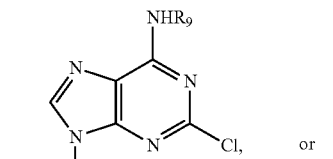
yet more preferably
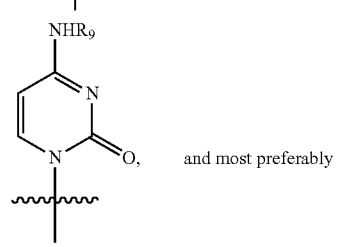
or
and most preferably
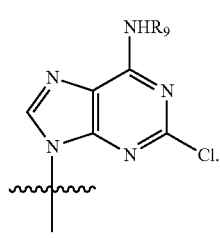
In embodiments, the compound is:
LCB-1992
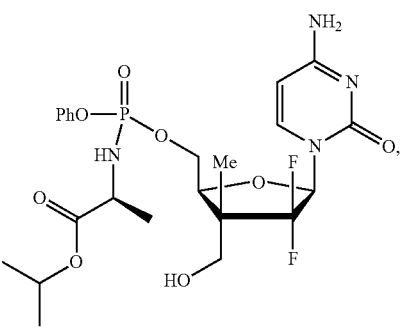
LCB-1998
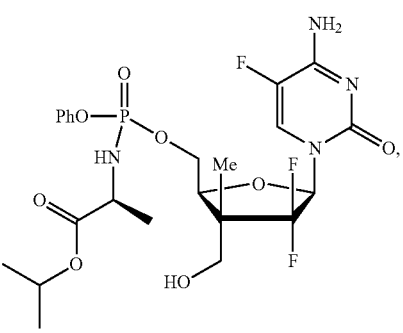
LCB-2000
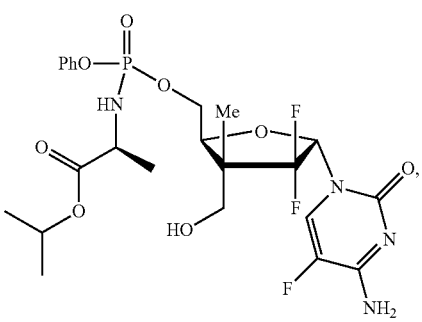
LCB-2001
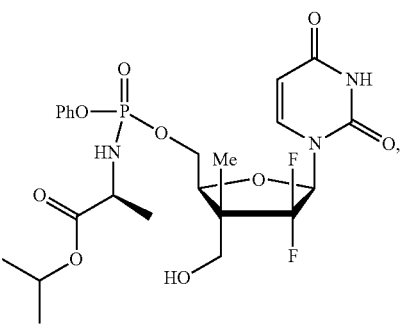

LCB-2018
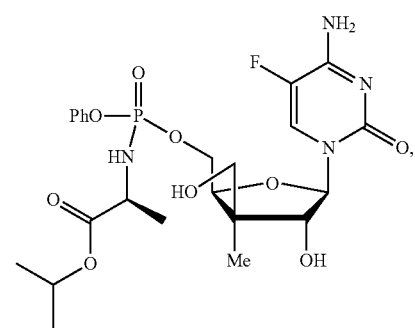
LCB-2027
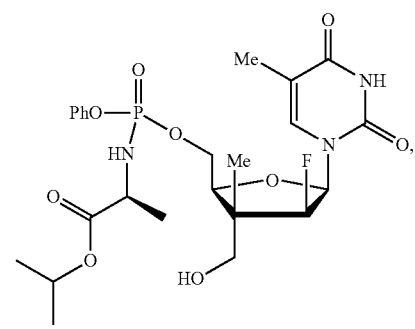
LCB-2028
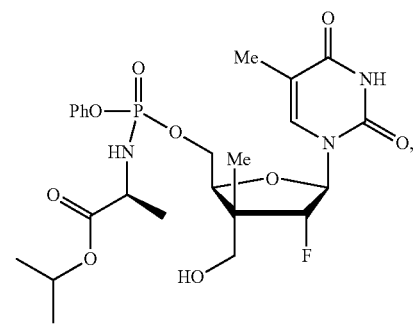
LCB-2034
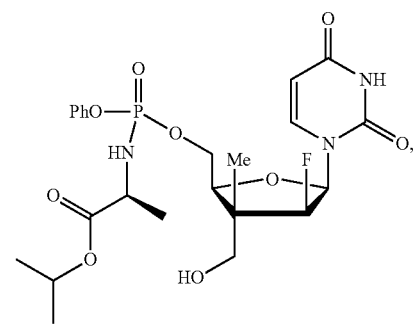
LCB-2093
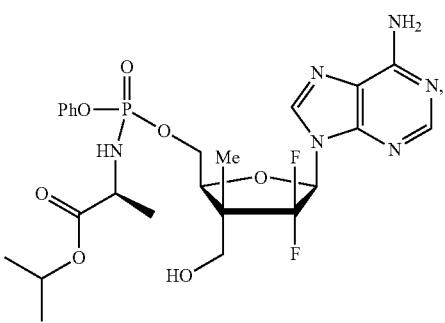
LCB-2106
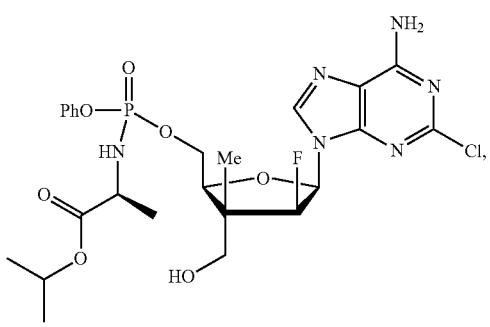
LCB-2142
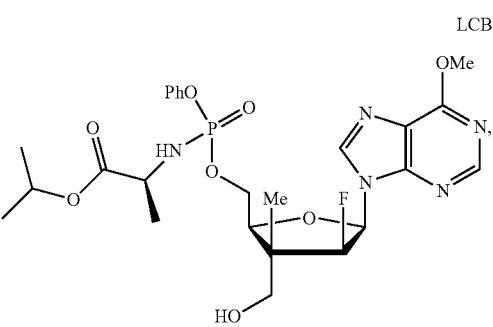
LCB-2146
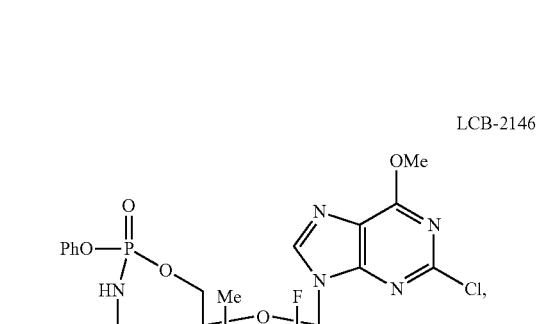
LCB-2147
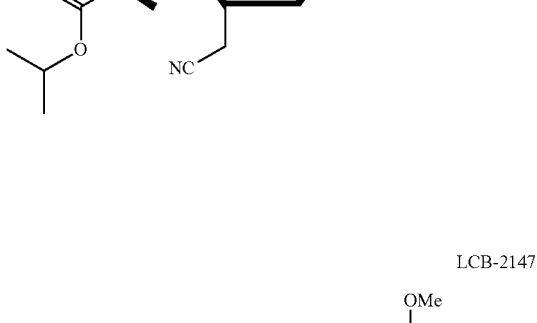

-continued
LCB-2168
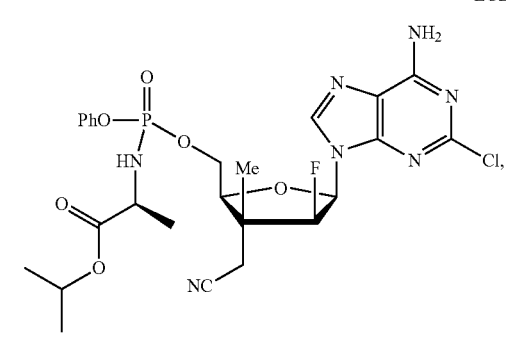
LCB-2172
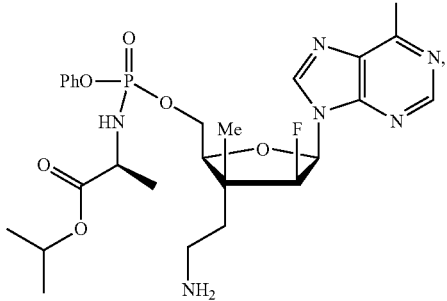
LCB-2173
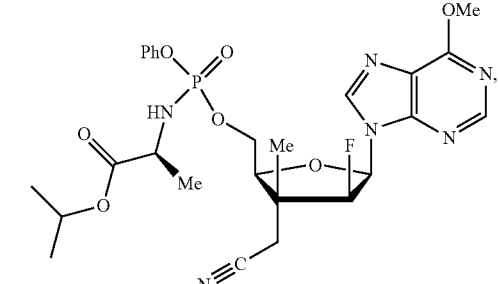
LCB-2174
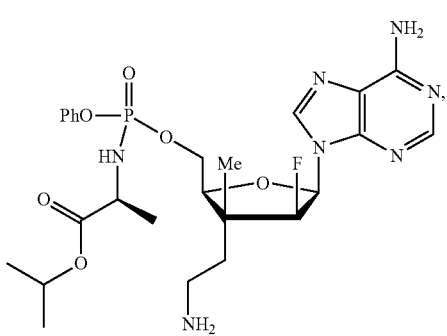
LCB-2175
-continued
LCB-2176
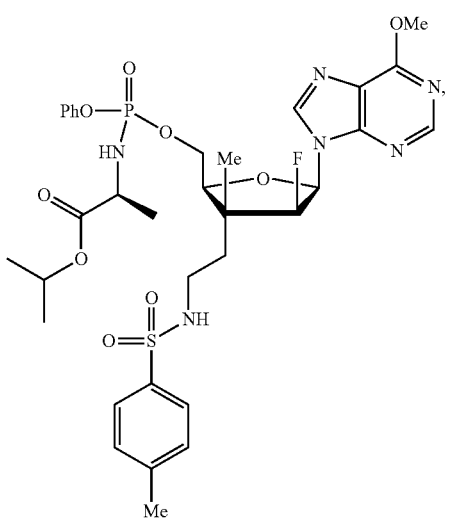
LCB-2187
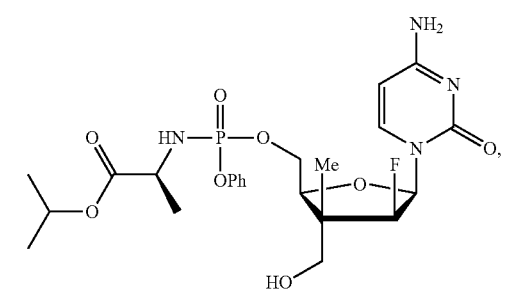
LCB-2189
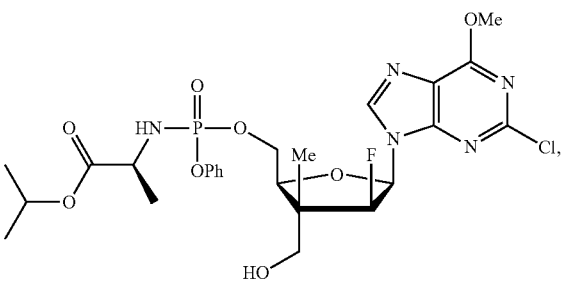
LCB-2201
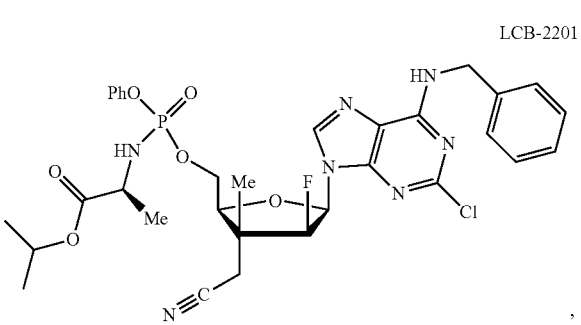

91
-continued
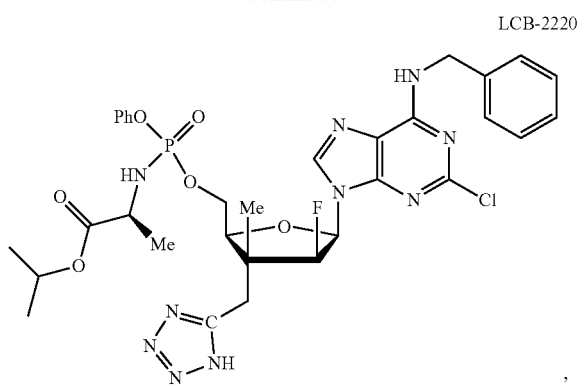
92
-continued
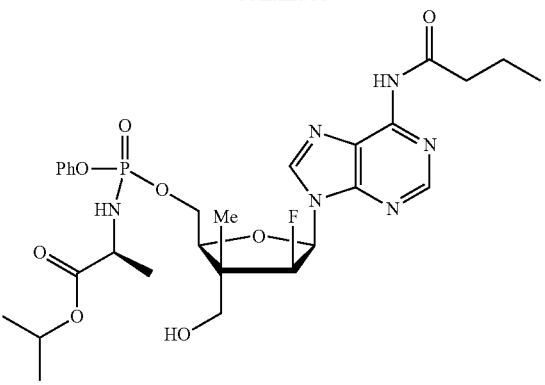
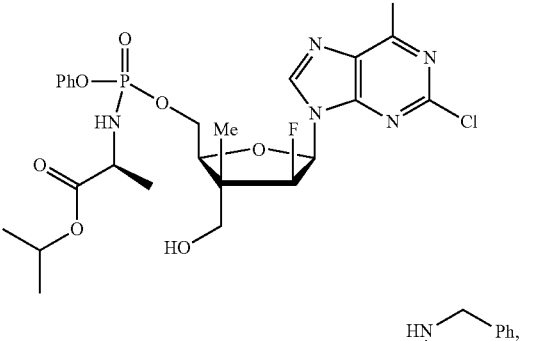
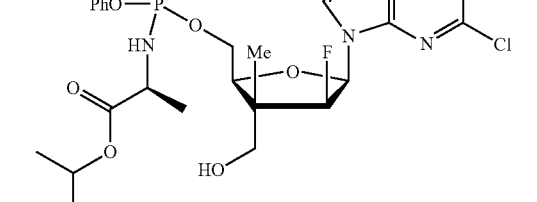
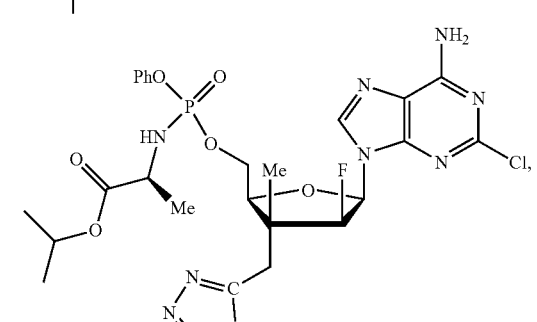
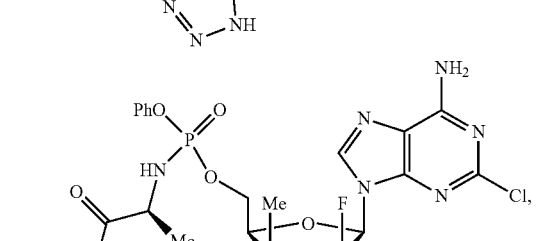
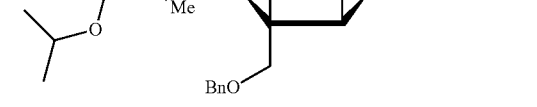

-continued
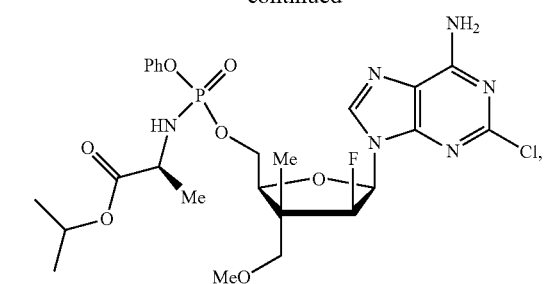
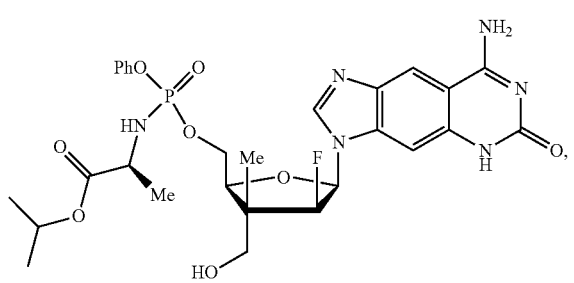
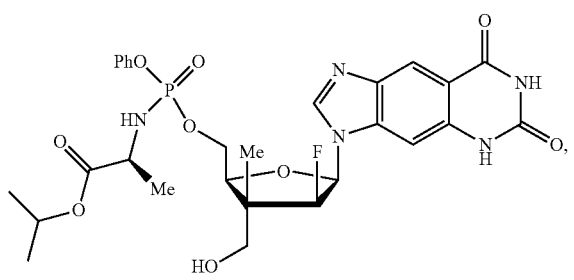
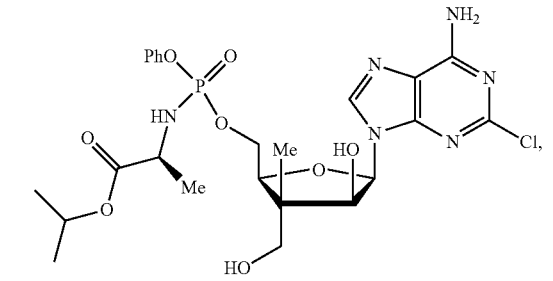
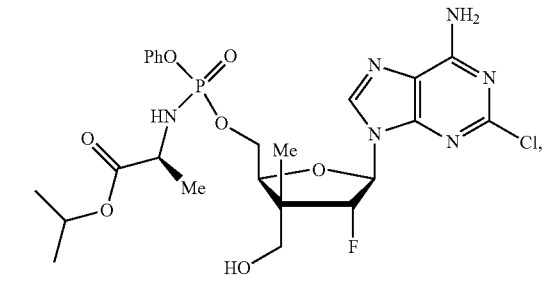
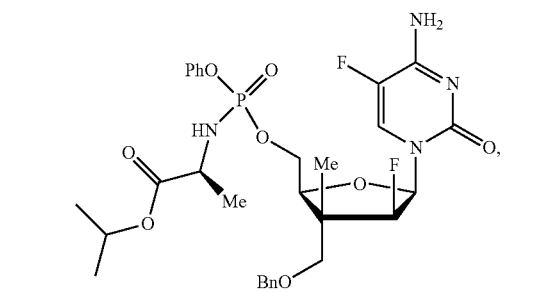
-continued
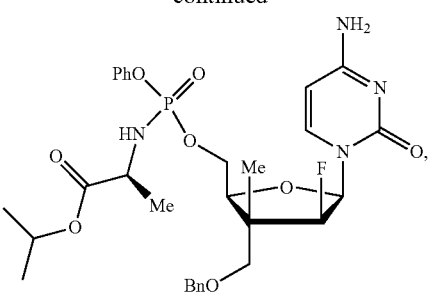
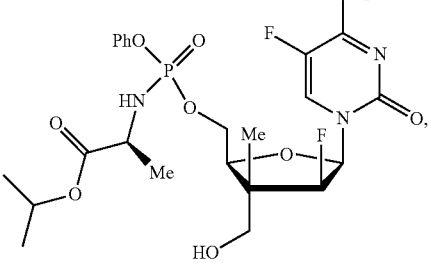
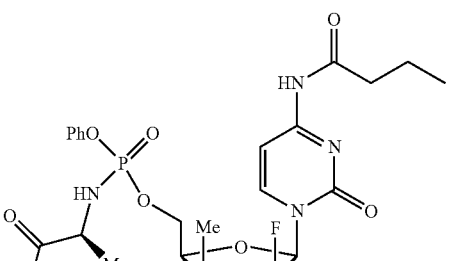
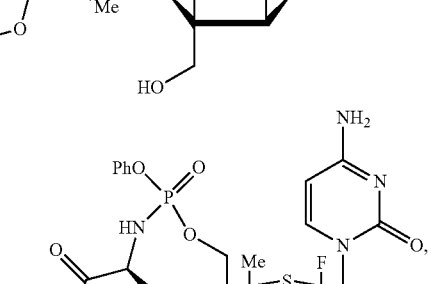
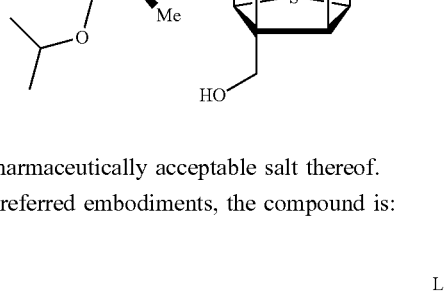
or a pharmaceutically acceptable salt thereof.
In preferred embodiments, the compound is:
LCB-1992
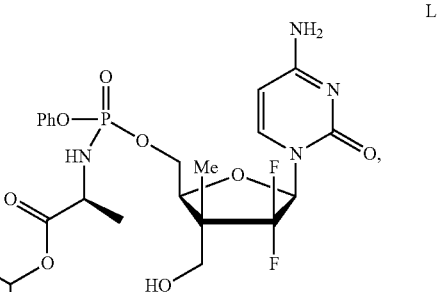

LCB-1998
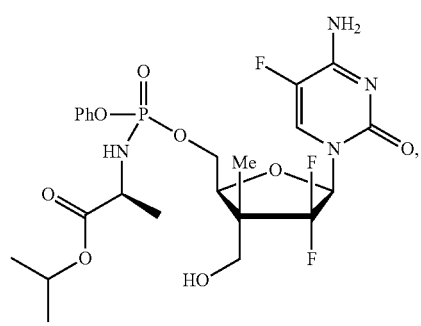
LCB-2000
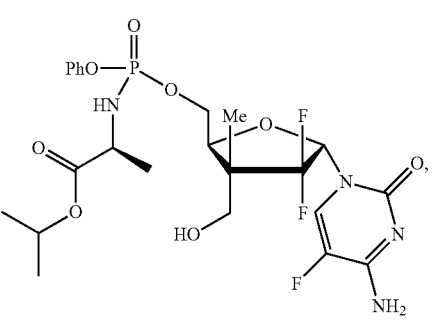
LCB-2001
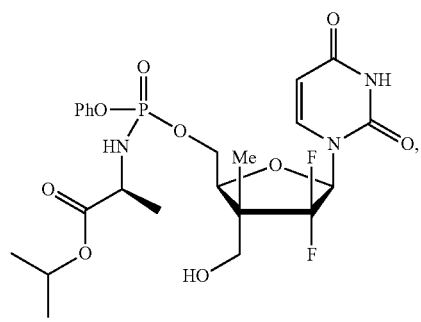
LCB-2018
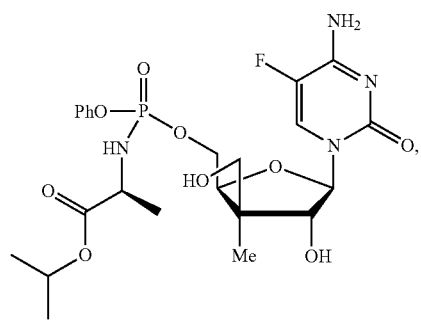
LCB-2027
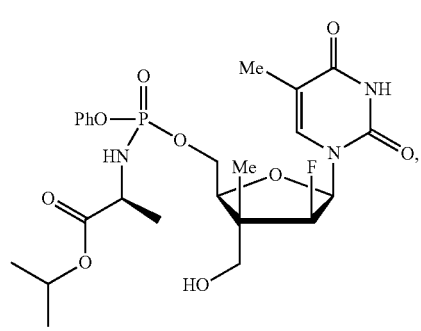
LCB-2028
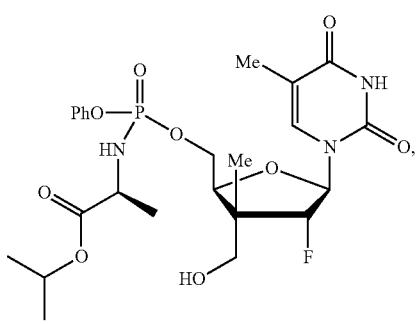
LCB-2034
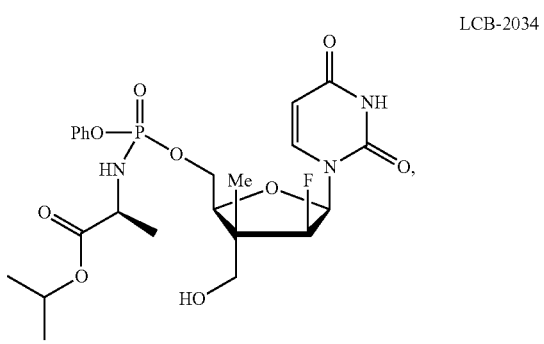
LCB-2093
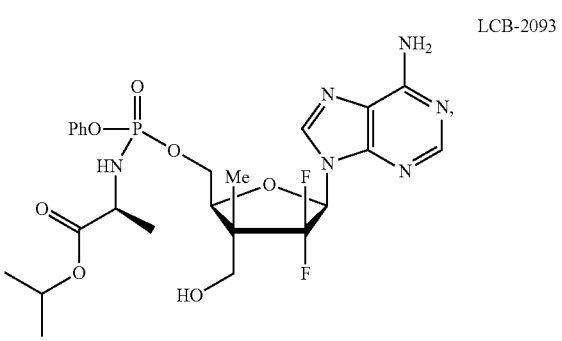
LCB-2106
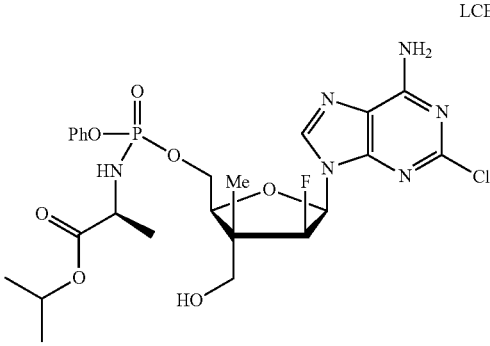
LCB-2142
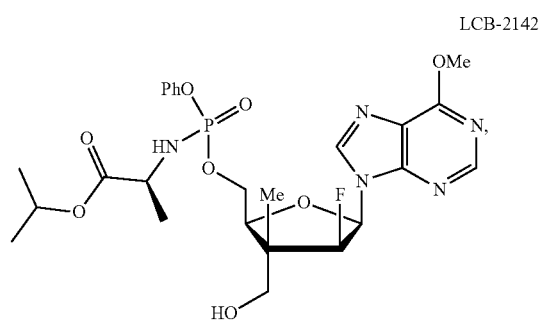

-continued
LCB-2146
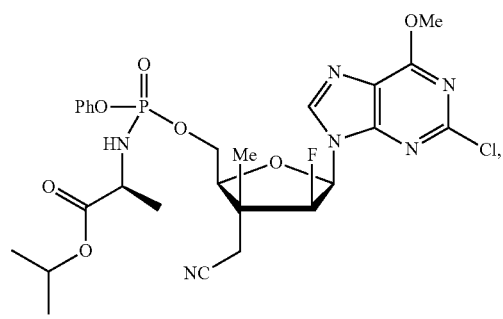
LCB-2147
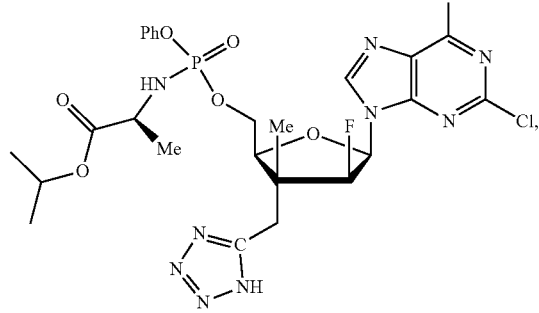
LCB-2168
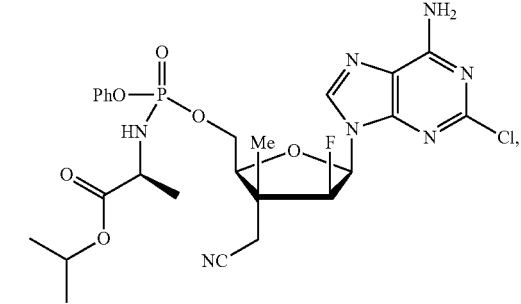
LCB-2172
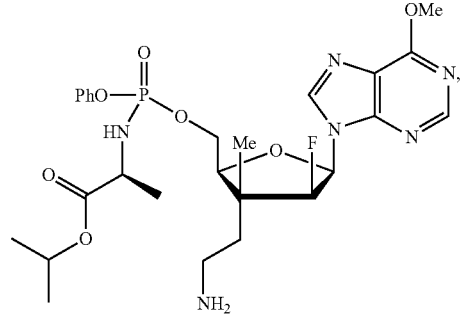
-continued
LCB-2173
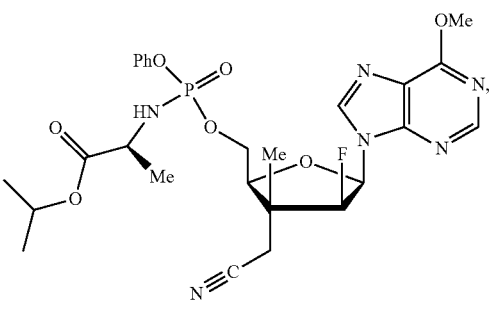
LCB-2174
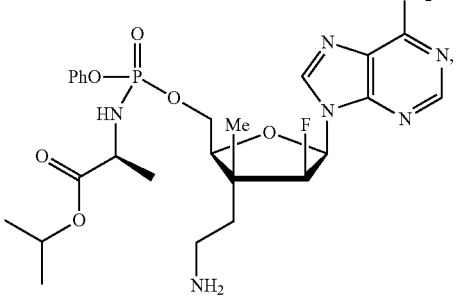
LCB-2175
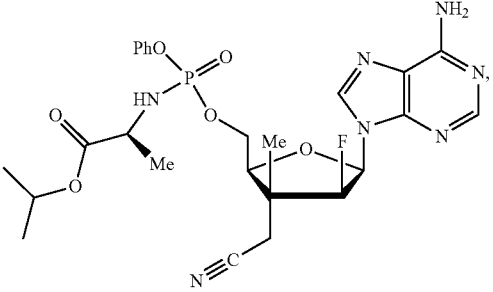
LCB-2176
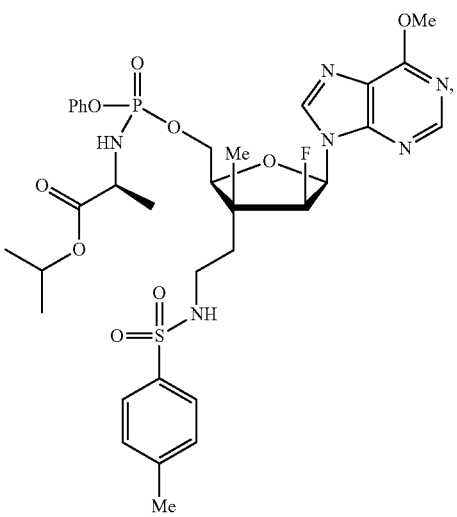

LCB-2187
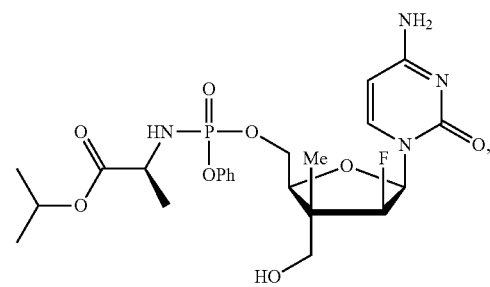
LCB-2189
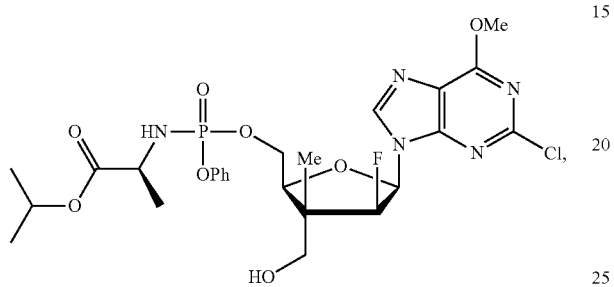
LCB-2201
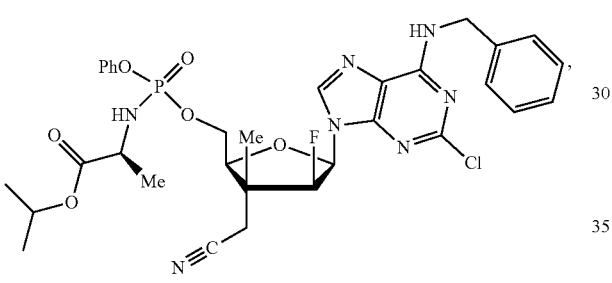
LCB-2220
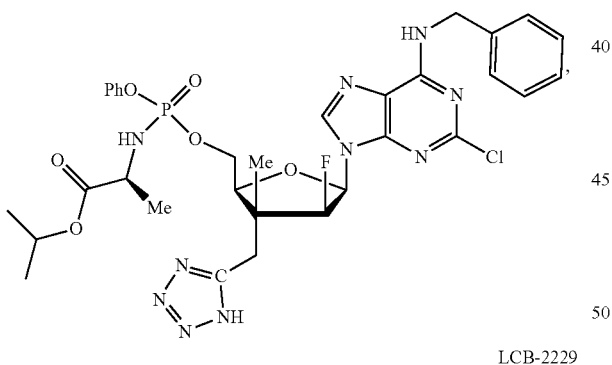
LCB-2229
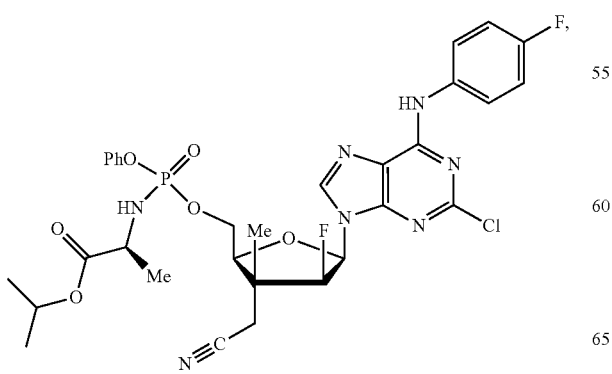
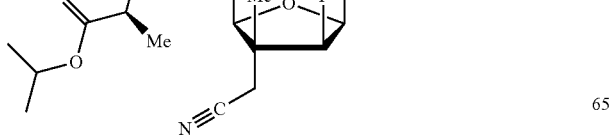
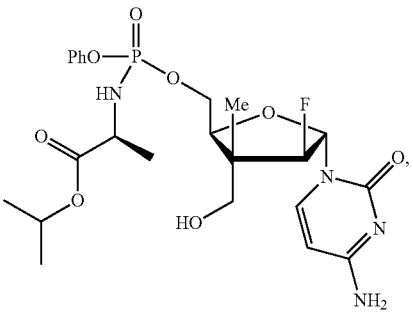
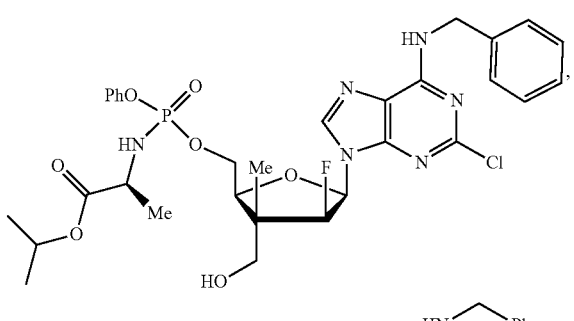
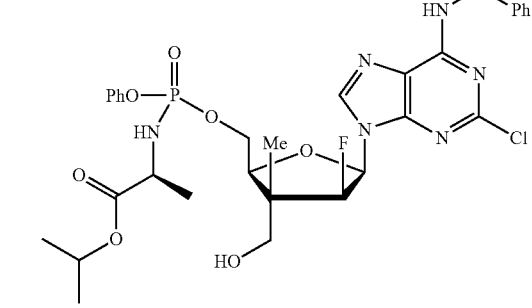
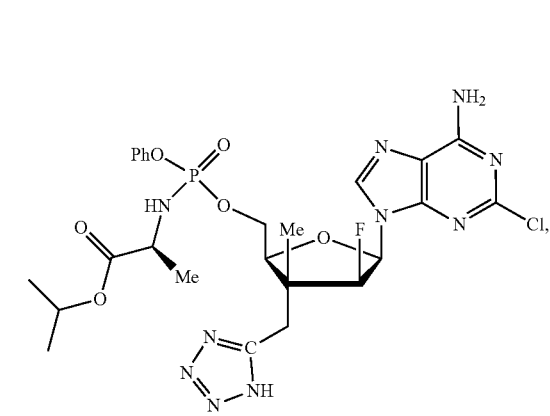
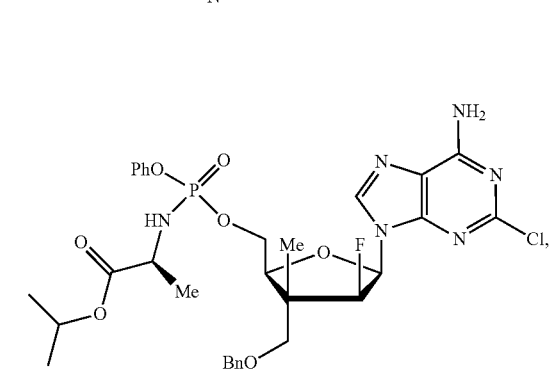
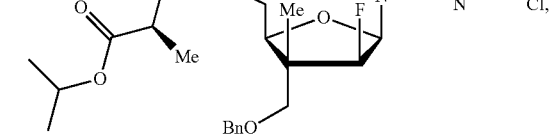

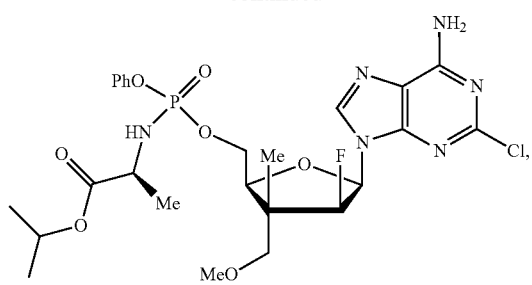
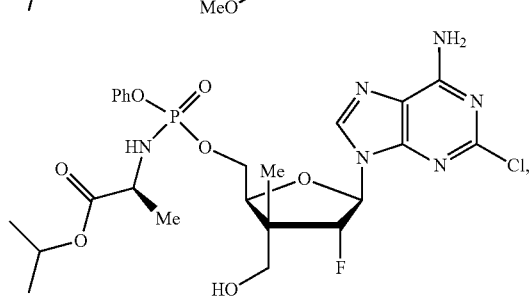
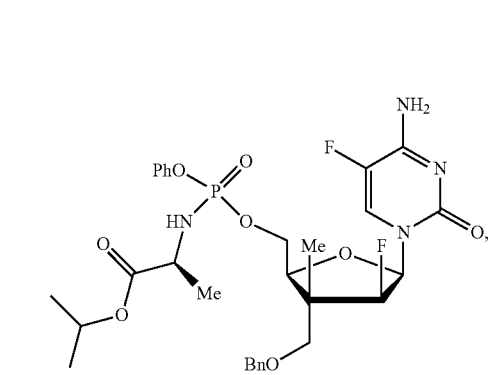
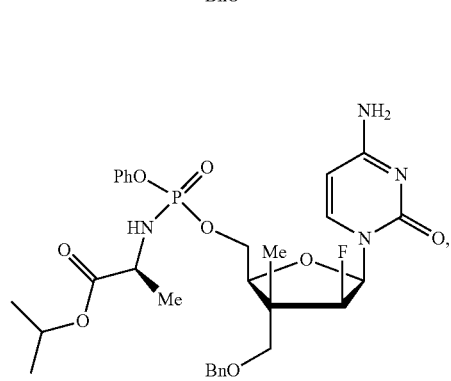
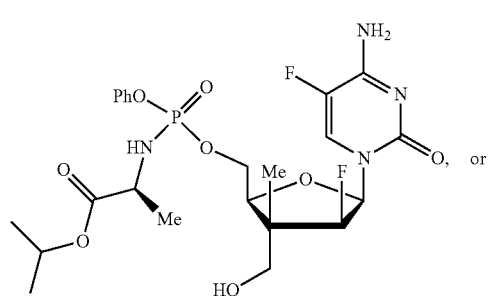
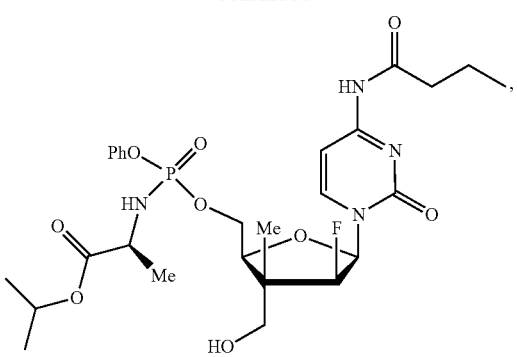
or a pharmaceutically acceptable salt thereof.
In more preferred embodiments, the compound is:
LCB-2027
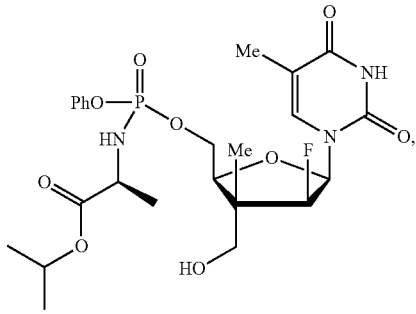
LCB-2028
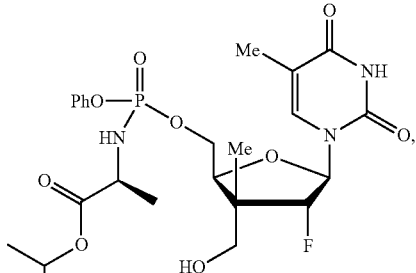
LCB-2034
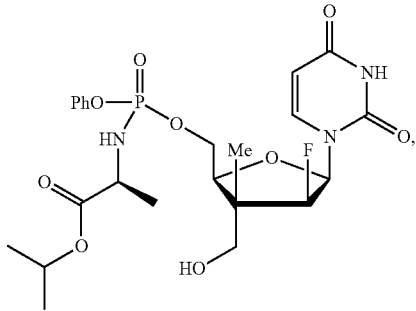

LCB-2106
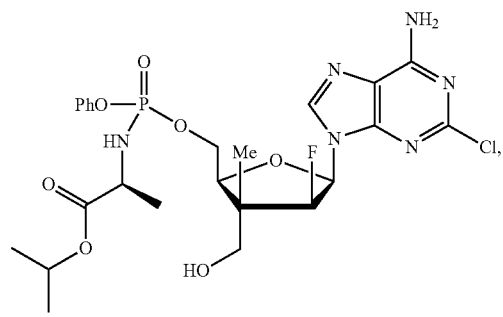
LCB-2142
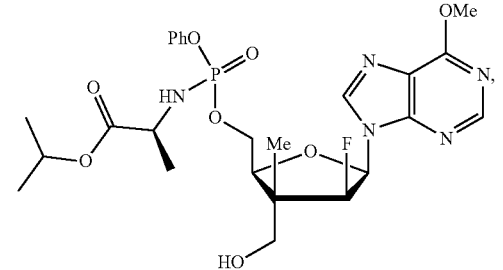
LCB-2146
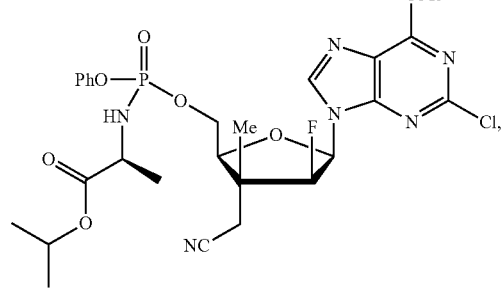
LCB-2147
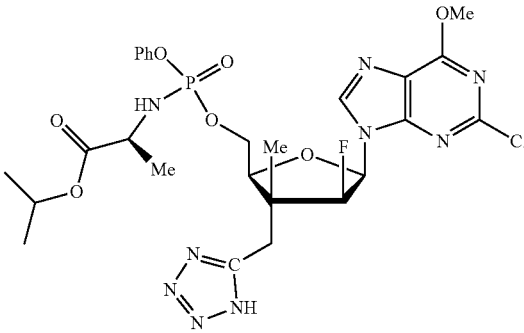
LCB-2168
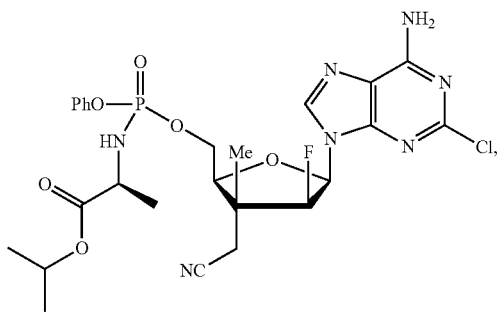
LCB-2173
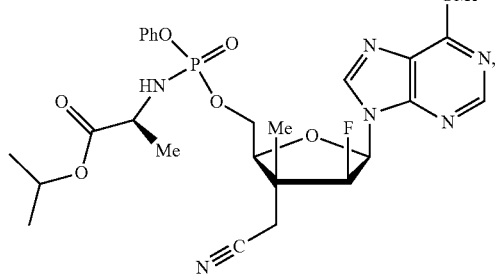
LCB-2174
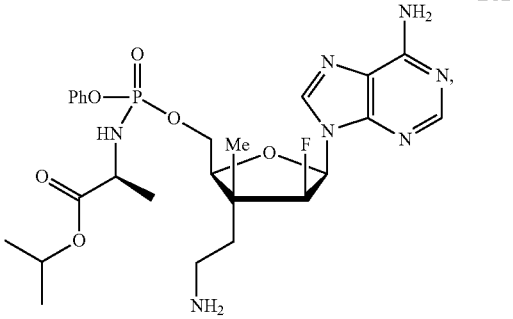
LCB-2175
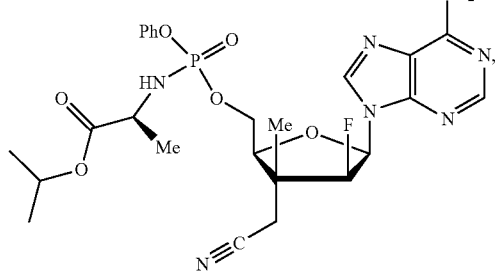
LCB-2187
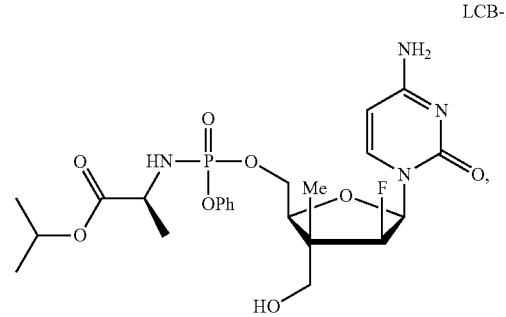

LCB-2189
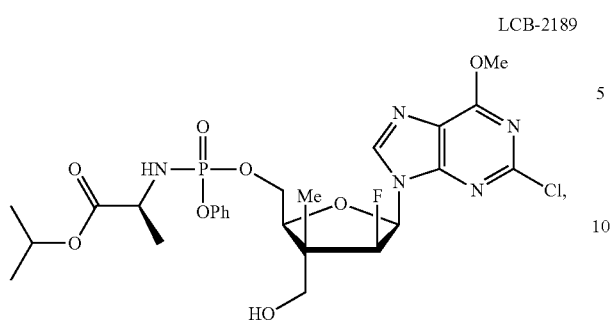
LCB-2201
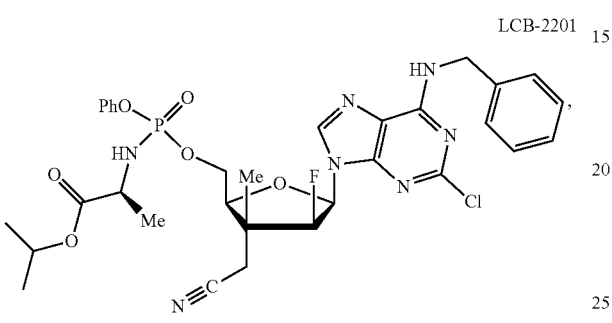
LCB-2220
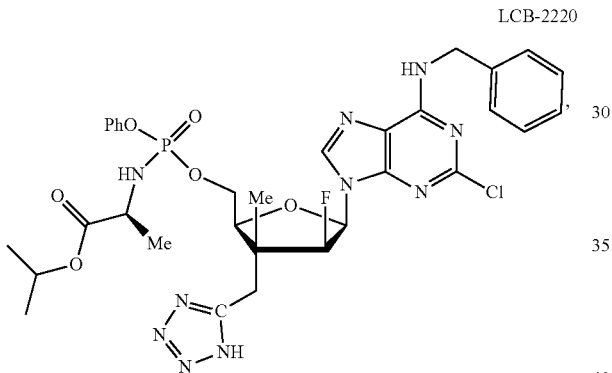
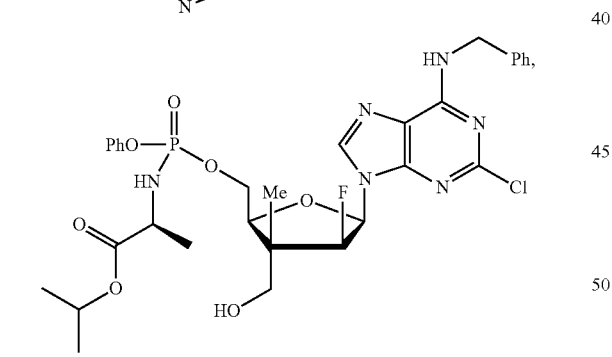
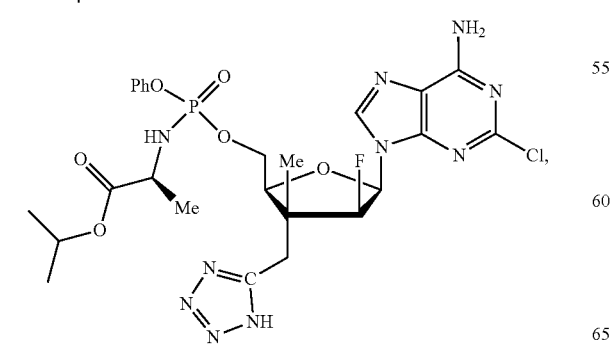
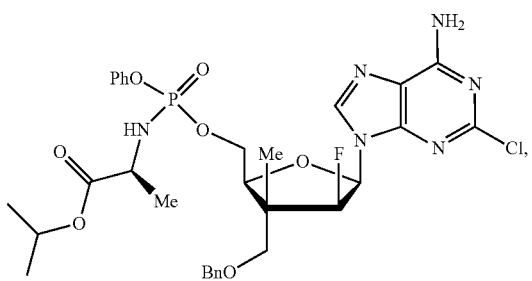
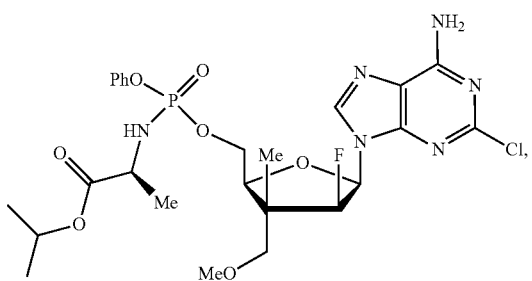
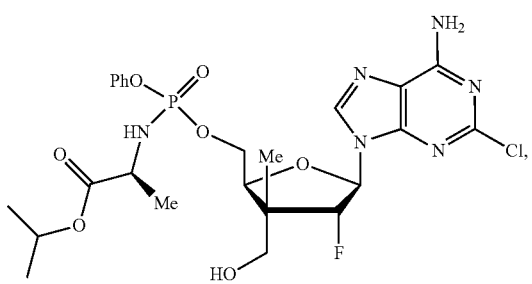
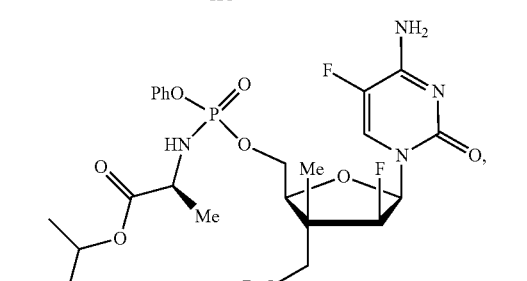
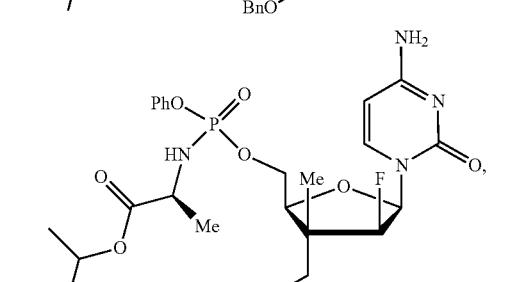
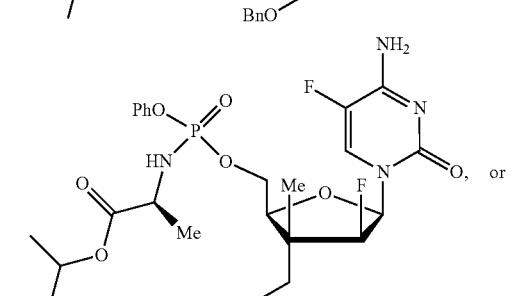

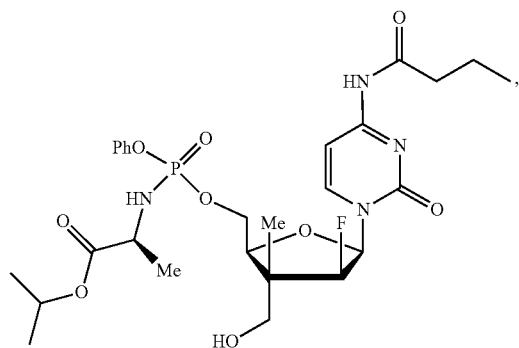
or a pharmaceutically acceptable salt thereof.
In yet more preferred embodiments, the compound is:
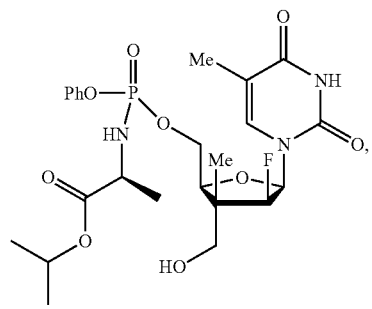
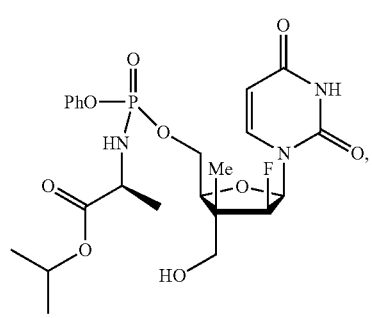
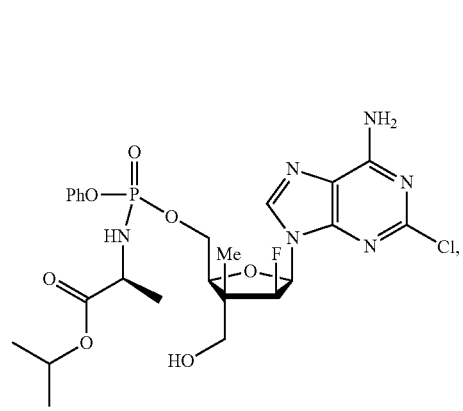
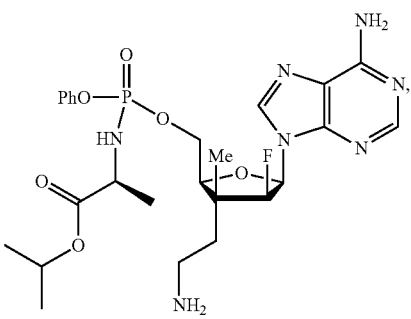
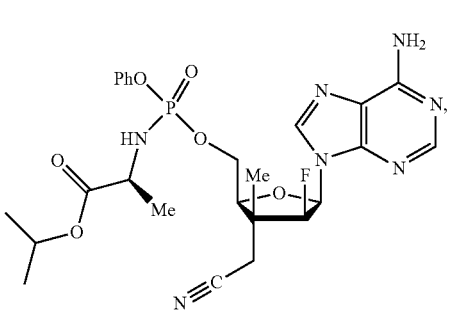
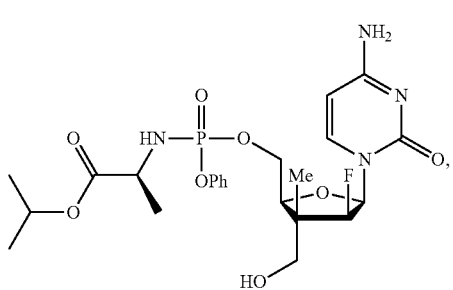
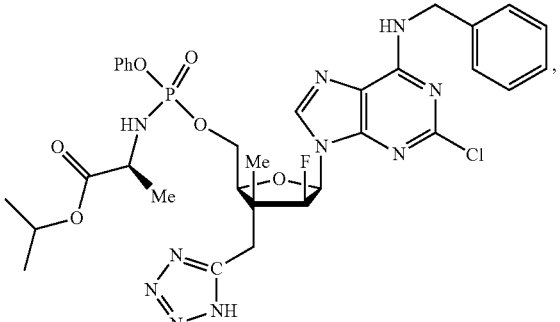

-continued

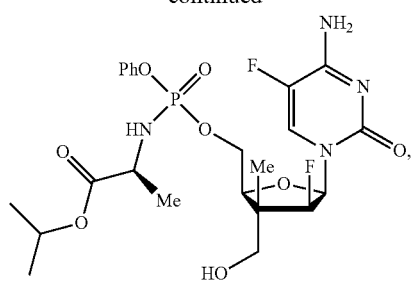

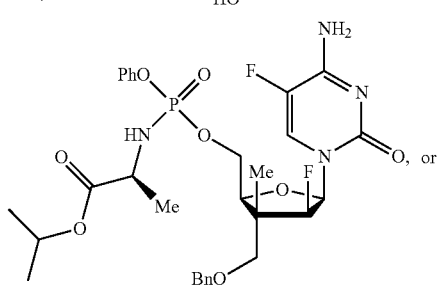

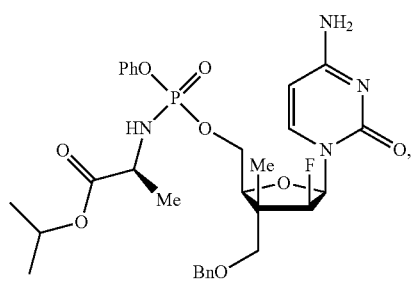

or a pharmaceutically acceptable salt thereof.

In even more preferred embodiments, the compound is:

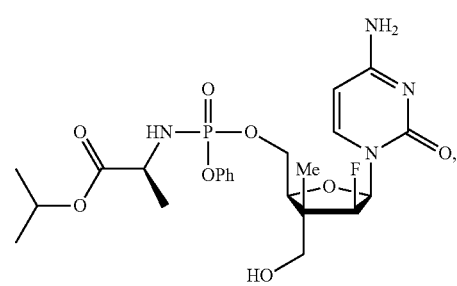
LCB-2187

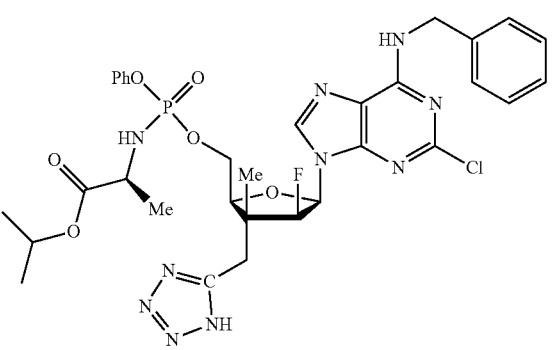
LCB-2220

-continued

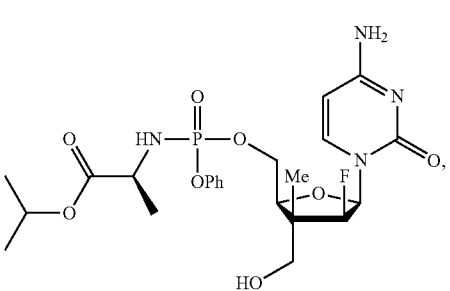

or a pharmaceutically acceptable salt thereof.

In most preferred embodiments, the compound is

LCB-2187 or a pharmaceutically acceptable salt thereof.

Compounds of Group A—with Two Phosphoryl Groups

In embodiments, the compound of the invention is a compound of Group A as described above, further characterized by the fact that it comprises only two phosphoryl group of formula (XX). In such compounds, $R_1$ represents one phosphoryl group and one of A and B is —$(CH_2)_nM$, M is $OR_2$, and $R_2$ represents the other phosphoryl group.

In embodiments, these compounds are of formula V, VI, IX, or X, preferably of formula V or IX, more preferably IX.

In embodiments, Base is:
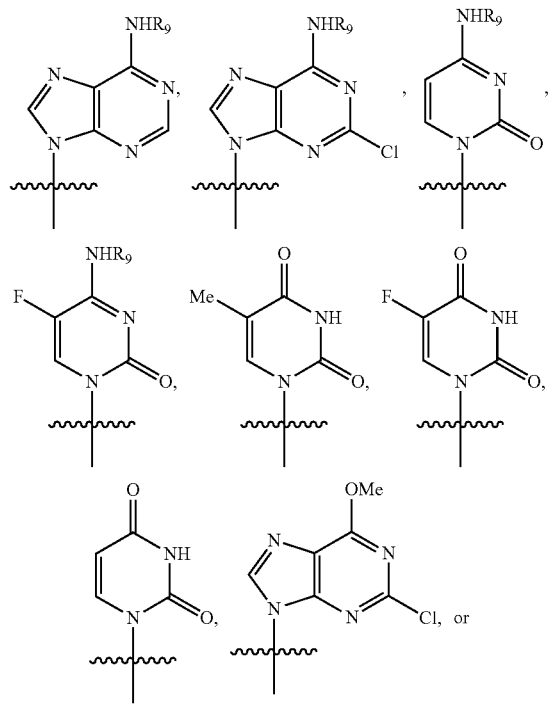
more preferably
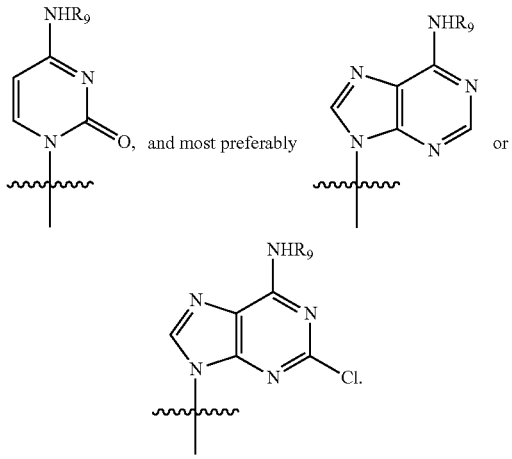
and most preferably
preferably
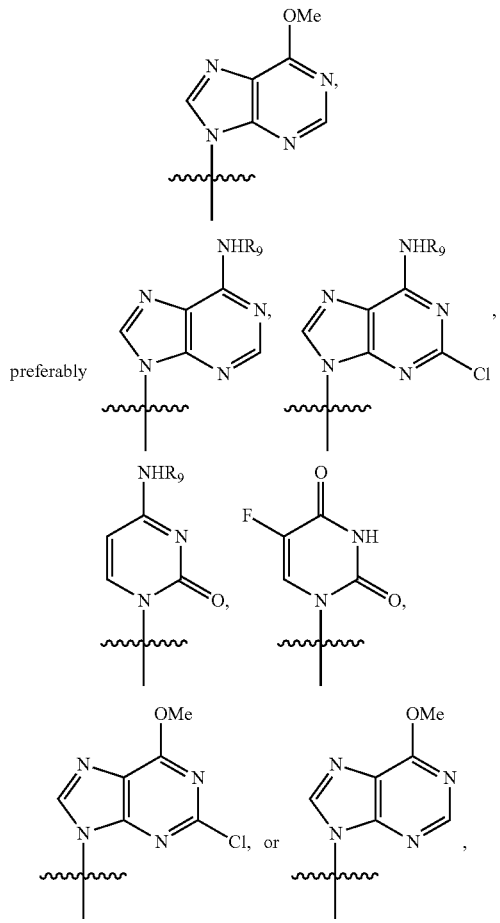
In embodiments, the compound is:
LCB-1993
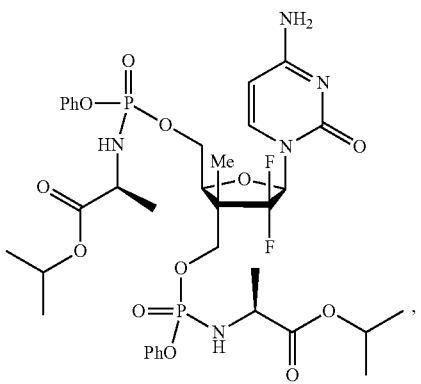
LCB-1995
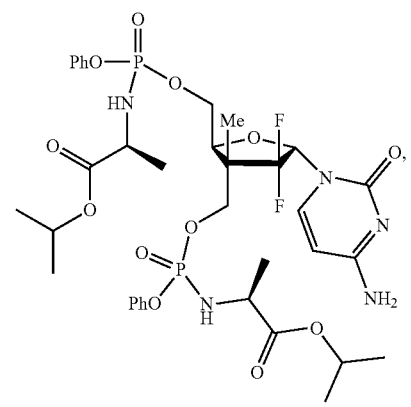

LCB-1996
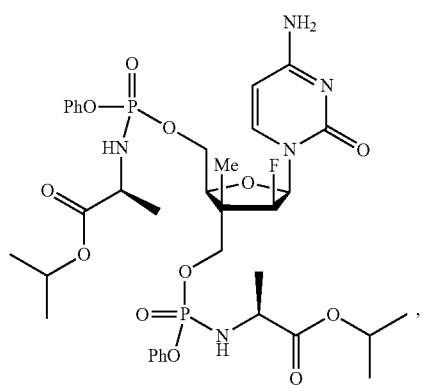
LCB-1997
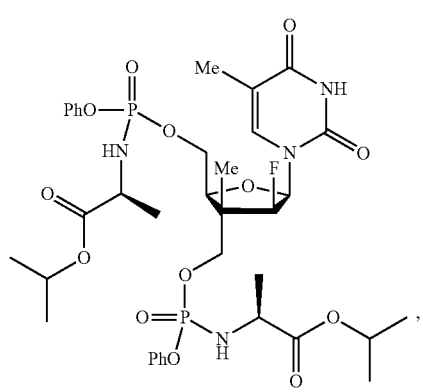
LCB-1999
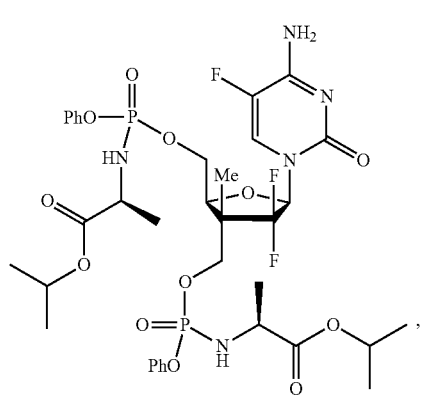
LCB-2002
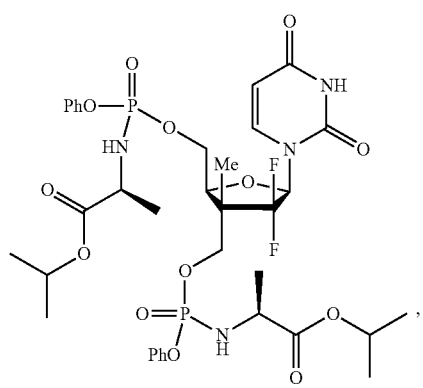
LCB-2009
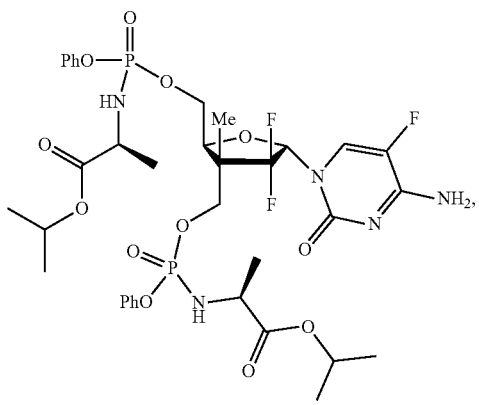
LCB-2015
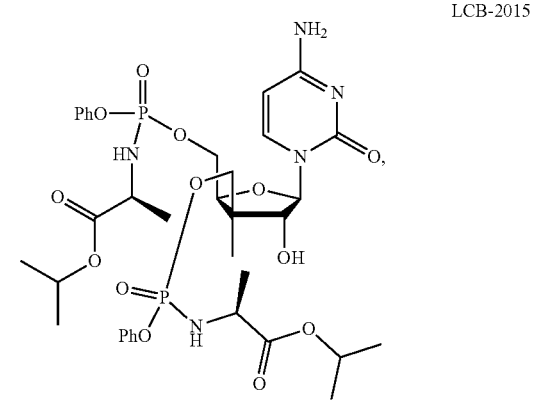
LCB-2016
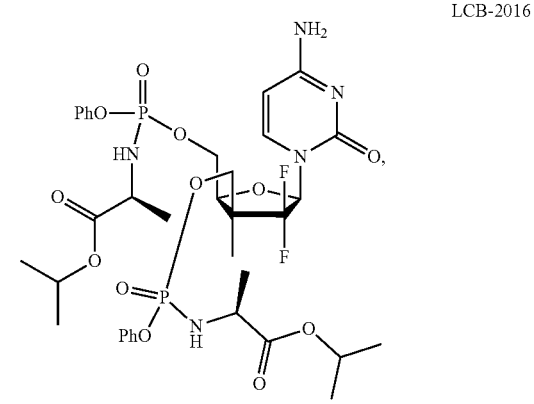
LCB-2017
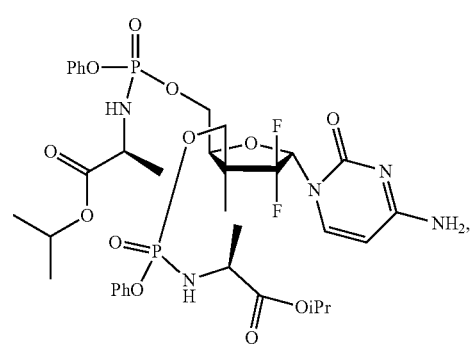

115
-continued
LCB-2029
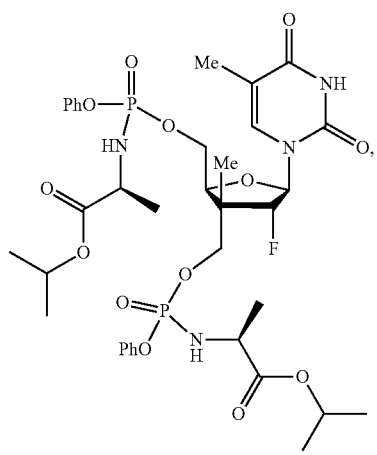
LCB-2035
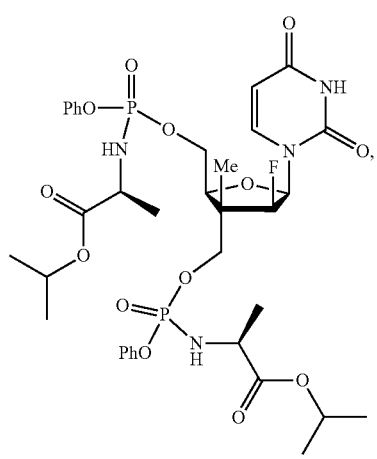
LCB-2036
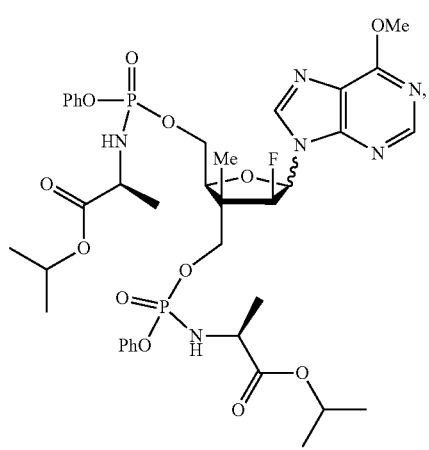
116
-continued
LCB-2045
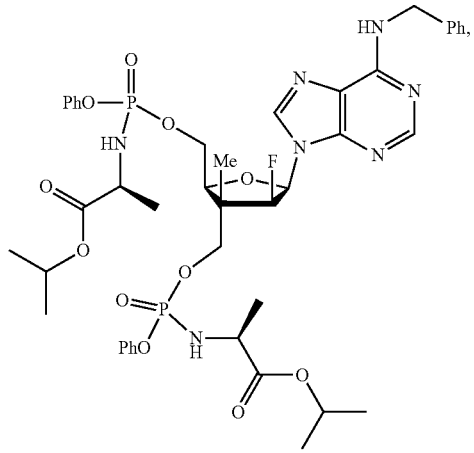
LCB-2076
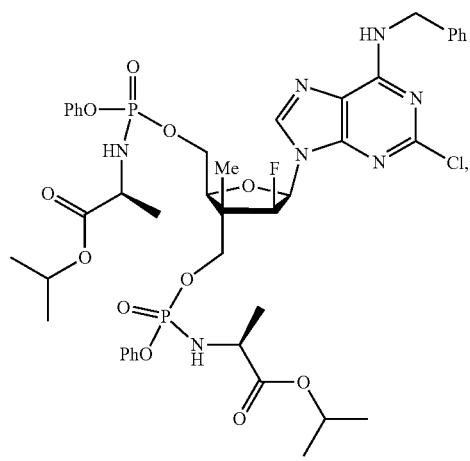
LCB-2079
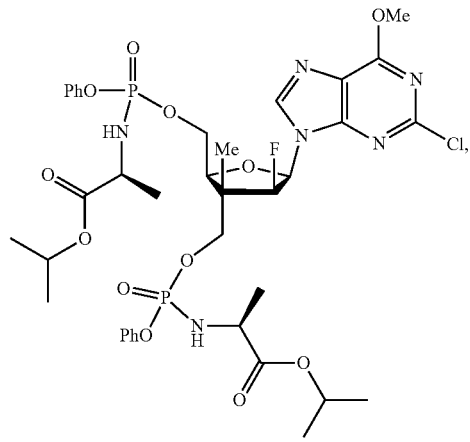

117
-continued
LCB-2080
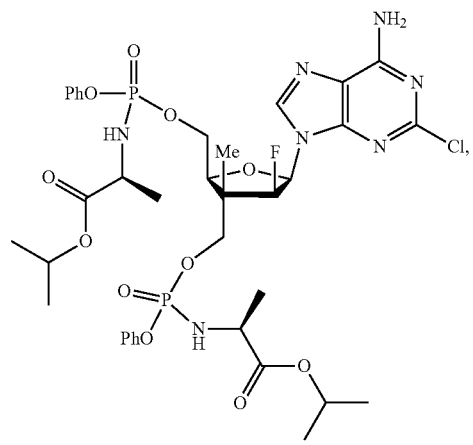
LCB-2088
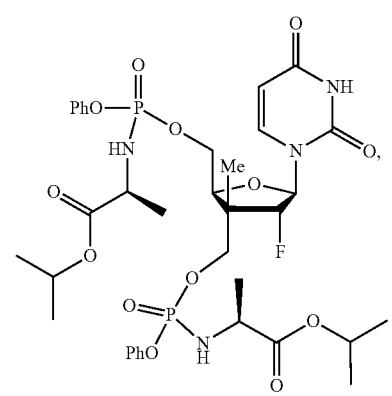
LCB-2092
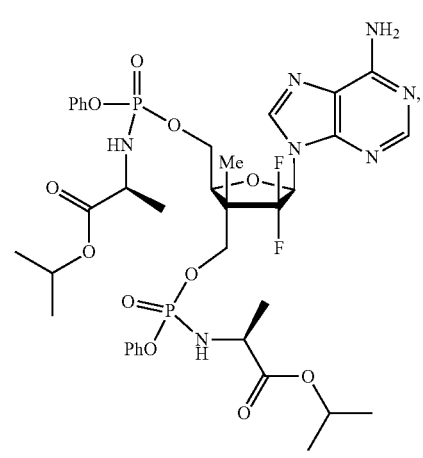
118
-continued
LCB-2095
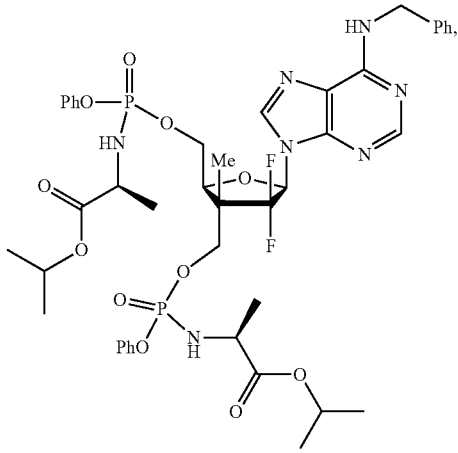
LCB-2105
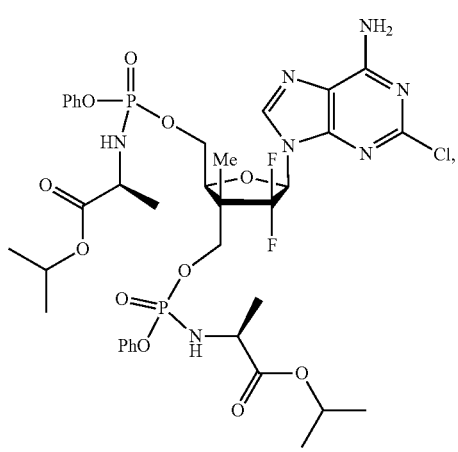
LCB-2127
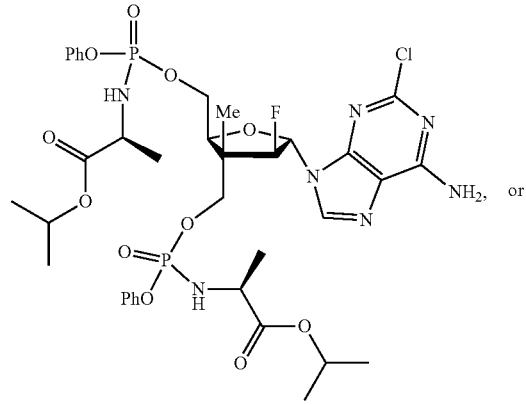

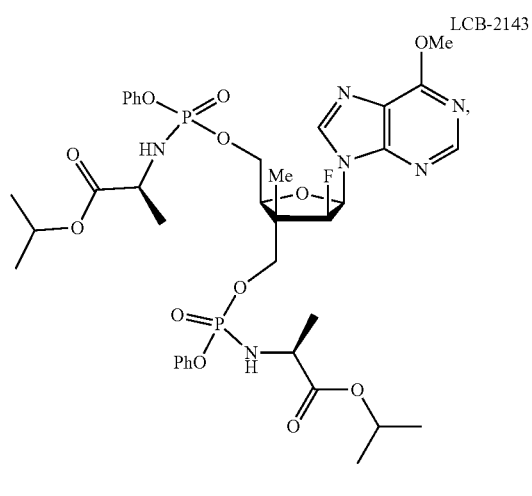
LCB-2143
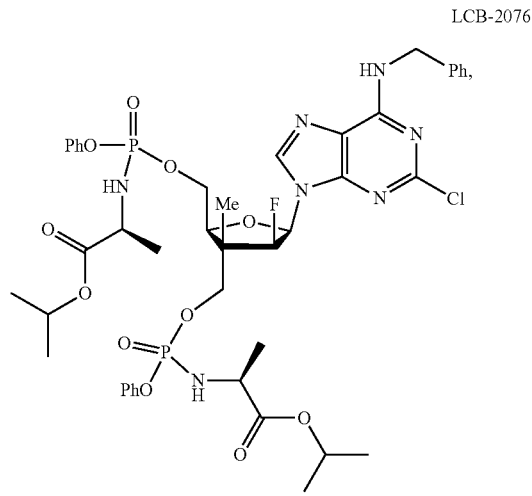
LCB-2076
or a pharmaceutically acceptable salt thereof.
In preferred embodiments, the compound is:
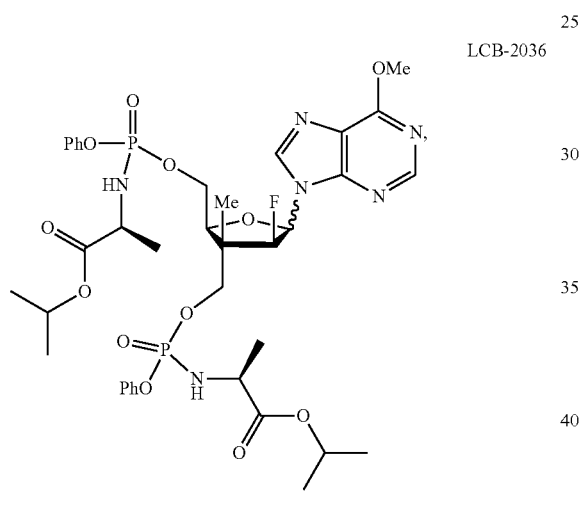
LCB-2036
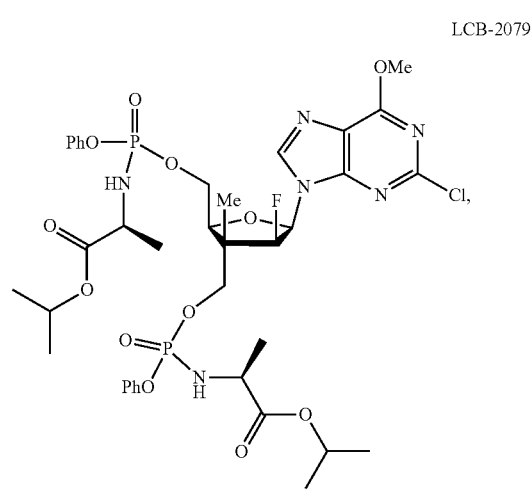
LCB-2079
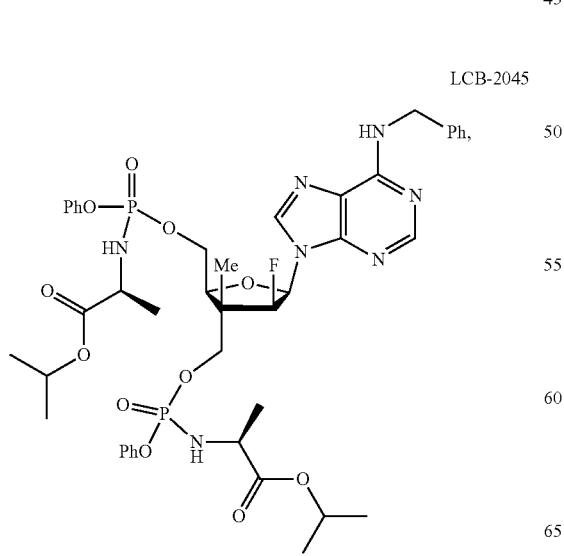
LCB-2045
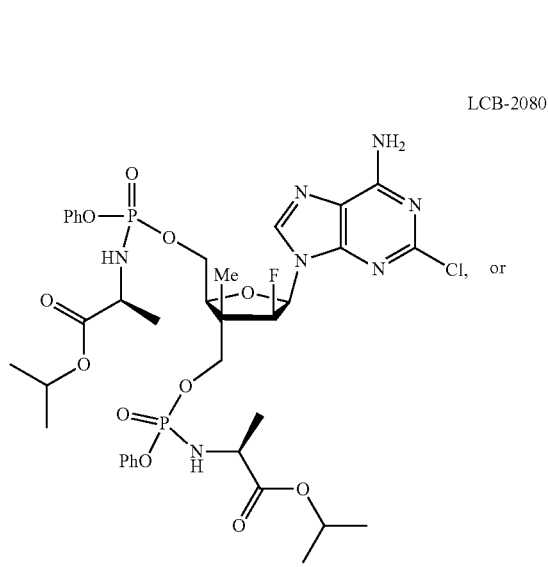
LCB-2080

-continued

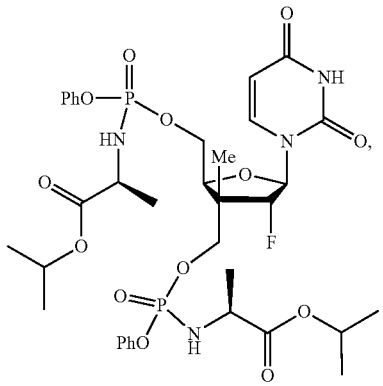
LCB-2088 or a pharmaceutically acceptable salt thereof.

Compounds of Groups B and C

In embodiments, the compound of the invention comprises one lipoate group of formula (XXI), said compound either being free of a phosphoryl group of formula (XX) or comprises a phosphoryl group of formula (XX) in $R_1$. These are compounds of Groups B and C as defined above, respectively.

In embodiments, the compounds are of formula I, II, V, VI, IX, X, XIII, XIV, or XVII, preferably I, V, IX, XIII, or XVII, more preferably V, XIII, or XVII or alternatively I, IX, or XVII, and more preferably of formula XIII or XVII.

In embodiments, C is H and D is halo or OH, preferably OH.

In embodiments, Base is:

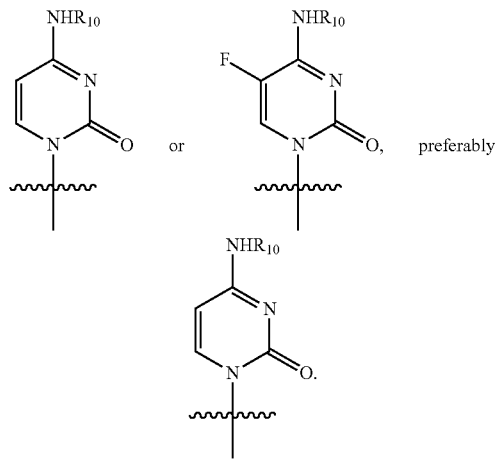

Compounds of Group B

In embodiments, the compound of the invention is a compound of Group B or C as described above, further characterized by the fact that it is free from phosphoryl group of formula (XX). These are compounds of Group B as defined above.

In embodiments, $R_1$ is H.

In embodiments, these compounds are of formula I, V, IX, XIII, or XVII. In preferred embodiments, these compounds of formula I, IX, or XVII, preferably IX or XVII. In alternative preferred embodiments, these compounds of formula V or XVII, preferably of formula XVII, or alternatively of formula V.

In embodiments, the compound is:

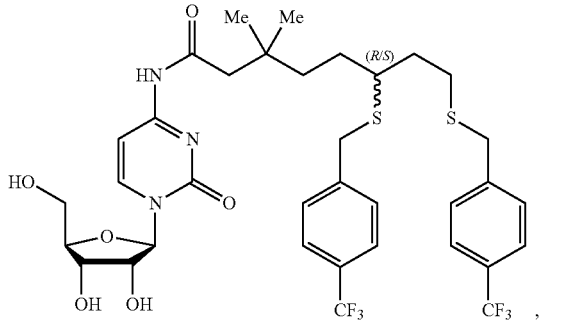
LCB-2125

LCB-2131

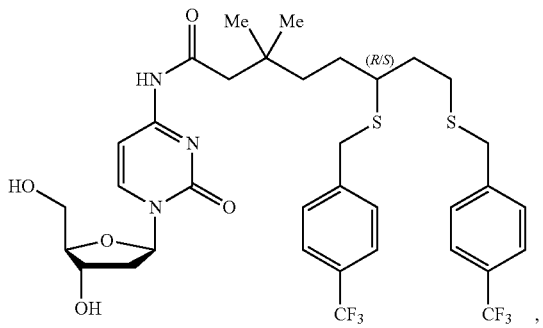
LCB-2132

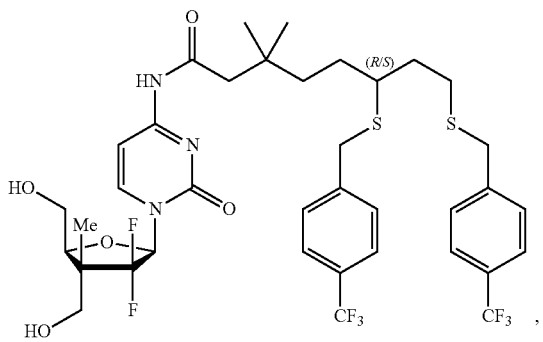
LCB-2139

-continued
LCB-2140
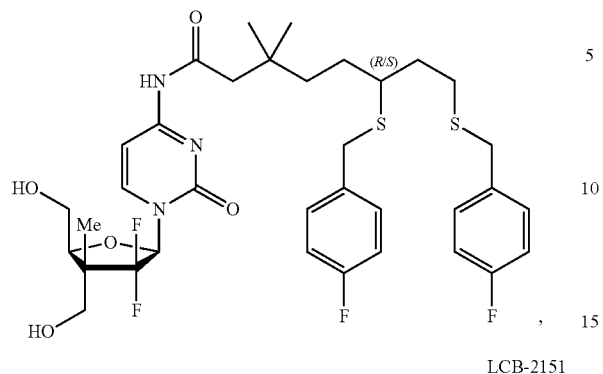
LCB-2151
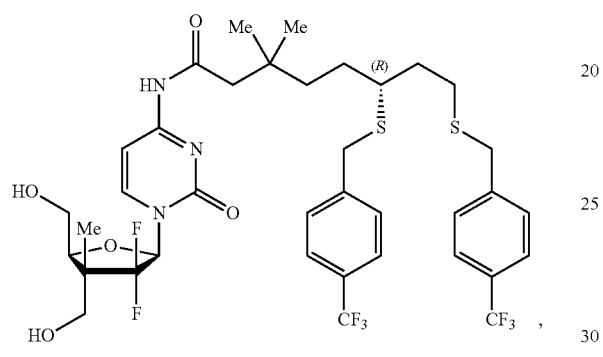
LCB-2216
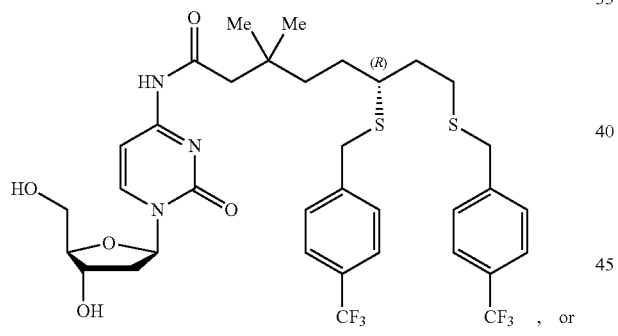
LCB-2227
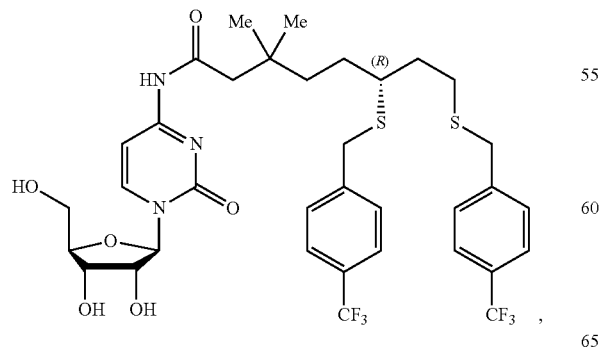
or a pharmaceutically acceptable salt thereof.
In preferred embodiments, the compound is:
LCB-2125
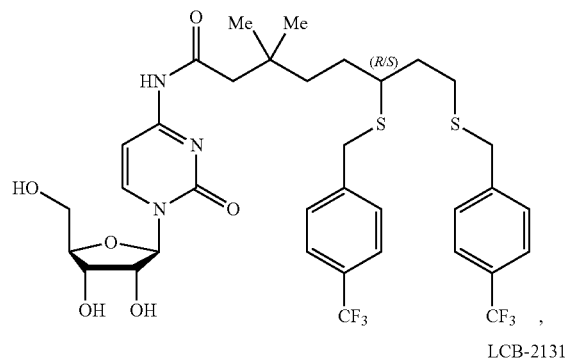
LCB-2131
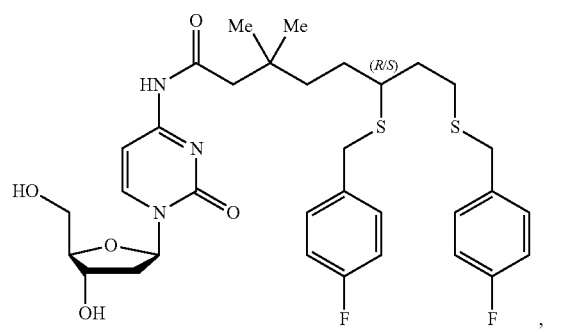
LCB-2132
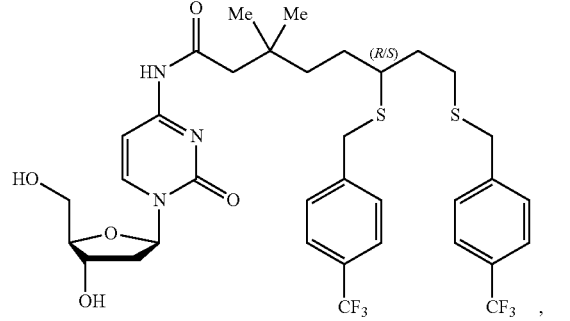
LCB-2140
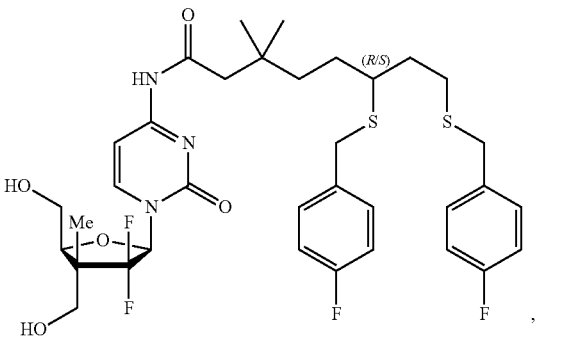

-continued

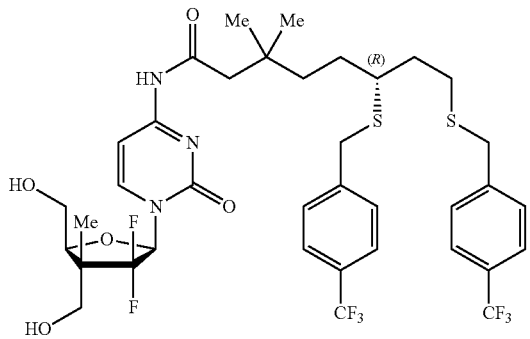

or a pharmaceutically acceptable salt thereof.

In most preferred embodiments, the compound is:

LCB-2151

[structure]

, or

LCB-2132

[structure]

or a pharmaceutically acceptable salt thereof.

Compounds of Group C

In embodiments, the compound of the invention is a compound of Group B or C as described above, further characterized by the fact that it comprises a phosphoryl group of formula (XX) in $R_1$. These are compounds of Group C as defined above.

In embodiments, the compounds are of formula I, V, IX, XIII, or XVII, preferably I, V, IX, or XIII. In preferred embodiments, the compounds are of formula I, IX, or XIII, preferably IX or XIII. In alternative preferred embodiments, the compounds are of formula V or XIII, preferably XIII.

In embodiments, the compound is:

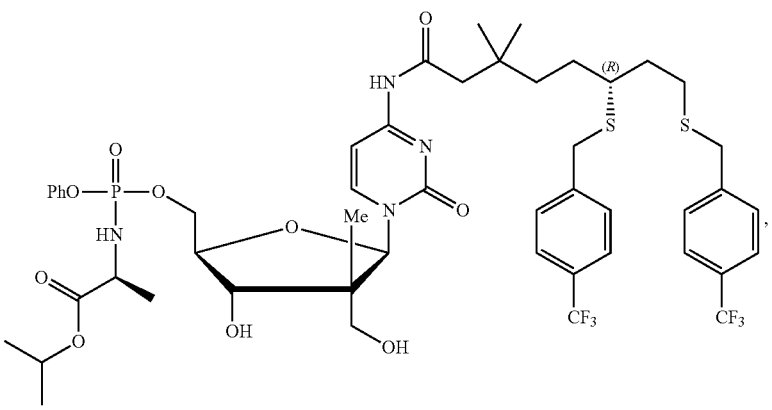

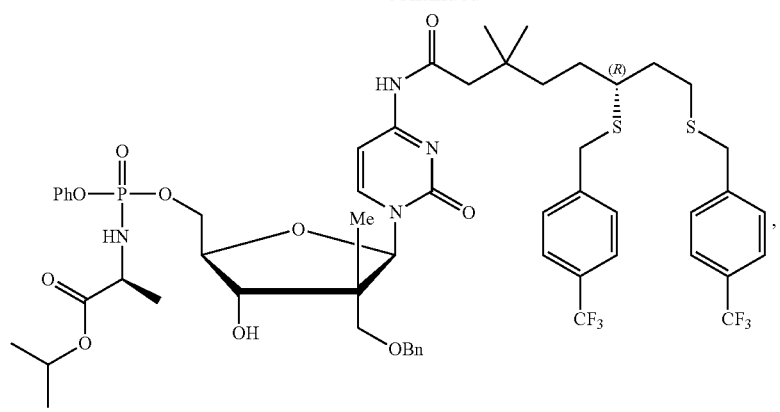
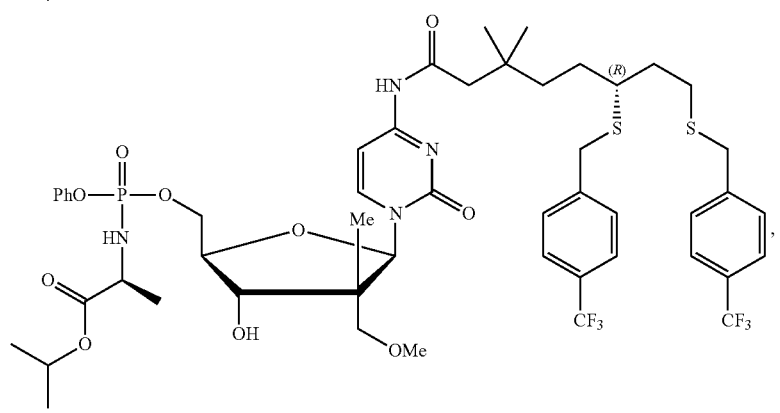
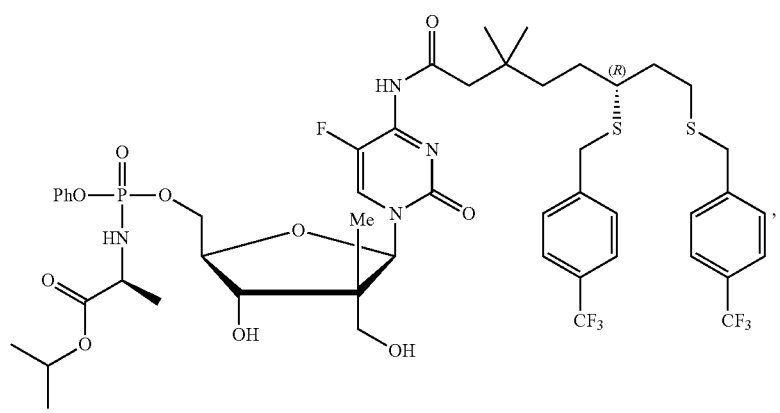
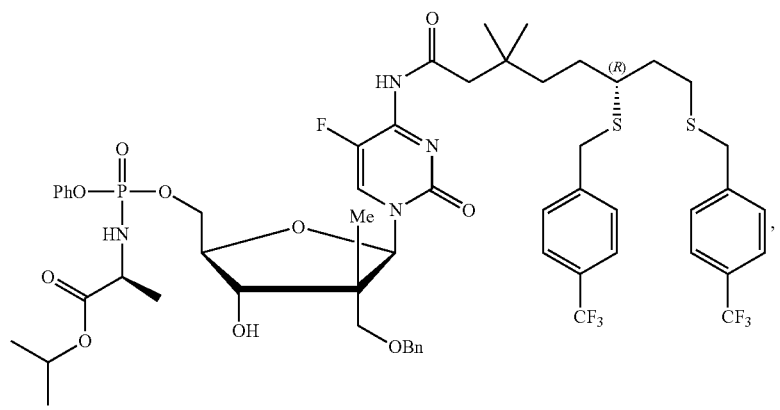

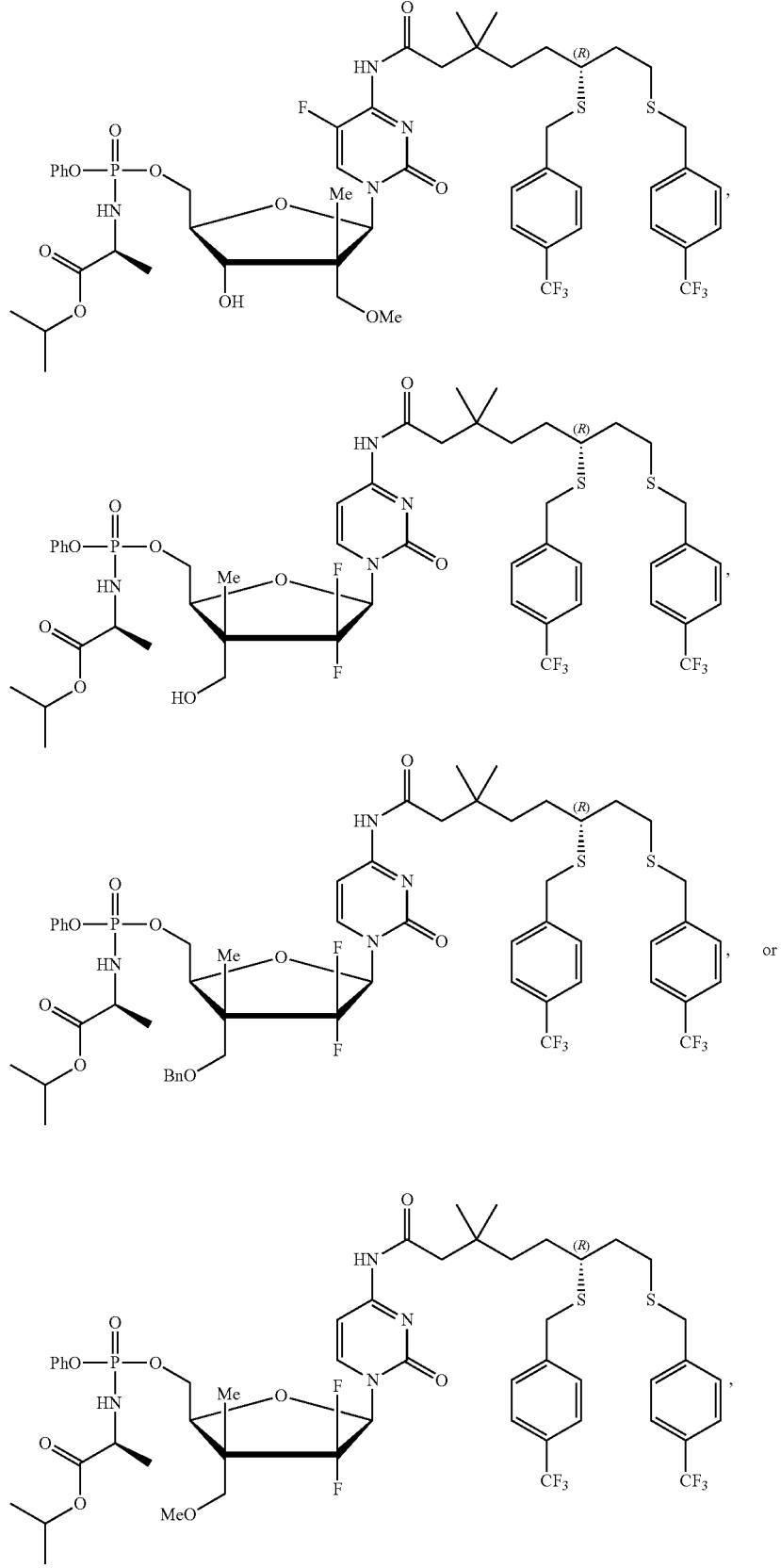
or a pharmaceutically acceptable salt thereof.

In preferred embodiments, the compound is:

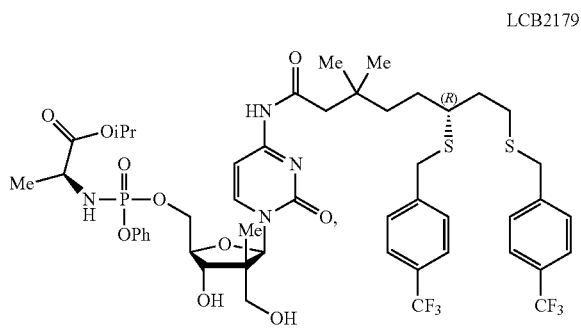

LCB2179 or a pharmaceutically acceptable salt thereof.

As noted above, "pharmaceutically acceptable salts" of all of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium and magnesium salts. Salts derived from pharmaceutically acceptable organic non-toxic bases include salts or primary, secondary, and tertiary amines, substituted amines including naturally occurring substituted amines, cyclic amines and basic ion exchange resin, such as isopropylamine, tri-methylamine, diethanolamine, diethylamine, triethylamine, tripropylamine, ethanolamine, 2-dimethylaminoethanol, 2-diethyl-amino-ethanol, tometheamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethylmorpholine, polyamine resins and the like. "Pharmaceutically acceptable salts" also refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. See, for example, S. M. Berge, et al., "Pharmaceutical Salts," J. Pharm. Sci., 1977; 66:1-19 which is incorporated herein by reference.[12]

Pharmaceutical Composition

The present invention also relates to pharmaceutical compositions comprising a pharmaceutically acceptable carrier, excipient or diluent and a compound of the invention as defined above or a pharmaceutically acceptable salt thereof.

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as, for example, tablets, suppositories, pills, soft elastic and hard gelatin capsules, powders, solutions, suspensions, or erosols, or the like, preferably in unit dosage forms suitable for simple administration of precise dosages. In embodiments, administration may preferably be by the oral route.

The compositions of the invention include a conventional pharmaceutical carrier or excipient and a compound of the invention as the/an active agent, and, in addition, may include other medicinal agents, pharmaceutical agents, carriers, adjuvants, etc. In particular, compositions of the invention may be used in combination with anticancer or other agents that are generally administered to a patient being treated for cancer. Adjuvants include preserving, wetting, suspending, sweetening, flavoring, perfuming, emulsifying, and dispensing agents.

Prevention of the action of microorganisms can be ensured by various antibacterial and antifungal agents, for example, parabens, chlorobutanol, phenol, ascorbic acid, and the like. It may also be desirable to include isotonic agents, for example sugars, sodium chloride, and the like. Prolonged absorption of injectable pharmaceutical forms can be brought about using agents delaying absorption, for example, aluminium monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms, as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18$^{th}$ Ed., (Mack Publishing Company, Easton, Pa., 1990)$^{12}$ The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Use of the Compounds Anticancer Agents and/or Antiviral Agents

The present invention relates to the use of the above compounds and the above pharmaceutical composition for treating cancer in a subject in need thereof. In other words, the invention relates to a method of treating cancer in a subject in need thereof, the method comprising administering the compound or pharmaceutical composition to the subject.

The present invention relates to the use of the above compounds and the above pharmaceutical composition for inhibiting tumor growth in a subject in need thereof. In other words, the invention relates to a method of inhibiting tumor growth in a subject in need thereof, the method comprising administering the compound or pharmaceutical composition to the subject.

The present invention also relates to the use of the above compounds for in vitro inhibition of tumor cell growth. In other words, the invention relates to a method of inhibiting tumor cell growth in vitro, the method comprising contacting the compound with the tumor cell.

In embodiments, the compound is a compound of group A as defined above.

In embodiments, the compound is a compound of group B as defined above.

In embodiments, the compound is a compound of group C as defined above.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carci-noma), cervix (cervical carcinoma, pre-tumor cervical dysplasia), ovaries (ovarian carcinoma [scrous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In preferred embodiments, the cancer is breast cancer, lung cancer, liver cancer, pancreas cancer, or colon cancer, more preferably liver cancer or pancreas cancer.

A "tumor" refers to an abnormal growth of tissue due to a cancer.

A "tumor cell" refers is a cell of a tumor of a cancer.

The present invention also relates to the use of the above compounds (in particular those of groups A an C) and the above pharmaceutical composition for providing antiviral treatment in a subject in need thereof. In other words, the invention relates to a method of providing antiviral treatment in a subject in need thereof, the method comprising administering the compound to the subject.

The present invention also relates to the use of the above compounds and the above pharmaceutical composition for inhibiting viral replication in a subject in need thereof. In other words, the invention relates to a method of inhibiting viral replication in a subject in need thereof, the method comprising administering the compound to the subject.

The present invention also relates to the use of the above compounds for in vitro inhibition of viral replication. In other words, the invention relates to a method of inhibiting viral replication in vitro, the method comprising contacting the compound to cells infected with a virus.

In embodiments, the compound is a compound of group A as defined above.

In embodiments, the compound is a compound of group C as defined above.

Herein, viral replication refers to the replication of a virus, a virus being, as well known in the art, a small infectious agent that replicates only inside the living cells of other organisms.

Treatment of viruses such as HCMV, HBV (Hepatitis B virus), RSV (respiratory Virus), Influenza, $AH_1N_1$, HSV-2 (Herpes simplex Virus-1), and Zika virus infections are sought after. HCMV infection, for instance, remains a major problem in transplantation and resistance is encountered in all forms of transplantation. In solid organ transplantation resistance is largely found amongst CMV-positive donor to CMV-negative recipient for lung and kidney organs. Resistance is also found in stem cells transplantation. Significant increase in morbidity and mortality results from this infection.

In preferred embodiments, the virus is HCMV or HBV. In more preferred embodiments, the virus is HCMV.

General Synthetic Procedures

The compounds of the invention can be prepared by well-known to those skilled in the art using reagents readily available. See FIG. 3.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. For more certainty:

| Term | Definition |
| --- | --- |
| alkyl | monovalent saturated aliphatic hydrocarbon radical of general formula —$C_nH_{2n+1}$ |
| alkenyl | monovalent aliphatic hydrocarbon radical similar to an alkyl, but comprising at least one double bond |
| alkynyl | monovalent aliphatic hydrocarbon radical similar to an alkyl, but comprising at least one triple bond |
| alkyloxy or alkoxy | monovalent radical of formula —O-alkyl |
| alkynyloxy | monovalent radical of formula —O-alkynyl |

It is to be noted that, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1, or preferably 2 carbon atoms.

Herein, the terms "cycloalkyl", "aryl", "heterocycloalkyl", and "heteroaryl" have their ordinary meaning in the art. For more certainty:

| Term | Definition |
| --- | --- |
| aryl | a monovalent aromatic hydrocarbon radical presenting a delocalized conjugated π system, most commonly an arrangement of alternating single and double bonds, between carbon atoms arranged in one or more rings, wherein the rings can be fused (i.e. share two ring atoms), for example: | naphthalene: 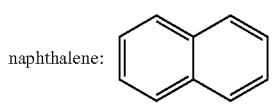

or linked together through a covalent bond, for example:

biphenyl: 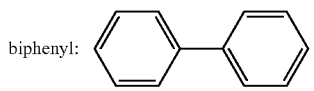 [SMILES: c1ccc(-c2ccccc2)cc1]

or linked together through a radical that allow continuation of the delocalized conjugated π system between the rings (e.g. —C(=O)—, —NRR—), for example:

benzophenone: 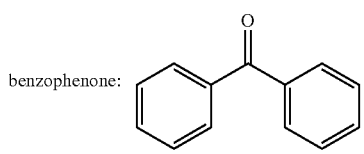 [SMILES: O=C(c1ccccc1)c1ccccc1]

| Term | Definition |
| --- | --- |
| Heteroaryl | aryl wherein at least one of the ring carbon atoms is replaced by a heteroatom, such as nitrogen or oxygen. Examples of heteroaryl include: | indole: 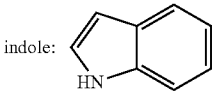

indole-5-carbonylbenzene: 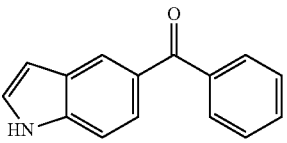

| | |
| --- | --- |
| cycloalkyl | monovalent saturated aliphatic hydrocarbon radical of general formula $C_nH_{2n-1}$, wherein the carbon atoms are arranged in one or more rings (also called cycles). |
| heterocycloalkyl | cycloalkyl wherein at least one of the carbon atoms is replaced by a heteroatom. |

It is to be noted that, unless otherwise specified, the ring(s) of the above groups can each comprise between 4 and 8 ring atoms, preferably between 5 or 6 ring atoms. Also, unless otherwise specified, the above groups may preferably comprise one or more rings, preferably 1 or 2 rings, more preferably a single ring.

Herein, the term "heteroatom" means nitrogen, oxygen, sulfur, phosphorus, preferably nitrogen or oxygen.

Herein, the term "arylalkyl" means an alkyl substituted with an aryl, the alkyl and aryl being as defined above. An arylalkyl groups attaches to the rest of a molecule via its alkyl moiety.

Herein, the term "alkylaryl" means an aryl substituted with an alkyl, the alkyl and aryl being as defined above. An alkylaryl groups attaches to the rest of a molecule via its aryl moiety.

Herein, "halo" refers to halogen atoms, which include fluorine (F), chlorine (Cl), bromine (Br), and iodine (I).

Herein, "azido" refers to a radical of formula $N_3$, i.e. —N=$N^+$=$N^-$, which is in resonance with —$N^-$—$N^+$≡N.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Preparation of Anti-tumor/Anti-viral Compounds

We prepared phosphorylated prodrugs of a series of nucleosides bearing an all-carbon stereogenic quaternary center at C3'. These prodrugs were installed at C5' and C3' or at both positions (Group A). They were evaluated for their antiproliferative and antiviral properties.

Nucleosides analogues having amino group on the nucleobase (e.g. cytosine, adenine) could be deaminated by a variety of enzymes (e.g. Cytidine deaminase or Adenine deaminase) in cells and plasma. Acylating the amino group prevented deamination.

Figure 1:
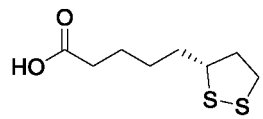
FIG. 1 shows the structure of lipoates and derivatives thereof.
Figure 1:
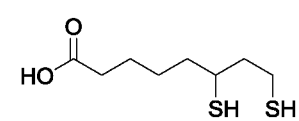
Figure 1:
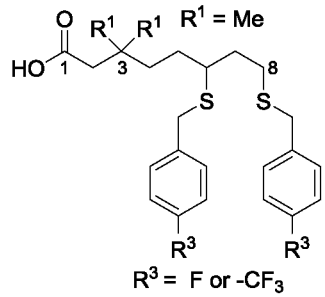
Figure 1:
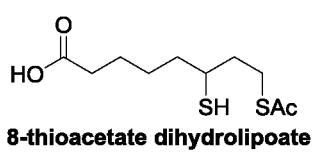
Figure 1:
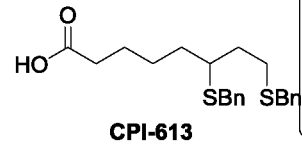
Figure 2:
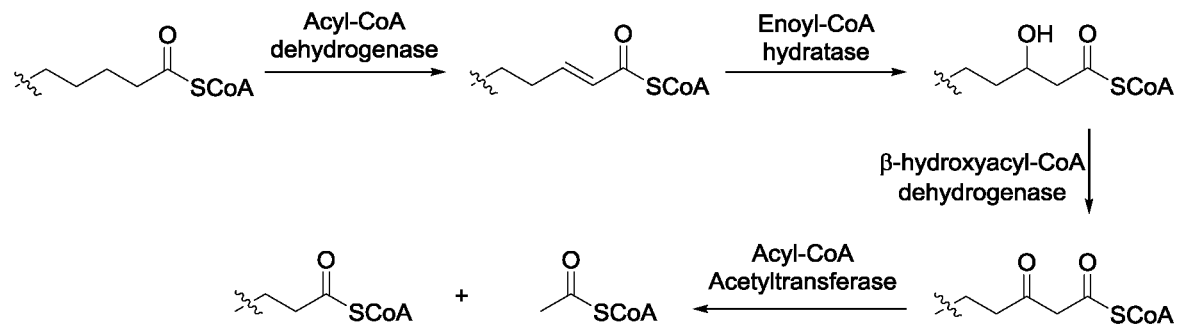
FIG. 2 shows the β-oxydation pathway of the lipoate.

Octanoic derivatives of the lipoates family (FIG. 1) were used. FIG. 1 shows different lipoate moieties, CPI-613 and our β-blocked lipoates, involved in the catalytic cycle of different enzymes. CPI-613, lipoates and lipids are metabolized through a β-oxidation pathway generating a novel molecule having two less, as seen in FIG. 2. This could be blocked by having gem-dimethyl at C-3 or a gem difluoride. The metabolism of the aromatic group is also protected through the introduction of a —CF3 or para fluoro group.

Lipid chain would also be metabolized through the β-oxidation pathway. FIG. 2 presents the lipoate catabolism following β-oxidation pathway, which can be blocked by preparing derivatives that are substituted at the C6 positions ($R_1$ groups). This strategy was employed to generate the lipoate chain installed on Group B and C molecules.

The above enzymes create unsaturated carbonyl, followed by addition of an hydroxy at the β-position. The later is then oxydized to a β-ketoacid, which decarboxylates with al loss of acetic acid. This could be prevented by adding gem substituents at C3' (e.g. gem dimethyl). This will also change the lipophilicity of the molecule while inducing a conformational bias. A —$CF_3$ was also introduced on the thiobenzyl to provent para-oxydation (FIG. 1). This modified lipoate was added to nucleosides having an —NH2 functionality on the base and an all-carbon stereogenic quaternary center at C3' and C2', as illustrated in FIG. 3 to give Group B molecules.

A mono-phosphorylated prodrug was also installed at the C5' position of the Group B molecules to give the Group C molecules. FIG. 3 shows the synthetic route to build nucleoside analogues with stereogenic all-carbon quaternary centers at C3' (shown) or C2' (not shown), which are then derivatized to groups A, B and C. Group A are generated by phosphorylation at C5' (shown) or/and C3' (not shown). Amide formation between the nucleobase —$NH_2$ group and lipoates obtained from the presented synthetic route provides Group B or Group C molecules, the later also bearing a phosphor group at C5'.

Figure 4:
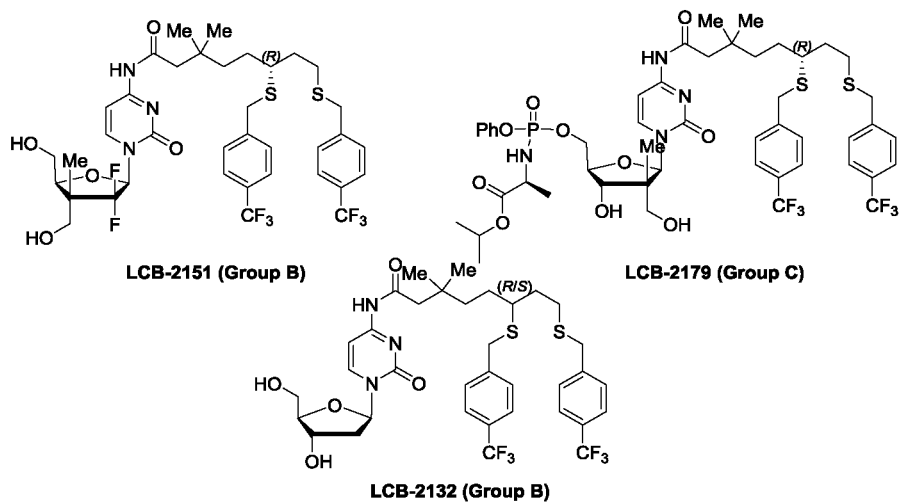
FIG. 4 shows the structure of LCB-2151, LCB-2132 (Group B), and LCB-2179 (group C).

FIG. 4 presents the structure of LCB-2151 (Group B) and LCB-2179 (Group C), which are representative examples of group B bearing a β-blocked lipoate derivatives and a quaternary center at C-3. LCB-2179 exemplifies a group C molecule having a lipoate and a phosphoramidate pro-drug at C-5' and a quaternary center at C-2'.

Anti-Tumor Activity of the Compounds

In spite of recent advances, certain cancers still have a poor survival rate, such as liver and pancreatic ones. For example, Table 1 shows worldwide statistics for liver and pancreatic cancer. In spite of significant improvements in the treatment of cancer patients, liver and pancreatic cancers treated with a variety of anticancer agents, including Gemcitabine, the gold standard, have poor 5-year survival rate; 38% for the former and 5% for the later.

TABLE 1

| Cancers | Treatments | Cases/ year | Deaths/ year | 5-year survival rate |
|---|---|---|---|---|
| Liver * | Tumor resection/Sorafenib | 792000 | 818000 | 28% |
| Pancreas+ | Tumor resection/ Gemcitabine/FOLFIRINOX | 338000 | 257000 | 5% |

*(Global Burden of Disease Cancer Collaboration et al., 2015; Harlan, Parsons, Wiggins, Stevens, & Patt, 2015).
+(Kaltsas et al., 2014).

The fourth aspect of the invention comprises methods for inhibiting tumor cell growth, viral replication in vitro by molecules of formulae of Group A, B and C or pharmaceutically acceptable salts thereof.

The fifth aspect of the invention comprises pharmaceutical compositions comprising a pharmaceutically acceptable carrier, excipient or diluent and compounds according to formulae of Group A, B and C and pharmaceutically acceptable salts thereof.

In the sixth aspect, the invention comprises methods for treating a patient with tumor or viral diseases with a pharmaceutical composition according to the fifth aspect of the invention.

The anti proliferative activities of Group A representatives are listed in Table 2. In fact, Table 2 presents the percentage of growth inhibition of representative molecules of Group A in MCF-7, A549, HepG2, Capan-2, BxPC3 and HCT-116 human cancer cells lines obtained with various compounds. Of particular importance are the compounds effect on liver and pancreatic cell lines.

TABLE 2

| | | MCF-7 (Breast) | | A549 (Lung) | | HepG2 (Liver) | | Capan-2 (Pancreas) | | BxPC3 (Pancreas) | | HCT-116 (Colon) | |
|---|---|---|---|---|---|---|---|---|---|---|---|---|---|
| | | Growth Inhibition (%) At | | | | | | | | | | | |
| Group | | 20 μM | 50 μM | 20 μM | 50 μM | 20 μM | 50 μM | 20 μM | 50 μM | 20 μM | 50 μM | 20 μM | 50 μM |
| A | LCB2036 | 52 | 93 | — | — | 0 | 0 | 0 | 0 | NT | NT | 41 | 65 |
| | LCB2045 | 73 | 77 | 7 | 20 | 0 | 0 | 61 | 86 | NT | NT | 28 | 29 |
| | LCB2076 | 69 | NT | NT | NT | 0 | NT | 14 | NT | 25 | NT | 10 | NT |
| | LCB2079 | 96 | >96 | 70 | NT | 72 | NT | 50 | NT | 40 | NT | 51 | NT |
| | LCB2080 | 79 | NT | 34 | NT | 0 | NT | 58 | NT | 16 | NT | 40 | NT |
| | LCB2092 | 54 | NT | 25 | NT | 16 | NT | 48 | NT | 62 | NT | 60 | NT |
| | LCB2093 | 14 | NT | 0 | NT | 6 | NT | 22 | NT | 6 | NT | 28 | NT |
| | LCB2095 | 49 | NT | 3 | NT | 0 | NT | 46 | NT | 67 | NT | 31 | NT |
| | LCB2105 | NT | NT | NT | NT | NT | NT | 48 | NT | 47 | NT | 53 | NT |

NT: Not tested.

Representative LCB-2151, LCB-2132 and LCB-2179 (FIG. 4) show $EC_{90}$ activity against KRAS mutated in human pancreatic and liver cancer cell lines (HepG-2, Panc-1, Capan-2) that are resistant to Gemcitabine, the clinical gold standard. Liver and pancreatic cancer patients have an extremely poor survival rate (Table 1).

Figure 5:
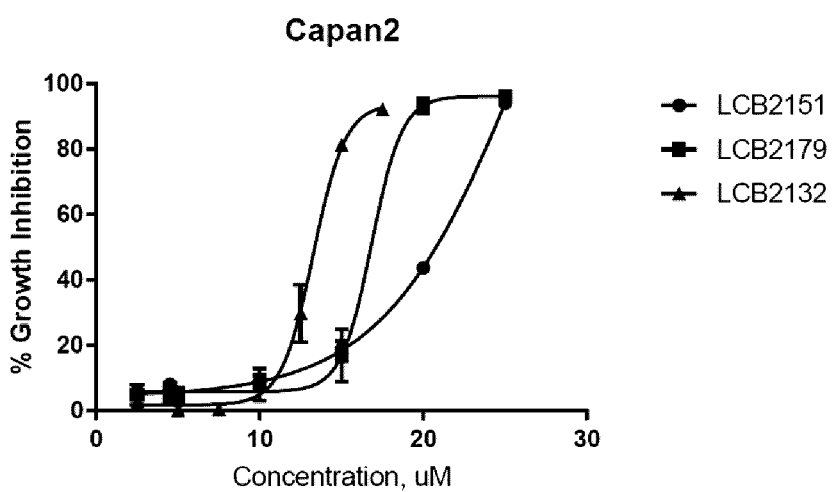
FIG. 5 shows the activity of LCB-2151, LCB-2132 and LCB-2179 in human cancer cell lines.
Figure 5:
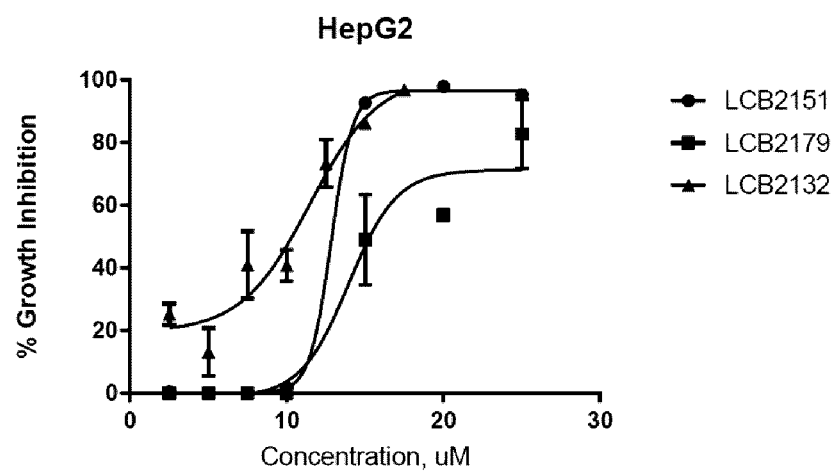
Figure 5:
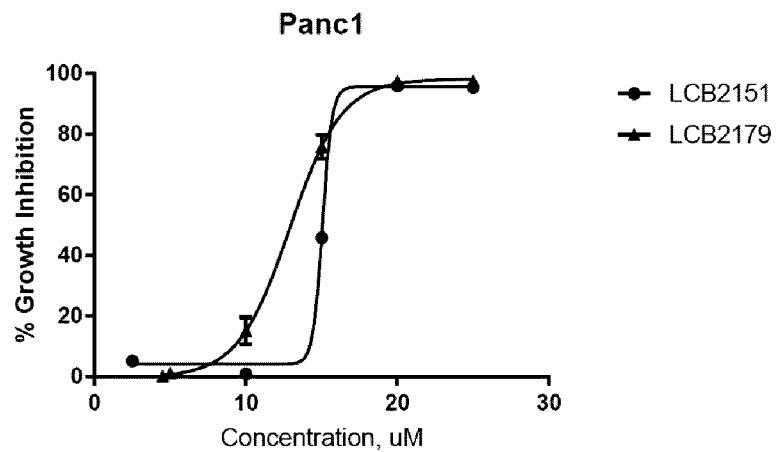
Figure 5:
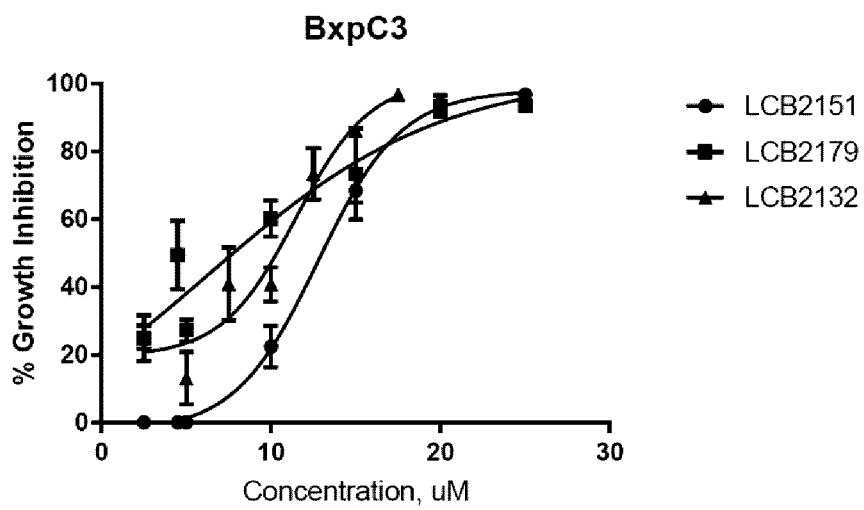
Figure 5:
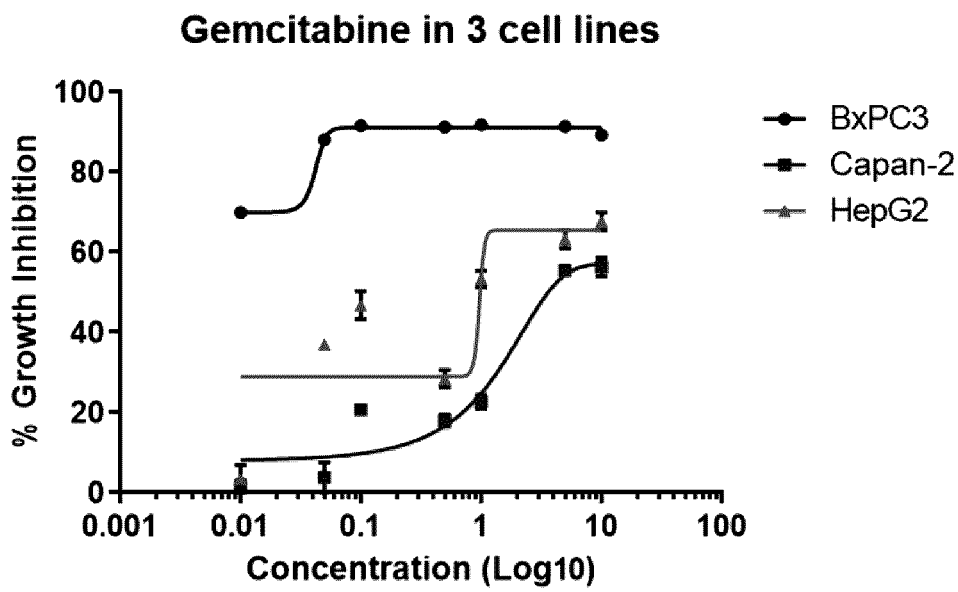

Molecules such as LCB-2151 and LCB-2132 (Group B) and LCB-2179 (Group C) indeed show antiproliferative activities against cancer cell lines with KRAS mutations. FIG. 5 presents the activity of LCB-2151, LCB-2179, LCB-2132 and Gemcitabine in different cancer cell lines. Most liver and pancreas cell lines have the KRAS protein (oncogene identified in Kiersten rat sarcoma virus), which alters its signal transduction pathway, are resistant to Gemcitabine. As seen in FIG. 5, Capan-2 cells treated with Gemcitabine showed no growth inhibition. Both HepG-2 (liver) and Panc-1 (pancreas) have the KRAS mutation and are resistant to Gemcitabine. A plateau at 50% and 30% inhibition is observed, while in BXPC3 (pancreas) that is KRAS wild type, growth is blocked by Gemcitatine at low concentrations. Both LCB-2151 and LCB-2179 block completely the growth in the four cell lines, including Capan-2.

Table 3 presents in vitro $IC_{50}$ for the antiproliferative activities of representative molecules of Group B and C for HepG2, BxPC3 and Capan-2 human cancer cells lines at two concentrations (20 and 50 micromolar).

TABLE 3

| Group | Compounds | HepG2 (Liver) | BxPC3 (Pancreas) $IC_{50}$ (μM) | Capan-2 (Pancreas) |
|---|---|---|---|---|
| B | LCB-2139 | 8 | 8 | 8 |
|   | LCB-2140 | 8 | 8 | 12.5 |
|   | LCB-2151 | 8 | 5 | 8 |
| C | LCB-2179 | 15 | 7 | 15 |

Experimental Section—Anti-Tumor Activity

Growth inhibition of the compound comprises in the invention was tested in vitro using human cancer cell cultures Cell Culture HepG2 (liver human hepatocellular carcinoma), BxPC3 and Capan-2 (adenocarcinomas), A549 (lung carcinoma), HCT-116 (colorectal carcinoma) and MCF-7 (breast tumor) cell lines were obtained from ATCC. The HepG2, BxPC3, Capan-2 and MCF-7 cells were placed into 75 ccm$^3$ tissue culture flasks and grown at 37° C. under a humidified 5% $CO_2$ atmosphere in EMEM and RPMI-1640 medium respectively with 10% fetal bovine serum and 2% penicillin-streptomycin. Trypsin (0.05%) was used to detach cells from the bottom of flask.

Cell Viability Assay

Cells were plated in 96 well plates at a density of $10^4$ cells/well and grown for 24 h. Cells were treated with different concentrations of the test compounds or vehicle alone (DMSO) and grown at 37° C. under a humidified 5% $CO_2$ atmosphere. Their corresponding medium was used to dilute the 10 mM stocks of each compound to obtain 1 mM stock solutions and subsequently, the treatment concentrations. After 96 hours of incubation, the plates were equilibrated at room temperature for 30 minutes, 100 mL of Cell Titer Glo® Luminometric Cell Viability Assay reagent (Promega) was added into each well, put on an orbital shaker for 2 minutes and incubated for 10 minutes at room temperature. The plate was transferred to a luminometer (Glomax Promega) and the luminescent signal was recorded. Each treatment at different concentration and the control group were triplicates or duplicates.

This is a homogeneous method to determine the number of viable cells in culture based on quantification of the ATP present which signals the presence of metabolically active cells.

Anti-Viral Activity of the Compounds

Table 4 presents results for Human cytomegalovirus (HCMV), which causes serious diseases in immune compromised hosts, particularly for transplantation recipient. Cytopathic effect (CPE) of A1-169 HMCV variant virus was measured using Human fibroblast cell lines (HFF). Cell titer were measured using Cellglo assay and luminescence in presence or absence of group A of molecules. As seen in Table 4, 50% of the viral load was observed at less than 0.05 μM of LCB-2187. 90% reduction of viral load was attained at 0.25 μM and no cell death was measured in presence of 150 μM of the tested compound, testifying of its lack of intrinsic cell toxicity. Ganciclovir the clinical gold standard in the treatment of HCMV has bee reported as active against the same strand at 1 to 3 μM.

TABLE 4

Example of Antiviral effect

| Structure | Virus/Strain | Cell | $EC_{50}$ (μM) | $EC_{90}$ (μM) | $CC_{50}$ (μM) |
|---|---|---|---|---|---|
| LCB-2187 | HCMV/AD169 | HFF | <0.05 | 0.25 | >150 |
| LCB-2147 | HBV/ayW1 | HepG-2 | 4 | 16 | >100 |

Example 1—Chemical Synthesis Details—Group A Compounds

Example 1.1—Intermediate Compound

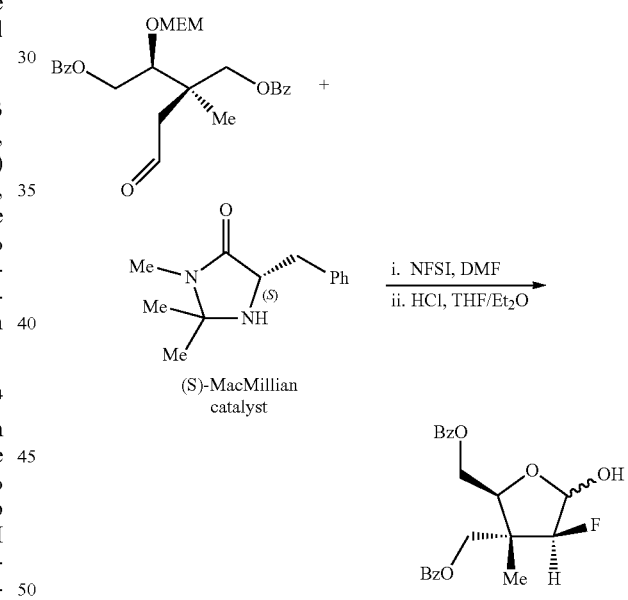

((2S,3R,4S)-4-fluoro-5-hydroxy-3-methyltetrahydrofuran-2,3-diyl)bis(methylene) dibenzoate. To a solution of aldehyde[13] (2.15 g, 4.38 mmol) in anhydrous DMF (4.4 mL, 1.0 M) at 0° C. was added (S)-MacMillan's catalyst ((5S)-5-benzyl-2,2,3-trimethyl-4-imidazolidine, 1.00 g, 4.60 mmol) and N-fluorobenzenesulfonimide (1.52 g, 4.81 mmol) and stirred until homogeneous. The reaction mixture was then maintained at 0° C. without stirring for 24 hours. $Et_3N$ (0.5 mL) and $Et_2O$ (10 mL) were added and the resulting mixture was filtered through a pad of Davisil Silica Gel, eluting with $Et_2O$. After in vacuo evaporation, THE (5 mL), $Et_2O$ (5 mL) and 10 mL of 6.0 N HCl were added to the crude mixture. After stirring at 25° C. for 3 hours, 25 mL of $Et_2O$ was added and the organic phase was separated, washed with a saturated solution of $NaHCO_3$, dried over $MgSO_4$, filtered, and concentrated in vacuo. Purification by flash chromatography (Hexanes:EtOAc gradient) provided the lactol (1.33 g, 73%) as a waxy white solid in an inseparable 4:1 anomeric mixture. $^1$H NMR (500 MHz, CDCl$_3$) δ 8.14-8.00 (m, 4H, major and minor), 7.66-7.56 (m, 2H, major and minor), 7.52-7.39 (m, 4H, major and minor), 5.66 (dd, J=13.1, 2.4 Hz, 1H, major), 5.62-5.57 (m, 1H, minor), 4.92 (dd, J=52.2, 0.7 Hz, 1H, major), 4.84 (d, J=51.7 Hz, 1H, minor), 4.67-4.38 (m, 5H, major and minor), 1.58 (s, J=12.5 Hz, 3H, major), 1.31 (d, J=4.3 Hz, 3H, minor) ppm; HRMS calcd for C$_{21}$H$_{21}$O$_6$FO$_6$Na (M+Na)$^+$: 411.1220, found: 411.1216 (+0.4 ppm).

Example 1.2—Intermediate Compound

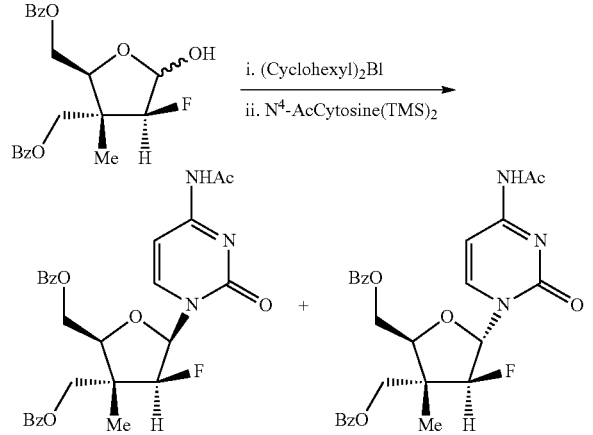

((2S,3R,4S,5R)-5-(4-acetamido-2-oxopyrimidin-1(2H)-yl)-4-fluoro-3-methyltetrahydrofuran-2,3-diyl)bis(methylene) dibenzoate and ((2S,3R,4S,5S)-5-(4-acetamido-2-oxopyrimidin-1(2H)-yl)-4-fluoro-3-methyltetrahydrofuran-2,3-diyl)bis(methylene) dibenzoate. To a solution of lactol (0.100 g, 0.257 mmol) in anhydrous dichloroethane (2.9 mL, 0.1 M) at 25° C. was added (cyclohexyl)$_2$BI (0.618 mL, 0.309 mmol, 0.5 M solution in DCM) under an inert atmosphere. The reaction mixture was then stirred at 25° C. for 90 minutes before the addition of silylated N$^4$-AcCytosine (0.73 mL of 0.6 M solution in DCM, 0.51 mmol). The resulting mixture was stirred 5 hours at 80° C. and then cooled to room temperature. A saturated NaHCO$_3$ (10 ml) solution was then added. The organic layer was separated and the aqueous phase was extracted with EtOAc (2×). The combined organic layers were dried over MgSO$_4$, filtered, and concentrated in vacuo. Purification by flash chromatography (Hexanes:EtOAc gradient) provided the β-anomer (78.6 mg, 58%) and the α-anomer (15.1 mg, 12%) as white foams.

β-anomer (major): [α]$_D^{25}$ +83.7 (c 1.0, CH$_2$Cl$_2$); $^1$H NMR (500 MHz, CDCl$_3$) δ 9.89 (s, 1H), 8.11-8.02 (m, 5H), 7.66-7.56 (m, 2H), 7.54-7.42 (m, 5H), 6.37 (dd, J=19.9, 3.0 Hz, 1H), 5.35 (dd, J=52.3, 3.1 Hz, 1H), 4.62 (dd, J=11.0, 2.9 Hz, 1H), 4.60-4.51 (m, 2H), 4.42 (d, J=11.6 Hz, 1H), 4.39 (d, J=11.3 Hz, 1H), 2.28 (s, 3H), 1.38 (d, J=3.1 Hz, 3H) ppm. $^{13}$C NMR (126 MHz, CDCl$_3$) δ 171.0, 166.3, 166.15, 163.29, 154.9, 145.1, 133.70 (d, $^4J_{13C\ to\ 19F}$=11.7 Hz), 129.8, 129.4, 129.2, 128.76 (d, $^4J_{13C\ to\ 19F}$=8.4 Hz), 96.6, 93.9 (d, $^1J_{13C\ to\ 19F}$=195.7 Hz), 87.8 (d, $^2J_{13C\ to\ 19F}$=17.0 Hz), 81.5, 77.4, 68.33 (d, $^3J_{13C\ to\ 19F}$=7.8 Hz), 64.29, 48.79 (d, $^2J_{13C\ to\ 19F}$=18.7 Hz), 25.0, 12.7 (d, $^3J_{13C\ to\ 19F}$=11.2 Hz) ppm. HRMS calcd for C$_{27}$H$_{27}$N$_3$O$_7$F (M+H)$^+$: 524.1833, found: 524.1821 (−1.2 ppm).

α-anomer (minor): $^1$H NMR (500 MHz, CDCl$_3$) δ 9.35 (s, 1H), 8.16-7.94 (m, 4H), 7.74 (d, J=7.5 Hz, 1H), 7.67-7.53 (m, 2H), 7.52-7.36 (m, 5H), 5.82 (dd, J=16.8, 3.5 Hz, 1H), 5.70 (dd, J=53.6, 3.6 Hz, 1H), 4.96 (dd, J=7.1, 4.3 Hz, 1H), 4.66-4.51 (m, 2H), 4.44-4.36 (m, 2H), 2.26 (s, J=5.8 Hz, 3H), 1.36 (d, J=3.8 Hz, 3H) ppm. HRMS calcd for C$_{27}$H$_{27}$N$_3$O$_7$F (M+H)$^+$: 524.1833, found: 524.1826 (−0.30 ppm).

Example 1.3—Intermediate Compound

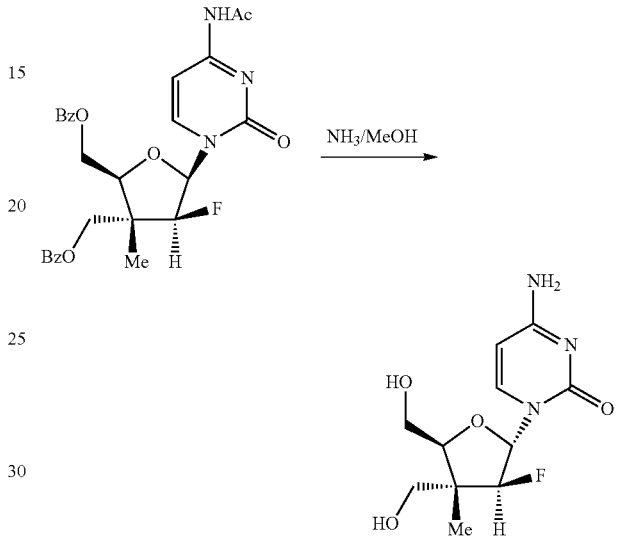

4-amino-1-((2R,3S,4R,5S)-3-fluoro-4,5-bis(hydroxymethyl)-4-methyltetrahydrofuran-2-yl)pyrimidin-2(1H)-one. A solution of β-anomer (0.201 g, 0.384 mmol) in MeOH (4 mL, 0.1 M) at 25° C. was saturated with NH$_3$ gas in a glass pressure vessel sealed with a PTFE bushing. The reaction mixture was stirred at 25° C. for 72 hours before being concentrated in vacuo. Purification by C18 reverse phase flash chromatography (MeOH:H$_2$O gradient) provided the product (92.3 mg, 88%) as white foam. $^1$H NMR (500 MHz, CD$_3$OD) δ 7.88 (d, J=7.5 Hz, 1H), 6.15 (dd, J=20.3, 3.2 Hz, 1H), 5.91 (d, J=7.5 Hz, 1H), 5.00 (dd, J=53.7, 3.2 Hz, 1H), 4.06 (dd, J=6.7, 5.6 Hz, 1H), 3.75-3.68 (m, 2H), 3.54 (s, 2H), 1.09 (d, J=3.1 Hz, 3H) ppm (Labile protons were not observed due to exchange with deuterated solvent). $^{13}$C NMR (126 MHz, CD$_3$OD) δ 167.9, 158.0, 143.4, 95.2, 88.2, 84.5, 67.9, 63.6, 63.3, 50.9, 11.3 ppm. HRMS calcd for C$_{11}$H$_{17}$N$_3$O$_4$F (M+H)$^+$: 274.1203, found: 274.1200 (−1.2 ppm).

Example 1.4—Intermediate Compound

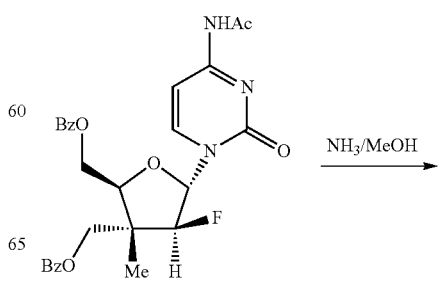

-continued

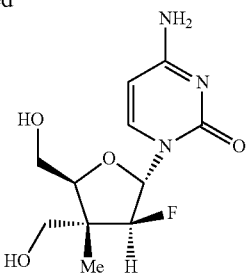

4-amino-1-((2S,3S,4R,5S)-3-fluoro-4,5-bis(hydroxymethyl)-4-methyltetrahydrofuran-2-yl)pyrimidin-2(1H)-one. A solution of α-anomer (0.086 g, 0.16 mmol) in MeOH (2 mL, 0.1 M) at 25° C. was saturated with $NH_3$ gas in a glass pressure vessel sealed with a PTFE bushing. The reaction mixture was then stirred at 25° C. for 72 hours before being concentrated in vacuo. Purification by C18 reverse phase flash chromatography (MeOH:$H_2O$ gradient) provided the product (35.6 mg, 79%) as a white foam. $^1$H NMR (500 MHz, $CD_3OD$) δ 7.89 (bs, 1H), 5.95 (dd, J=20.3, 4.5 Hz, 1H), 5.94 (d, J=1.1 Hz, 1H), 5.22 (dd, J=53.9, 4.2 Hz, 1H), 3.92 (s, 1H), 3.72 (d, J=5.9 Hz, 2H), 3.56-3.48 (m, 2H), 1.08 (d, J=3.6 Hz, 3H) ppm (Labile protons were not observed due to exchange with deuterated solvent). HRMS calcd for $C_{11}H_{17}N_3O_4F$ (M+H)$^+$: 274.1203, found 274.1195 (−1.1 ppm).

Example 1.5—Intermediate Compound

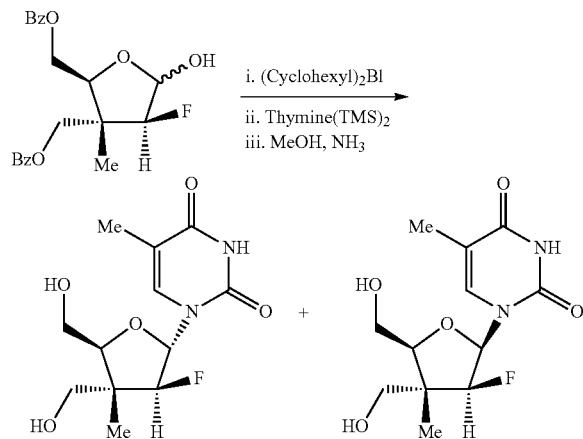

1-((2S,3S,4R,5S)-3-fluoro-4,5-bis(hydroxymethyl)-4-methyltetrahydrofuran-2-yl)-5-methylpyrimidine-2,4(1H,3H)-dione and 1-((2R,3S,4R,5S)-3-fluoro-4,5-bis(hydroxymethyl)-4-methyltetrahydrofuran-2-yl)-5-methylpyrimidine-2,4(1H,3H)-dione. To a solution of lactol (0.20 g, 0.51 mmol) in anhydrous dichloroethane (5.1 mL, 0.1 M) at 25° C. was added (cyclohexyl)$_2$BI (1.24 mL of a 0.5 M solution in DCM, 0.62 mmol) under an inert atmosphere. The reaction mixture was then stirred at 25° C. for 90 minutes before addition of silylated thymine (1.5 mL of 0.65 M solution in DCM, 1.28 mmol). The resulting mixture was stirred 5 hours at 80° C. and cooled to room temperature. 0.5 g of silica was added and the resulting mixture was concentrated in vacuo. The residue was then dissolved in DCM and passed through a pad of silica gel eluting with EtOAc. After in vacuo evaporation, the residue was dissolved in MeOH and the resulting solution was saturated with $NH_3$ gas. The reaction mixture was then stirred at 25° C. for 72 hours before being concentrated in vacuo. Purification by C18 reverse flash chromatography (MeOH:$H_2O$ gradient) provided the α-anomer (18.1 mg, with 10% of β-anomer) and the β-anomer (79.1 mg, 53%) as white foams.

α-anomer (6:1 mixture of α-anomer and β-anomer): $^1$H NMR (500 MHz, $CD_3OD$) δ 7.49 (d, J=5.6 Hz, 1H), 5.96 (dd, J=15.6, 4.8 Hz, 1H), 5.27 (dd, J=54.2, 4.7 Hz, 1H), 4.40 (dd, J=6.2, 5.4 Hz, 1H), 3.70 (dd, J=9.9, 6.9 Hz, 2H), 3.58-3.52 (m, 2H), 1.90 (s, 3H), 1.06 (d, J=2.9 Hz, 3H) ppm (Labile protons were not observed due to exchange with deuterated solvent). HRMS calcd for $C_{12}H_{17}N_2O_5FNa$ (M+Na)$^+$: 311.1019, found: 311.1015 (−1.1 ppm).

β-anomer: $^1$H NMR (500 MHz, $CD_3OD$) δ 7.68 (s, 1H), 6.13 (dd, J=20.7, 3.3 Hz, 1H), 4.94 (dd, J=53.9, 3.3 Hz, 1H), 4.03 (dd, J=7.1, 4.9 Hz, 1H), 3.76-3.69 (m, 2H), 3.57-3.42 (m, 2H), 1.89 (s, 3H), 1.08 (d, J=3.3 Hz, 3H) ppm (Labile protons were not observed due to exchange with deuterated solvent). $^{13}$C NMR (126 MHz, $CD_3OD$) δ 165.4, 151.1, 137.7, 109.0, 95.3, 85.9, 83.8, 66.8, 62.1, 49.6, 11.3, 10.4 ppm. HRMS calcd for $C_{12}H_{17}N_2O_5FNa$ (M+Na)$^+$: 311.1019, found: 311.1013 (−1.9 ppm).

Example 1.6—Intermediate Compound

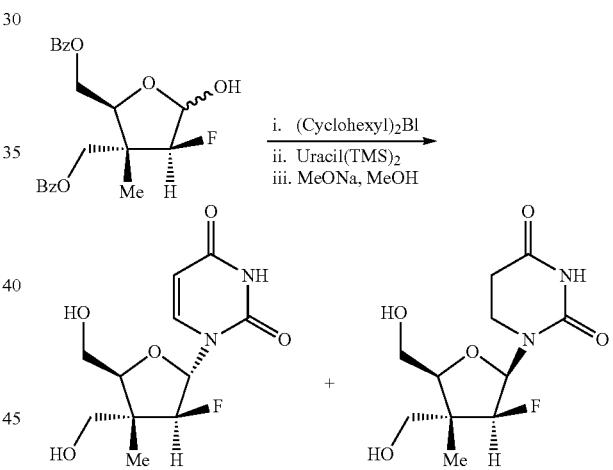

1-((2S,3S,4R,5S)-3-fluoro-4,5-bis(hydroxymethyl)-4-methyltetrahydrofuran-2-yl)pyrimidine-2,4(1H,3H)-dione and 1-((2R,3S,4R,5S)-3-fluoro-4,5-bis(hydroxymethyl)-4-methyltetrahydrofuran-2-yl)pyrimidine-2,4(1H,3H)-dione. To a solution of lactol (0.050 g, 0.13 mmol) in anhydrous dichloroethane (1.3 mL, 0.1 M) at 25° C. was added (Cyclohexyl)$_2$BI (0.309 mL of a 0.5 M solution in DCM, 0.15 mmol) under an inert atmosphere. The reaction mixture was stirred at 25° C. for 60 minutes before addition of silylated uracil (0.35 mL, 0.26 mmol, 0.74 M solution in DCM). The resulting mixture was stirred 16 hours at 25° C. 0.1 g of silica was added and the resulting mixture was concentrated in vacuo. The residue was dissolved in DCM and passed through a pad of silica gel eluting with EtOAc. After in vacuo evaporation, the residue obtained was dissolved in 2 mL of MeOH and a MeONa solution (0.065 ml, 0.061 mmol, 3.6 M solution) was added. The reaction mixture was stirred at 25° C. for 16 hours before addition of formic acid to reach a neutral pH. In vacuo concentration and purification by flash chromatography (MeOH:DCM gradient) provided the β-anomer (18.1 mg, 51%) as a white foam (the α-anomer was not recovered): β-anomer (major): $^1$H NMR (500 MHz, CD$_3$OD) δ 7.82 (d, J=8.0 Hz, 1H), 6.15 (dd, J=20.4, 3.3 Hz, 1H), 5.68 (d, J=7.9 Hz, 1H), 4.96 (dd, J=54.3, 3.4 Hz, 1H), 4.03 (dd, J=7.1, 5.0 Hz, 1H), 3.75-3.67 (m, 2H), 3.56-3.50 (m, 2H), 1.09 (d, J=3.3 Hz, 3H) ppm (Labile protons were not observed due to exchange with deuterated solvent). $^{13}$C NMR (126 MHz, CD$_3$OD) δ 168.8, 153.7, 142.9, 101.6, 96.5 (d, $^1J_{13C\ to\ 19F}$=192.5 Hz), 87.5 (d, $^2J_{13C\ to\ 19F}$=16.5 Hz), 85.0, 67.9 (d, $^3J_{13C\ to\ 19F}$=7.7 Hz), 63.2, 50.8 (d, $^2J_{13C\ to\ 19F}$=16.7 Hz), 11.9 (d, $^3J_{13C\ to\ 19F}$=12.2 Hz) ppm. HRMS calcd for C$_{11}$H$_{15}$N$_2$O$_5$FNa (M+Na)$^+$: 297.0863, found: 297.0861 (1.4 ppm).

Example 1.7—Antitumor/Antiviral Compounds LCB-1997 and LCB-2027

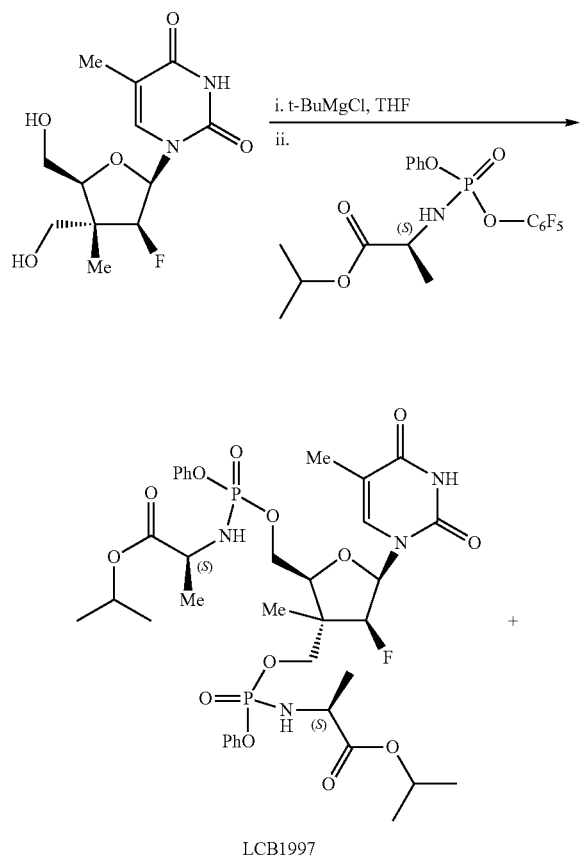

LCB1997

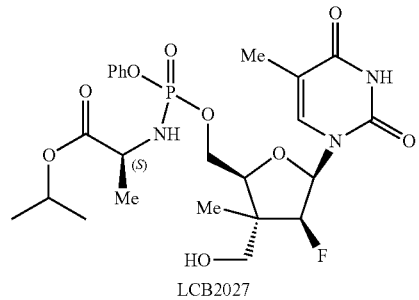

LCB2027

5',3'-Bisphosphoramidate nucleoside analogue (LCB-1997) and 5'-Phosphoramidate nucleoside analogue (LCB- 2027). To a solution of the nucleoside (0.030 g, 0.104 mmol) in anhydrous THF (0.3 mL) at 25° C. was added tBuMgCl (0.26 mmol, 1.0 M solution in THF) under an inert atmosphere. The reaction mixture was stirred at 25° C. for 30 minutes before the addition of a solution of Protide Reagent (0.071 g, 0.16 mmol) in 0.4 mL of THF. After 16 hours at 25° C., 0.1 ml of MeOH was added and the mixture was concentrated in vacuo. Purification by flash chromatography (MeOH:DCM gradient) provided LCB-1997 (0.021 g, 24%) and LCB-2027 (0.0101 g, 18%) as white foams.

LCB-1997: $^1$H NMR (500 MHz, CD$_3$OD) δ 7.62 (s, 1H), 7.42-7.34 (m, 4H), 7.33-7.24 (m, 4H), 7.24-7.18 (m, 2H), 6.12 (dd, J=20.8, 3.1 Hz, 1H), 5.02 (dd, J=53.0, 3.5 Hz, 1H), 5.05-4.92 (m, 2H), 4.32-4.22 (m, 3H), 4.10 (d, J=4.6 Hz, 2H), 4.02-3.88 (m, 2H), 1.88 (d, J=12.8 Hz, 3H), 1.36 (t, J=6.5 Hz, 6H), 1.27-1.20 (m, 12H), 1.14 (d, J=3.3 Hz, 3H) ppm (Labile protons were not observed due to exchange with deuterated solvent). $^{13}$C NMR (126 MHz, CD$_3$OD) δ 174.33 (d, $^3J_{13C\ to\ 31P}$=5.2 Hz), 174.31 (d, $^3J_{13C\ to\ 31P}$=5.7 Hz), 166.31, 152.2 (d, $^2J_{13C\ to\ 31P}$=11.4 Hz), 152.1 (d, $^2J_{13C\ to\ 31P}$=11.5 Hz), 151.9, 138.3, 130.9, 130.8, 126.3, 126.2, 121.55 (s, $^2J_{13C\ to\ 31P}$=10.9 Hz), 121.47 (d, $^2J_{13C\ to\ 31P}$=10.9 Hz), 121.4, 110.7, 95.5 (d, $^1J_{13C\ to\ 19F}$=194.7 Hz), 86.9 (d, $^2J_{13C\ to\ 19F}$=16.6 Hz), 81.8 (d, $^2J_{13C\ to\ 31P}$=7.9 Hz), 71.41-71.11 (m), 70.23, 70.17, 67.4 (d, $^2J_{13C\ to\ 31P}$=5.5 Hz), 51.7 (d, $^2J_{13C\ to\ 31P}$=5.8 Hz), 50.1 (dd, $^2J_{13C\ to\ 19F}$ and $^3J_{13C\ to\ 31P}$=18.5, 8.3 Hz), 22.0, 21.97, 21.92, 21.90, 20.6, 20.5, 12.5, 11.9 (d, $^3J_{13C\ to\ 19F}$=12.3 Hz) ppm. HRMS calcd for C$_{36}$H$_{49}$N$_4$O$_{13}$FP$_2$Na (M+Na)$^+$: 849.2643, found: 849.2663 (1.8 ppm).

LCB-2027: $^1$H NMR (500 MHz, CD$_3$OD) δ 7.65 (s, 1H), 7.41-7.35 (m, 2H), 7.33-7.26 (m, 2H), 7.23-7.17 (m, 1H), 6.19 (dd, J=21.3, 3.2 Hz, 1H), 5.01-4.94 (m, 1H), 4.97 (dd, J=53.7, 3.1 Hz, 1H), 4.32-4.23 (m, 3H), 3.97-3.88 (m, 1H), 3.57-3.50 (m, 2H), 1.87 (s, 3H), 1.35 (d, J=7.2 Hz, 3H), 1.25-1.21 (m, 6H), 1.12 (d, J=3.2 Hz, 3H) ppm (Labile protons were not observed due to exchange with deuterated solvent). HRMS calcd for C$_{24}$H$_{33}$N$_3$O$_9$FNaP (M+H)$^+$: 580.1836, found: 580.1834 (0.5 ppm).

Example 1.8—Antitumor/Antiviral Compounds LCB-2035 and LCB-2034

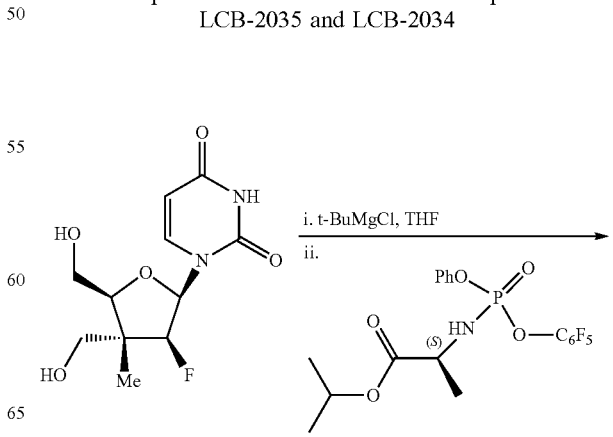

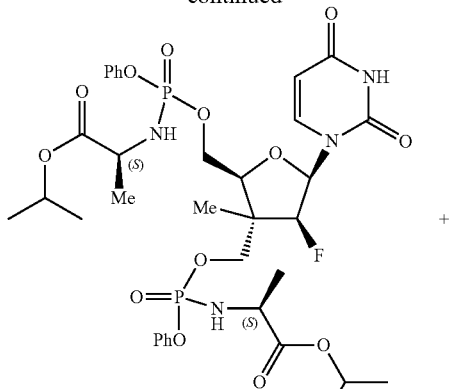

LCB2035

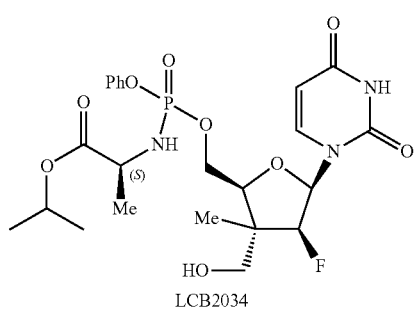

LCB2034

5',3'-Bisphosphoramidate nucleoside analogue (LCB-2035) and 5'-Phosphoramidate nucleoside analogue (LCB-2034). To a solution of the nucleoside (0.015 g, 0.055 mmol) in anhydrous THF (0.5 mL) at 25° C. was added tBuMgCl (0.18 ml of a 1.0 M solution in THF, 0.17 mmol) under an inert atmosphere. The reaction mixture was stirred at 25° C. for 30 minutes before the addition of a solution of Protide Reagent (0.060 g, 0.13 mmol) in 0.5 mL of THF. After 16 hours at 25° C., 0.1 ml of MeOH was added and the mixture was concentrated in vacuo. Purification by flash chromatography (MeOH:DCM gradient) provided LCB-2035 (18 mg, 64%) and LCB-2034 (5.1 mg, 18%) as white foams.

LCB-2035: $^1$H NMR (500 MHz, CD$_3$OD) δ 7.8 (dd, J=8.1, 1.4 Hz, 1H), 7.43-7.34 (m, 4H), 7.28 (appt, J=8.6 Hz, 4H), 7.21 (appt, J=7.4 Hz, 2H), 6.13 (dd, J=20.5, 3.3 Hz, 1H), 5.67 (d, J=8.1 Hz, 1H), 5.03 (dd, J=55.6, 5.9 Hz, 1H), 5.05-4.95 (m, 2H), 4.26 (d, J=4.7 Hz, 3H), 4.11 (d, J=4.6 Hz, 2H), 4.02-3.87 (m, 2H), 1.36 (dd, J=7.1, 1.2 Hz, 6H), 1.27-1.21 (m, 12H), 1.14 (d, J=3.5 Hz, 3H) ppm (Labile protons were not observed due to exchange with deuterated solvent). HRMS calcd for C$_{35}$H$_{47}$N$_4$O$_{13}$FP$_2$Na (M+Na)$^+$: 835.2497, found 835.2484 (−0.8 ppm).

LCB-2034: $^1$H NMR (500 MHz, CD$_3$OD) δ 7.79 (dd, J=8.2, 1.7 Hz, 1H), 7.36 (t, J=7.8 Hz, 2H), 7.30-7.22 (m, 2H), 7.19 (t, J=7.4 Hz, 1H), 6.17 (dd, J=21.0, 3.2 Hz, 1H), 5.64 (d, J=8.1 Hz, 1H), 5.00-4.94 (m, 1H), 4.96 (dd, J=53.6, 3.2 Hz, 1H), 4.24 (d, J=5.2 Hz, 3H), 3.91 (dd, J=9.8, 7.1 Hz, 1H), 3.57-3.44 (m, 2H), 1.34 (dd, J=7.1, 0.7 Hz, 3H), 1.24-1.20 (m, 6H), 1.10 (d, J=3.2 Hz, 3H). HRMS calcd for C$_{23}$H$_{32}$N$_3$O$_9$FP (M+H)$^+$: 544.1860, found: 544.1843 (−2.2 ppm).

Example 1.9—Antitumor/Antiviral Compounds LCB-1993 and LCB-1992

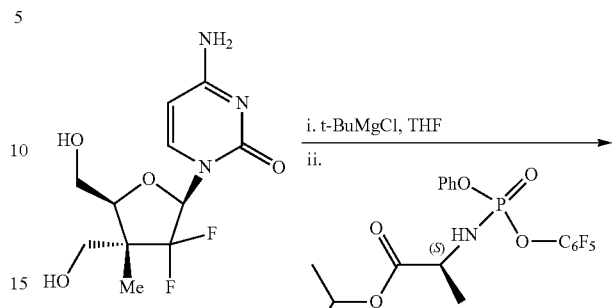

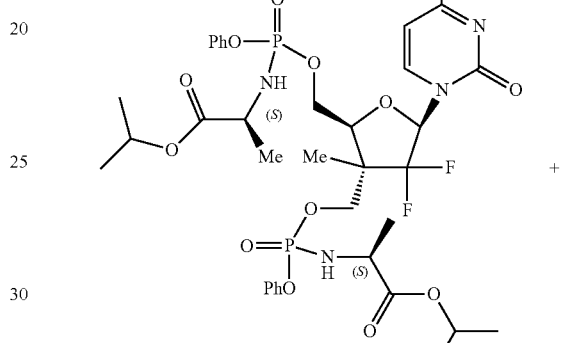

LCB1993

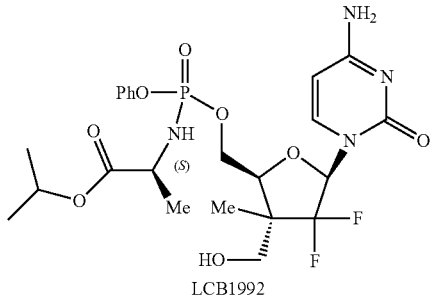

LCB1992

5',3'-Bisphosphoramidate nucleoside analogue (LCB1993) and 5'-Phosphoramidate nucleoside analogue (LCB1992). To a solution of the nucleoside[13] (0.050 g, 0.171 mmol) in anhydrous THF (0.6 mL) at 25° C. was added tBuMgCl (0.41 mmol, 1.0 M solution in THF) under an inert atmosphere. The reaction mixture was stirred at 25° C. for 30 minutes before the addition of a solution of Protide Reagent (0.41 mmol in 0.4 mL of THF). After 16 hours at 25° C., 1 mL of MeOH was added and the mixture was concentrated in vacuo. Purification by flash chromatography (MeOH:DCM gradient) provided LCB1993 (99.6 mg, 71%) and LCB1992 (4.0 mg, 3%) as white foams.

LCB1993: $[α]_D^{25}$ +21.3 (c 1.0, MeOH); IR (neat) $v_{max}$ 3194, 2983, 1731, 1651, 1491 cm$^{-1}$, $^1$H NMR (500 MHz, CD$_3$OD) δ 7.53 (d, J=7.5 Hz, 1H), 7.42-7.30 (m, 4H), 7.26 (d, J=1.4 Hz, 4H), 7.23-7.16 (m, 2H), 6. (dd, J=13.3, 4.1 Hz, 1H), 5.94 (d, J=7.6 Hz, 1H), 5.03-4.92 (m, 2H), 4.55 (t, J=5.5 Hz, 1H), 4.31-4.23 (m, 3H), 4.14 (dd, J=10.5, 4.6 Hz, 3H), 3.96-3.86 (m, 2H), 1.38-1.32 (m, 6H), 1.28-1.18 (m, 15H) ppm (Labile protons were not observed due to exchange with deuterated solvent). $^{13}$C NMR (126 MHz, CD$_3$OD) δ 173.3, 173.1, 166.4, 156.6, 150.94 (d, $^2J_{13C\ to\ 31P}$=6.9 Hz), 150.90 (d, $^2J_{13C\ to\ 31P}$=7.0 Hz), 141.4, 129.73, 129.70, 125.8 (dd, $^1J_{13C\ to\ 19F}$=506.7, 242.8 Hz), 125.2, 120.4, 120.39, 120.35, 120.3, 95.3, 85.0 (dd, $^2J_{13C\ to\ 19F}$=39.7, 20.6 Hz), 79.3, 69.04, 69.03, 68.08, 67.7 ($^2J_{13C\ to\ 31P}$ and $^3J_{13C\ to\ 19F}$, m), 65.4, 65.3, 50.5 (dd, $^2J_{13C\ to\ 19F}$=4.0, 1.0 Hz), 20.89, 20.87, 20.81, 20.80, 19.5 (d, $^3J_{13C\ to\ 19F}$=4.4 Hz), 19.4 (d, $^3J_{13C\ to\ 31P}$=4.5 Hz), 10.2 (d, J=10.9 Hz) ppm. HRMS calcd for C$_{35}$H$_{48}$F$_2$N$_5$O$_{12}$P$_2$(M+H)$^+$: 830.2743, found: 830.2736 (−0.4 ppm).

LCB1992: IR (neat) v$_{max}$ 0.3338, 3193, 2984, 1647, 1490 cm$^{-1}$, $^1$H NMR (500 MHz, CD$_3$OD) δ 7.72 (dd, J=7.6, 2.4 Hz, 1H), 7.43-7.34 (m, 2H), 7.27 (d, J=8.7 Hz, 2H), 7.22 (t, J=7.4 Hz, 1H), 6.42 (dd, J=13.4, 5.6 Hz, 1H), 5.90 (d, J=7.6 Hz, 1H), 5.02-4.91 (m, 1H), 4.49 (dd, J=6.4, 3.7 Hz, 1H), 4.43-4.21 (m, 2H), 4.03-3.84 (m, 1H), 3.72 (d, J=10.9 Hz, 1H), 3.53 (d, J=11.1 Hz, 1H), 1.34 (t, J=13.9 Hz, 3H), 1.29-1.18 (m, 6H), 1.09 (d, J=2.8 Hz, 3H) ppm (Labile protons were not observed due to exchange with deuterated solvent). $^{13}$C NMR (126 MHz, CD$_3$OD) δ 174.4 (d, J=5.7 Hz), 167.7, 158.0, 152.2 (d, J=6.9 Hz), 143.1 (d, J=3.5 Hz), 130.8, 126.3, 125.45 (dd, J=503.8, 239.3 Hz), 121.47 (d, J=4.7 Hz), 96.2, 88.5, 85.9 (dd, J=38.0, 20.2 Hz), 81.2 (dd, J=7.5, 5.1 Hz), 70.2, 67.3 (d, J=5.1 Hz), 65.5 (dd, J=8.3, 3.1 Hz), 51.7, 21.96, 21.89, 20.5 (d, J=6.3 Hz), 11.1 (d, J=11.1 Hz) ppm. HRMS calcd for C$_{23}$H$_{32}$F$_2$N$_4$O$_8$P (M+H)$^+$: 561.1926, found: 561.1925 (0.9 ppm).

Example 1.10—Antitumor/Antiviral Compound LCB-1995

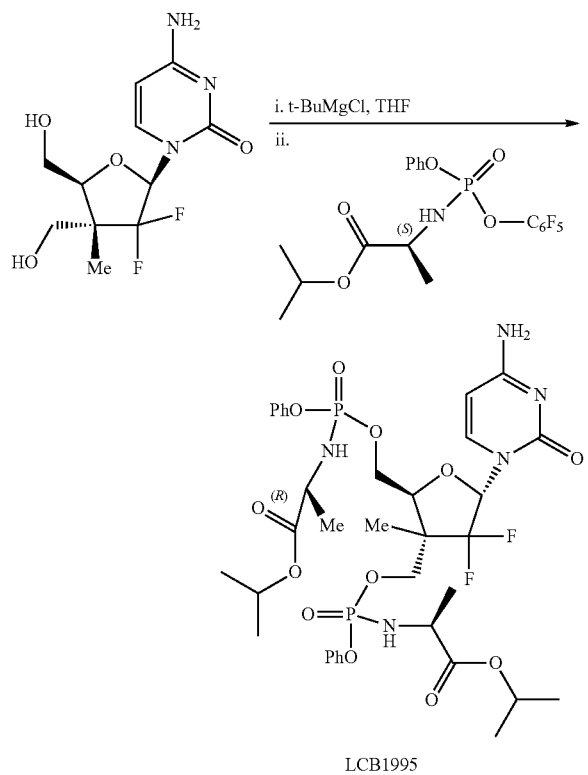

5',3'-Bisphosphoramidate nucleoside analogue (LCB1995). To a solution of the nucleoside (0.050 g, 0.171 mmol) in anhydrous THF (0.6 mL) at 25° C. was added tBuMgCl (0.41 mmol, 1.0 M solution in THF) under an inert atmosphere. The reaction mixture was stirred at 25° C. for 30 minutes before the addition of a solution of Protide Reagent (0.41 mmol in 0.4 mL of THF). After 16 hours at 25° C., 1 mL of MeOH was added and the mixture was concentrated in vacuo. Purification by flash chromatography (MeOH:DCM gradient) provided LCB1995 (α-anomer, 69.1 mg, 49%) as a white foam. [α]$_D^{25}$ −1.0 (c 1.0, MeOH); IR (neat) v$_{max}$ 0.3333, 3199, 2981, 1731, 1651, 1209 cm$^{-1}$, $^1$H NMR (500 MHz, CD$_3$OD) δ 7.70 (d, J=7.8 Hz, 1H), 7.41-7.34 (m, 4H), 7.28 (t, J=7.3 Hz, 4H), 7.21 (dd, J=12.9, 6.5 Hz, 2H), 6.35 (dd, J=11.7, 6.9 Hz, 1H), 5.90 (d, J=7.6 Hz, 1H), 5.05-4.93 (m, 2H), 4.43 (t, J=4.9 Hz, 1H), 4.36-4.26 (m, 2H), 4.22-4.13 (m, 2H), 4.04-3.88 (m, 2H), 1.35 (dd, J=7.0, 2.0 Hz, 6H), 1.23 (d, J=6.2 Hz, 12H), 1.14 (d, J=2.6 Hz, 3H) ppm (Labile protons were not observed due to exchange with deuterated solvent). $^{13}$C NMR (126 MHz, CD$_3$OD) δ 174.33 (d, $^3J_{13C\ to\ 31P}$=5.3 Hz), 174.3 (d, $^3J_{13C\ to\ 31P}$=5.7 Hz), 167.6, 157.8, 152.06 (d, $^2J_{13C\ to\ 31P}$=7.9 Hz), 152.0 (d, $^2J_{13C\ to\ 31P}$=8.1 Hz), 142.3, 130.8, 130.1, 126.4 (dd, $^1J_{13C\ to\ 19F}$=531, 100 Hz), 126.3, 126.2, 121.53, 121.50, 121.40, 121.36, 96.5, 86.0 (dd, $^2J_{13C\ to\ 19F}$=35.7, 19.9 Hz), 82.7-82.5 (m), 70.14, 70.13, 68.1-67.7 (dd, $^2J_{13C\ to\ 19F}$=35.7, 19.9 Hz), 67.13-66.77 (m), 66.4 (d, J=6.4 Hz), 51.6 (d, $^2J_{13C\ to\ 19F}$=4.8 Hz), 22.00, 21.94, 21.91, 21.90, 20.6 (d, $^3J_{13C\ to\ 31P}$=6.0 Hz), 20.5 (d, $^3J_{13C\ to\ 31P}$=6.4 Hz), 12.6-12.5 (m, $^3J_{13C\ to\ 19F}$) ppm. HRMS calcd for C$_{35}$H$_{48}$F$_2$N$_5$O$_{12}$P$_2$ (M+H)$^+$: 830.2743, found: 830.2763 (3.0 ppm).

Example 1.11—Intermediate Compound

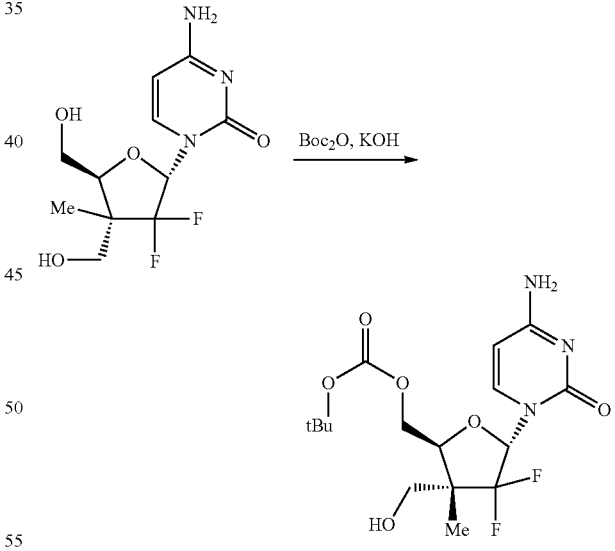

((2S,3R,5S)-5-(4-amino-2-oxopyrimidin-1(2H)-yl)-4,4-difluoro-3-(hydroxymethyl)-3-methyltetrahydrofuran-2-yl)methyl tert-butyl carbonate. To a solution of the nucleoside (0.020 g, 0.069 mmol) in a 0.05 M KOH solution (1.4 mL) at 25° C. was added Boc$_2$O (120 mg, 0.550 mmol) in 0.3 mL of dioxane. The reaction mixture was stirred at 25° C. for 30 minutes before extracting with EtOAc (3×5 ml). In vacuo evaporation and purification by flash chromatography (MeOH:DCM gradient) provided the product (14.1 mg, 52%) as a white foam. IR (neat) v$_{max}$ 3354, 2980, 1743, 1654 cm$^{-1}$. $^1$H NMR (500 MHz, CD$_3$OD) δ 7.59 (dd, J=7.6, 1.9

Hz, 1H), 6.46 (dd, J=13.4, 4.5 Hz, 1H), 5.95 (d, J=7.6 Hz, 1H), 4.58 (dd, J=7.6, 2.8 Hz, 1H), 4.35 (dd, J=11.8, 3.3 Hz, 1H), 4.26 (dd, J=11.8, 7.8 Hz, 1H), 3.75-3.66 (m, 2H), 1.48 (s, 9H), 1.28 (d, J=1.8 Hz, 3H) ppm (Labile protons were not observed due to exchange with deuterated solvent). $^{13}$C NMR (126 MHz, CD$_3$OD) δ 167.8, 158.0, 154.7, 142.6, 96.2, 86.2 (dd, J=37.0, 20.2 Hz), 83.4, 83.1 (d, J=5.0 Hz), 67.2, 62.9 (d, J=9.8 Hz), 27.9, 12.6-12.4 (m).

Example 1.12—Antitumor/Antiviral Compound LCB-1994

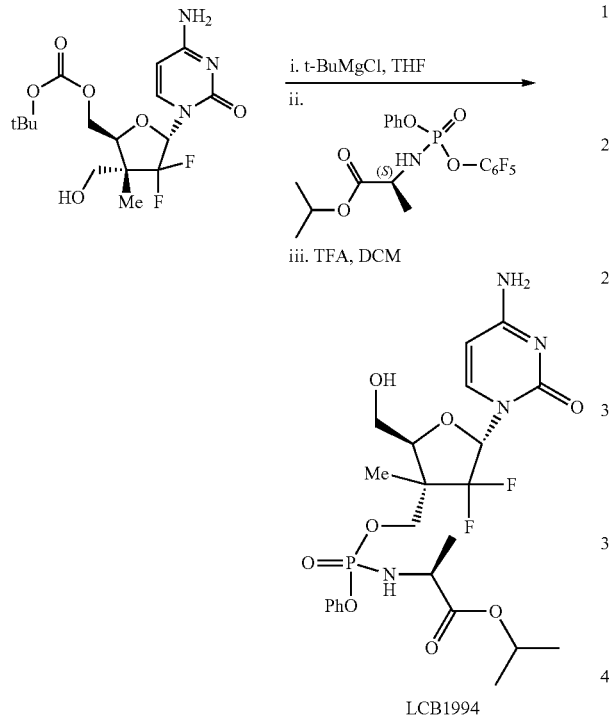

Isopropyl(((((2S,3R,5S)-5-(4-amino-2-oxopyrimidin-1 (2H)-yl)-4,4-difluoro-2-(hydroxymethyl)-3-methyl tetrahydrofuran-3-yl)methoxy)(phenoxy)phosphoryl)-L-alaninate (LCB1994). To a solution of protected nucleoside (0.016 g, 0.041 mmol) in anhydrous THF (0.2 mL) at −30° C. was added tBuMgCl (0.082 ml, 0.082 mmol, 1.0 M solution in THF) under an inert atmosphere. The reaction mixture was stirred at −30° C. for 30 minutes before the addition of a solution of Protide Reagent (0.037 g in 0.3 mL of THF, 0.082 mmol). After 1 hour at 0° C., 0.1 mL of MeOH was added and the mixture was concentrated in vacuo. The residue was dissolved in 1 mL of DCM and treated with 0.5 mL of triflic acid at 0° C. under an inert atmosphere and maintained at that temperature for 5 minutes. In vacuo concentration of the reaction mixture and purification by C18 reverse phase flash chromatography (MeOH:H$_2$O gradient) provided LCB1994 (12.3 mg, 56% over two steps) as a white foam. $^1$H NMR (500 MHz, CD$_3$OD) δ 7.56 (dd, J=7.6, 1.9 Hz, 1H), 7.41-7.30 (m, 2H), 7.27-7.12 (m, 2H), 6.42 (dd, J=13.5, 4.2 Hz, 1H), 5.93 (d, J=7.6 Hz, 1H), 4.99-4.91 (m, 1H), 4.35-4.28 (m, 1H), 4.24 (m, J=10.4, 3.9 Hz, 1H), 4.18-4.07 (m, 1H), 3.94-3.80 (m, 1H), 3.70 (qd, J=11.7, 5.9 Hz, 2H), 1.36 (dd, J=20.7, 7.0 Hz, 3H), 1.25-1.17 (m, 10H) ppm (Labile protons were not observed due to exchange with deuterated solvent). $^{13}$C NMR (126 MHz, CD$_3$OD) δ 174.4, 167.8, 158.0, 152.1 (d, J=7.1 Hz), 142.5, 130.8, 126.3, 121.5 (d, J=4.6 Hz), 96.3, 84.6, 70.2, 67.3 (dd, J=10.0, 4.8 Hz), 61.7, 51.6, 21.9, 21.9, 20.2 (d, J=6.2 Hz), 12.49-12.39 (m). HRMS calcd for C$_{23}$H$_{32}$N$_4$O$_8$F$_2$P (M+H)$^+$: 561.1926, found: 561.1928 (1.3 ppm).

Example 1.13—Antitumor/Antiviral Compound LCB-2002 and LCB-2001

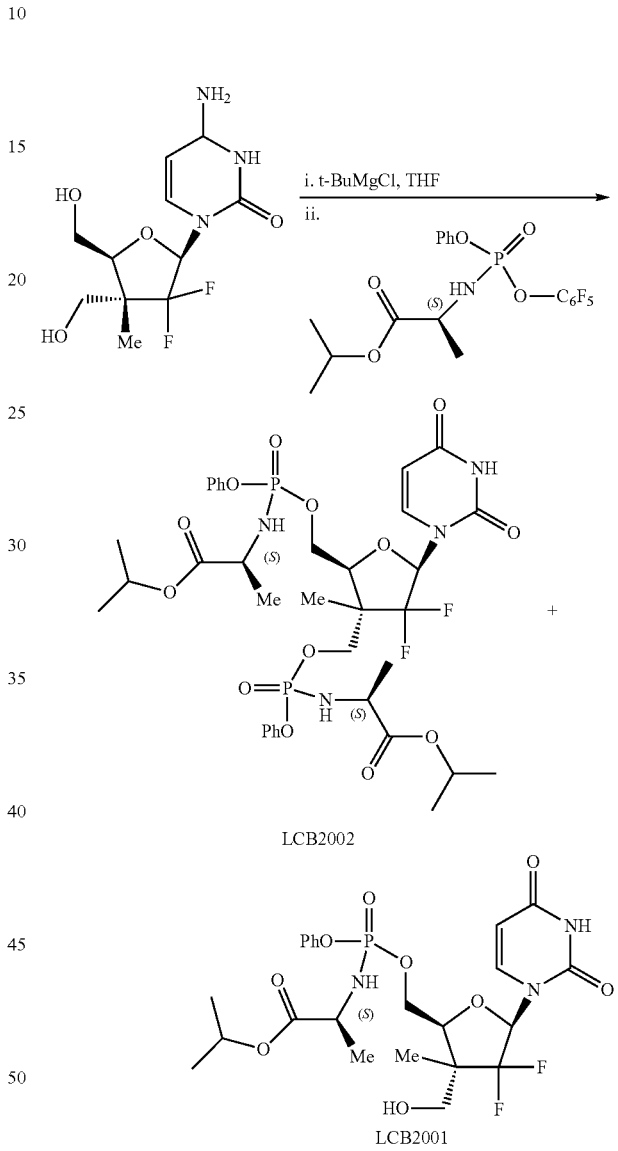

5',3'-Bisphosphoramidate nucleoside analogue (LCB2002) and 5'-Phosphoramidate nucleoside analogue (LCB2001). To a solution of the nucleoside (0.024 g, 0.82 mmol) in anhydrous THF (0.3 mL) at 25° C. was added tBuMgCl (0.205 mL, 0.205 mmol, 1.0 M solution in THF) under an inert atmosphere. The reaction mixture was stirred at 0° C. for 30 minutes before addition of a solution of Protide Reagent (0.056 g, 0.12 mmol) in 0.3 mL of THF. After 18 hours at 0° C., 0.1 mL of MeOH was added and the mixture was concentrated in vacuo. Purification by C$_{18}$ reverse phase flash chromatography (MeOH:H$_2$O gradient) provided LCB2002 (11.2 mg, 17%) and LCB2001 (2.1 mg, 3.7%) as white foams.

LCB2002: $^1$H NMR (500 MHz, CD$_3$OD) δ 7.72 (dd, J=8.2, 2.1 Hz, 1H), 7.43-7.34 (m, 4H), 7.28 (t, J=7.6 Hz, 4H), 7.25-7.17 (m, 1H), 6.28 (dd, J=12.4, 6.5 Hz, 1H), 5.71 (d, J=8.2 Hz, 1H), 5.04-4.95 (m, 2H), 4.59 (s, 1H), 4.47 (t, J=4.9 Hz, 1H), 4.36-4.27 (m, 2H), 4.22-4.14 (m, 2H), 4.03-3.88 (m, 2H), 1.36 (d, J=7.1 Hz, 6H), 1.27-1.21 (m, 12H), 1.17 (d, J=2.8 Hz, 3H) ppm (Labile protons were not observed due to exchange with deuterated solvent). $^{13}$C NMR (126 MHz, CD$_3$OD) δ 173.10 (d, J=5.6 Hz), 164.37 (s), 150.93 (d, J=5.4 Hz), 150.87 (d, J=5.4 Hz), 150.7 140.9, 129.7 (dd, J=2.7, 0.8 Hz), 129.4 (d, J=0.9 Hz), 125.1, 124.55 (dd, J=344.7, 179.4 Hz), 124.5 (d, J=1.3 Hz), 120.4-120.3 (m), 120.4, 120.3 (d, J=4.8 Hz), 101.8, 84.3 (dd, J=39.4, 20.2 Hz), 83.8 (d, J=7.8 Hz), 79.6, 69.0 (d, J=3.1 Hz), 68.8 (s), 68.0-67.8 (m), 65.3 (d, J=5.0 Hz), 50.5 (dd, J=6.0, 1.1 Hz), 29.1 (d, J=4.2 Hz), 20.82, 20.80, 20.7, 20.7, 19.4 (d, J=6.3 Hz), 10.0 (d, J=11.0 Hz). H RMS calcd for C$_{35}$H$_{46}$N$_4$O$_{13}$F$_2$P$_2$Na (M+Na)$^+$: 853.2402 and: 853.2415 (2.1 ppm).

LCB2001: $^1$H NMR (500 MHz, CD$_3$OD) δ 7.73 (dd, J=8.2, 2.7 Hz, 1H), 7.39 (t, J=7.9 Hz, 2H), 7.27 (d, J=8.7 Hz, 2H), 7.22 (t, J=7.4 Hz, 1H), 6.38 (dd, J=14.1, 5.2 Hz, 1H), 5.69 (d, J=8.2 Hz, 1H), 5.03-4.94 (m, 1H), 4.54-4.49 (m, 1H), 4.33 (ddt, J=17.9, 11.4, 8.9 Hz, 2H), 3.98-3.88 (m, 1H), 3.71 (d, J=11.3 Hz, 1H), 3.53 (d, J=10.9 Hz, 1H), 1.36 (d, J=7.1 Hz, 3H), 1.24 (dt, J=6.2, 3.1 Hz, 6H), 1.10 (d, J=2.6 Hz, 3H) ppm (Labile protons were not observed due to exchange with deuterated solvent). HRMS calcd for C$_{23}$H$_{30}$N$_3$O$_9$F$_2$PNa (M+Na)$^+$: 584.1585, found: 584.1577 (−0.5 ppm).

Example 1.14—Intermediate Compound

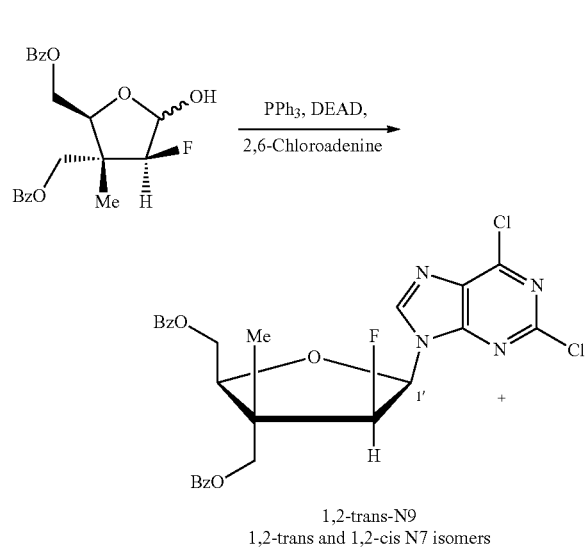

((2S,3R,4S,5R)-5-(2,6-dichloro-9H-purin-9-yl)-4-fluoro-3-methyltetrahydrofuran-2,3-diyl)bis(methylene) dibenzoate. To a solution of PPh$_3$ (1.66 g, 6.33 mmol) and 2,6-chloropurine (1.20 g, 6.35 mmol) in anhydrous THF (6 mL) at 25° C. was added diethyl azodicarboxylate (1.0 ml, 6.33 mmol) under an inert atmosphere. The reaction mixture was stirred at 25° C. for 15 minutes before addition of the nucleoside (1.89 g, 4.87 mmol) in 4 mL of THF. After 16 hours at 25° C., the reaction mixture was concentrated in vacuo. Purification by flash chromatography (AcOEt:Hexanes gradient) provided the β-anomer (1.21 g, 44%) as a white foam with impurities from the decomposition of the diethyl azodicarboxylate reagent. A second fraction consisting of a mixture of isomers was also isolated (1.0 g, 37%). β-anomer (major): $^1$H NMR (500 MHz, CDCl$_3$) δ 8.44 (d, J=2.9 Hz, 1H), 8.12 (dd, J=8.2, 1.1 Hz, 2H), 8.06 (dd, J=8.3, 1.1 Hz, 3H), 7.68-7.62 (m, 1H), 7.62-7.56 (m, 1H), 7.56-7.51 (m, 2H), 7.49-7.42 (m, 2H), 6.71 (dd, J=21.5, 3.1 Hz, 1H), 5.18 (dd, J=52.8, 3.2 Hz, 1H), 4.68 (dd, J=11.9, 7.6 Hz, 1H), 4.62 (dd, J=12.1, 4.0 Hz, 1H), 4.56-4.50 (m, 2H), 1.47 (d, J=3.3 Hz, 3H) ppm. calcd for C$_{26}$H$_{21}$Cl$_2$FN$_4$O$_5$Na (M+Na)$^+$: 581.0771, found: 581.0761 (−0.6 ppm). The product obtained was carried onto the next step without further purification.

Example 1.15—Intermediate Compound

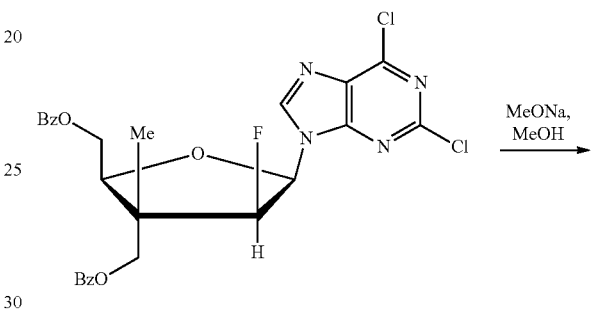

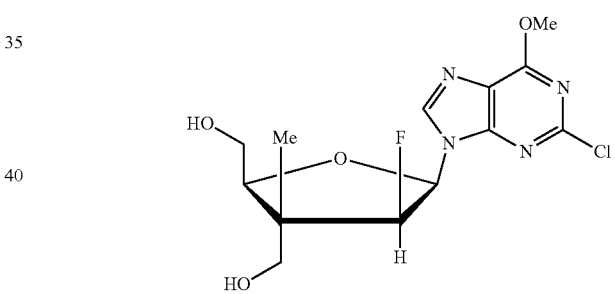

((2S,3R,4S,5R)-5-(2-chloro-6-methoxy-9H-purin-9-yl)-4-fluoro-3-methyltetrahydrofuran-2,3-diyl)dimethanol. To a solution of protected nucleoside (0.053 g, 0.13 mmol) in MeOH (1.3 mL) was added MeONa (0.037 ml, 0.16 mmol, 4.4 M solution) at 25° C. The reaction mixture was stirred at 25° C. for 16 hours before addition of formic acid to neutral pH. In vacuo concentration and purification by flash chromatography (MeOH:DCM gradient) provided the product (31 mg, 94%) as a white powder. [α]$_D^{25}$ +54.6 (c 1.0, MeOH); $^1$H NMR (500 MHz, CD$_3$OD) δ 8.46 (d, J=2.4 Hz, 1H), 6.57 (dd, J=20.8, 3.4 Hz, 1H), 5.07 (dd, J=53.8, 3.4 Hz, 1H), 4.19 (d, J=17.9 Hz, 3H), 4.14 (dd, J=7.4, 4.1 Hz, 1H), 3.86-3.74 (m, 2H), 3.62 (d, J=1.6 Hz, 2H), 1.19 (d, J=3.2 Hz, 3H) ppm (Labile protons were not observed due to exchange with deuterated solvent). $^{13}$C NMR (126 MHz, CD$_3$OD) δ 162.5, 154.4, 153.8, 144.3 (d, $^4J_{13C\ to\ 19F}$=4.6 Hz), 120.8, 96.8 (d, $^1J_{13C\ to\ 19F}$=193.4 Hz), 86.5 (d, $^2J_{13C\ to\ 19F}$=16.4 Hz), 85.4, 68.2 (d, $^3J_{13C\ to\ 19F}$=7.7 Hz), 63.4, 55.7, 51.2 ($^2J_{13C\ to\ 19F}$, J=16.7 Hz), 12.0 (d, $^3J_{13C\ to\ 19F}$=11.8 Hz) ppm. HRMS calcd for C$_{27}$H$_{27}$N$_3$O$_7$F (M+H)$^+$: 369.0742, found: 369.0743 (1.8 ppm).

Example 1.16—Intermediate Compound

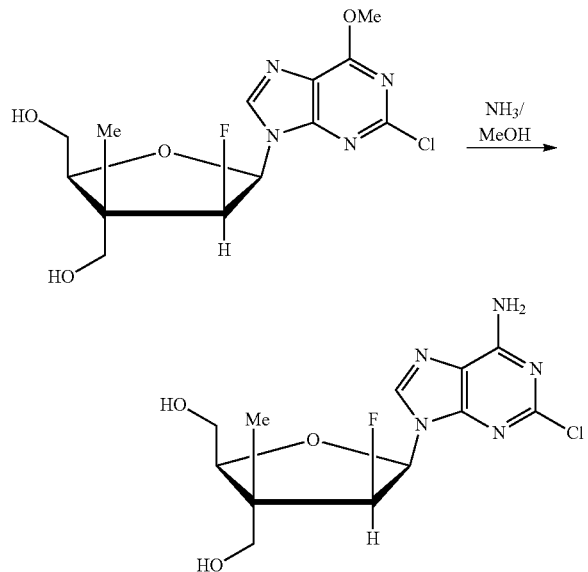

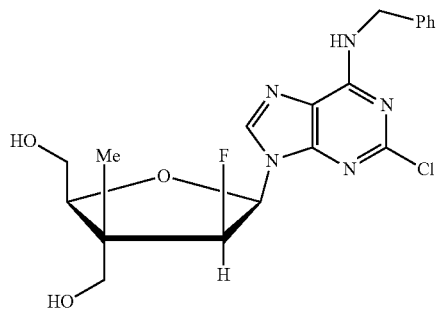

((2S,3R,4S,5R)-5-(6-amino-2-chloro-9H-purin-9-yl)-4-fluoro-3-methyltetrahydrofuran-2,3-diyl)dimethanol. The nucleoside (40.0 mg, 0.115 mmol) was dissolved in MeOH in a glass pressure vessel sealed with a PTFE bushing and the resulting solution was saturated with $NH_3$ gas. The reaction mixture was stirred at 95° C. for 16 hours before being concentrated in vacuo. Purification by C18 reverse flash chromatography ($MeOH:H_2O$ gradient) provided the product (28 mg, 73%) as a white foam. $[\alpha]D_{25}$ +64 (c 1.0, MeOH); $^1H$ NMR (500 MHz, $CD_3OD$) δ 8.23 (d, J=2.4 Hz, 1H), 6.44 (dd, J=21.1, 3.4 Hz, 1H), 5.00 (dd, J=53.8, 3.3 Hz, 1H), 4.09 (dd, J=7.3, 4.1 Hz, 2H), 3.78 (qd, J=11.9, 5.7 Hz, 1H), 3.64-3.55 (m, 2H), 1.17 (d, J=3.2 Hz, 3H) ppm (Labile protons were not observed due to exchange with deuterated solvent). $^{13}C$ NMR (126 MHz, $CD_3OD$) δ 158.0, 155.4, 151.5, 141.9 (d, $^4J_{13C\ to\ 19F}$=4.5 Hz), 118.6 (s), 96.7 (d, $^1J_{13C\ to\ 19F}$=193.5 Hz), 86.2 (d, $^2J_{13C\ to\ 19F}$=16.4 Hz), 85.1 (s), 68.1 (d, $^3J_{13C\ to\ 19F}$=7.8 Hz), 63.4, 51.17 (d, $^2J_{13C\ to\ 19F}$=16.7 Hz), 12.0 (d, $^3J_{13C\ to\ 19F}$=11.9 Hz). HRMS calcd for $C_{12}H_{15}ClFN_5O_3Na$ (M+Na)$^+$: 354.0745, found: 354.0747 (2.0 ppm).

((2S,3R,4S,5R)-5-(6-(benzylamino)-2-chloro-9H-purin-9-yl)-4-fluoro-3-methyltetrahydrofuran-2,3-diyl)dimethanol. To a solution of protected nucleoside (31.0 mg, 0.0551 mmol) in i-PrOH in a glass pressure vessel sealed with a PTFE bushing was added benzylamine (0.008 mL, 0.072 mmol) and DIEA (0.029 mL, 0.166 mmol) under an inert atmosphere. The reaction mixture was stirred at 50° C. for 48 hours before being concentrated in vacuo. The mixture was then dissolved in MeOH (0.5 mL) and treated with MeONa (0.006 mL of 3.6 M solution in MeOH, 0.024 mmol). The reaction mixture was stirred at 25° C. for 16 hours before addition of enough formic acid to reach a neutral pH. In vacuo concentration and purification by flash chromatography (MeOH:DCM gradient) provided the product (9.7 mg, 42%) as a white powder. $[\alpha]_D^{25}$ +42 (c 1.0, MeOH); $^1H$ NMR (500 MHz, $CD_3OD$) δ 8.17 (d, J=1.8 Hz, 1H), 7.39-7.34 (m, 2H), 7.32-7.27 (m, 2H), 7.26-7.20 (m, 1H), 6.43 (dd, J=21.1, 3.3 Hz, 1H), 4.99 (dd, J=53.8, 3.3 Hz, 1H), 4.74 (s, 2H), 4.07 (dd, J=7.3, 4.1 Hz, 1H), 3.83-3.71 (m, 2H), 3.61-3.55 (m, 2H), 1.16 (d, J=3.0 Hz, 3H) ppm (Labile protons were not observed due to exchange with deuterated solvent). $^{13}C$ NMR (126 MHz, $CD_3OD$) δ 159.1, 158.4, 153.5, 144.3 (d, $^4J_{13C\ to\ 19F}$=2.9 Hz), 142.6, 132.3, 131.6, 131.1, 121.8, 99.4 (d, $^1J_{13C\ to\ 19F}$=193.5 Hz), 88.9 (d, $^2J_{13C\ to\ 19F}$=15.8 Hz), 87.9, 70.85 (d, $^3J_{13C\ to\ 19F}$=7.7 Hz), 66.2, 53.9 (d, $^2J_{13C\ to\ 19F}$=16.6 Hz), 48.0, 14.8 (d, $^3J_{13C\ to\ 19F}$=11.9 Hz). HRMS calcd for $C_{19}H_{21}N_5O_3ClFNa$ (M+Na)$^+$: 444.1215, found: 444.1202 (−1.5 ppm).

Example 1.17—Intermediate Compound

Example 1.18—Antitumor/Antiviral Compound LCB-2079

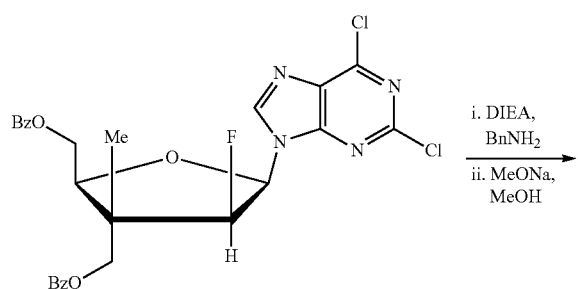

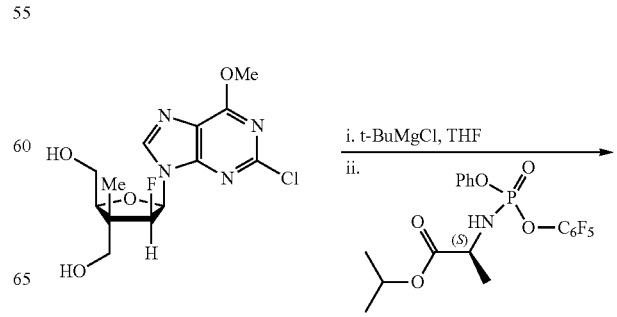

159

-continued

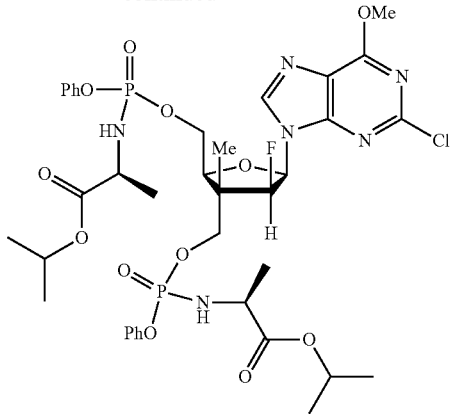

LCB2079

5′,3′-Bisphosphoramidate nucleoside analogue (LCB2079). To a solution of the nucleoside (0.029 g, 0.0.084 mmol) in anhydrous THF (0.3 mL) at 25° C. was added tBuMgCl (0.21 mL of a 1.0 M solution in THF, 0.21 mmol) under an inert atmosphere. The reaction mixture was stirred at 25° C. for 30 minutes before the addition of a solution of Protide Reagent (0.095 g in 0.3 mL of THF, 0.21 mmol). After 16 hours at 25° C., two drops of MeOH were added and the mixture was concentrated in vacuo. Purification by flash chromatography (MeOH:DCM gradient) provided LCB2079 (0.048 g, 65%) as a white foam. $[\alpha]_D^{25}$ +13.9 (c 1.0, MeOH); $^1$H NMR (500 MHz, CD$_3$OD) δ 8.42 (d, J=2.6 Hz, 1H), 7.41-7.15 (m, 10H), 6.49 (dd, J=21.0, 3.4 Hz, 1H), 5.11 (dd, J=52.8, 3.4 Hz, 1H), 4.99-4.90 (m, 2H), 4.41-4.27 (m, 3H), 4.18 (s, 3H), 4.20-4.14 (m, 2H), 4.03 (dd, J=10.0, 7.2 Hz, 1H), 3.89 (dd, J=9.9, 7.2 Hz, 1H), 1.38 (d, J=7.1 Hz, 3H), 1.31 (d, J=7.0 Hz, 3H), 1.27-1.08 (m, 15H) ppm (Labile protons were not observed due to exchange with deuterated solvent). $^{13}$C NMR (126 MHz, CD$_3$OD) δ 174.4 (d, $^4J_{13C\ to\ 31P}$=4.9 Hz), 174.3 (d, $^4J_{13C\ to\ 31P}$=5.7 Hz), 162.5, 154.5, 153.8, 152.10 (d, $^2J_{13C\ to\ 31P}$=10.4 Hz), 152.08 (d, $^2J_{13C\ to\ 31P}$=10.4 Hz), 144.09 (d, $^4J_{13C\ to\ 19F}$=5.3 Hz), 130.9, 130.8, 130.7, 126.4, 126.2, 121.6, 121.5, 121.4 (d, $^2J_{13C\ to\ 31P}$=4.8 Hz), 120.7, 95.7 (d, $^1J_{13C\ to\ 19F}$=194.9 Hz), 85.9 (d, $^2J_{13C\ to\ 19F}$=16.5 Hz), 82.0 (d, $^2J_{13C\ to\ 31P}$=8.3 Hz), 71.41-71.17 (m), 70.14 (d, J=9.6 Hz), 67.50-67.34 (m), 55.74, 51.7 (d, J=13.6 Hz), 50.5 (dd, $^3J_{13C\ to\ 19F}$=18.5, 8.2 Hz), 21.96, 21.95, 21.9, 21.88, 20.60 (d, $^3J_{13C\ to\ 31P}$=9.9 Hz), 20.55 (d, $^3J_{13C\ to\ 31P}$=9.6 Hz), 11.91 (d, $^3J_{13C\ to\ 19F}$=12.1 Hz). HRMS calcd for C$_{37}$H$_{48}$N$_6$O$_{12}$ClFP$_2$Na (M+Na)$^+$: 907.2376, found: 907.2390 (2.2 ppm).

Example 1.19—Antitumor/Antiviral Compound LCB-2080

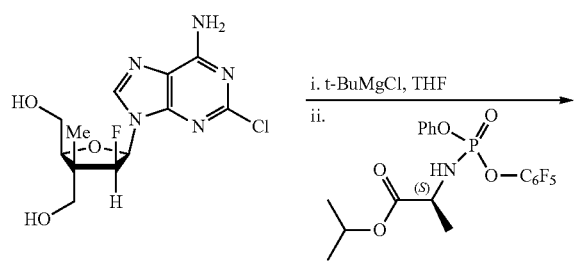

160

-continued

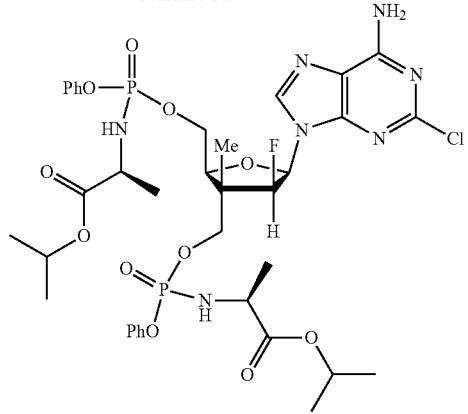

LCB2080

3′,5′-Bisphosphoramidate nucleoside analogue (LCB2080). To a solution of nucleoside (0.455 g, 1.37 mmol) in anhydrous THF (8.6 mL) at 25° C. was added tBuMgCl (3.43 mL, 3.43 mmol, 1.0 M solution in THF) under an inert atmosphere. The reaction mixture was stirred at 25° C. for 30 minutes before addition of a solution of Protide Reagent (1.55 g, 3.43 mmol). After 16 hours at 25° C., 2 ml of MeOH was added and the mixture was concentrated in vacuo. Purification by flash chromatography (MeOH:DCM gradient) provided LCB2080 (0.951 g, 80%) as a white foam. $[\alpha]_D^{25}$ +23.2 (c 1.0, MeOH); $^1$H NMR (500 MHz, CD$_3$OD) δ 8.25 (d, J=2.8 Hz, 1H), 7.43-7.31 (m, 6H), 7.28 (d, J=8.6 Hz, 2H), 7.21 (t, J=7.0 Hz, 2H), 6.43 (dd, J=21.3, 3.4 Hz, 1H), 5.07 (dd, J=56.1, 3.2 Hz, 1H), 5.00-4.90 (m, 2H), 4.39-4.26 (m, 3H), 4.17 (d, J=4.6 Hz, 2H), 4.06 (dd, J=10.0, 7.1 Hz, 1H), 3.92 (dd, J=9.8, 7.1 Hz, 1H), 1.40 (d, J=6.8 Hz, 3H), 1.33 (d, J=7.0 Hz, 3H), 1.23-1.17 (m, 15H) ppm (Labile protons were not observed due to exchange with deuterated solvent). $^{13}$C NMR (126 MHz, CD$_3$OD) δ 174.4 (d, $^4J_{13C\ to\ 31P}$=8.2 Hz), 174.3 (d, $^4J_{13C\ to\ 31P}$=8.9 Hz), 158.1, 155.6, 152.2 (d, $^2J_{13C\ to\ 31P}$=10.1 Hz), 152.1 (d, $^2J_{13C\ to\ 31P}$=10.2 Hz), 151.6, 141.8 (d, $^4J_{13C\ to\ 19F}$=5.6 Hz), 130.9, 130.8, 126.4, 126.2, 121.6 (d, $^1J_{13C\ to\ 19F}$=4.6 Hz), 121.5 (d, J=4.8 Hz), 95.7 (d, $^1J_{13C\ to\ 19F}$=194.8 Hz), 85.6 (d, $^2J_{13C\ to\ 31P}$=16.6 Hz), 81.8 (d, $^2J_{13C\ to\ 31P}$=8.4 Hz), 71.3 (dd, $^2J_{13C\ to\ 31P}$ and $^3J_{13C\ to\ 19F}$=6.9, 5.8 Hz), 70.2, 70.1, 67.5 (d, J=5.2 Hz), 51.7 (d, $^3J_{13C\ to\ 19F}$=11.2 Hz), 50.5 (dd, $^2J_{13C\ to\ 19F}$=18.6, 8.1 Hz), 21.95, 21.92, 21.88, 20.6 (d, $^3J_{13C\ to\ 31P}$=6.9 Hz), 20.5 (d, $^3J_{13C\ to\ 31P}$=6.3 Hz), 11.9 (d, $^3J_{13C\ to\ 19F}$=12.2 Hz). HRMS calcd for C$_{36}$H$_{47}$N$_7$O$_{11}$ClFP$_2$Na (M+Na)$^+$: 892.2379, found: 892.2345 (−3.2 ppm).

Example 1.20—Antitumor/Antiviral Compound LCB-2106

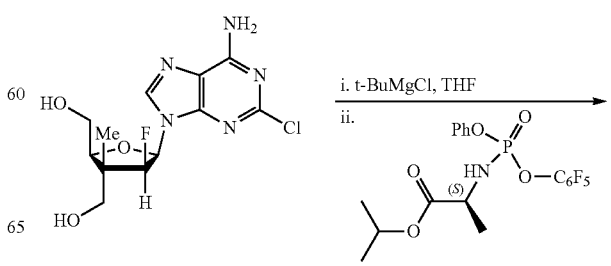

-continued
LCB2080 +

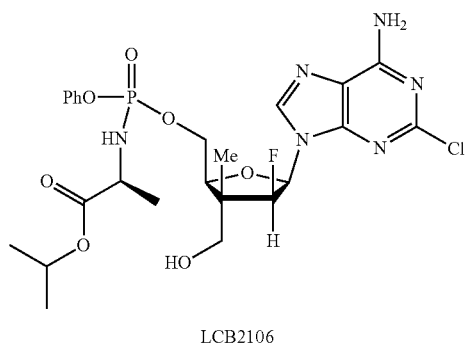

LCB2106

5'-Phosphoramidate nucleoside analogue (LCB2106). To a solution of nucleoside (0.0509 g, 0.154 mmol) in anhydrous THF (0.5 mL) at 0° C. was added tBuMgCl (3.43 mL, 3.43 mmol, 1.0 M solution in THF) under an inert atmosphere. The reaction mixture was stirred at 0° C. for 30 minutes before addition of a solution of Protide Reagent (0.175 g, 0.385 mmol). After 16 hours at 0° C., 0.1 mL of MeOH was added and the mixture was concentrated in vacuo. Purification by flash chromatography (MeOH:DCM gradient) provided LCB2106 (0.0102 g, 7.6%) as a white foam. $^1$H NMR (500 MHz, CD$_3$OD) δ 8.26 (d, J=2.7 Hz, 1H), 7.37 (t, J=7.8 Hz, 2H), 7.28 (d, J=7.8 Hz, 2H), 7.20 (t, J=7.4 Hz, 1H), 6.49 (dd, J=21.7, 3.2 Hz, 1H), 5.03 (dd, J=53.8, 3.0 Hz, 1H), 4.97-4.88 (m, 1H), 4.32 (tdd, J=11.2, 9.1, 5.2 Hz, 3H), 3.92 (dq, J=14.0, 7.0 Hz, 1H), 3.66-3.55 (m, 2H), 1.33 (d, J=7.1 Hz, 3H), 1.25-1.16 (m, 9H) ppm (Labile protons were not observed due to exchange with deuterated solvent). HRMS calcd for C$_{24}$H$_{32}$N$_6$O$_7$ClFP (M+H)$^+$: 601.1743, found: 601.1736 (−0.3 ppm).

Example 1.21—Antitumor/Antiviral Compound LCB-2076

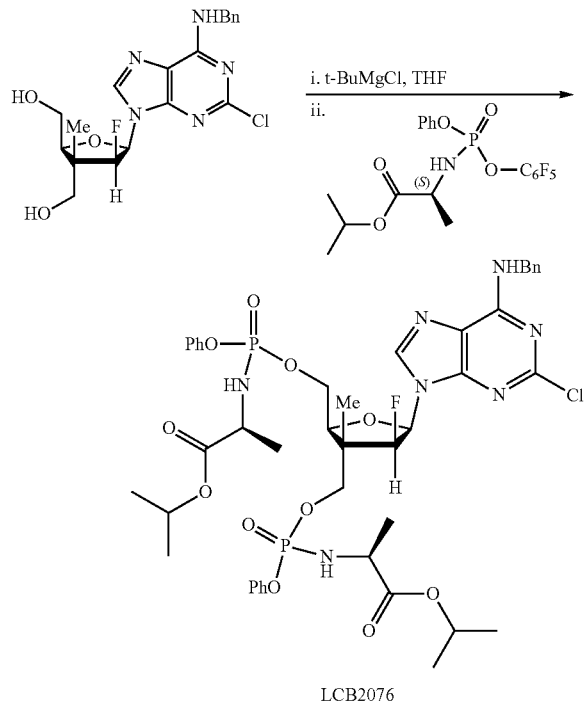

LCB2076

3',5'-Bisphosphoramidate nucleoside analogue (LCB2076). To a solution of nucleoside (0.018 g, 0.043 mmol) in anhydrous THF (0.2 mL) at 25° C. was added tBuMgCl (0.128 mL, 0.128 mmol, 1.0 M solution in THF) under an inert atmosphere. The reaction mixture was stirred at 25° C. for 30 minutes before addition of a solution of Protide Reagent (0.058 g, 0.128 mmol). After 16 hours at 25° C., 0.1 mL of MeOH were added and the mixture was concentrated in vacuo. Purification by flash chromatography (MeOH:DCM gradient) provided LCB2076 (0.021 g, 51%) as a white foam: $^1$H NMR (500 MHz, CD$_3$OD) δ 8.19 (s, 1H), 7.50-7.06 (m, 15H), 6.42 (dd, J=21.4, 3.2 Hz, 1H), 5.06 (dd, J=56.7, 4.0 Hz, 1H), 5.00-4.89 (m, 2H), 4.77 (s, 2H), 4.40-4.22 (m, 3H), 4.16 (d, J=4.5 Hz, 2H), 4.11-4.00 (m, 1H), 3.95-3.83 (m, 1H), 1.39 (d, J=7.1 Hz, 3H), 1.31 (d, J=7.1 Hz, 3H), 1.22-1.10 (m, 15H) ppm (Labile protons were not observed due to exchange with deuterated solvent). HRMS calcd for C$_{43}$H$_{53}$N$_7$O$_{11}$FClP$_2$Na(M+Na)$^+$: 982.2849, found: 982.2844 (−0.05 ppm).

Example 1.22—Intermediate Compounds

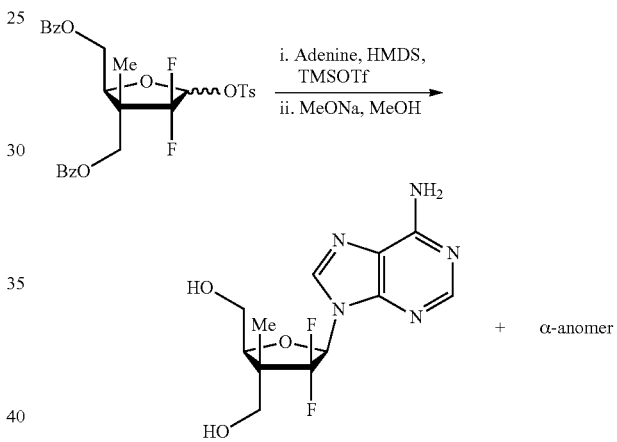

((2S,3R,5R)-5-(6-amino-9H-purin-9-yl)-4,4-difluoro-3-methyltetrahydrofuran-2,3-diyl)dimethanol. Adenine (0.238 g, 1.76 mmol), HMDS (2.0 ml, 9.6 mmol) and a few crystals of NH$_4$SO$_4$ were placed in a round bottomed flask equipped with a reflux condenser under an inert atmosphere. The mixture was refluxed for 2 hours (130° C.). The volatiles were evaporated in vacuo before addition of the nucleoside[13] (0.45 g, 0.80 mmol) dissolved in DCE (17 mL) and TMSOTf (0.35 mL, 1.89 mmol). The reaction mixture was heated to 60° C. for 16 hours, followed by addition of aqueous NaHCO$_3$. The aqueous phase was extracted with AcOEt (3×20 mL). The volatiles were then evaporated in vacuo. The resulting residue was dissolved in MeOH (5 mL) and treated with MeONa (0.361 mL, 1.3 mmol, 3.6 M solution). After 16 hours at 25° C., the reaction mixture was neutralized (pH=7) with HCl 6N and concentrated. Purification by C18 reverse flash chromatography (MeOH:H$_2$O gradient) provided the product (β-anomer 0.027 g, 11% over 2 steps) and the corresponding α-anomer (0.040 g, 16% over 2 steps) as white foams. β-anomer: $^1$H NMR (500 MHz, CD$_3$OD) δ 8.30 (d, J=2.4 Hz, 1H), 8.21 (d, J=20.8 Hz, 1H), 6.49 (dd, J=14.1, 5.9 Hz, 1H), 4.43-4.32 (m, 1H), 3.88 (dd, J=12.3, 3.9 Hz, 1H), 3.81 (dd, J=12.4, 5.5 Hz, 1H), 3.77 (d, J=11.0 Hz, 1H), 3.58 (d, J=11.0 Hz, 1H), 1.20 (d, J=2.5 Hz, 3H) ppm (Labile protons were not observed due to exchange with deuterated solvent). $^{13}$C NMR (126 MHz, CD$_3$OD) δ 157.5, 154.1, 150.8, 141.5, 126.2, 120.0, 86.1 (dd, J=38.7, 20.9 Hz), 84.5 (d, J=5.3 Hz), 66.2 (dd, J=8.2, 3.6 Hz), 62.7, 11.1 (d, J=10.6 Hz) ppm. HRMS calcd for C$_{12}$H$_{16}$N$_5$O$_3$F$_2$ (M+H)$^+$: 316.1221, found: 316.1206 (−3.0 ppm).

Example 1.23—Antitumor/Antiviral Compound LCB2092 and LCB2093

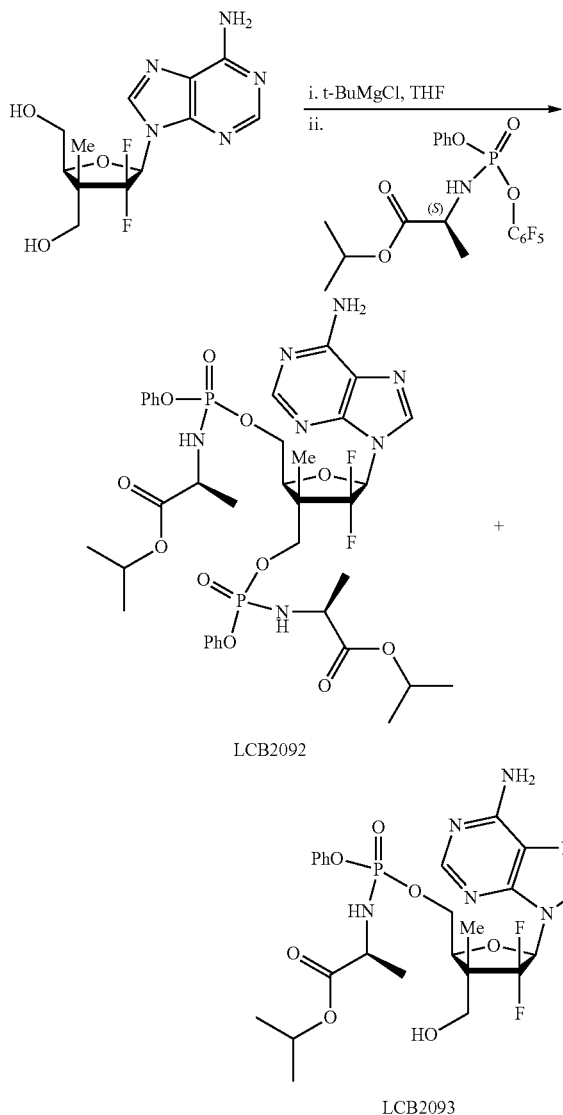

LCB2092: $^1$H NMR (500 MHz, CD$_3$OD) δ 8.30 (d, J=2.8 Hz, 1H), 8.23 (s, 1H), 7.39-7.34 (m, 4H), 7.34-7.29 (m, 2H), 7.29-7.25 (m, 2H), 7.23-7.15 (m, 2H), 6.48 (dd, J=13.1, 6.4 Hz, 1H), 5.02-4.88 (m, 2H), 4.55 (t, J=5.0 Hz, 1H), 4.37 (t, J=5.6 Hz, 2H), 4.32-4.17 (m, 2H), 4.08-3.97 (m, 1H), 3.95-3.84 (m, 1H), 1.36 (d, J=7.1 Hz, 3H), 1.32 (d, J=7.1 Hz, 3H), 1.25 (d, J=2.6 Hz, 3H), 1.20-1.14 (m, 12H) ppm (Labile protons were not observed due to exchange with deuterated solvent). HRMS calcd for C$_{36}$H$_{46}$N$_7$O$_{11}$F$_2$P$_2$ (M+H)$^+$: 854.2855, found: 854.2837 (−1.4 ppm).

LCB2093: $^1$H NMR (500 MHz, CD$_3$OD) δ 8.32 (d, J=3.2 Hz, 1H), 8.23 (s, 1H), 7.40-7.33 (m, 2H), 7.31-7.24 (m, 2H), 7.24-7.18 (m, 1H), 6.57 (dd, J=14.6, 5.3 Hz, 1H), 5.01-4.91 (m, 1H), 4.62-4.59 (m, 1H), 4.44-4.33 (m, 2H), 3.93 (dd, J=9.9, 7.1 Hz, 1H), 3.80 (d, J=11.0 Hz, 1H), 3.59 (d, J=10.8 Hz, 1H), 1.34 (d, J=7.1 Hz, 3H), 1.23-1.16 (m, 9H). ppm (Labile protons were not observed due to exchange with deuterated solvent). HRMS calcd for C$_{24}$H$_{32}$N$_6$O$_7$F$_2$P (M+H)$^+$: 585.2038, found: 585.2018 (−2.5 ppm).

Example 1.24—Intermediate Compound

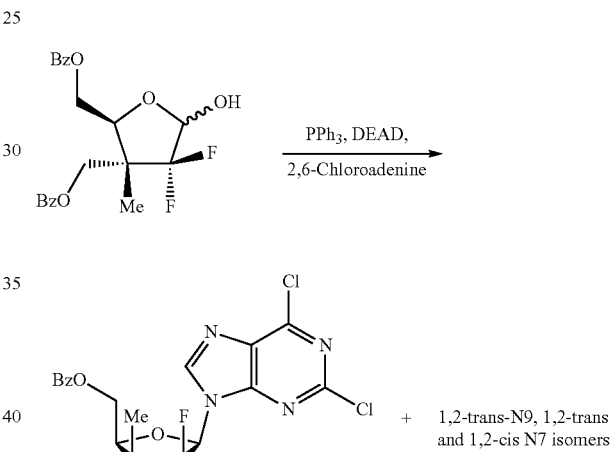

((2S,3R,5R)-5-(2,6-dichloro-9H-purin-9-yl)-4,4-difluoro-3-methyltetrahydrofuran-2,3-diyl)bis(methylene) dibenzoate. To a solution of PPh$_3$ (0.167 g, 0.640 mmol) and 2,6-chloropurine (0.121 g, 0.640 mmol) in anhydrous THF (1.0 mL) at 25° C. was added diethyl azodicarboxylate (0.100 mL, 0.640 mmol) under an inert atmosphere. The reaction mixture was stirred at 25° C. for 15 minutes before addition of the lactol (0.200 g, 0.492 mmol). After 16 hours at 25° C., the reaction mixture was concentrated in vacuo. Purification by flash chromatography (AcOEt:Hexanes gradient) provided the β-anomer (0.078 g, 28%) as a white foam with impurities from the decomposition of the diethyl azodicarboxylate reagent. A second fraction consisting of a mixture of isomers was also isolated (0.086 g, 30%). β-anomer: $^1$H NMR (500 MHz, CDCl$_3$) δ 8.37 (d, J=3.1 Hz, 1H), 8.18-8.13 (m, 2H), 8.10-8.00 (m, 2H), 7.68-7.40 (m, 6H), 6.69 (dd, J=14.0, 5.3 Hz, 1H), 4.78-4.59 (m, 4H), 4.48 (d, J=11.6 Hz, 1H), 1.49 (d, J=2.6 Hz, 3H) ppm. HRMS calcd for C$_{26}$H$_{21}$Cl$_2$F$_2$N$_4$O$_5$Na (M+Na)$^+$: 599.0677, found: 599.0659 (−2.0 ppm). The product obtained was carried onto the next step without further purification.

3',5'-Bisphosphoramidate nucleoside analogue (LCB2092) and 5'-Phosphoramidate nucleoside analogue (LCB2093). To a solution of nucleoside (0.011 g, 0.034 mmol) in anhydrous THF (0.25 mL) at 25° C. was added tBuMgCl (0.105 mL, 0.105 mmol, 1.0 M solution in THF) under an inert atmosphere. The reaction mixture was stirred at 25° C. for 30 minutes before addition of a solution of Protide Reagent (0.045 g, 0.105 mmol). After 16 hours at 25° C., 0.1 mL of MeOH was added and the mixture was concentrated in vacuo. Purification by C$_{18}$ reverse phase flash chromatography (MeOH:H$_2$O gradient) provided LCB2092 (0.011 g, 38%) and LCB2093 (0.0019 g, 9.5%) as white foams.

Example 1.25—Intermediate Compound

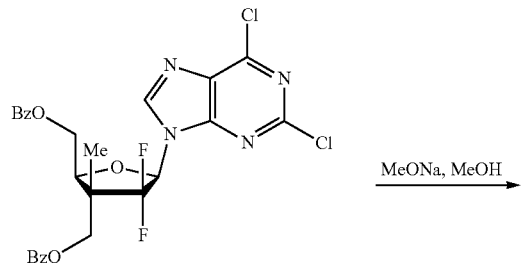

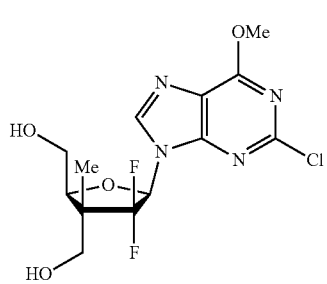

((2S,3R,5R)-5-(2-chloro-6-methoxy-9H-purin-9-yl)-4,4-difluoro-3-methyltetrahydrofuran-2,3-diyl)dimethanol. To a solution of protected nucleoside (0.078 g, 0.135) in MeOH (1.4 mL) was added MeONa (0.043 mL, 0.189 mmol, 4.4 M solution) at 25° C. The reaction mixture was stirred at 25° C. for 4 hours before addition of formic acid to neutral pH. In vacuo concentration and purification by flash chromatography (MeOH:DCM gradient) provided the product (31 mg, 63%) as a white foam. IR (neat) $v_{max}$ 0.3354, 2952, 1597 cm$^{-1}$, $^1$H NMR (500 MHz, CD$_3$OD) δ 8.48 (d, J=2.6 Hz, 1H), 6.52 (dd, J=13.9, 5.6 Hz, 1H), 4.42 (t, J=4.5 Hz, 1H), 4.19 (d, J=2.8 Hz, 3H), 3.92-3.73 (m, 3H), 3.61-3.55 (m, J=11.1, 2.1 Hz, 1H), 1.18 (d, J=2.6 Hz, 3H) ppm (Labile protons were not observed due to exchange with deuterated solvent). $^{13}$C NMR (126 MHz, CD$_3$OD) δ 162.6, 154.7, 154.2, 144.0, 127.0 (dd, J=498.6, 238.8 Hz), 120.9, 86.0 (dd, J=38.9, 20.2 Hz), 84.6 (d, J=5.0 Hz), 66.1 (dd, J=7.5, 3.8 Hz), 62.7, 55.8, 11.0 (d, J=10.6 Hz) ppm.

Example 1.26—Intermediate Compound

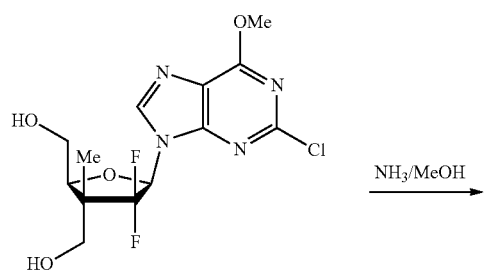

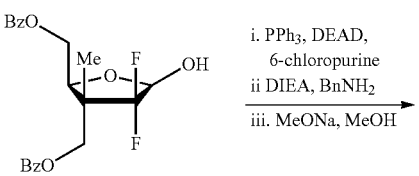

((2S,3R,5R)-5-(6-amino-2-chloro-9H-purin-9-yl)-4,4-difluoro-3-methyltetrahydrofuran-2,3-diyl)dimethanol. The deprotected nucleoside (31.1 mg, 0.085 mmol) was dissolved in MeOH (1 mL) in a glass pressure vessel sealed with a PTFE bushing and the resulting solution was saturated with NH$_3$ gas. The reaction mixture was stirred at 95° C. for 16 hours before being concentrated in vacuo. Purification by C18 reverse flash chromatography (MeOH:H$_2$O gradient) provided the product (18.1 mg, 63%) as a white foam. $[\alpha]_D^{25}$ +5.4 (c 1.0, MeOH); $^1$H NMR (500 MHz, CD$_3$OD) δ 8.25 (d, J=2.5 Hz, 1H), 6.42 (dd, J=14.1, 5.8 Hz, 1H), 4.39 (t, J=4.7 Hz, 1H), 3.88-3.73 (m, 2H), 3.64-3.51 (m, 1H), 1.17 (dd, J=20.1, 2.5 Hz, 3H) ppm (Labile protons were not observed due to exchange with deuterated solvent). $^{13}$C NMR (126 MHz, CD$_3$OD) δ 158.2, 155.7, 152.0, 141.7 (d, J=3.7 Hz), 126.38-125.45 (m), 66.1 (dd, J=7.5, 4.0 Hz), 62.7, 11.0 (d, J=10.6 Hz) ppm. HRMS calcd for C$_{12}$H$_{15}$ClF$_2$N$_5$O$_3$(M+H)$^+$: 350.0831, found: 350.0822 (−1.1 ppm).

Example 1.27—Intermediate Compound

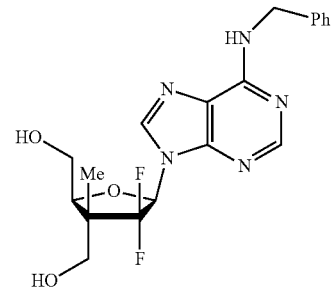

((2S,3R,5R)-5-(6-(benzylamino)-9H-purin-9-yl)-4,4-difluoro-3-methyltetrahydrofuran-2,3-diyl)dimethanol. To a solution of PPh$_3$ (0.168 g, 0.640 mmol) and 6-chloropurine (0.100 g, 0.640 mmol) in anhydrous THF (1.0 mL) at 25° C. was added diethyl azodicarboxylate (0.100 mL, 0.640 mmol) under an inert atmosphere. The reaction mixture was stirred at 25° C. for 15 minutes before the addition of the lactol (0.200 g, 0.492 mmol). After 16 hours at 0° C., the reaction mixture was concentrated in vacuo. Purification by flash chromatography (AcOEt:Hexanes gradient) provided the β-anomer (0.061 g, 28%) as a white foam with impurities from the decomposition of the diethyl azodicarboxylate reagent. A second fraction consisting of a mixture of isomers was also isolated. In a glass pressure vessel sealed with a PTFE bushing, a solution of the nucleoside (0.061 g, 0.112 mmol) in i-PrOH was added benzylamine (0.018 mL, 0.169 mmol) and DIEA (0.059 mL, 0.337 mmol) under an inert atmosphere. The reaction mixture was stirred at 50° C. for 48 hours before being concentrated in vacuo. The mixture was then dissolved in MeOH (0.5 mL) and treated with MeONa (0.0127 ml of 4.4 M solution in MeOH, 0.0562 mmol). The reaction mixture was stirred at 25° C. for 16 hours before addition of formic acid to reach a neutral pH (pH=7). In vacuo concentration and purification by C18 reverse flash chromatography (MeOH:H$_2$O gradient) provided the product (21.2 mg, 47%) as a white powder. $[\alpha]_D^{25}$ −6.4 (c 1.0, MeOH); $^1$IR (neat) $v_{max}$ 0.3296, 2937, 1623 cm$^{-1}$, H NMR (500 MHz, CD$_3$OD) δ 8.26 (s, J=1.9 Hz, 1H), 8.25 (s, 1H), 7.42-7.35 (m, 2H), 7.35-7.27 (m, 2H), 7.27-7.19 (m, 1H), 6.49 (dd, J=14.0, 6.0 Hz, 1H), 4.82 (d, J=7.2 Hz, 2H), 4.41 (t, J=4.6 Hz, 1H), 3.88 (dd, J=12.3, 3.9 Hz, 1H), 3.81 (dd, J=11.9, 5.0 Hz, 1H), 3.78 (d, J=11.0 Hz, 1H), 3.59 (d, J=11.0 Hz, 1H), 1.21 (d, J=2.5 Hz, 3H) ppm (Labile protons were not observed due to exchange with deuterated solvent). $^{13}$C NMR (126 MHz, CD$_3$OD) δ 155.0, 153.0, 139.9, 139.1, 128.4, 127.3, 127.1, 125.0, 122.9, 119.2 (m), 85.0 (dd, J=33.7, 23.7 Hz), 83.3 (d, J=5.1 Hz), 65.0 (dd, J=7.8, 3.4 Hz), 61.6, 43.9, 9.9 (d, J=10.5 Hz) ppm. HRMS calcd for C$_{19}$H$_{22}$N$_5$O$_3$F$_2$ (M+H)$^+$: 406.1691, found: 406.1683 (−0.6 ppm).

g, 0.0441 mmol) in anhydrous THF (0.3 mL) at 25° C. was added tBuMgCl (0.088 ml, 0.088 mmol, 1.0 M solution in THF) under an inert atmosphere. The reaction mixture was stirred at 25° C. for 30 minutes before addition of a solution of Protide Reagent (0.040 g, 0.088 mmol). After 16 hours at 25° C., 0.1 mL of MeOH was added and the mixture was concentrated in vacuo. Purification by C18 reverse phase flash chromatography (MeOH:H$_2$O gradient) provided LCB2105 (0.018 g, 46%). $[\alpha]_D^{25}$ +1.9 (c 1.0, DCM); IR (neat) $v_{max}$ 0.3204, 2984, 1728, 1615, 1486 cm$^{-1}$, $^1$H NMR (500 MHz, CD$_3$OD) δ 8.25 (s, 1H), 7.40-7.14 (m, 10H), 6.39 (dd, J=13.5, 6.2 Hz, 1H), 5.02-4.89 (m, 2H), 4.58-4.51 (m, 1H), 4.40-4.33 (m, 2H), 4.29-4.17 (m, 2H), 4.11-3.99 (m, 1H), 3.96-3.86 (m, 1H), 1.38 (d, J=7.1 Hz, 3H), 1.34 (d, J=7.0 Hz, 3H), 1.28-1.12 (m, 15H) ppm (Labile protons were not observed due to exchange with deuterated solvent). $^{13}$C NMR (126 MHz, CD$_3$OD) δ 174.34 (d, J=5.6 Hz), 174.28 (d, J=5.9 Hz), 158.2, 156.0, 152.18-152.07 (m), 141.2, 130.9 (d, J=4.6 Hz), 126.3, 121.54 (d, J=4.6 Hz), 121.46 (d, J=4.7 Hz), 80.9 (m), 70.2, 66.7, 51.7, 21.9, 21.9, 20.7 (d, J=6.6 Hz), 20.6 (d, J=6.4 Hz), 11.1 (dd, J=10.9, 2.4 Hz) ppm. HRMS calcd for C$_{36}$H$_{47}$N$_7$ClO$_{11}$F$_2$P$_2$ (M+H)$^+$: 888.2465, found: 888.2461 (0.1 ppm).

Example 1.29—Antitumor/Antiviral Compound LCB2095

Example 1.28—Antitumor/Antiviral Compound LCB2105

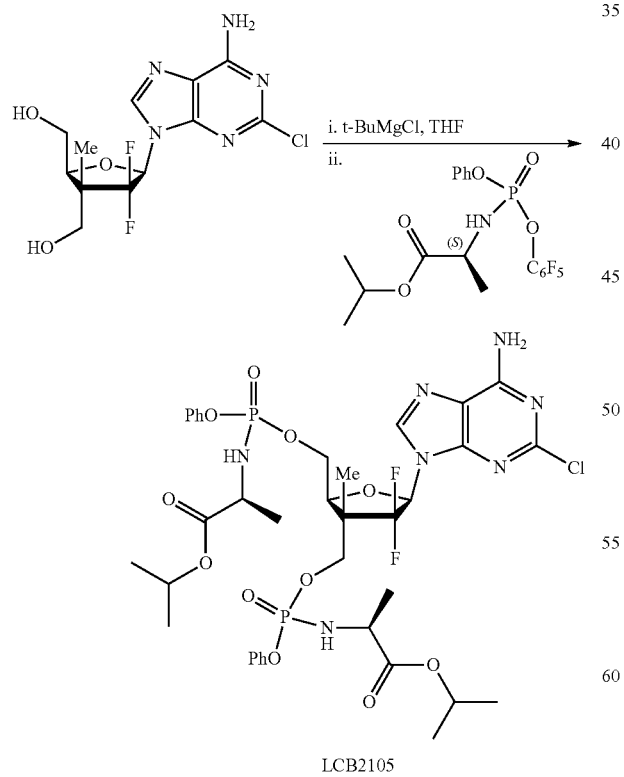

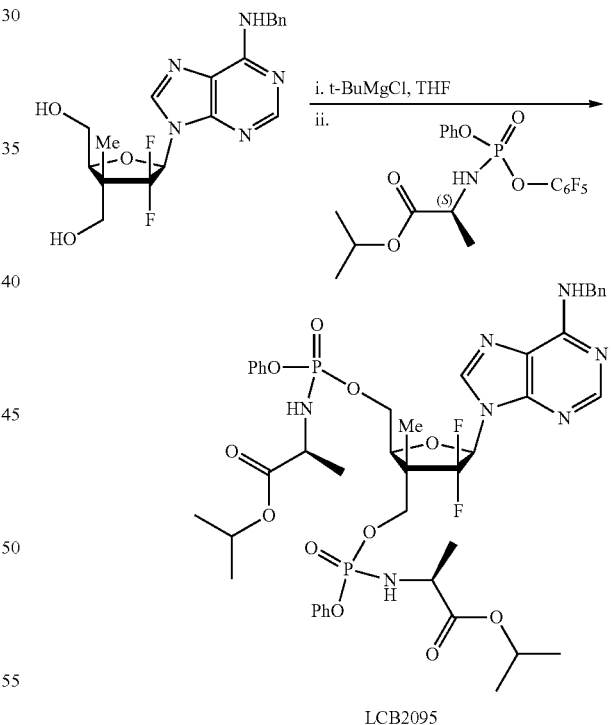

LCB2105

3',5'-Bisphosphoramidate nucleoside analogue (LCB2105). To a solution of deprotected nucleoside (0.0161

3',5'-Bisphosphoramidate nucleoside analogue (LCB2095). To a solution of deprotected nucleoside (0.018 g, 0.043 mmol) in anhydrous THF (0.2 mL) at 25° C. was added tBuMgCl (0.133 mL, 0.133 mmol, 1.0 M solution in THF) under an inert atmosphere. The reaction mixture was stirred at 25° C. for 30 minutes before addition of a solution of Protide Reagent (0.0604 g, 0.133 mmol). After 16 hours at 25° C., 0.1 mL of MeOH was added and the mixture was concentrated in vacuo. Purification by C18 reverse phase flash chromatography (MeOH:H₂O gradient) provided LCB2095 (0.027 g, 65%) as a white foam: $[\alpha]_D^{25}$ −2.4 (c 1.0, MeOH); IR (neat) $v_{max}$ 0.3210, 2980, 1731, 1608 cm$^{-1}$; $^1$H NMR (500 MHz, CD₃OD) δ 8.30 (s, 1H), 8.27 (s, 1H), 7.45-7.15 (m, 15H), 6.50 (dd, J=13.0, 6.prev Hz, 1H), 5.02-4.94 (m, 1H), 4.95-4.90 (m, 1H), 4.86-4.77 (m, 2H), 4.58-4.53 (m, 1H), 4.41-4.35 (m, 2H), 4.31-4.20 (m, 2H), 4.08-4.00 (m, 1H), 3.98-3.83 (m, 1H), 1.38 (d, J=7.0 Hz, 3H), 1.33 (d, J=7.0 Hz, 3H), 1.28-1.22 (m, 3H), 1.21-1.10 (m, 11H) ppm (Labile protons were not observed due to exchange with deuterated solvent); $^{13}$C NMR (126 MHz, CD₃OD) δ 174.3 (dd, J=5.7, 1.7 Hz), 154.8-154.2 (m), 152.1 (dd, J=8.2, 1.3 Hz), 140.6-140.4 (m), 140.2, 130.9, 129.5, 128.5, 128.2, 126.3 (d, J=6.9 Hz), 121.5 (dd, J=9.0, 4.7 Hz), 85.1 (dd, J=41.4, 23.8 Hz), 81.0 (dd, J=9.5, 4.7 Hz), 70.1 (d, J=4.1 Hz), 69.5-68.91 (m), 66.7-66.6 (m), 51.7 (d, J=6.2 Hz), 21.9 (s), 21.9 (d, J=2.6 Hz), 20.6 (d, J=5.9 Hz), 20.6 (d, J=6.3 Hz), 11.2 (d, J=10.8 Hz) ppm; HRMS calcd for $C_{43}H_{54}N_7O_{11}F_2P_2$ (M+H)$^+$: 944.3325, found: 944.3301 (−2.0 ppm).

Example 1.30—Antitumor/Antiviral Compound LCB2029 and LCB2028

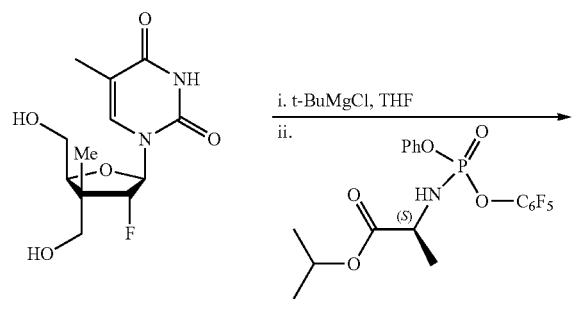

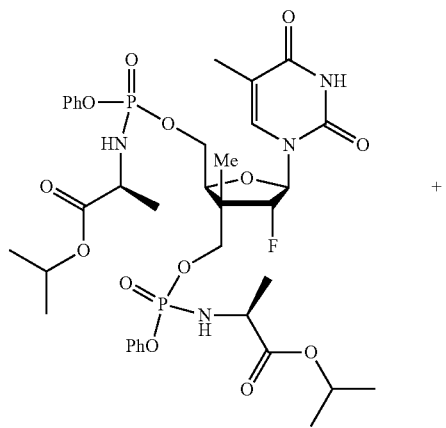

LCB2029

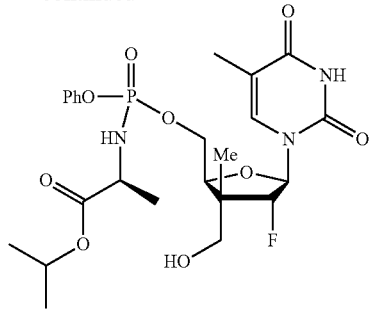

LCB2028

3',5'-Bisphosphoramidate nucleoside analogue (LCB2029) and 5'-Phosphoramidate nucleoside analogue (LCB2028). To a solution of nucleoside$^{14}$ (24 mg, 0.09 mmol) in anhydrous THF (0.30 mL) at 25° C. was added tBuMgCl (0.20 mL, 0.20 mmol, 1.0 M solution in THF) under an inert atmosphere. The reaction mixture was stirred at 25° C. for 30 minutes before addition of a solution of Protide Reagent (92 mg, 0.20 mmol). After 16 hours at 25° C., 0.5 mL of MeOH was added and the mixture was concentrated in vacuo. Purification by flash chromatography (DCM:MeOH 95:5) provided LCB2029 (33 mg, 47%) and LCB2028 (5 mg).

LCB2029: $R_f$=0.32 (DCM/MeOH, 95:5); $[\alpha]^{25}_D$ +9 (c 0.97, CD₃OD); IR (neat) $v_{max}$ 0.3418, 2523, 1658 cm$^{-1}$; $^1$H NMR (500 MHz, CD₃OD) δ 7.61 (s, 1H), 7.41-7.11 (m, 11H), 5.91 (dd, J=18.3, 3.3 Hz, 1H), 5.07-4.92 (m, 3H), 4.36-4.27 (m, 3H), 4.18 (apps, 2H), 3.97-3.87 (m, 2H), 1.89 (s, 3H), 1.34 (appt, J=6.6 Hz, 7H), 1.22 (appdd, J=9.2, 3.9 Hz, 13H), 1.09 (s, 3H) ppm; $^{13}$C NMR (125 MHz, CD₃OD) δ 174.4 (d, J=5.5 Hz), 174.3 (d, J=5.6 Hz), 166.3, 152.21, 152.15 (d, J=7.0 Hz), 152.07 (d, J=6.8 Hz), 137.1, 130.86, 130.84, 126.27, 126.26, 121.6 (d, J=4.7 Hz), 121.5 (d, J=4.7 Hz), 112.0, 100.7 (d, J=190.9 Hz), 90.3 (d, J=36.9 Hz), 82.9 (d, J=8.4 Hz), 70.2 (d, J=1.4 Hz), 69.1 (d, J=5.4 Hz), 69.0 (d, J=6.1 Hz), 66.9 (d, J=5.1 Hz), 51.7, 48.0 (d, J=8.7 Hz), 47.8 (d, J=8.8 Hz), 22.0 (d, J=1.8 Hz), 21.9 (d, J=3.4 Hz), 20.6 (d, J=1.9 Hz), 20.5 (d, J=1.9 Hz), 15.6 (d, J=3.0 Hz), 12.5 ppm; HRMS calcd for $C_{36}H_{49}FN_4O_{13}P_2Na$ [M+Na$^+$]: 849.2648, found: 849.2670 (2.59 ppm).

LCB2028: $R_f$=0.20 (DCM/MeOH, 95:5); $^1$H NMR (500 MHz, CD₃OD) δ 7.65 (s, 1H), 7.40-7.18 (m, 6H), 5.98 (dd, J=17.8, 3.7 Hz, 1H), 5.00-4.93 (m, 2H), 4.42-4.27 (m, 3H), 3.94-3.87 (m, 1H), 3.68 (dd, J=10.9, 1.9 Hz, 1H), 3.61 (dd, J=11.1, 1.7 Hz, 1H), 1.89 (s, 3H), 1.36-1.20 (m, 10H), 1.08 (s, 3H) ppm OH signal missing possibly due to exchange in CD₃OD; HRMS calcd for $C_{24}H_{33}FN_3O_9PNa$ [M+Na$^+$]: 580.1831, found: 580.1841 (1.82 ppm).

Example 1.31—Antitumor/Antiviral Compound LCB2088

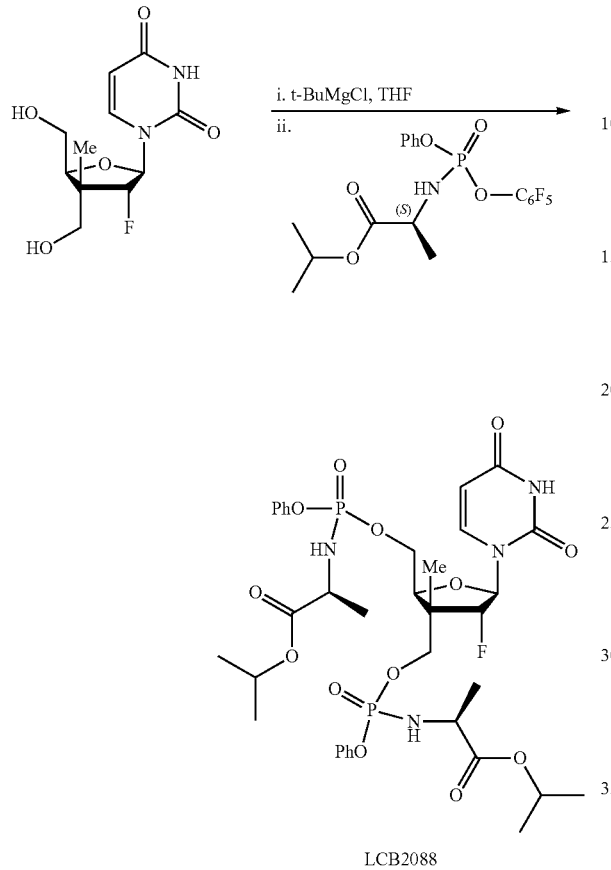

LCB2088

3',5'-Bisphosphoramidate nucleoside analogue (LCB2088). To a solution of nucleoside[14] (30 mg, 0.11 mmol) in anhydrous THF (0.40 mL) at 25° C. was added tBuMgCl (0.26 mL, 0.26 mmol, 1.0 M solution in THF) under an inert atmosphere. The reaction mixture was stirred at 25° C. for 30 minutes before addition of a solution of Protide Reagent (0.12 g, 0.26 mmol). After 16 hours at 25° C., 0.5 mL of MeOH was added and the mixture was concentrated in vacuo. Purification by flash chromatography (DCM:MeOH 95:5) provided LCB2088 (46 mg, 52%). $R_f$=0.19 (DCM/MeOH, 95:5); $[\alpha]^{25}_D$ +19 (c 1.5, $CD_3OD$); IR (neat) $v_{max}$ 2981, 2938, 1718, 1690 $cm^{-1}$; $^1H$ NMR (500 MHz, $CD_3OD$) δ 7.81 (d, J=8.2 Hz, 1H), 7.38-7.16 (m, 11H), 5.89 (dd, J=18.8, 2.8 Hz, 1H), 5.70 (d, J=8.1 Hz, 1H), 4.99 (dd, J=51.4, 2.7 Hz, 1H), 5.01-4.95 (m, 2H), 4.37-4.27 (m, 3H), 4.23-4.13 (m, 2H), 3.96-3.87 (m, 2H), 1.34 (appd, J=7.1 Hz, 7H), 1.25-1.20 (m, 13H), 1.06 (s, 3H) ppm; $^{13}C$ NMR (125 MHz, $CD_3OD$) δ 174.4 (d, J=5.5 Hz), 174.3 (d, J=5.6 Hz), 166.0, 152.1192, 152.1185 (d, J=14.6 Hz), 152.0, 141.5, 130.87, 130.83, 126.27, 126.25, 121.5 (d, J=4.7 Hz), 121.4 (d, J=4.8 Hz), 102.9, 101.0 (d, J=190.6 Hz), 90.9 (d, J=37.7 Hz), 83.3 (d, J=8.3 Hz), 70.2 (d, J=3.0 Hz), 69.0 (d, J=4.9 Hz), 68.9 (d, J=4.9 Hz), 66.8 (d, J=5.1 Hz), 51.7, 48.1 (d, J=8.8 Hz), 48.0 (d, J=8.8 Hz), 22.0, 21.9 (d, J=2.9 Hz), 20.6 (d, J=2.5 Hz), 20.5 (d, J=2.6 Hz), 15.4 (d, J=3.6 Hz) ppm; HRMS calcd for $C_{35}H_{47}FN_4O_{13}P_2Na$ [M+Na$^+$]: 835.2491, found: 835.2516 (2.97 ppm).

Example 2—Chemical Synthesis Details—Group B Compounds Synthesis of Gem-Dimethyl Lipoate Analogues

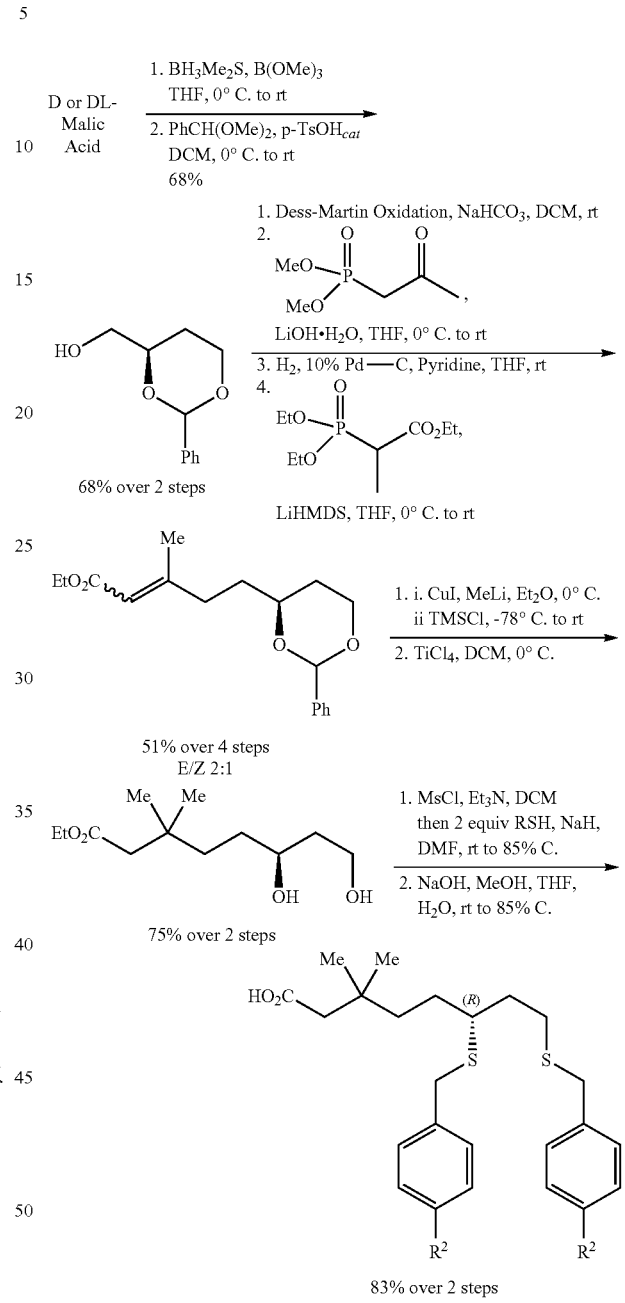

$R^2$ = $CF_3$; C6-(R) LCB2152
$R^2$ = F; C6-(R;S) LCB2111

Example 2.1—Intermediate Compound

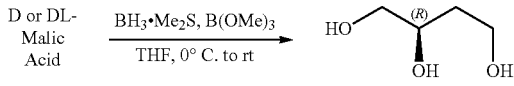

(R)-butane-1,2,4-triol. To a solution of D- or DL-malic acid (20.0 g, 149.1 mmol) in 250 mL of THF under $N_2$ atmosphere was added B(OMe)$_3$ (65.0 mL, 583 mmol). The resulting mixture was stirred at room temperature for 1 h. BH$_3$·Me$_2$S (34.0 mL, 354.0 mmol) was added dropwise and stirred for 24 hours. Following evaporation, the residue was dissolved in MeOH (200 mL) and silica gel (60 g) was added. The resulting slurry was stirred overnight at room temperature. Filtration of the slurry on Celite, washing with MeOH (×2) and evaporation afforded the triol which was used as a crude without purification. Formula: $C_4H_{10}O_3$; MW: 106.12 g/mol; $^1$H NMR (500 MHz, CD$_3$OD): δ 3.78-3.68 (m, 3H), 3.52-3.43 (m, 2H), 1.78-1.70 (m, 1H), 1.65-1.56 (m, 1H); $^{13}$C NMR (126 MHz, CD$_3$OD): δ 70.8, 67.6, 60.1, 37.2; HRMS (ESI+): m/z=129.0530, calcd. for $C_4H_{10}O_3$[M+Na]+:129.0528; $[\alpha]^{25}_D$: +25.1 (c 0.31, MeOH) {lit: $[\alpha]^{25}_D$: +24.6 (c 2.6, MeOH)}[15]

Example 2.2—Intermediate Compound

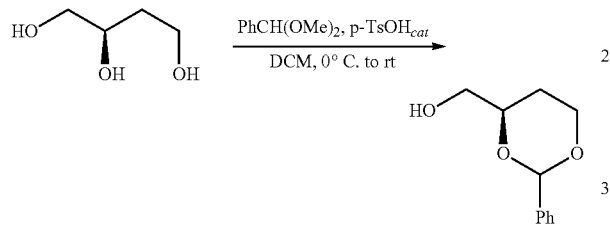

((4R)-2-Phenyl-1,3-dioxan-4-yl)methanol. To a solution of the crude triol (150.0 mmol) and benzaldehyde dimethyl acetal (23.5 mL, 157.5 mmol) in dry CH$_2$Cl$_2$ (150 mL) at 0° C., under $N_2$ atmosphere, was added p-TsOH·H$_2$O (1.42 g, 7.5 mmol). The solution was brought to room temperature and stirred for 24 h. Et$_3$N (2.1 mL, 15.0 mmol) was added and the mixture stirred for 10 minutes before evaporation. The benzylidene (19.4 g, 68% over 2 steps) was obtained following flash chromatography (Hex/EtOAc 7:3→1:1). R$_f$=0.12 (Hexanes/EtOAc 7:3); Formula: $C_{11}H_{14}O_3$; MW: 194.23 g/mol; $^1$H NMR (500 MHz, CDCl$_3$): δ 7.53-7.33 (m, 5H), 5.56 (s, 1H), 4.31 (ddd, J=11.4, 5.2, 1.3, 1H), 4.09-3.92 (m, 2H), 3.72-3.65 (m, 2H), 2.10 (bs, 1H), 2.04-1.83 (m, 1H), 1.51-1.41 (m, 1H); $^{13}$C NMR (125 MHz, CDCl$_3$): δ 138.4, 128.9, 128.4, 128.4, 126.1, 126.0, 101.3, 77.6, 66.6, 65.6, 26.8; $[\alpha]_D^{25D}$: −9.8 (c 1.18, CHCl$_3$) {lit: $[\alpha]^{25}_D$: −10.0 (c 1.18, CHCl$_3$).[16]

Example 2.3—Intermediate Compound

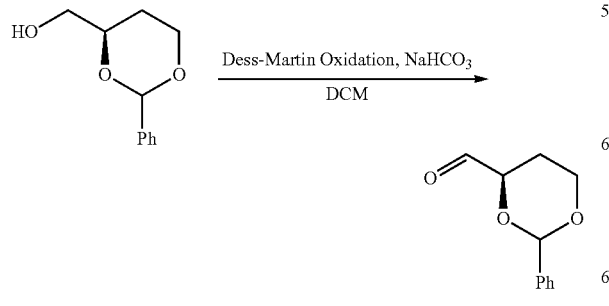

(4R)-2-Phenyl-1,3-dioxane-4-carbaldehyde. To a stirred suspension of Dess-Martin Periodinane (9.33 g, 22.0 mmol) and NaHCO$_3$ (16.8 g, 200.0 mmol) in CH$_2$Cl$_2$ (80 mL) at room temperature was cannulated a solution of the free alcohol (3.88 g, 20.0 mmol) in CH$_2$Cl$_2$ (40 mL). After 18 h, the volatiles were evaporated. Hexanes were added and the slurry filtrated on a short pad of silica gel (Et$_2$O). Evaporation of the solvents afforded the unstable aldehyde that was used immediately in the next step. R$_f$=0.24 (Hexanes/EtOAc 7:3); Formula: $C_{11}H_{12}O_3$; MW: 192.21 g/mol; $^1$H NMR (500 MHz, CDCl$_3$): δ 9.75 (s, 1H), 7.57-7.32 (m, 5H), 5.63 (s, 1H), 4.42-4.36 (m, 2H), 4.05 (ddd, J=12.2, 7.2, 2.5 Hz, 1H), 2.06-1.96 (m, 1H), 1.85-1.80 (m, 1H).

Example 2.4—Intermediate Compound

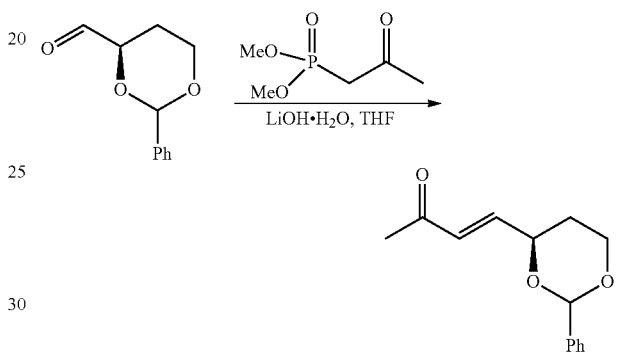

(E)-4-((4R)-2-Phenyl-1,3-dioxan-4-yl)but-3-en-2-one. To a suspension of LiOH·H$_2$O (0.92 g, 22.0 mmol) in anhydrous THF (60 mL) at 0° C. was added dimethyl acetylmethylphosphonate (3.0 mL, 22.0 mmol) and the resulting mixture was stirred for 15 min at 0° C. A solution of the aldehyde (20.0 mmol) in THF (20 mL) was cannulated into the mixture. After 15 min at 0° C., the reaction was brought to room temperature and stirred for 5 h before addition of a saturated aqueous solution of NH$_4$Cl. The aqueous layer was extracted with Et$_2$O (×3) and combined organic fractions were washed with brine, dried (MgSO$_4$), filtered and concentrated in vacuo to afford the α,β-unsaturated ketone that was used as a crude. R$_f$=0.11 (Hexanes/EtOAc 8:2); Formula: $C_{14}H_{16}O_3$; MW: 232.27 g/mol; $^1$H NMR (500 MHz, CDCl$_3$): δ 7.55-7.52 (m, 2H), 7.43-7.37 (m, 3H), 6.80 (dd, J=16.1, 4.3 Hz, 1H), 6.38 (dd, J=16.1, 1.6 Hz, 1H), 5.62, (s, 1H), 4.63-4.58 (m, 1H), 4.39-4.32 (m, 1H), 4.06 (td, J=12.0, 2.5 Hz, 1H), 2.30 (s, 3H), 2.01-1.91 (m, 1H), 1.74-1.69 (m, 1H); $^{13}$C NMR (126 MHz, CDCl$_3$): δ 198.5, 144.7, 138.2, 129.6, 129.2, 128.5, 126.2, 101.4, 75.7, 67.0, 30.9, 27.7; $[\alpha]^{25}_D$: +4.4 (c 0.18, CHCl$_3$).

Example 2.5—Intermediate Compound

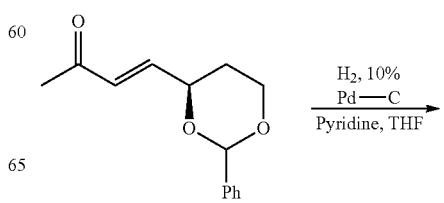

-continued

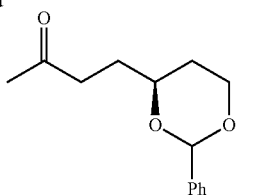

4-((4S)-2-Phenyl-1,3-dioxan-4-yl)butan-2-one. To a solution of crude α,β-unsaturated ketone (20.0 mmol) and pyridine (11.0 mmol) in THF (100 mL) at room temperature was added 10 wt. % Pd on activated carbon (800 mg). Inert gas atmosphere was purged by 3 cycles of vacuum/$H_2$ gas before stirring the reaction mixture until judged completed by TLC (18 h). Mixture was then filtered on a pad of silica gel ($Et_2O$) and washed with $Et_2O$. Filtrate was concentrated in vacuo to afford the saturated ketone that was used without purification. $R_f$=0.36 (Hexanes/EtOAc 7:3); Formula: $C_{14}H_{18}O_3$; MW: 234.29 g/mol; $^1H$ NMR (500 MHz, $CDCl_3$): δ 7.51-7.46 (m, 2H), 7.41-7.33 (m, 3H), 5.50 (s, 1H), 4.28 (dd, J=11.4, 4.9 Hz, 1H), 3.97 (td, J=11.9, 2.3 Hz, 1H), 3.87 (td, J=8.4, 3.1 Hz, 1H), 2.72-2.60 (m, 2H), 2.17 (s, 3H), 1.98-1.90 (m, 1H), 1.90-1.79 (m, 2H), 1.57-1.52 (m, 1H); $^{13}C$ NMR (126 MHz, $CDCl_3$): δ 208.6, 138.9, 128.9, 128.4, 126.1, 101.3, 76.2, 67.1, 39.1, 31.5, 30.2, 29.9.

Example 2.6—Intermediate Compound

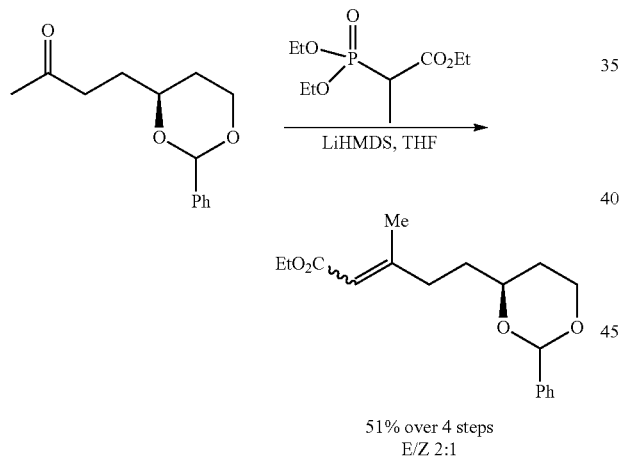

51% over 4 steps
E/Z 2:1

(Z) and (E)-Ethyl 3-methyl-5-((4S)-2-phenyl-1,3-dioxan-4-yl)pent-2-enoate. To a solution of triethyl phosphonacetate (13.0 mL, 64.0 mmol) in anhydrous THF (45 mL) at 0° C. was added a 1 M THF solution of LiHMDS (64.0 mL, 64.0 mmol) and the resulting mixture was stirred for 15 min at 0° C. A solution of the saturated ketone (13.0 mmol) in THF (15 mL) was cannulated. After 15 min at 0° C., the reaction was brought to room temperature and the stirred overnight before addition of a saturated aqueous solution of $NH_4Cl$. The aqueous layer was extracted with $Et_2O$ (×3) and combined organic fractions were washed with brine, dried ($MgSO_4$), filtered and concentrated in vacuo to afford a 2:1 E/Z mixture of α,β-unsaturated ester (3.13 g, 51% over 4 steps) that was purified with flash chromatography (Hex/EtOAc 8:2). $R_f$=0.52 (Hexanes/EtOAc 8:2); Formula: $C_{18}H_{24}O_4$; MW: 304.38 g/mol; $^1H$ NMR (500 MHz, $CDCl_3$): δ 7.53-7.49 (m, 2H), 7.41-7.33 (m, 3H), 5.50 (s, 1H), 5.72 (d, J=1.0 Hz, $1H_E$), 5.71 (s, 1 Hz), 5.53 (s, 1 Hz), 5.52 (s, $1H_E$), 4.29 (dd, J=11.1, 4.7 Hz, $1H_{E+Z}$); $[α]^{25}_D$: −36.4 (c 1.14, $CHCl_3$).

Example 2.7—Intermediate Compound

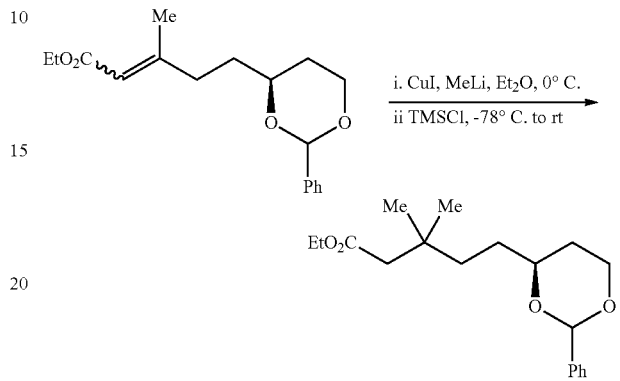

Ethyl 3,3-dimethyl-5-((4S)-2-phenyl-1,3-dioxan-4-yl)pentanoate. To a suspension of CuI (7.82 g, 41.1 mmol) in anhydrous $Et_2O$ (30 mL) at 0° C. was added a 1.6 M $Et_2O$ solution of MeLi (51.4 mL, 82.2 mmol) and the resulting colorless mixture was stirred for 15 min at 0° C. then brought to −78° C. After 30 min at −78° C., TMSCl (10.0 mL, 82.2 mmol) was added. After 15 min, a solution of the unsaturated ester (3.13 g, 10.3 mmol) in THF (15 mL) was added. The resulting yellow suspension was stirred at room temperature for 48 h (formation of a black precipitate). The reaction mixture was filtered on silica gel ($Et_2O$) and concentrated in vacuo to afford the corresponding gem-dimethyl ester that was used without purification. $R_f$=0.14 (Hexanes/EtOAc 9:1); Formula: $C_{19}H_{28}O_4$; MWeight: 320.42 g/mol; $^1H$ NMR (500 MHz, $CDCl_3$): δ 7.52-7.49 (m, 2H), 7.41-7.31 (m, 3H), 5.52 (s, 1H), 4.29 (dd, J=11.5, 4.0 Hz, 1H), 4.13 (q, J=7.1 Hz, 2H), 3.97 (t, J=10.7 Hz, 1H), 3.82-3.75 (m, 1H), 2.22 (s, 2H), 1.87-1.77 (m, 1H), 1.75-1.67 (m, 1H).

Example 2.8—Intermediate Compound

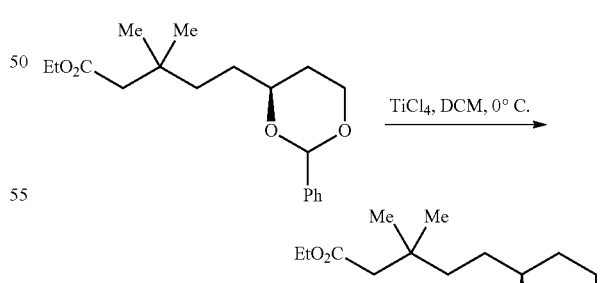

(S)-Ethyl 6,8-dihydroxy-3,3-dimethyloctanoate. To a solution of the gem-dimethyl ester (3.0 g, 7.3 mmol) in anhydrous $CH_2Cl_2$ (20 mL) at 0° C. was added $TiCl_4$ (2.4 mL, 21.8 mmol) and the resulting mixture was stirred for 30 min at 0° C. before addition of a saturated aqueous solution of $NH_4Cl$. The aqueous layer was extracted with EtOAc (×3)

and combined organic fractions were washed with brine, dried (MgSO$_4$), filtered and concentrated in vacuo to afford the diol (1.27 g, 75% over 2 steps) that was purified with flash chromatography (Hex/EtOAc 1:1→100% EtOAc). Formula: C$_{12}$H$_{24}$O$_4$; MW: 232.32 g/mol.

Example 2.9—Intermediate Compound

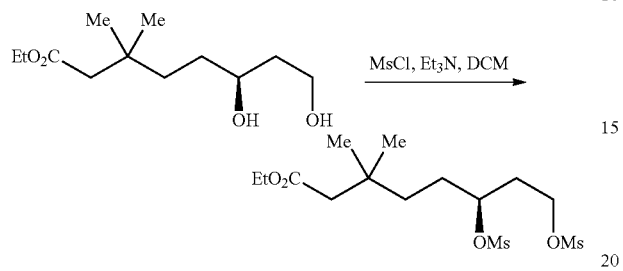

(R)-Ethyl 3,3-dimethyl-6,8-bis((4-(trifluoromethyl)benzyl)thio)octanoate. To a solution of the diol (3.1 g, 13.5 mmol) and Et$_3$N (4.3 mL, 31.0 mmol) in anhydrous CH$_2$Cl$_2$ (60 mL) at 0° C. was added MsCl (2.2 mL, 28.3 mmol) and the resulting mixture was stirred for 2 h at 0° C. before addition of a saturated aqueous solution of NH$_4$Cl. The aqueous layer was extracted with CH$_2$Cl$_2$ (×3) and combined organic fractions were washed with brine, dried (MgSO$_4$), filtered and concentrated in vacuo to afford the dimesylate that was used without purification.

Example 2.10—Intermediate Compound

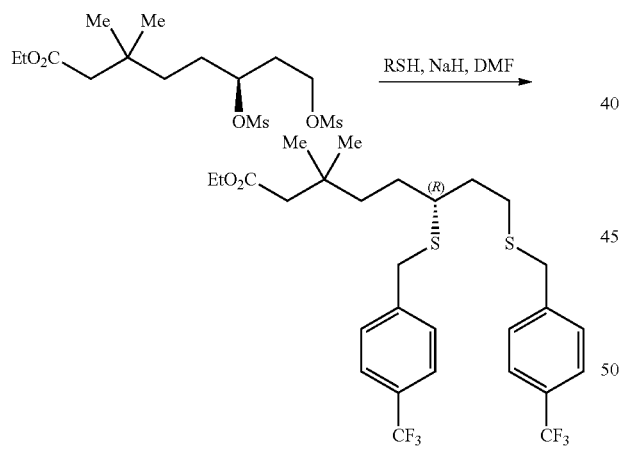

Ethyl (R)-3,3-dimethyl-6,8-bis((4-(trifluoromethyl)benzyl)thio)octanoate. To a suspension of NaH (60% wt in oil, 1.24 g, 31.0 mmol) in anhydrous DMF at 0° C. was added dropwise (4-(trifluoromethyl)phenyl)methanethiol (5.71 g, 29.7 mmol) and stirred for 1 h. A solution of the crude dimesylate (13.5 mmol) in DMF (20 mL) was cannulated into the sodium thiolate reaction mixture at 0° C. The reaction was brought to 85° C. and stirred for 18 h. After the reaction mixture was brought back to room temperature, brine was added. The aqueous layer was extracted with Et$_2$O (×3) and the combined organic fractions were washed with brine, dried (MgSO$_4$), filtered and concentrated in vacuo to afford the dithioether that was used without purification.

Example 2.11—Intermediate Compound (LCB-2152)

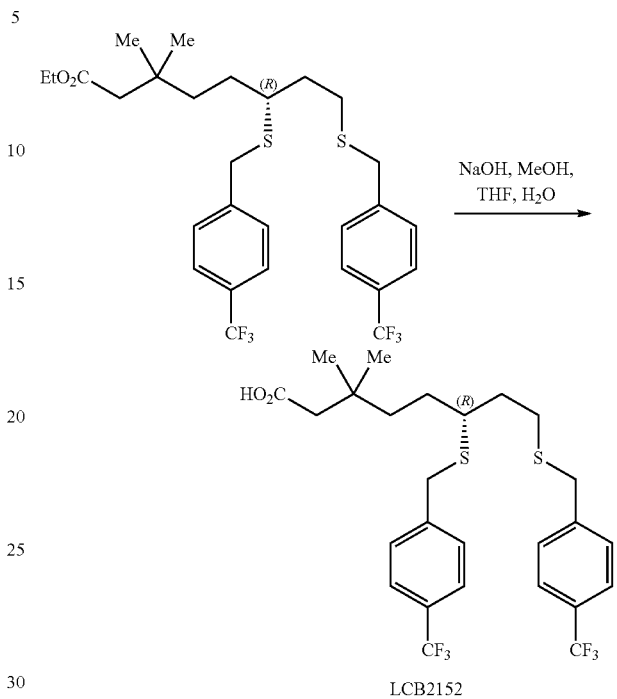

(R)-3,3-Dimethyl-6,8-bis((4-(trifluoromethyl)benzyl)thio)octanoic acid (LCB2152). To a solution of the crude dithioether (13.5 mmol) in THF (92 mL) and MeOH (150 mL) at 0° C. was added a 1M aqueous solution of NaOH (27.0 mL, 27.0 mmol) and the resulting mixture was stirred for 15 min at 0° C. The reaction mixture was then heated to 85° C. for 18 h. Upon bringing the reaction back to 0° C., a 6N aqueous solution was added until pH=2 followed by a saturated solution of NaCl. The aqueous layer was extracted with Et$_2$O (×3) and combined organic fractions were dried (MgSO$_4$), filtered and concentrated in vacuo to afford the corresponding lipoate analogue LCB2152 (6.20 g, 83% over 2 steps) that was purified with flash chromatography (Hex/EtOAc 9:1→6:4). Formula: C$_{26}$H$_{30}$F$_6$O$_2$S$_2$; MW: 552.63 g/mol; $^1$H NMR (500 MHz, CDCl$_3$): δ 7.61-7.55 (m, 4H), 7.46-7.40 (m, 4H), 3.74-3.67 (m, 4H), 2.58-2.47 (m, 3H), 2.19 (s, 2H), 1.81-1.67 (m, 2H), 1.56-1.36 (m, 3H), 1.35-1.26 (m, 1H), 0.98 (s, 6H). $^{13}$C NMR (126 MHz, CDCl$_3$) δ 178.3, 143.1, 142.9, 129.7, 129.4, 129.3, 129.1, 127.6, 127.6, 125.7, 125.7, 125.6, 125.6, 125.4, 123.3, 121.1, 45.6, 45.2, 38.7, 36.2, 35.0, 34.1, 33.2, 29.5, 29.0, 27.5, 27.5. HRMS (ESI+) m/z=calcd. for C$_{26}$H$_{30}$F$_6$O$_2$NaS$_2$ [M+Na]+: 575.1484; found 575.1490 (+1.09 ppm).

Example 2.12—Intermediate Compound (LCB-2111)

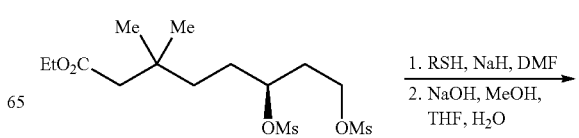

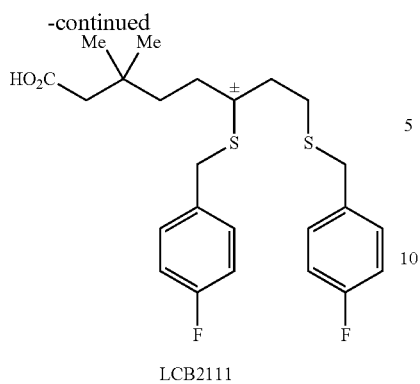

LCB2111

Following a similar procedure as in Example 2.11, the p-fluoro benzyl lipoate analogue (LCB2111) could be obtained:

(R,S)-6,8-bis((4-Fluorobenzyl)thio)-3,3-dimethyloctanic acid (LCB2111). Formula: $C_{24}H_{30}F_2O_2S_2$; MW: 452.62 g/mol; $^1$H NMR (500 MHz, CDCl$_3$): δ 7.32-7.23 (m, 4H), 7.06-6.96 (m, 4H), 3.70-3.60 (m, 4H), 2.59-2.45 (m, 3H), 2.20 (s, 2H), 1.80-1.66 (m, 2H), 1.53-1.39 (m, 3H), 1.36-1.27 (m, 1H), 1.00 (s, 6H); $^{13}$C NMR (126 MHz, CDCl$_3$) δ 178.2, 143.1, 143.1, 142.9, 129.7, 129.7, 129.4, 129.4, 129.1, 127.6, 125.7, 125.7, 125.7, 125.6, 125.6, 125.4, 123.3, 121.1, 45.6, 45.3, 38.7, 36.2, 35.0, 34.2, 33.2, 29.5, 29.1, 27.5, 27.5; HRMS (ESI+): m/z=calcd. for $C_{24}H_{30}F_2O_2S_2Na$ [M+Na]$^+$: 475.1551; found 452.1655 (+0.75 ppm).

Example 2.13—Intermediate Compounds (CPI613, LCB2059, LCB2058, LCB2055, LCB2081, LCB2056)

To racemic or (R)-lipoic acid (10.0 g, 48.5 mmol) was added a 0.5 M aqueous solution of NaOH (97.0 mL, 48.5 mmol) at room temperature and stirring was continued for 15 min. The reaction mixture was heated to 50° C. before careful addition of NaBH$_4$ (1.83 g, 48.5 mmol) in 5 portions over 1 h. A 1 M aqueous solution of NaOH (97.0 mL, 97.0 mmol) was then added at 50° C. before slow addition of the appropriate substituted benzyl bromide (2 equiv). Stirring was maintained at 50° C. for 2 h before the reaction mixture was cooled to 0° C. Concentrated HCl was added until reaching pH=1. EtOAc was added and the aqueous layer extracted with EtOAc (×3) and combined organic fractions washed with brine, dried (MgSO$_4$), filtered and concentrated in vacuo to afford the corresponding lipoate analogues (>70%) that were purified with flash chromatography (Hex/EtOAc 8:2→6:4).

Example 2.14—Representative Experimental Procedure for the Synthesis Group B Compounds

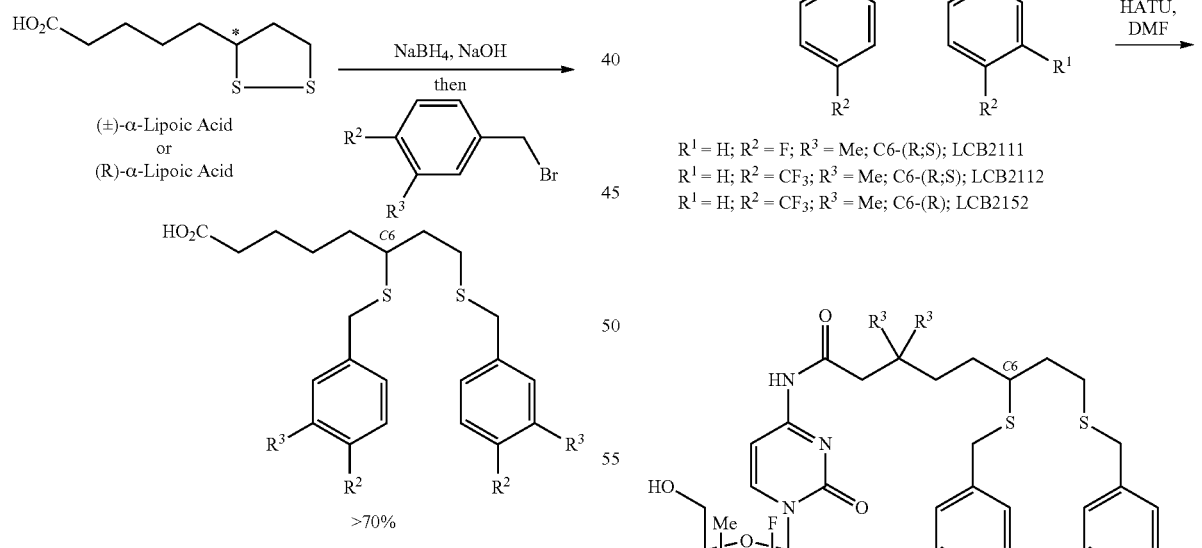

Example 2.15—Antitumor Compound LCB2140

N-(1-((2R,4R,5S)-3,3-difluoro-4,5-bis(hydroxymethyl)-4-methyltetrahydrofuran-2-yl)-2-oxo-1,2-dihydropyrimidin-4-yl)-6,8-bis((4-fluorobenzyl)thio)-3,3-dimethyloctanamide (LCB2140)

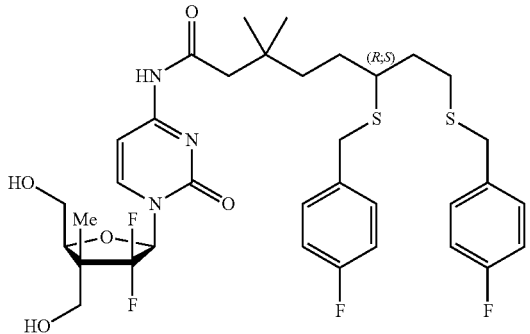

LCB2140

To a solution of LCB2111 (49.8 mg, 0.11 mmol) in anhydrous DMF (1 mL) at room temperature was added DIEA (19.0 mL, 0.11 mmol) and the resulting mixture stirred for 5 min at room temperature. HATU (42.0 mg, 0.11 mmol) was added and the reaction mixture stirred 1 h before addition of LCB1180 (58.2 mg, 0.2 mmol). The reaction was stirred at 55° C. for 18 h and concentrated in vacuo to afford the corresponding nucleoside-lipoate analogue LCB2140 (59.6 mg, 75%) that was purified with reverse-phase flash chromatography (H$_2$O→MeCN).

$R_f$=0.37 (EtOAc+2% MeOH); [α]$^{25}_D$ +44 (c 0.2, MeOH); Formula: C$_{35}$H$_{43}$F$_4$N$_3$O$_5$S$_2$; MW: 725.86 g/mol; IR (neat) $v_{max}$ 3064, 2307, 1653, 1508, 1116 cm$^{-1}$; $^1$H NMR (500 MHz, CD$_3$OD) δ 8.23 (d, J=7.6 Hz, 1H), 7.53 (d, J=7.6 Hz, 1H), 7.34-7.27 (m, 4H), 7.04-6.97 (m, 4H), 6.39 (dd, J=11.2, 6.3 Hz, 1H), 4.39-4.33 (m, 1H), 3.84 (dd, J=12.0, 4.3 Hz, 1H), 3.79 (dd, J=12.0, 6.5 Hz, 1H), 3.73 (d, J=11.1 Hz, 1H), 3.66 (s, 4H), 3.59 (d, J=11.1 Hz, 1H), 2.58-2.43 (m, 3H), 2.30 (s, 2H), 1.79-1.62 (m, 2H), 1.54-1.43 (m, 3H), 1.38-1.29 (m, 1H), 1.10 (s, 3H), 1.00 (s, 6H) ppm (Labile protons were not observed due to exchange with deuterated solvent); $^{13}$C NMR (125 MHz, CD$_3$OD) δ 174.30, 164.57, 164.15, 162.21, 157.81, 146.63, 136.34 (d, J=3.0 Hz), 136.23 (d, J=3.2 Hz), 131.74 (d, J=6.7 Hz), 131.67 (d, J=6.7 Hz), 126.97 (appt, J=262.3 Hz), 116.13 (d, J=2.7 Hz), 115.95 (d, J=2.7 Hz), 97.97, 87.19 (dd, J=39.1, 20.8 Hz), 84.44, 65.50, 62.29, 50.15 (appt, J=19.3 Hz), 46.05, 39.76, 36.10, 35.36, 35.09, 34.70, 30.40, 29.62, 29.61, 27.89, 27.87, 11.11 (d, J=10.4 Hz) ppm; HRMS calcd for: C$_{35}$H$_{44}$F$_4$N$_3$O$_5$S$_2$ [M+H]$^+$: 726.2653; found 726.2667 (+1.90 ppm).

Example 2.16—Antitumor Compound LCB2139

N-(1-((2R,4R,5S)-3,3-difluoro-4,5-bis(hydroxymethyl)-4-methyltetrahydrofuran-2-yl)-2-oxo-1,2-dihydropyrimidin-4-yl)-3,3-dimethyl-6,8-bis((4-(trifluoromethyl)benzyl)thio)octanamide (LCB2139)

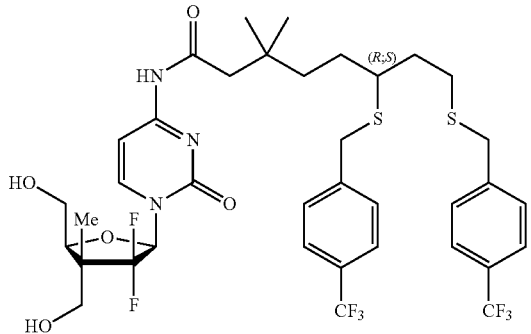

LCB2139

To a solution of LCB2112 (120 mg, 0.22 mmol) in anhydrous DMF (2 mL, 0.1 M) at room temperature was added DIEA (80 μL, 0.44 mmol) and the resulting mixture was stirred for 5 minutes at room temperature. HATU (84 mg, 0.22 mmol) was added and the reaction mixture stirred 1 hour before addition of LCB1180 (60 mg, 0.2 mmol). The reaction was stirred at 55° C. for 18 hours and concentrated in vacuo to afford the corresponding nucleoside-lipoate analogue LCB2139 (123 mg, 75%) that was purified by C18 reverse flash chromatography (H$_2$O→MeCN).

$R_f$=0.29 (EtOAc+2% MeOH); Formula: C$_{37}$H$_{43}$F$_8$N$_3$O$_5$S$_2$; MW: 825.87 g/mol; $^1$H NMR (500 MHz, CD$_3$OD) δ 8.18 (dd, J=7.6, 1.5 Hz, 1H), 7.56-7.50 (m, 4H), 7.48 (d, J=7.6 Hz, 1H), 7.44 (dd, J=15.9, 6.9 Hz, 4H), 6.34 (dd, J=11.3, 6.2 Hz, 1H), 4.33-4.28 (m, 1H), 3.76 (ddd, J=20.1, 12.9, 6.3 Hz, 2H), 3.70-3.63 (m, 5H), 3.53 (d, J=11.2 Hz, 1H), 3.27 (dt, J=3.2, 1.6 Hz, 1H), 2.54-2.39 (m, 3H), 2.27-2.20 (m, 2H), 1.76-1.57 (m, 2H), 1.49-1.32 (m, 3H), 1.27 (ddd, J=13.3, 7.1, 2.7 Hz, 1H), 1.06-1.02 (m, 3H), 0.93 (s, 6H) ppm (Labile protons were not observed due to exchange with deuterated solvent); $^{13}$C NMR (125 MHz, CD$_3$OD) δ 174.28, 164.57, 157.80, 146.63, 145.28 (d, J=1.2 Hz), 145.08 (d, J=1.2 Hz), 130.62, 130.56, 130.06 (q, J=32.3 Hz), 129.99 (q, J=32.3 Hz), 126.30 (appqd, J=3.9, 1.6 Hz, 2C), 125.70 (q, J=271.5 Hz, 2CF$_3$), 97.95, 87.18, 84.40, 65.51, 65.44, 62.28, 50.19 (t, J=19.0 Hz), 46.28, 39.64, 36.37, 35.43, 35.25, 34.68, 30.43, 30.40, 29.69, 27.92, 27.86, 11.09 (d, J=10.7 Hz) ppm; HRMS calcd for: C$_{37}$H$_{44}$F$_8$N$_3$O$_5$S$_2$ [M+H]$^+$: 826.2589; found 826.2607 (+2.12 ppm).

Example 2.17—Antitumor Compound LCB2151

(R)—N-(1-((2R,4R,5S)-3,3-difluoro-4,5-bis(hydroxymethyl)-4-methyltetrahydrofuran-2-yl)-2-oxo-1,2-dihydropyrimidin-4-yl)-3,3-dimethyl-6,8-bis((4-(trifluoromethyl)benzyl)thio) octanamide (LCB2151)

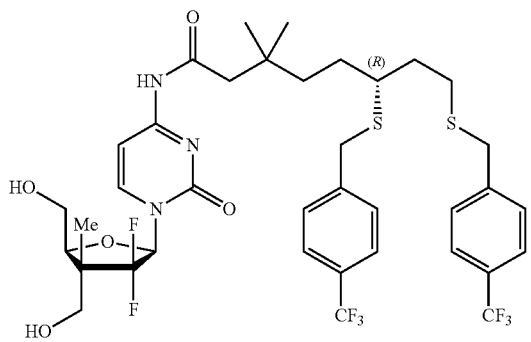

LCB2151

To a solution of LCB2152 (61.0 mg, 0.11 mmol) in anhydrous DMF (1 mL) at room temperature was added DIEA (19.0 mL, 0.11 mmol) and the resulting mixture stirred for 5 min at room temperature. HATU (42.0 mg, 0.11 mmol) was added and the reaction mixture stirred 1 h before addition of LCB1180 (58.2 mg, 0.2 mmol). The reaction was stirred at 55° C. for 18 h and concentrated in vacuo to afford the corresponding nucleoside-lipoate analogue LCB2151 (68.2 mg, 78%) that was purified with reverse-phase flash chromatography (H$_2$O→MeCN).

R$_f$=0.29 (EtOAc+4% MeOH); [α]$^{25}_D$ −5.4 (c 1.2, MeOH); Formula: C$_{37}$H$_{43}$F$_8$N$_3$O$_5$S$_2$; MW: 825.87 g/mol; IR (neat) v$_{max}$ 0.2946, 1653, 1492, 1325, 1123 cm$^{-1}$; $^1$H NMR (500 MHz, CD$_3$OD) δ 8.18 (dd, J=7.6, 1.6 Hz, 1H), 7.52 (dd, J=17.5, 6.8 Hz, 4H), 7.48 (d, J=7.6 Hz, 1H), 7.47-7.41 (m, 4H), 6.34 (dd, J=11.3, 6.3 Hz, 1H), 4.34-4.28 (m, 1H), 3.76 (ddd, J=19.0, 12.2, 5.7 Hz, 2H), 3.69-3.66 (m, 5H), 3.53 (d, J=11.2 Hz, 1H), 3.27 (dt, J=3.0, 1.5 Hz, 1H), 2.55-2.40 (m, 3H), 2.24 (s, 2H), 1.76-1.57 (m, 2H), 1.49-1.35 (m, 3H), 1.32-1.20 (m, 1H), 1.04 (s, 3H), 0.93 (s, 6H) ppm (Labile protons were not observed due to exchange with deuterated solvent); $^{13}$C NMR (125 MHz, CD$_3$OD) δ 174.17, 164.46, 157.69, 146.52, 145.22 (d, J=1.2 Hz), 145.03 (d, J=1.2 Hz), 130.51, 130.45, 130.02 (q, J=32.3 Hz), 129.95 (q, J=32.3 Hz), 126.25 (appqd, J=3.9, 1.6 Hz, 2C), 125.65 (q, J=271.5 Hz, 2CF$_3$), 97.84, 87.07, 84.29, 65.51, 65.44, 62.28, 50.19 (t, J=19.0 Hz), 46.28, 39.64, 36.35, 35.43, 35.25, 34.68, 30.43, 30.32, 29.66, 27.85, 27.83, 11.04 (d, J=10.7 Hz) ppm; HRMS calcd for: C$_{37}$H$_{44}$F$_8$N$_3$O$_5$S$_2$ [M+H]$^+$: 826.2589; found 826.2607 (+2.12 ppm).

Example 2.18—Antitumor Compound LCB2216

N-(1-((2R,4S,5R)-4-hydroxy-5-(hydroxymethyl)tetrahydrofuran-2-yl)-2-oxo-1,2-dihydropyrimidin-4-yl)-3,3-dimethyl-6,8-bis((4-(trifluoromethyl)benzyl)thio)octanamide (LCB-2216)

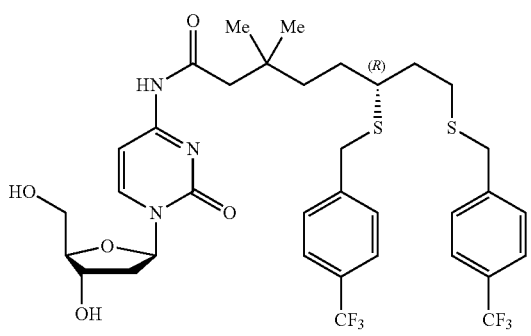

LCB2216

To the LCB2152 lipoate (92.1 mg, 0.5 eq., 171 umol) as a 0.1 M solution in anhydrous DMF (1.7 ml) was added DIEA (29.9 uL, 0.5 eq., 172 umol) followed by HATU (66.6 mg, 0.51 eq., 175 umol). The reaction mixture was stirred at room temperature for 1 hour. Commercially available deoxycytidine (78.1 mg, 1.0 eq., 344 uL) was added and the mixture stirred for 16 hours at 60° C. Upon cooling to room temperature, the mixture was evaporated. Two purifications by silica gel flash chromatography (100% EtOAc+6% MeOH) followed by one purification by reverse phase C18 (100% H$_2$O to 100% MeOH) provided the product (65.6 mg, 25% yield).

R$_f$=0.64 (94:6 EtOAc:MeOH); IR (neat) 3355, 2933, 1650, 1326 cm$^{-1}$; Formula C$_{35}$H$_{41}$F$_6$N$_3$O$_5$S$_2$; MW 761.84; $^1$H NMR (500 MHz, CD$_3$OD) δ 8.47 (d, J=7.5 Hz, 1H), 7.61-7.54 (m, 4H), 7.51-7.45 (m, 5H), 6.20 (t, J=6.2 Hz, 1H), 4.36 (dt, J=6.2, 4.0 Hz, 1H), 4.00 (q, J=3.7 Hz, 1H), 3.83 (dd, J=12.1, 3.3 Hz, 1H), 3.77-3.69 (m, 5H), 2.60-2.41 (m, 4H), 2.26 (s, 2H), 2.20-2.08 (m, 1H), 1.81-1.62 (m, 2H), 1.56-1.38 (m, 3H), 1.36-1.24 (m, 1H), 0.97 (s, 6H) OH and NH signal missing possibly due to exchange in CD$_3$OD; $^{13}$C NMR (125 MHz, CD$_3$OD) δ 174.3, 164.1, 157.9, 146.3, 145.3, 145.1, 130.668, 130.665, 130.60, 130.59, 126.33, 126.32, 126.30, 126.29, 97.9, 89.5, 88.7, 71.7, 62.5, 46.2, 42.5, 39.7, 36.3, 35.4, 35.2, 34.7, 30.4, 29.6, 27.9; HRMS calcd for [M+H]$^+$: 762.2465, found: 762.2466 (0.14 ppm); [α]$_D$ +19 (c 0.92, CD$_3$OD).

Example 2.19—Antitumor Compound LCB2131

(R,S)-6,8-bis((4-Fluorobenzyl)thio)-N-(1-((2R,4S,5R)-4-hydroxy-5-(hydroxymethyl)tetrahydrofuran-2-yl)-2-oxo-1,2-dihydropyrimidin-4-yl)-3,3-dimethyl-octanamide (LCB 2131)

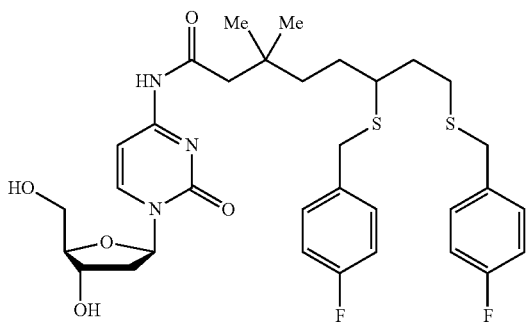

LCB2131

To a solution of LCB2111 (50.0 mg, 0.1 mmol) in anhydrous DMF (1 mL) at room temperature was added DIEA (19.0 μL, 0.1 mmol) and the resulting mixture is stirred for 5 min at room temperature. HATU (42.0 mg, 0.1 mmol) is added and the reaction mixture stirred for 1 h before addition of deoxycytidine (50.0 mg, 0.2 mmol). The reaction was stirred at 55° C. for 18 h and concentrated in vacuo to afford the corresponding nucleoside-lipoate analogue LCB2131 (56.8 mg, 78%) that was purified with reverse-phase flash chromatography (H$_2$O→MeCN).

$R_f$=0.24 (EtOAc+6% MeOH); Formula: C$_{33}$H$_{41}$F$_2$N$_3$O$_5$S$_2$. Molecular Weight: 661.82 g/mol; $^1$H NMR (500 MHz, CD$_3$OD): δ=8.47 (d, J=7.5 Hz, 1H), 7.48 (d, J=7.5 Hz, 1H), 7.33-7.26 (m, 4H), 7.04-6.96 (m, 4H), 6.21 (t, J=6.1 Hz, 1H), 4.38 (dt, J=6.1, 4.1 Hz, 1H), 4.03-4.00 (m, 1H), 3.85 (dd, J=12.1, 3.3 Hz, 1H), 3.76 (dd, J=12.1, 3.8 Hz, 1H), 3.66-3.62 (m, 4H), 2.57-2.42 (m, 4H), 2.28 (s, 2H), 2.19-2.12 (m, 1H), 1.78-1.62 (m, 2H), 1.53-1.40 (m, 3H), 1.35-1.28 (m, 1H), 0.99 (s, 6H); $^{13}$C NMR (126 MHz, CD$_3$OD): δ=173.9, 163.8, 163.7, 161.8, 157.5, 145.9, 136.0, 135.96, 135.88, 135.8, 131.4, 131.3, 131.3, 115.8, 115.77, 115.63, 115.60, 97.5, 89.1, 88.3, 71.3, 62.1, 49.2, 49.0, 48.8, 48.7, 48.5, 48.3, 48.1, 45.7, 42.1, 39.4, 35.7, 35.0, 34.7, 34.3, 30.1, 29.3, 27.5; HRMS (ESI+): m/z=calcd. for C$_{33}$H$_{41}$F$_2$N$_3$O$_5$S$_2$Na [M+Na]$^+$: 684.2348; found 684.2350 (+0.38 ppm).

Example 2.20—Intermediate Compound

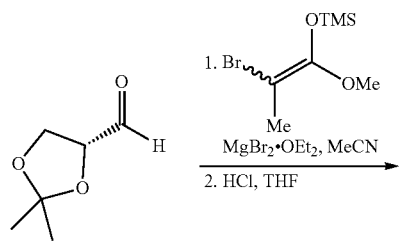

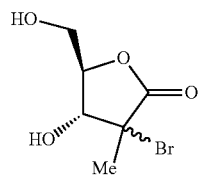

(4R,5R)-3-bromo-4-hydroxy-5-(hydroxymethyl)-3-methyldihydrofuran-2(3H)-one. To a solution of precooled glyceraldehyde (24 g, 185 mmol) in dry acetonitrile (710 mL) at −10° C. under Ar, MgBr$_2$.OEt$_2$ (37 g, 142 mmol) was added. After 15 min all the solids were in solution and neat enolate (50.7 g, 142 mmol) precooled at −20° C. was added via cannula during 10 min. The mixture was stirred for 23 h at 0° C., and quenched by addition of 200 mL ice-H$_2$O at 0° C. The mixture was diluted with ethyl acetate, washed 2×200 mL with distilled water, the organic phase was dried over MgSO$_4$, and concentrated to produce clear brown oil (50.7 g), which was used for the next step. HCl conc (10 mL, 121.8 mmol) was added dropwise to a solution of aldol adducts (50.7 g, 137 mmol) in THF (275 mL) at 0° C. and open atmosphere for 20 min. After 50 min the reaction was warmed to room temperature. After 5 h, the reaction mixture was concentrated producing dark green oil that was passed through a bed of SiO$_2$ (200 mL) and rinsed with a mixture of CH$_2$Cl$_2$/EtOAc 50%. The produced dark brown solid was washed with hexanes, then twice with Hexanes/EtOAc (95:5) producing a clear brown solid (19 g, 59% over 2 steps).

A: major lactone (3,4-anti). $^1$H NMR (500 MHz, Methanol-d$_4$) δ 4.18 (ddd, J=8.4, 4.2, 2.1 Hz, 1H), 3.97 (dd, J=13.0, 2.1 Hz, 1H), 3.82 (d, J=8.4 Hz, 1H), 3.73 (dd, J=13.0, 4.2 Hz, 1H), 1.86 (s, 3H). $^{13}$C NMR (126 MHz, CD$_3$OD) δ 174.4, 84.3, 74.3, 62.4, 59.9, 24.4.

B: minor lactone (3,4-anti) $^1$H NMR (500 MHz, Methanol-d$_4$) δ 4.64 (d, J=6.3 Hz, 1H), 4.24 (ddd, J=6.3, 5.0, 3.2 Hz, 1H), 3.96-3.84 (m, 2H), 3.82-3.75 (m, 1H), 1.82 (s, 3H). $^{13}$C NMR (126 MHz, CD$_3$OD) δ 175.7, 86.1, 78.0, 61.4, 58.8, 22.3. $R_f$=0.05 (30% ethyl acetate in hexanes).

Example 2.21—Intermediate Compound

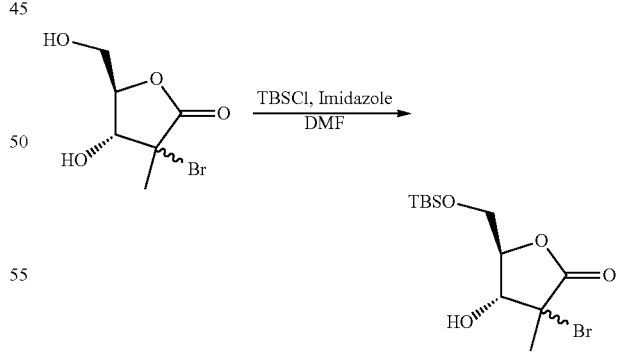

(4R, 5R)-3-bromo-5-(((tert-butyldimethylsilyl)oxy)methyl)-4-hydroxy-3-methyl dihydrofuran-2(3H)-one. TBSCl (12.7 g, 84.4 mmol) was added to a mixture of lactones (19 g, 84.4 mmol), and imidazole (23 g, 337.7 mmol) in dry DMF (420 mL) under Ar at −40° C. The reaction was followed by TLC, and after 5 h, 0.06 equiv of TBS-Cl (0.77 g, 5.10 mmol) was added. After 7 h in total, the reaction mixture was diluted with ethyl acetate (800 mL), washed sequentially with citric acid [0.1M] (400 mL), distilled water, brine, dried over MgSO$_4$ and concentrated to produce a brown oil (27 g, 94% yield). R$_f$=0.37 (30% ethyl acetate in hexanes); IR (neat) 3457, 2952, 2931, 2855, 1771, 1256, 1132 cm$^{-1}$; Formula C$_{12}$H$_{23}$BrO$_4$Si; MW 339.2981; For major diastereomer from 3,4-anti aldol adduct: $^1$H NMR (500 MHz, CDCl$_3$) δ 4.13 (dt, J=8.1, 2.8 Hz, 1H), 4.01 (dd, J=12.1, 2.5 Hz, 1H), 3.94-3.83 (m, 2H), 1.94 (s, 3H), 0.95-0.82 (m, 9H), 0.08 (d, J=7.8 Hz, 6H); $^{13}$C NMR (125 MHz, CDCl$_3$) δ 171.5, 82.7, 74.0, 62.3, 60.0, 26.0, 24.4, 18.4, −5.2, −5.3; For minor diastereomer from 3,4-anti aldol adduct: $^1$H NMR (500 MHz, CDCl$_3$) δ 4.82 (dd, J=6.6, 2.5 Hz, 1H), 4.22 (ddd, J=6.4, 5.3, 3.8 Hz, 1H), 4.00-3.88 (m, 2H), 1.88 (s, 3H), 0.90 (s, 9H), 0.10 (s, 6H); $^{13}$C NMR (125 MHz, CDCl$_3$) δ 173.1, 83.0, 78.1, 61.7, 57.0, 26.0, 22.1, 18.4, −5.2, −5.2; HRMS calcd for [M+H$^+$]: 339.0627, found: 339.0621; calcd for [M+Na$^+$]: 361.0447, found: 361.0442.

Example 2.22—Intermediate Compound

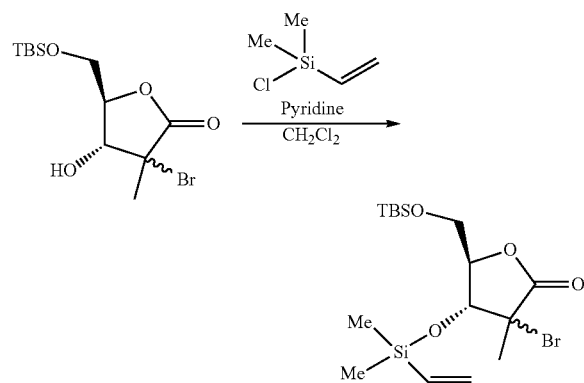

(4R,5R)-3-bromo-5-(((tert-butyldimethylsilyl)oxy) methyl)-4-((dimethyl(vinyl)silyl) oxy)-3-methyldihydrofuran-2(3H)-one. Chlorodimethylvinylsilane (11.2 g, 13.2 mL, 92.9 mmol) was added to a mixture of TBS-lactones (84.43 mmol) and dry pyridine (16.6 g, 17.0 mL, 211.1 mmol) in dry CH$_2$Cl$_2$ (422 mL) under Ar at 0° C. The mixture was allowed to reach room temperature slowly and after 23 h, 0.05 equiv of chlorodimethylvinylsilane was added (509 mg, 0.6 mL). After 28 h, the reaction mixture was concentrated, the resulted mixture was suspended in a mixture of 20% ethyl acetate in hexanes, passed through a pad of SiO$_2$, rinsed with 500 mL of (20% ethyl acetate in hexanes), and concentrated to produce yellow oil (32.5 g, 96% yield).

R$_f$=0.6 (30% ethyl acetate in hexanes); IR (neat) 2952, 2925, 2850, 1787, 1256, 1138 cm$^{-1}$; Formula C$_{16}$H$_{31}$BrO$_4$Si$_2$; MW 423.4899; For major diastereomer from 3,4-anti aldol adduct: $^1$H NMR (500 MHz, CDCl$_3$) δ 6.20-6.05 (m, 2H), 5.86 (dd, J=19.4, 4.6 Hz, 1H), 4.16 (dt, J=7.9, 1.9 Hz, 1H), 4.03-3.98 (m, 2H), 3.78 (dd, J=12.6, 2.0 Hz, 1H), 1.84 (s, 3H), 0.87 (s, 9H), 0.28 (s, 6H), 0.07 (d, J=10.4 Hz, 6H); $^{13}$C NMR (125 MHz, CDCl$_3$) δ 172.4, 136.4, 134.9, 82.5, 73.4, 60.1, 58.6, 25.9, 24.9, 18.3, −1.3, −1.5, −5.2, −5.3; For minor diastereomer from 3,4-anti aldol adduct: $^1$H NMR (500 MHz, CDCl$_3$) δ 6.20-6.05 (m, 2H), 5.83 (dd, J=19.9, 4.1 Hz, 1H), 4.84 (d, J=6.0 Hz, 1H), 4.13 (ddd, J=6.0, 4.0, 3.2 Hz, 1H), 3.96 (dd, J=12.0, 3.8 Hz, 1H), 3.81 (dd, J=11.9, 3.6 Hz, 1H), 1.80 (s, 3H), 0.90 (s, 9H), 0.30-0.28 (m, 6H), 0.08 (s, 6H); $^{13}$C NMR (125 MHz, CDCl$_3$) δ 173.5, 136.3, 134.7, 84.2, 77.4, 60.5, 57.5, 25.9, 22.5, 18.4, −1.4, −1.5, −5.2, −5.3; HRMS calcd for [M+H$^+$]: 423.1023, found: 423.1009; [M+NH$_4^+$]: 440.1288, found: 440.1274; calcd for [M+Na$^+$]: 445.0842, found: 445.0831.

Example 2.23—Intermediate Compound

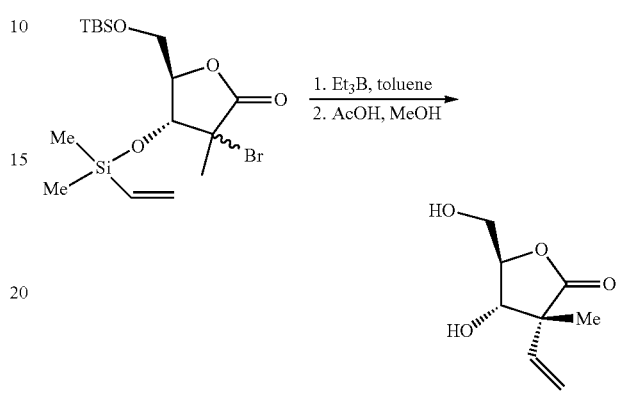

(3R,4S,5R)-4-hydroxy-5-(hydroxymethyl)-3-methyl-3-vinyldihydrofuran-2-(3H)-one. Et$_3$B [1 M] in hexane (76.8 mL, 76.8 mmol) was added via syringe with a rate of 15.4 mL/h to a solution of lactones (32.5 g, 76.8 mmol) in dry toluene (153 mL) at 0° C., open atmosphere and vigorous stirring. After 7 h, 0.1 equiv of BEt$_3$ [1 M] in hexane (7.7 mL, 7.7 mmol) were added. The reaction was quenched after 8 h in total by consecutive addition of methanol (153 mL) and acetic acid (9.2 g, 8.8 mL, 153.6 mmol) at 0° C. and allowed to reach room temperature slowly overnight. The reaction mixture was concentrated after 17 h, the resulting brown oil was washed with hexanes (×1), passed through a pad of SiO$_2$ and rinsed with a gradient of 50% ethyl acetate in hexanes to 100% ethyl acetate. The brown solid was dissolved in CH$_2$Cl$_2$ and the title product was formed as a white solid (7.08 g, 53% yield, only one diastereomer). The remaining brown oil (8.52 g) was fractionated by FCC (30% ethyl acetate in hexanes) to yield the title product as a beige solid (4.68 g, 35%, 5:1 mixture of diastereomers). Overall yield 88% and ca. 14:1 (3,4-anti:3,4-syn).

R$_f$=0.09 (30% ethyl acetate in hexanes); IR (neat) cm$^{-1}$ 3419, 2936, 1766, 1100, 1041; Formula C$_8$H$_{12}$O$_4$; MW 172.1785; $^1$H NMR (500 MHz, CDCl$_3$) δ 6.07-5.92 (m, 1H), 5.27 (d, J=10.7 Hz, 1H), 5.13 (d, J=17.7 Hz, 1H), 4.12-4.03 (m, 2H), 3.97-3.89 (m, 1H), 3.68 (dd, J=13.1, 3.8 Hz, 1H), 1.32 (s, 3H); $^{13}$C NMR (125 MHz, CD$_3$OD) δ 178.9, 135.7, 117.0, 83.6, 75.8, 60.8, 52.7, 20.9; HRMS calcd for [M+H$^+$]: 173.0814, found: 173.0804; calcd for [M+Na$^+$]: 195.0633, found: 195.0625; [α]D +53 (c 1.4, CH$_3$OH).

Example 2.24—Intermediate Compound

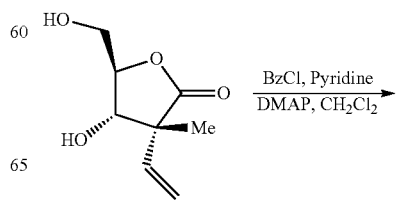

-continued

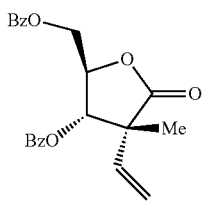

((2R,3S,4R)-3-(benzoyloxy)-4-methyl-5-oxo-4-vinyltetrahydrofuran-2-yl)methyl benzoate. Benzoyl chloride (26.9 g, 22.2 mL, 191.14 mmol) was added slowly to a mixture of lactone (10.97 g, 63.71 mmol), DMAP (778 mg, 6.371 mmol) and pyridine (30.2 g, 31 mL, 382.3 mmol) under Ar at 0° C. The mixture was allowed to reach room temperature slowly. After 21 h, the reaction was cooled to 0° C., diethylamine (3.8 g, 4.2 mL, 63.7 mmol) was added dropwise, allowed to reach room temperature and stirred overnight. The mixture was concentrated, suspended in a mixture of 30% ethyl acetate in hexanes, passed through a pad of $SiO_2$, and concentrated to yield yellow oil (23.12 g, 95% yield).

$R_f$=0.49 (30% ethyl acetate in hexanes); IR (neat) 1787, 1723, 1449, 1267, 1111 $cm^{-1}$; Formula $C_{22}H_{20}O_6$; MW 380.3906; $^1$H NMR (500 MHz, $CDCl_3$) δ 8.03-7.98 (m, 4H), 7.62 (td, J=7.4, 1.3 Hz, 1H), 7.55 (td, J=7.4, 1.4 Hz, 1H), 7.47 (td, J=7.9, 7.5, 1.4 Hz, 2H), 7.41-7.37 (m, 2H), 5.95 (dd, J=17.5, 10.7 Hz, 1H), 5.55 (d, J=7.5 Hz, 1H), 5.44-5.30 (m, 2H), 4.76-4.71 (m, 2H), 4.59-4.54 (m, 1H), 1.56 (s, 3H); $^{13}$C NMR (125 MHz, $CDCl_3$) δ 175.1, 166.0, 165.5, 134.0, 133.5, 132.6, 130.0, 129.9, 128.8, 128.6, 118.5, 77.2, 63.2, 51.0, 21.6; $^1$H NMR (500 MHz, $C_6D_6$) δ 8.04 (dd, J=8.3, 1.3 Hz, 2H), 7.96 (dd, J=8.3, 1.3 Hz, 2H), 7.17-7.12 (m, 1H), 7.11-7.06 (m, 1H), 7.07-7.01 (m, 2H), 6.99 (ddd, J=8.2, 6.8, 1.2 Hz, 2H), 5.68 (dd, J=17.5, 10.7 Hz, 1H), 5.40 (d, J=7.6 Hz, 1H), 5.23 (d, J=17.5 Hz, 1H), 5.03 (d, J=10.7 Hz, 1H), 4.46 (dd, J=12.1, 3.5 Hz, 1H), 4.38 (ddd, J=7.7, 5.8, 3.4 Hz, 1H), 4.30 (dd, J=12.1, 5.8 Hz, 1H), 1.38 (s, 3H); $^{13}$C NMR (125 MHz, $C_6D_6$) 5174.4, 165.8, 165.3, 133.7, 133.3, 133.2, 130.1, 130.0, 128.8, 128.6, 117.9, 77.4, 77.4, 77.1, 63.6, 50.9, 21.5; HRMS calcd for [M+H$^+$]: 381.1338, found: 381.1317; calcd for [M+NH$_4^+$]: 398.1604, found: 398.1580; calcd for [M+Na$^+$]: 403.1158, found: 403.1137; [α]$_D$ +90 (c 2.0, $CH_2Cl_2$).

Example 2.25—Intermediate Compound

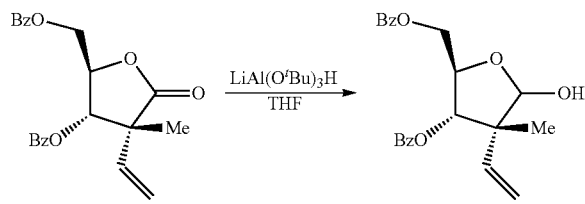

((2R,3S,4R)-3-(benzoyloxy)-5-hydroxy-4-methyl-4-vinyltetrahydrofurna-2-yl)methylbenzoate. LiAlH(OtBu)$_3$ 1M in THF (45 mL, 45 mmol) was added dropwise at 0° C. to solution of lactone (13.16 g, 34.60 mmol) in THF (115 mL) under Ar. The mixture was allowed to reach room temperature slowly. After 3 days reaction, $Na_2SO_4 \cdot 10H_2O$ (16.7 g, 51.90 mmol) was added and stirred vigorously for 1 h. The mixture was concentrated, suspended in ethyl acetate and filtered through a pad of celite-$SiO_2$, washed with ethyl acetate and concentrated to yield a clear yellow oil (11.08 g, 83%, mixture of anomers in a 1.4:1 ratio of anomers).

$R_f$=0.3 (×2, 20% ethyl acetate in hexanes); IR (neat) 3457, 1723, 1449, 1272, 1116 $cm^{-1}$; Formula $C_{22}H_{22}O_6$; MW 382.4065; For mixture of both anomers: $^1$H NMR (500 MHz, $CDCl_3$) δ 8.08-7.98 (m, 9H), 7.60-7.35 (m, 17H), 6.29 (dd, J=17.8, 11.0 Hz, 1H), 6.10 (dd, J=17.6, 11.0 Hz, 1.4H), 5.57 (d, J=6.8 Hz, 1.4H), 5.36-5.15 (m, 8H), 4.77-4.57 (m, 7H), 4.42 (td, J=6.5, 4.2 Hz, 1.4H), 3.20 (dd, J=3.3, 1.7 Hz, 1H), 2.99 (dd, J=5.3, 1.4 Hz, 1H), 1.35 (×2s, 7H); $^{13}$C NMR (125 MHz, $CDCl_3$) δ 166.6, 166.1, 138.1, 135.3, 133.5, 133.2, 133.1, 129.9, 128.6, 128.6, 128.5, 128.5, 117.8, 116.3, 104.4, 103.4, 81.1, 80.8, 79.9, 79.6, 66.4, 65.0, 52.6, 51.8, 20.8, 16.9; HRMS calcd for [M+NH$_4^+$]: 400.1760, found: 400.1755; calcd for [M+Na$^+$]: 405.1314, found: 405.1311.

Example 2.26—Intermediate Compound

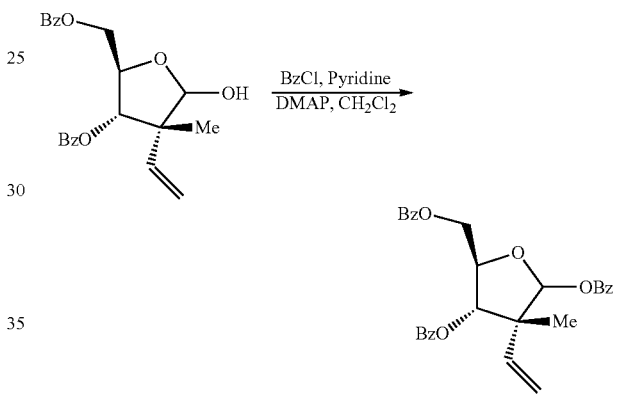

(3R,4S,5R)-5-((benzoyloxy)methyl)-3-methyl-3-vinyltetrahydrofuran-2,4-diyl dibenzoate. Benzoyl chloride (7.7 g, 6.4 mL, 55.0 mmol) was added slowly to a mixture of lactols (16.18 g, 42.31 mmol), DMAP (517 mg, 4.23 mmol) and pyridine (10.0 g, 10.3 mL, 126.93 mmol) under Ar at 0° C. The mixture was allowed to reach room temperature slowly. After 21 h, 0.2 equiv of benzoyl chloride (1.19 g, 0.98 mL, 8.46 mmol) was added. After 42 h, the reaction was cooled to 0° C., diethylamine (1.3 g, 1.4 mL, 21.16 mmol) was added dropwise (yellow precipitate formed). The mixture was concentrated, suspended in a mixture 20% ethyl acetate in hexanes, passed through a pad of $SiO_2$, concentrated to yield a clear yellow oil (18.06 g, 88% yield, 3:1 mixture of anomers) and another fraction containing 3 diastereomers (1.73 g in a 16:27:57 ratio, the first 2 coming from 3,4-anti aldol adduct and the last from 3,4-syn aldol adduct).

$R_f$=0.4 (30% ethyl acetate in hexanes); IR (neat) 3065, 2968, 1728, 1599, 1449, 1272 $cm^{-1}$; Formula $C_{29}H_{26}O_7$; MW 486.5125; For major anomer: $^1$H NMR (500 MHz, $CDCl_3$) δ 8.14 (dd, J=8.4, 1.4 Hz, 1H), 8.05 (ddd, J=13.9, 8.3, 1.4 Hz, 4H), 7.93-7.90 (m, 2H), 7.59 (ddt, J=7.7, 6.1, 1.6 Hz, 2H), 7.47-7.41 (m, 4H), 7.20 (t, J=7.8 Hz, 2H), 6.43 (s, 1H), 6.18 (dd, J=17.5, 11.2 Hz, 1H), 5.81 (d, J=7.6 Hz, 1H), 5.45 (s, 1H), 5.42 (d, J=7.3 Hz, 1H), 4.70 (dd, J=11.5, 4.1 Hz, 1H), 4.60 (ddd, J=7.5, 5.6, 4.1 Hz, 1H), 4.54 (dd, J=11.6, 5.6 Hz, 1H), 1.42 (s, 3H); $^{13}$C NMR (125 MHz, $CDCl_3$) δ 166.2, 165.8, 165.2, 136.5, 133.6, 133.5, 133.0, 130.6, 129.9, 129.9, 129.7, 129.3, 128.9, 128.6, 128.6, 128.2, 117.2, 102.1, 79.6, 78.5, 65.1, 52.1, 17.5; HRMS calcd for [M+NH₄⁺]: 504.2022, found: 504.2021; calcd for [M+Na⁺]: 509.1576, found: 509.1576.

Example 2.27—Intermediate Compound

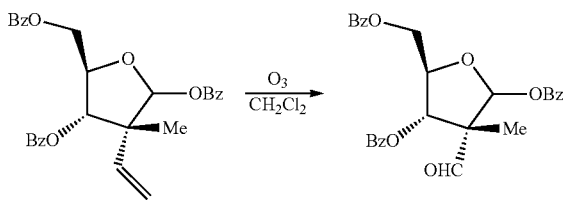

(3S,4S,5R)-5-((benzoyloxy)methyl)-3-formyl-3-methyl-tetrahydrofuran-2,4-diyl dibenzoate. $O_3$ was flowed into a mixture of benzoylated lactols (18.06 g, 37.12 mmol) in $CH_2Cl_2$ (150 mL) and pyridine (8.8 g, 9.0 mL, 111.36 mmol) at –78° C. After 5.5 h, the excess of $O_3$ was removed under vacuum, a balloon with $N_2$ was attached, $Et_3N$ (3.7 g, 5.2 mL, 37.12 mmol) was added, and allowed to reach rt. The mixture was concentrated, diluted with ethyl acetate, washed (×1) with citric acid [0.1 M], (×1) $NaHCO_3$ saturated solution, and dried over $MgSO_4$ to yield the title compound as a mixture of anomers in a 4:1 ratio (clear oil, 16.9 g, 93%).

$R_f$=0.15 (20% ethyl acetate in hexanes); IR (neat) 1728, 1599, 1449, 1267 cm⁻¹; Formula $C_{28}H_{24}O_8$; MW 488.4854; ¹H NMR (500 MHz, CDCl₃) δ 10.06 (s, 1H), 9.97 (s, 4H), 8.08-7.23 (m, aromatics), 6.70 (s, 4H), 6.54 (s, 1H), 5.88 (d, J=6.7 Hz, 4H), 5.48 (d, J=3.7 Hz, 1H), 4.87-4.56 (m, 15H), 1.50 (s, 3H), 1.48 (s, 12H); ¹³C NMR (125 MHz, CDCl₃) δ 198.2, 197.5, 166.0, 165.8, 165.5, 165.4, 164.6, 164.6, 133.8, 133.8, 133.6, 133.6, 133.1, 132.9, 132.8, 129.7, 129.7, 129.7, 129.7, 129.6, 129.6, 129.6, 129.5, 129.5, 129.4, 129.4, 129.2, 129.0, 128.7, 128.6, 128.6, 128.5, 128.5, 128.4, 128.4, 128.3, 128.3, 128.2, 128.1, 128.0, 101.7, 98.5, 84.7, 80.8, 80.1, 79.2, 64.7, 63.7, 60.3, 58.1, 17.9, 13.3; HRMS calcd for [M+NH₄⁺]: 506.1815, found: 506.1800; calcd for [M+Na⁺]: 511.1369, found: 511.1362.

Example 2.28—Intermediate Compound

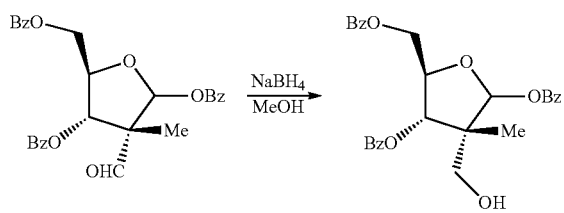

(3R,4S,5R)-5-((benzoyloxy)methyl)3-(hydroxymethyl)-3-methyltetrahydrofuran-2,4-diyldibenzoate. $NaBH_4$ (1.34 g, 34.64 mmol) was slowly added in portions to a mixture of aldehydes (16.92 g, 34.64 mmol) in THF/MeOH (1:2) (345 mL) under Ar at 0° C. After 2 h, the reaction was quenched at 0° C. by addition of 20 mL of distilled water and stirred at room temperature for 40 min. The mixture was concentrated, suspended in ethyl acetate, and washed with distilled water. The aqueous phase was back extracted ×3 with ethyl acetate, the organics were mixed and dried over $MgSO_4$, concentrated and fractionated (30% ethyl acetate in hexanes) to yield the title compound as a white solid (12.26 g, 72%, mixture of anomers 1.6:1).

$R_f$=0.2 (30% ethyl acetate in hexanes); IR (neat) 3483, 3070, 2947, 1723, 1599, 1449, 1272 cm⁻¹; Formula $C_{28}H_{26}O_8$; MW 490.5012; For major anomer: ¹H NMR (500 MHz, CDCl₃) δ 8.08 (dd, J=8.0, 1.4 Hz, 2H), 7.99-7.94 (m, 4H), 7.61-7.54 (m, 2H), 7.50 (t, J=7.6 Hz, 1H), 7.45 (t, J=7.7 Hz, 2H), 7.38 (t, J=7.7 Hz, 2H), 7.28 (t, J=8.0 Hz, 2H), 6.59 (s, 1H), 4.62-4.51 (m, 5H), 4.42 (dd, J=8.0, 5.5 Hz, 1H), 4.37 (dt, J=8.1, 4.2 Hz, 1H), 1.35 (s, 3H); ¹³C NMR (125 MHz, CDCl₃) δ 167.0, 166.8, 165.4, 133.5, 133.4, 133.3, 129.9, 129.9, 129.8, 128.7, 128.7, 128.5, 100.7, 82.4, 77.9, 65.6, 65.2, 49.9, 16.4; HRMS calcd for [M+NH₄⁺]: 508.1971, found: 508.1970; calcd for [M+Na⁺]: 513.1525, found: 513.1518. For mixture of anomers: ¹H NMR (500 MHz, CDCl₃) δ 8.11-7.32 (m, 19H), 7.28 (t, J=7.9 Hz, 1H), 7.22 (t, J=7.8 Hz, 1H), 6.60 (d, J=4.8 Hz, 1H), 5.79 (d, J=6.4 Hz, 0.6H), 4.72-4.31 (m, 8H), 4.02 (d, J=11.3 Hz, 0.6H), 3.95-3.91 (m, 1H), 1.35 (5H); ¹³C NMR (125 MHz, CDCl₃) δ 167.0, 166.8, 166.3, 165.9, 165.5, 165.4, 133.8, 133.6, 133.5, 133.4, 133.3, 133.1, 129.9, 129.9, 129.8, 129.8, 129.8, 129.8, 129.7, 129.7, 129.6, 128.8, 128.7, 128.7, 128.6, 128.5, 128.4, 128.3, 101.4, 100.7, 82.4, 80.8, 79.1, 77.6, 65.6, 65.6, 65.2, 64.7, 51.4, 49.8, 16.4, 16.2.

Example 2.29—Intermediate Compound

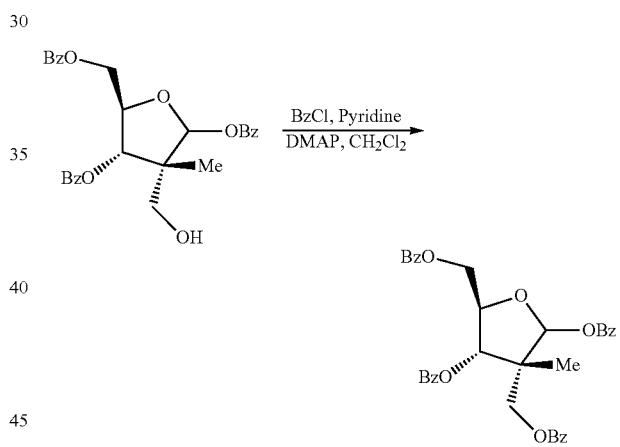

(3R,4S,5R)-3,5-bis((benzoyloxy)methyl)-3-methyltetrahydrofuran-2,4-diyl dibenzoate. Benzoyl chloride (6.6 g, 5.4 mL, 46.89 mmol) was added slowly to a mixture of alcohols (11.5 g, 23.44 mmol) DMAP (286 mg, 2.34 mmol) and pyridine (7.4 g, 7.6 mL, 93.78 mmol) under Ar at 0° C. The mixture was allowed to reach room temperature slowly. After 21 h, the reaction was cooled to 0° C., diethylamine (1.41 g, 1.57 mL, 23.44 mmol) was added dropwise and stirred for 4 h at room temperature. The mixture was concentrated, suspended in a mixture 20% ethyl acetate in hexane, passed through a pad of $SiO_2$, and concentrated to yield white foam (12.73 g, 91%, mixture of anomers with an 8:1 ratio).

$R_f$=0.38 (30% ethyl acetate in hexanes); IR (neat) 1728, 1449, 1261, 1106 cm⁻¹; Formula $C_{35}H_{30}O_9$; MW 594.6073; For major anomer: ¹H NMR (500 MHz, CDCl₃) δ 8.11-8.00 (m, 6H), 7.96-7.88 (m, 2H), 7.63-7.52 (m, 3H), 7.44 (td, J=7.8, 4.5 Hz, 7H), 7.23 (t, J=7.7 Hz, 2H), 6.72 (s, 1H), 5.90 (d, J=6.6 Hz, 1H), 4.75-4.52 (m, 5H), 1.47 (s, 3H); ¹³C NMR (125 MHz, CDCl₃) δ 166.4, 166.2, 165.8, 165.3, 133.9, 133.7, 133.5, 133.1, 130.0, 130.0, 130.0, 129.8, 129.8, 129.8, 128.8, 128.7, 128.3, 101.0, 80.7, 78.6, 65.7, 65.5, 50.3, 16.7; HRMS calcd for [M+NH$_4^+$]: 612.2234, found: 612.2234; calcd for [M+Na$^+$]: 617.1788, found: 617.1789.

Example 2.30—Intermediate Compound

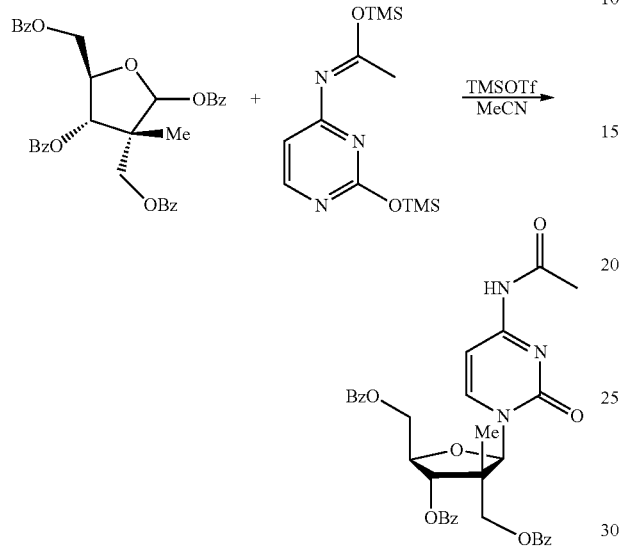

((2R,3S,4R,5R)-5-(4-acetamido-2-oxopyrimidin-1(2H)-yl)-3-(benzoyloxy)-4-methyltetrahydrofuran-2,4-diyl)bis(methylene) dibenzoate. TMSOTf (2.2 g, 1.8 mL, 9.64 mmol) was added dropwise to a mixture of Bz-sugar (2.87 g, 4.82 mmol) and silylated N4-acetyl-cytosine [1M] in dry acetonitrile (9.64 mL, 9.64 mmol) under Ar at 0° C. (reaction mixture turned colorless). After 6 h, the mixture was quenched by addition of H$_2$O (10 mL) at 0° C., diluted with ethyl acetate, washed with distilled water and sat. NaHCO$_3$ solution. The organics were dried over MgSO$_4$, concentrated and fractionated (30% ethyl acetate in hexanes, 10% methanol in dichloromethane, and 20% methanol in dichloromethane) to yield the title compound as a white solid (2.81 g, 93% yield, ca.8:1 mixture of anomers β:α).

R$_f$=0.7 (10% MeOH in CH$_2$Cl$_2$); IR (neat) 2968, 1723, 1658, 1492, 1261, 1089 cm$^{-1}$; Formula C$_{34}$H$_{31}$N$_3$O$_9$; MW 625.6246; $^1$H NMR (500 MHz, CDCl$_3$) δ10.46 (s, 1H), 8.29-7.76 (m, 5H), 7.70-7.29 (m, 10H), 6.57 (s, 1H), 5.62-5.42 (m, 1H), 4.91-4.50 (m, 6H), 2.29 (s, 3H), 1.15 (s, 3H); $^{13}$C NMR (125 MHz, CDCl$_3$) δ 171.5, 166.2, 165.9, 165.6, 163.2, 155.4, 144.4, 133.8, 133.6, 133.3, 129.8, 129.7, 129.6, 129.6, 129.6, 129.6, 129.5, 128.7, 128.6, 128.6, 128.5, 128.5, 97.1, 89.4, 80.1, 77.3, 66.3, 63.1, 49.5, 24.9, 17.5; $^1$H NMR (500 MHz, CDs) δ 8.16-8.09 (m, 4H), 8.04-8.00 (m, 2H), 7.51 (d, J=7.5 Hz, 1H), 7.15-7.05 (m, 6H), 7.00 (t, J=7.6 Hz, 2H), 6.58 (s, 1H), 5.47 (s, 1H), 4.81-4.68 (m, 2H), 4.66-4.50 (m, 2H), 4.39 (d, J=4.2 Hz, 1H), 4.29 (d, J=7.5 Hz, 1H), 1.97 (s, 3H), 0.86 (s, 3H); $^{13}$C NMR (125 MHz, C$_6$D6) δ 171.0, 166.2, 166.1, 165.7, 163.3, 156.3, 144.3, 133.7, 133.5, 133.2, 130.1, 130.0, 129.9, 128.8, 128.8, 128.7, 97.2, 89.6, 80.2, 77.9, 66.5, 63.6, 49.8, 24.4, 17.1; HRMS calcd for [M+H$^+$]: 626.2139, found: 626.2141; calcd for [M+Na$^+$]: 648.1958, found: 648.1959.

Example 2.31—Intermediate Compound

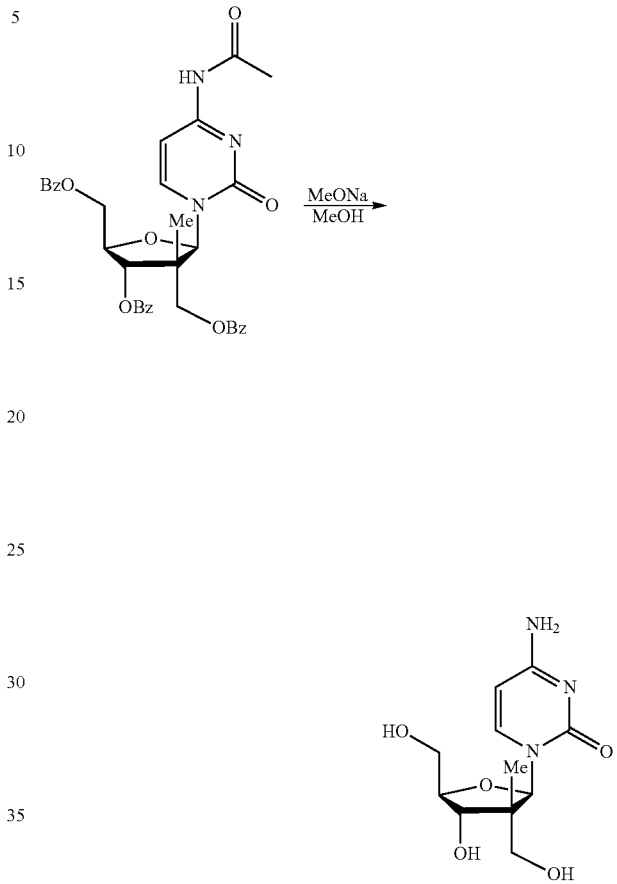

4-amino-1-((2R,3R,4S,5R)-4-hydroxy-3,5-bis(hydroxymethyl)-3-methyltetrahydro furan-2-yl)pyrimidin-2(1H)-one. NaOMe in MeOH 25% wt (1 mL, 4.4 mmol) was added to a solution of protected nucleosides (2.77 g, 4.40 mmol) in dry MeOH (34 mL) under Ar at rt. After 20 h, HCl 1N (4.4 mL, 4.4 mmol) was added, verifying that pH=7. The reaction mixture was concentrated to produce the crude as yellow foam (1.75 g, 9:1 mixture of anomers β:α). The crude was purified by reverse phase (C18) column chromatography with a gradient of H$_2$O:MeOH for compound characterization. Otherwise, the crude mixture was used for the next reaction.

R$_f$=0.04 (10% MeOH in CH$_2$Cl$_2$); IR (neat) 3344, 3215, 1648, 1492, 1046 cm$^{-1}$; Formula C$_{11}$H$_{17}$N$_3$O$_5$; MW 271.2698; $^1$H NMR (500 MHz, CD$_3$OD) δ 8.19 (d, J=7.4 Hz, 1H), 6.17 (s, 1H), 5.95 (d, J=7.2 Hz, 1H), 4.04-3.89 (m, 3H), 3.81 (d, J=11.5 Hz, 1H), 3.76 (dd, J=12.0, 2.3 Hz, 1H), 3.72 (d, J=10.6 Hz, 1H), 0.83 (s, 3H); $^{13}$C NMR (125 MHz, CD$_3$OD) δ 166.3, 157.0, 144.1, 95.3, 91.0, 85.1, 76.7, 66.1, 61.1, 51.3, 17.5; HRMS calcd for [M+H$^+$]: 272.1246, found: 272.1238; calcd for [M+Na$^+$]: 294.1066, found: 294.1058; [α]$_D$ +124 (c 1.0, CH$_3$OH). For α-anomer: $^1$H NMR (500 MHz, CD$_3$OD) δ 7.84 (d, J=7.5 Hz, 1H), 5.94 (s, 1H), 5.86 (d, J=7.5 Hz, 1H), 4.31 (td, J=5.9, 3.5 Hz, 1H), 3.99 (d, J=6.5 Hz, 1H), 3.79 (dd, J=12.0, 3.5 Hz, 1H), 3.65 (dd, J=12.0, 5.5 Hz, 1H), 3.54 (d, J=11.4 Hz, 1H), 3.45 (d, J=11.4 Hz, 1H), 1.26 (s, 3H).

195
Example 2.32—Intermediate Compound

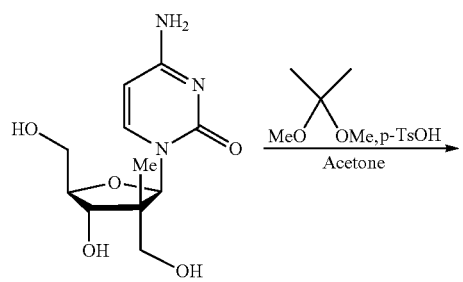

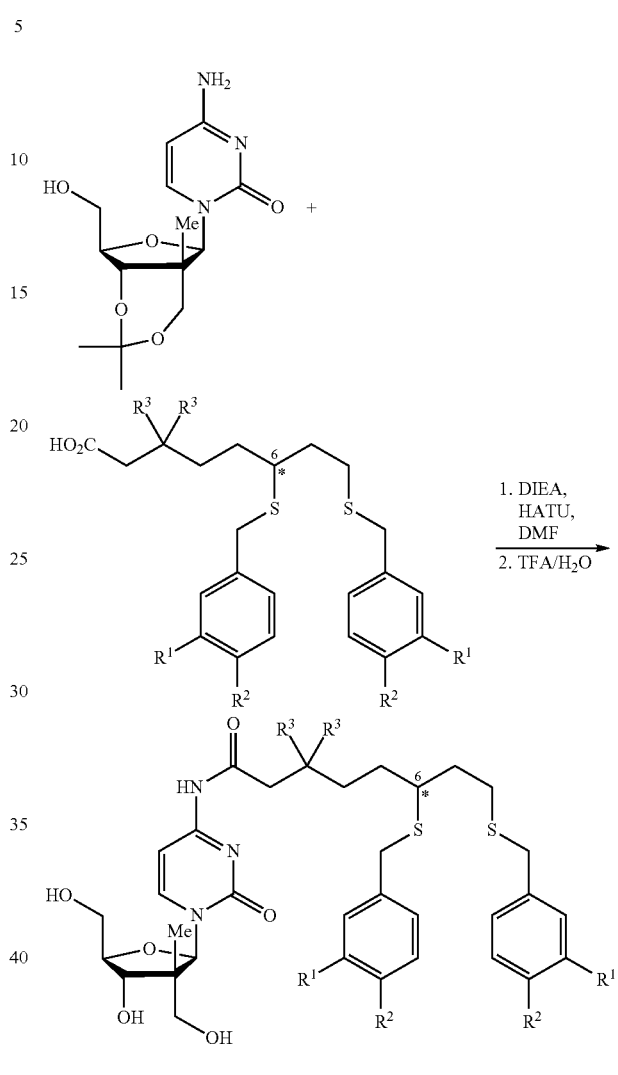

4-amino-1-((4aR,5R,7R,7aS)-7-(hydroxymethyl)-2,2,4a-trimethyltetrahydro-4H-furo [3,4-d][1,3]dioxin-5-yl)pyrimidin-2(1H)-one. 2,2-dimethoxy propane (6.7 g, 8.0 mL, 64.14 mmol) was added to a crude mixture of nucleoside (1.75 g, 4.4 mmol), p-TsOH.H$_2$O (1.2 g, 6.41 mmol), molecular sieves 3 Å, and dry acetone (160 mL). After 23 h, the reaction mixture was concentrated, suspended in MeOH and basic resin was added (2.7 g). After 2 h, the mixture was filtered, rinsed with MeOH, concentrated, and fractionated (10% methanol in dichloromethane) to yield 1.25 g of the title compound mixed with pTsOH.H$_2$O. The fraction was suspended in 20 mL of MeOH and stirred for 1 h with basic resin (2 g). After filtration and concentration, the title compound was obtained as a white solid (1.156 g, 84% yield, 12:1 mixture of anomers β:α).

R$_f$=0.5 (10% MeOH in CH$_2$Cl$_2$); IR (neat) 3339, 3199, 2979, 2936, 1642, 1487, 1379, 1282, 1224, 1057 cm$^{-1}$; Formula C$_{14}$H$_{21}$N$_3$O$_5$; MW 311.3336; $^1$H NMR (500 MHz, CD$_3$OD) δ 7.91 (d, J=7.3 Hz, 1H), 5.91 (s, 1H), 5.87 (dd, J=7.7, 3.1 Hz, 1H), 4.08 (d, J=13.0 Hz, 1H), 4.04-3.98 (m, 1H), 3.92 (t, J=2.5 Hz, 1H), 3.83 (dt, J=12.6, 2.6 Hz, 1H), 3.76-3.69 (m, 1H), 3.50 (d, J=11.9 Hz, 1H), 1.36 (d, J=8.5 Hz, 6H), 0.85 (s, 3H); $^{13}$C NMR (125 MHz, CD$_3$OD) δ 167.4, 157.8, 143.1, 126.9, 100.7, 95.0, 91.9, 85.3, 79.7, 67.4, 62.8, 25.8, 22.8, 17.1; HRMS calcd for [M+H$^+$]: 312.1559, found: 312.1557; calcd for [M+Na$^+$]: 334.1379, found: 334.1376; [α]$^D$ +123 (c 0.48, CH$_3$OH).

196
Example 2.33—Representative Experimental Procedure for the Synthesis of C2'-Nucleoside-Lipoate Conjugates

Example 3—Chemical Synthesis Details—Group C Compounds

Example 3.1—Preparation of Intermediate

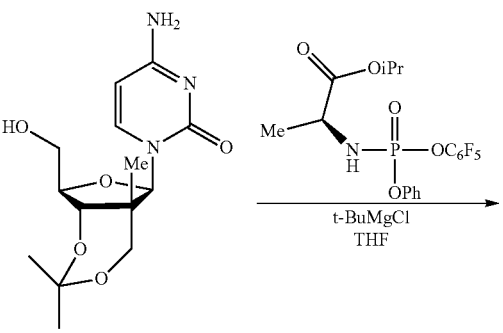

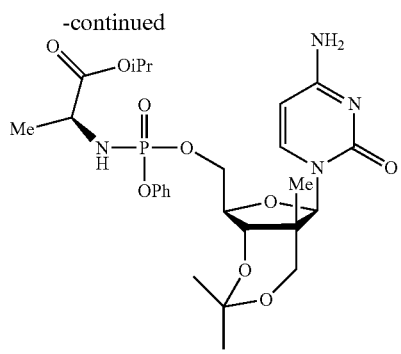

(2S)-isopropyl 2-(((((4aR,5R,7R,7aS)-5-(4-amino-2-oxopyrimidin-1(2H)-yl)-2,2,4a-trimethyltetrahydro-4H-furo[3,4-d][1,3]dioxin-7-yl)methoxy)(phenoxy)phosphoryl)amino)propanoate. tBuMgCl [1M] in THF (4.0 mL, 4.0 mmol) was added dropwise to a solution of nucleoside (952 mg, 3.058 mmol) in THF (18 mL) under Ar at room temperature. After 40 min, a solution of phosphoramidate (1.8 g, 3.98 mmol) in THF (20 mL) was added via cannula. After 2 h, the reaction was quenched at room temperature with MeOH (5 mL), concentrated, diluted with dichloromethane and washed with distilled water. The aqueous phase was extracted ×3 with dichloromethane, the organics were dried over MgSO$_4$, concentrated and fractionated (50% Ethyl acetate in dichloromethane, 10%-20% methanol in dichloromethane) to yield the title compound as a white solid (1.46 g, 95% yield, 9:1 mixture of β:α anomers).

R$_f$=0.3 (10% MeOH in CH$_2$Cl$_2$); IR (neat) 3333, 3199, 2984, 2941, 1734, 1648, 1492, 1207 cm$^{-1}$; Formula C$_{26}$H$_{37}$N$_4$O$_9$P; MW 580.5671; $^1$H NMR (500 MHz, CDCl$_3$) δ 7.72 (dd, J=7.8, 4.3 Hz, 1H), 7.33 (t, J=7.9 Hz, 2H), 7.22 (d, J=8.0 Hz, 2H), 7.17 (t, J=7.4 Hz, 1H), 5.92 (d, J=2.9 Hz, 1H), 5.67 (d, J=7.5 Hz, 1H), 5.01 (pd, J=6.3, 3.0 Hz, 1H), 4.37 (ddd, J=11.0, 7.4, 3.4 Hz, 1H), 4.24 (ddd, J=11.5, 7.1, 4.5 Hz, 1H), 4.18-4.07 (m, 2H), 4.03-3.90 (m, 1H), 3.79-371 (m, 2H), 3.54 (dd, J=12.2, 3.2 Hz, 1H), 1.41-1.35 (m, 6H), 1.31 (s, 3H), 1.27-1.18 (m, 6H), 0.77 (s, 3H); $^{13}$C NMR (125 MHz, CDCl$_3$) δ 172.9, 172.9, 165.7, 155.5, 150.7, 150.7, 141.5, 129.8, 125.1, 120.1, 120.1, 99.8, 94.1, 90.5, 81.1, 81.1, 78.4, 69.3, 66.4, 65.9, 50.4, 48.5, 25.2, 22.8, 21.7, 21.7, 20.9, 20.9, 16.7; HRMS calcd for [M+H$^+$]: 581.2376, found: 581.2377; calcd for [M+Na$^+$]: 603.2196, found: 603.2194; [α]$_D$ +90 (c 1.06, CH$_2$Cl$_2$).

Example 3.2—Representative Experimental Procedures for the Synthesis of Phosphoramidate Prodrug Nucleoside-Lipoate Conjugates

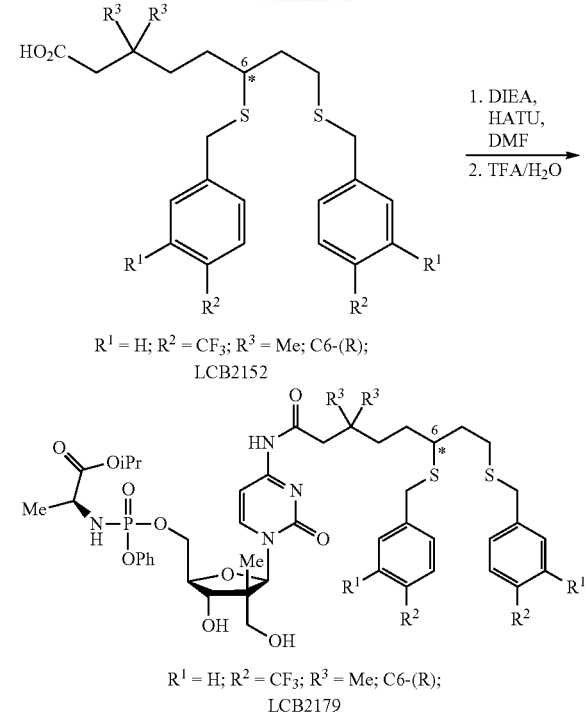

R$^1$ = H; R$^2$ = CF$_3$; R$^3$ = Me; C6-(R); LCB2152

R$^1$ = H; R$^2$ = CF$_3$; R$^3$ = Me; C6-(R); LCB2179

Et$_3$N (3 equiv) was added to a solution of the appropriate lipoate analogue (1.1 equiv) and HATU (1.1 equiv) in dry DMF (0.13 M) under Ar at room temperature. The mixture was stirred for 10 min and then transferred to a solution of prodrug (1 equiv) in DMF (0.13 M). After 28 h at room temperature, the mixture was diluted with ethyl acetate, washed with a saturated solution of NaCl, dried over MgSO$_4$, concentrated and fractionated (50-100% ethyl acetate in hexanes) to yield the acetonide-protected compound. To a solution of the latter (1 equiv) in THF (0.1M) at room temperature and open atmosphere) was added a mixture of TFA/H$_2$O (8:2) (0.1 M). After 30 minutes, the reaction was concentrated in vacuo and fractionated by FCC to yield the title compound.

Example 3.3—Intermediate Compound

Isopropyl (((((4aR,5R,7R,7aS)-5-(4-(3,3-dimethyl-6,8-bis((4-(trifluoromethyl)benzyl)thio)octanamido)-2-oxopyrimidin-1(2H)-yl)-2,2,4a-trimethyltetrahydro-4H-furo[3,4-d][1,3]dioxin-7-yl)methoxy)(phenoxy)phosphoryl)-L-alaninate

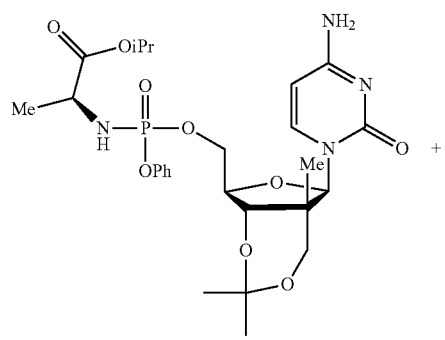

+

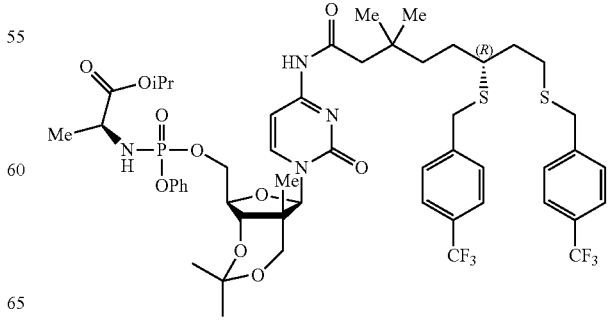

Reaction was performed with prodrug (26 mg, 44.4 umol) of using general procedure for 46 h at 60° C., and fractionated by FCC (50-100% ethyl acetate in hexanes) to yield the title compound (35.1 mg, 71% yield).

$R_f$=0.63 (100% EtOAc); IR (neat) 3419, 2984, 2931, 1653, 1491, 1324 cm$^{-1}$; Formula $C_{52}H_{65}F_6N_4O_{10}PS_2$; MW 1115.19; $^1$H NMR (500 MHz, CD$_3$OD) δ 8.14 (d, J=7.6 Hz, 1H), 7.57 (t, J=9.1 Hz, 4H), 7.51-7.43 (m, 5H), 7.36 (t, J=7.9 Hz, 2H), 7.29-7.23 (m, 2H), 7.19 (t, J=7.4 Hz, 1H), 5.94 (s, 1H), 4.98 (p, J=6.3 Hz, 1H), 4.41 (ddd, J=10.8, 6.7, 3.4 Hz, 1H), 4.30 (ddd, J=11.3, 6.9, 4.2 Hz, 1H), 4.21 (s, 1H), 4.12-4.06 (m, 2H), 3.97 (d, J=3.2 Hz, 1H), 3.93 (dt, J=10.5, 7.1 Hz, 1H), 3.72 (s, 4H), 3.49 (d, J=12.0 Hz, 1H), 2.58-2.53 (m, 1H), 2.50 (td, J=7.4, 7.0, 2.1 Hz, 2H), 2.27 (s, 2H), 1.81-1.61 (m, 2H), 1.54-1.40 (m, 2H), 1.39-1.32 (m, 11H), 1.22 (dt, J=6.1, 3.0 Hz, 6H), 0.97 (s, 6H), 0.72 (s, 3H) NH signal missing possibly due to exchange in CD$_3$OD; $^{13}$C NMR (125 MHz, CD$_3$OD) δ 174.29 (d, J=5.2 Hz), 174.22, 164.2, 157.7, 152.2, 146.5, 145.3 (d, J=1.3 Hz), 145.1 (d, J=1.3 Hz), 130.9, 130.7, 130.6, 126.36, 126.33, 126.30, 126.27, 121.3 (d, J=4.8 Hz), 101.0, 97.6, 92.6, 83.3 (d, J=7.5 Hz), 79.6, 70.2, 67.5, 66.97, 66.93, 51.8, 49.7, 49.5, 46.3, 39.6, 36.4, 35.5, 35.2, 34.7, 30.5, 29.7, 27.9 (d, J=1.7 Hz), 25.6, 22.9, 22.0, 21.9, 20.5 (d, J=6.6 Hz), 17.0; HRMS calcd for [M+Na$^+$]: 1137.3676, found: 1137.3674 (−0.15 ppm); [α]$_D$ +33 (c 0.94, CD$_2$Cl$_2$).

Example 3.4—Antitumor/Antiviral Compound-LCB2179

Isopropyl ((((2R,3S,4R,5R)-5-(4-(3,3-dimethyl-6,8-bis((4-(trifluoromethyl)benzyl)thio)octanamido)-2-oxopyrimidin-1(2H)-yl)-3-hydroxy-4-(hydroxymethyl)-4-methyltetrahydrofuran-2-yl)methoxy)(phenoxy)phosphoryl)-L-alaninate (LCB-2179)

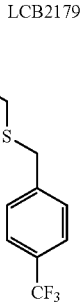

LCB2179

Reaction was performed with prodrug (26.5 mg, 23.8 umol) using general procedure for 30 min at rt, and fractionated by FCC (5% MeOH in CH$_2$Cl$_2$) to yield the title compound (15.3 mg, 60%).

$R_f$=0.38 (5:95 MeOH:DCM); IR (neat) 3199, 2936, 1653, 1492, 1324 cm$^{-1}$; Formula $C_{49}H_{61}F_6N_4O_{10}PS_2$; MW 1115.19; $^1$H NMR (500 MHz, CD$_3$OD) δ 8.12 (d, J=7.5 Hz, 1H), 7.57 (t, J=8.8 Hz, 4H), 7.48 (t, J=9.1 Hz, 5H), 7.36 (t, J=7.9 Hz, 2H), 7.27 (d, J=8.1 Hz, 2H), 7.18 (t, J=7.4 Hz, 1H), 6.25 (s, 1H), 4.97 (p, J=6.3 Hz, 1H), 4.50-4.43 (m, 1H), 4.39-4.31 (m, 1H), 4.22 (d, J=8.9 Hz, 1H), 3.99-3.88 (m, 2H), 3.84 (d, J=11.0 Hz, 1H), 3.72 (s, 6H), 2.55 (d, J=6.2 Hz, 1H), 2.50 (t, J=7.6 Hz, 2H), 2.26 (s, 2H), 1.71 (dp, J=29.3, 7.2 Hz, 2H), 1.53-1.40 (m, 2H), 1.39-1.26 (m, 5H), 1.20 (dt, J=4.6, 2.2 Hz, 6H), 0.97 (s, 6H), 0.71 (s, 3H) OH and NH signal missing possibly due to exchange in CD$_3$OD; $^{13}$C NMR (125 MHz, CD$_2$Cl$_2$) δ 173.4 (d, J=6.8 Hz), 172.0, 162.5, 156.2, 151.1 (d, J=6.7 Hz), 145.5, 143.8, 143.6 (d, J=1.3 Hz), 130.2, 129.7, 129.6, 125.78, 125.75, 125.72, 125.69, 125.5, 120.7 (d, J=4.9 Hz), 96.7, 89.3, 82.9, 78.5, 69.9, 65.7, 65.5, 50.9, 49.97, 49.3, 45.6, 39.1, 36.2, 35.0, 34.5, 34.1, 29.6, 29.2, 27.4 (d, J=6.4 Hz), 21.9, 21.8, 21.1 (d, J=5.4 Hz), 17.2; HRMS calcd for [M+Na$^+$]: 1097.3363, found: 1097.3371 (0.73 ppm); [α]$_D$ +26 (c 0.91, CD$_3$OD).

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

1. Basavapathruni, A.; Jin, L.; Daigle, S. R.; Majer, C. R. A.; Therkelsen, C. A.; Wigle, T. J.; Kuntz, K. W.; Chesworth, R.; Pollock, R. M.; Scott, M. P.; Moyer, M. P.; Richon, V. M.; Copeland, R. A.; Olhava, E. J. *Chem. Biol. Drug Des.* 2012, 80 (6), 971-980.
2. Giovannetti, E.; Del Tacca, M.; Mey, V.; Funel, N.; Nannizzi, S.; Ricci, S.; Orlandini, C.; Boggi, U.; Campani, D.; Del Chiaro, M.; Iannopollo, M.; Bevilacqua, G.; Mosca, F.; Danesi, R. *Cancer Res.* 2006, 66 (7), 3928-35.
3. Sofia, M. J.; Bao, D.; Chang, W.; Du, J.; Nagarathnam, D.; Rachakonda, S.; Reddy, P. G.; Ross, B. S.; Wang, P.; Zhang, H. R.; Bansal, S.; Espiritu, C.; Keilman, M.; Lam, A. M.; Steuer, H. M.; Niu, C.; Otto, M. J.; Furman, P. A. *J. Med. Chem.* 2010, 53 (19), 7202-18.
4. Global Burden of Disease Cancer, C. *JAMA Oncology* 2015, 1(4), 505-527.
5. Wilhelm, S.; Carter, C.; Lynch, M.; Lowinger, T.; Dumas, J.; Smith, R. A.; Schwartz, B.; Simantov, R.; Kelley, S. *Nat. Rev. Drug Discov.* 2006, 5 (10), 835-44.
6. Lönnberg, H.; Kulonpää, A. *Acta Chem. Scand.* 1977, 31, 306-312.
7. Shorr, R. R., L. Lakmal WO 2011/143593 A1.
8. (a) Stuart, S. D.; Schauble, A.; Gupta, S.; Kennedy, A. D.; Keppler, B. R.; Bingham, P. M.; Zachar, Z. *Cancer Metab* 2014, 2 (1), 4;
   (b) Nerstone Pharmaceuticals: WO 2011/143593 A1; (c) Zachar, Z.; Marecek, J.; Maturo, C.; Gupta, S.; Stuart, S. D.; Howell, K.; Schauble, A.; Lem, J.; Piramzadian, A.; Karnik, S.; Lee, K.; Rodriguez, R.; Shorr, R.; Bingham, P. M. *J. Mol. Med.* 2011, 89(11), 1137.
9. DeBerardinis, R. J.; Lum, J. J.; Hatzivassiliou, G.; Thompson, C. B. *Cell Metab.* 2008, 7(1), 11-20.
10. Bartlett, K.; Eaton, S. *Eur. J. Biochem.* 2004, 271 (3), 462-469.
11. (a) Abeysuriya, K.; Wu, X.; Franck, C. *Phys Rev B. Condens Matter* 1987, 35 (13), 6771-6778;
    (b) Quilici, M.; Dunan, S.; Dumon, H.; Franck, J.; Gambarelli, F.; Toga, I.; Perrimond, H.; Michel, G.; Mattei, M. *Ann. Pediatr.* (Paris) 1987, 34 (5), 369-73.
12. Remington's Pharmaceutical Sciences, t. E., (Mack Publishing Company, Easton, Pa., 1990).
13. Tambutet, G.; Becerril-Jimenez, F.; Dostie, S.; Simard, R.; Prevost, M.; Mochirian, P.; Guindon, Y. *Org. Lett.* 2014, 16 (21), 5698-5701.
14. Dostie, S.; Prevost, M.; Mochirian, P.; Tanveer, K.; Andrella, N.; Rostami, A.; Tambutet, G.; Guindon, Y. *J. Org. Chem.* 2016, 81(22), 10769-10790.

15. Hjeresen, D. L.; Franck, J. E.; Amend, D. L. *Dev. Psychobiol.* 1987, 20 (3), 355-63.
16. Cahilly-Snyder, L.; Yang-Feng, T.; Francke, U.; George, D. L. *Somat. Cell Mol. Genet.* 1987, 13 (3), 235-44.
17. Neelarapu, R.; Holzle, D. L.; Velaparthi, S.; Bai, H.; Brunsteiner, M.; Blond, S. Y.; Petukhov, P. A. *J. Med. Chem.* 2011, 54 (13), 4350-64.

The invention claimed is:
1. A compound of formula:

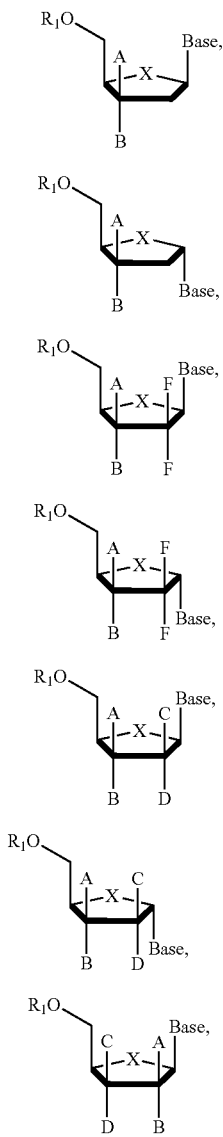

wherein:
A and B are $C_1$-$C_6$ alkyl, mono- to per-halo alkyl or —$(CH_2)_n$M, with the proviso that:
  A is different from B,
    when one of A and B is methyl, the other is $C_1$-$C_6$ alkyl, —$(CH_2)_n$M, or a mono- to per-halo alkyl other than —$CF_3$, and
  one of A and B is $C_2$-$C_6$ alkyl, the other is $C_1$-$C_6$ alkyl, —$(CH_2)_n$M, or a mono- to per-halo alkyl other than $C_2$-$C_6$ fluoroalkyl;

n is 1 to 3;
M is —$OR_2$, —$SR_2$, —CN, —C(O)$OR_3$, —OC(O)$R_4$,

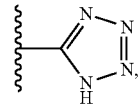

or —$NHR_{15}$;
$R_1$ is —H, —$C_1$-$C_6$ alkyl, alkylaryl, or a phosphoryl group of formula (XX):

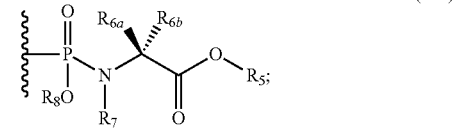

$R_2$ is H, $C_1$-$C_6$-alkyl, aryl-$C_1$-$C_6$ alkyl, or a phosphoryl group of formula (XX), each of the alkyl and aryl moieties being unsubstituted or substituted with one or more groups selected from halo, —CN, —C(O)OH, —C(O)$R_3$, —$N_3$, —$C_1$-$C_6$ alkyl, —C(O)$OR_4$, —$CF_3$, —$C_1$-$C_6$ alkyl-$N_3$, —$SiF_5$, and —$NHR_{15}$;
$R_3$ is H, $C_1$-$C_6$ alkyl, or aryl-$C_1$-$C_6$ alkyl, each of the alkyl and aryl moieties being unsubstituted or substituted with one or more groups selected from halo, —CN, —C(O)OH, —C(O)$OR_4$, —$N_3$, —$C_1$-$C_6$ alkyl-C(O)$OR_4$, —$CF_3$, —$C_1$-$C_6$ alkyl-$N_3$, and —$SiF_5$;
$R_4$ is $C_1$-$C_6$ alkyl, aryl, or aryl-$C_1$-$C_6$ alkyl, each of the alkyl and aryl moieties being unsubstituted or substituted with one or more groups selected from halo, —CN, —C(O)OH, —$N_3$, —$CF_3$, —$C_1$-$C_6$ alkyl-$N_3$, —$SiF_5$, and —$NHR_{15}$;
$R_5$ is H, $C_1$-$C_6$ alkyl, or arylalkyl;
$R_{6a}$ is H, methyl, isopropyl, n-propyl, or —$CH_2$—$CH_2$—SMe;
$R_{6b}$ is H or methyl;
$R_7$ is H or methyl;
$R_8$ is H, $C_1$-$C_6$ alkyl, or aryl, the aryl being unsubstituted or substituted with one group selected from $C_1$-$C_6$ alkyl and halo;
$R_{15}$ is H, $C_1$-$C_6$ alkyl, —$SO_2$-aryl or aryl, each of the aryl moieties being unsubstituted or substituted with one or more $C_1$-$C_6$ alkyl or halo;
X is O or S;
C and D are independently —H, —OH, halo, azido, —CN, —$NHR_2$, or —$CF_3$;
wherein when one of C and D is OH, the other is —H, —OH, azido, —CN, —$NHR_2$, or —$CF_3$,
Base is:

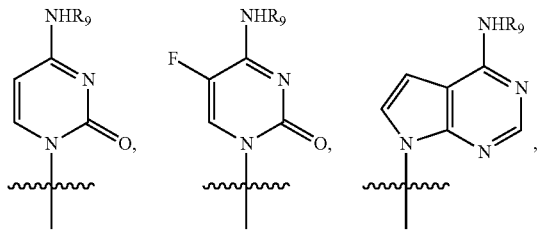

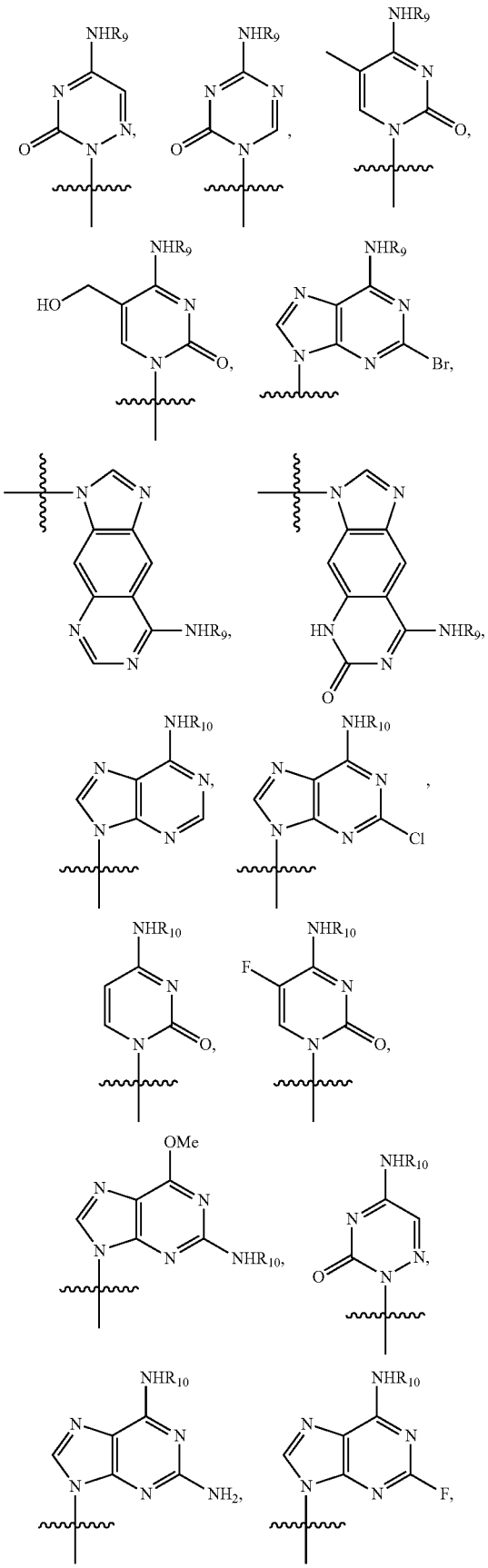

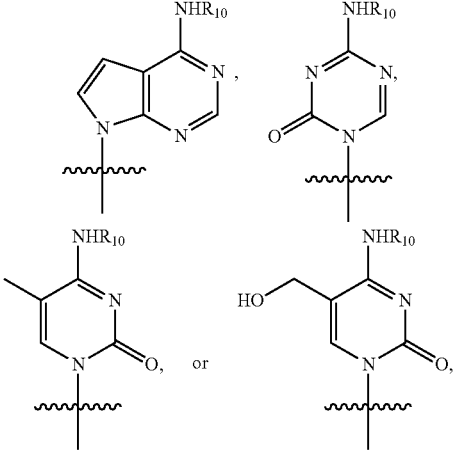

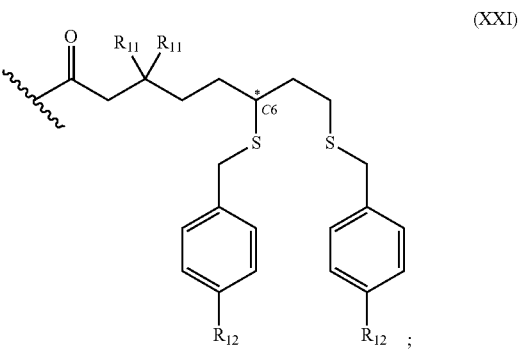

$R_9$ is $C_1$-$C_6$ alkyl, —C(O)—$C_1$-$C_6$ alkyl, —C(O)aryl, aryl, or arylalkyl, wherein each of the alkyl and aryl moieties is unsubstituted or substituted with one or more groups selected from halo, —$CF_3$, —$N_3$, and —$SF_5$;

$R_{10}$ represents a lipoate group of formula (XXI):

$R_{11}$ are the same of different, and represents F or methyl; and $R_{12}$ are the same of different, and represents F or —$CF_3$; and

* denotes the R, S, or R/S configuration, with the proviso that the compound comprises:
one or two phosphoryl groups of formula (XX), the compound being free of a lipoate group of formula (XXI),
one lipoate group of formula (XXI), the compound being free of a phosphoryl group of formula (XX), or
one lipoate group of formula (XXI) and only one phosphoryl group of formula (XX), said phosphoryl group being in $R_1$, and with the further proviso that when the compound is of formula XIII, the compound comprises one lipoate group of formula (XXI), or a pharmaceutically acceptable salt thereof.

2. The compound of claim 1, wherein the phosphoryl groups of formula (XX) is:

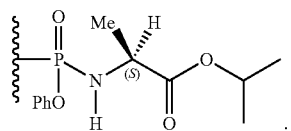

3. The compound of claim 1, wherein one of A and B is $C_1$-$C_6$ alkyl, and the other of A and B is —$(CH_2)_nM$, wherein M is —$OR_2$, —$OC(O)R_4$, —CN,

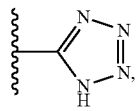

or —$NHR_{15}$, and wherein $R_2$ is H, $C_1$-$C_6$-alkyl, aryl-$C_1$-$C_6$ alkyl, or a phosphoryl group of formula (XX), each of the alkyl and aryl moieties being unsubstituted or substituted with one or more groups selected from halo, —CN, —C(O)OH, —C(O)$R_3$, —$N_3$, —$C_1$-$C_6$ alkyl, —C(O)$OR_4$, —$CF_3$, —$C_1$-$C_6$ alkyl-$N_3$, —$SiF_5$, and —$NHR_{15}$.

4. The compound of claim 1, wherein one of C and D is H and the other of C and D is halo or OH.

5. The compound of claim 1, wherein the lipoate group of formula (XXI) is:

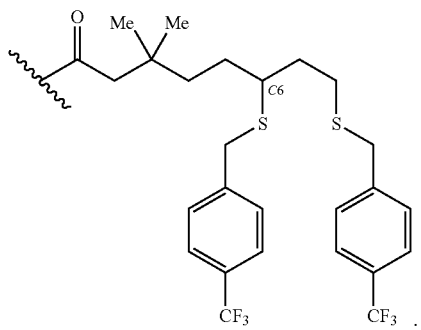 [SMILES: *C(=O)CC(C)(C)CCC(CCSCc1ccc(C(F)(F)F)cc1)SCc1ccc(C(F)(F)F)cc1]

6. The compound of claim 1, comprising one or two phosphoryl groups of formula (XX), and being free of a lipoate group of formula (XXI).

7. The compound of claim 6, comprising only one phosphoryl group of formula (XX).

8. The compound of claim 7, wherein one of A and B is —$(CH_2)_nM$, M is $OR_2$, and $R_2$ is a phosphoryl group of formula (XX).

9. A compound selected from:

LCB-1994

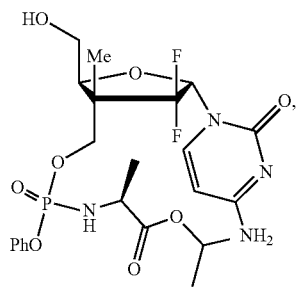

LCB-2137

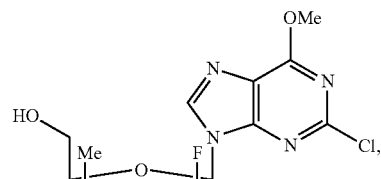

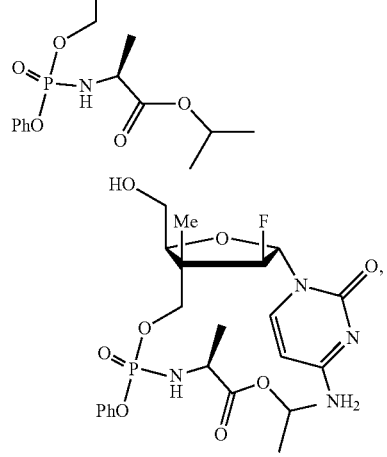

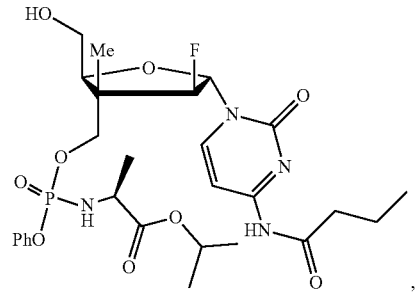

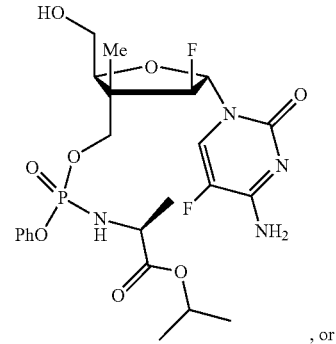

, or

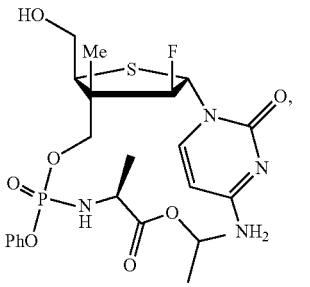

or a pharmaceutically acceptable salt thereof.

10. The compound of claim 7, wherein $R_1$ is a phosphoryl group of Formula (XX).

11. A compound selected from:
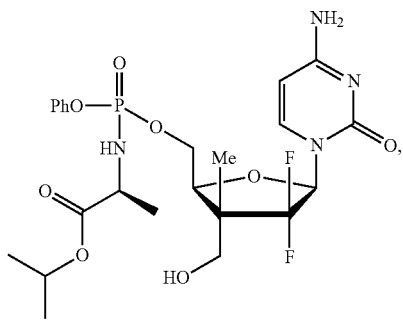
LCB-1992
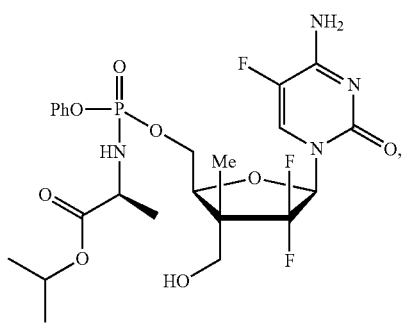
LCB-1998
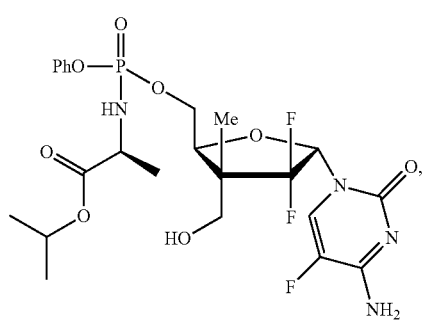
LCB-2000
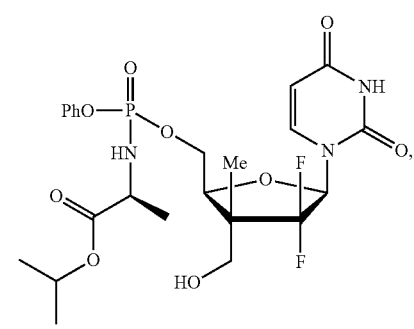
LCB-2001
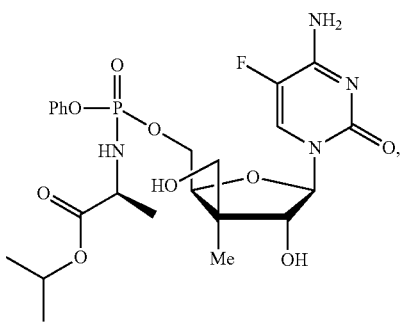
LCB-2018
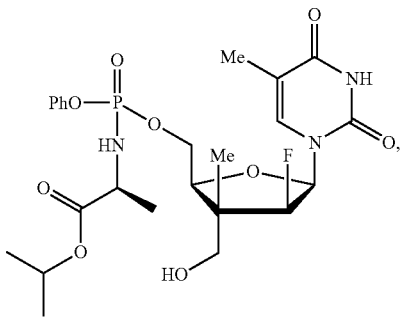
LCB-2027
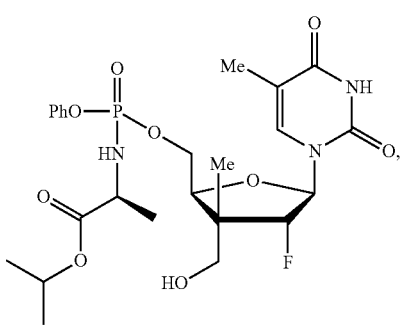
LCB-2028
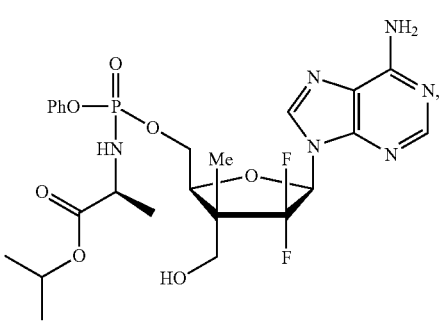
LCB-2034
LCB-2093

LCB-2106
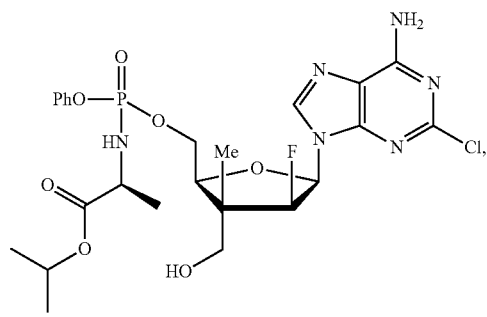
LCB-2142
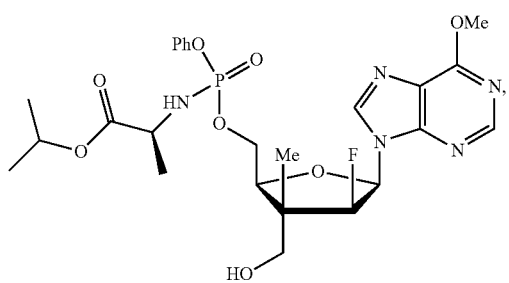
LCB-2146
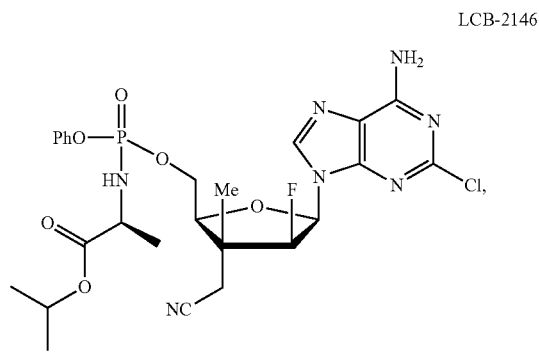
LCB-2147
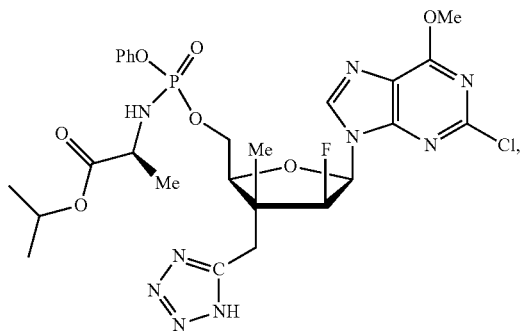
LCB-2168
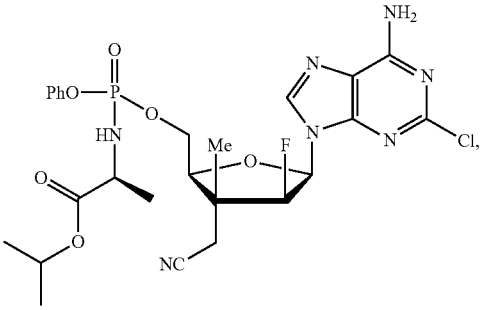
LCB-2172
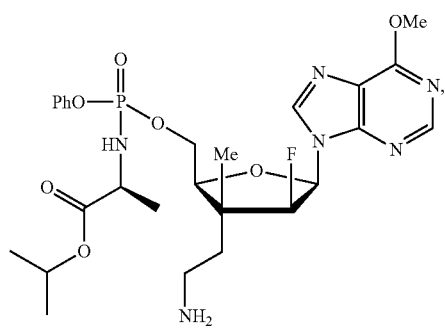
LCB-2173
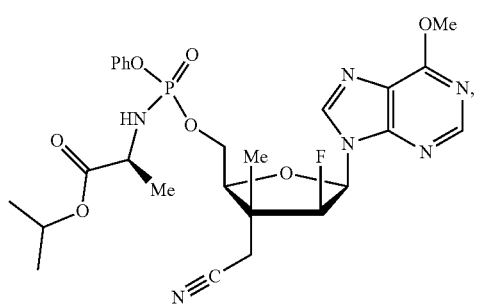
LCB-2174
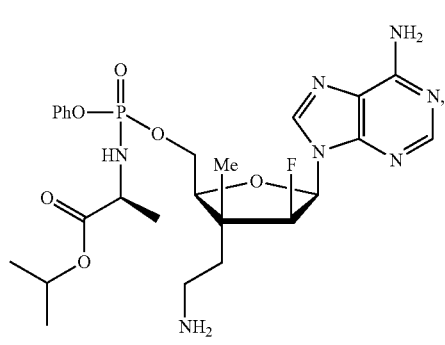
LCB-2175
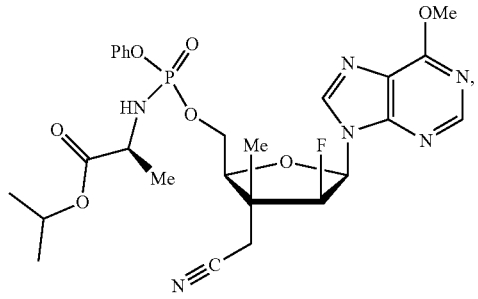

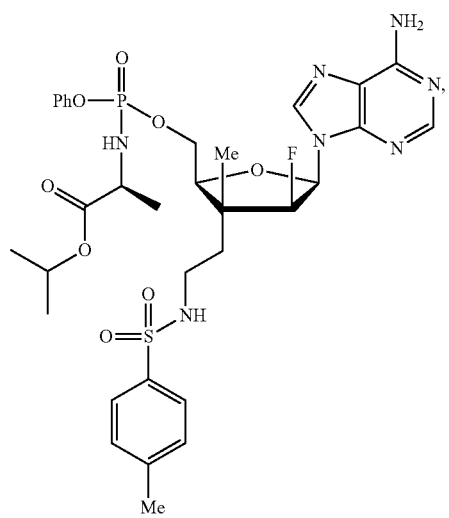
LCB-2176
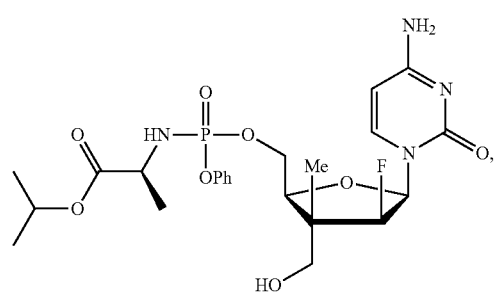
LCB-2187
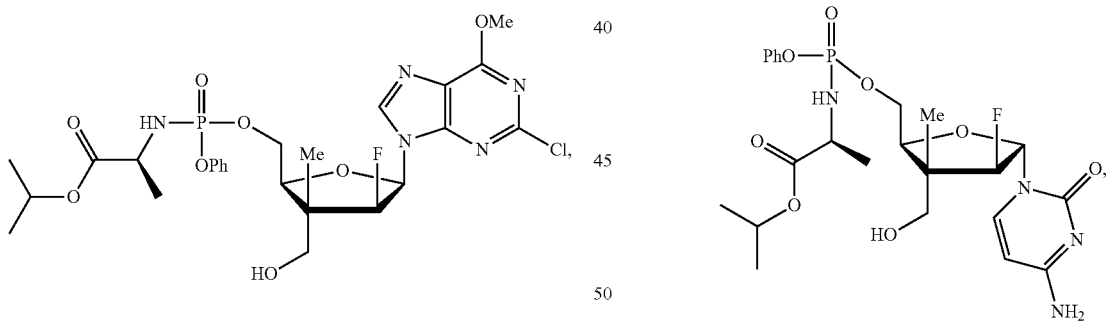
LCB-2189
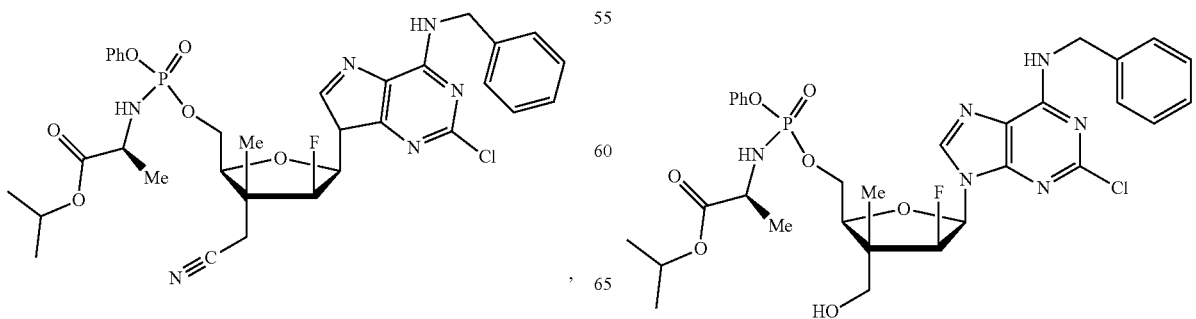
LCB-2201
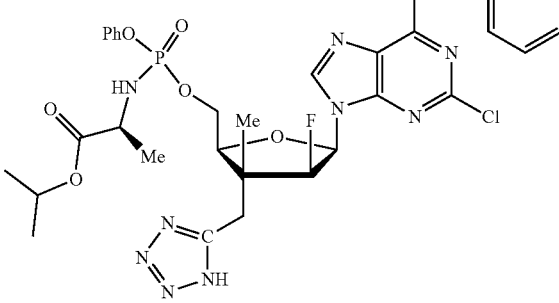
LCB-2220
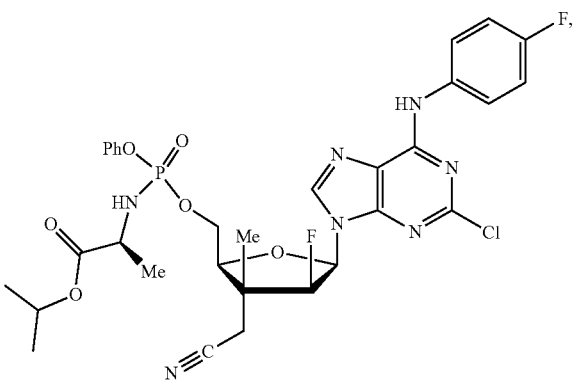
LCB-2229
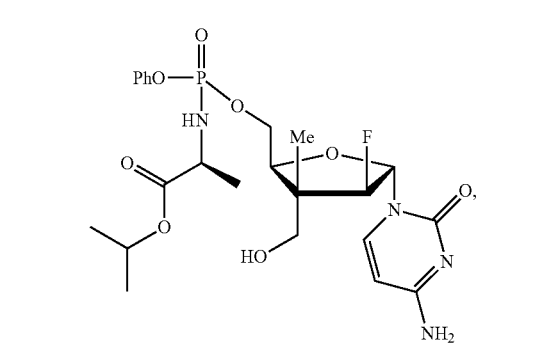
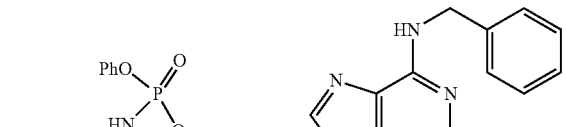

213
-continued
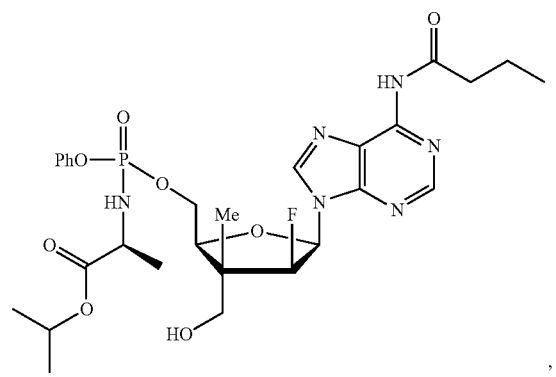
,
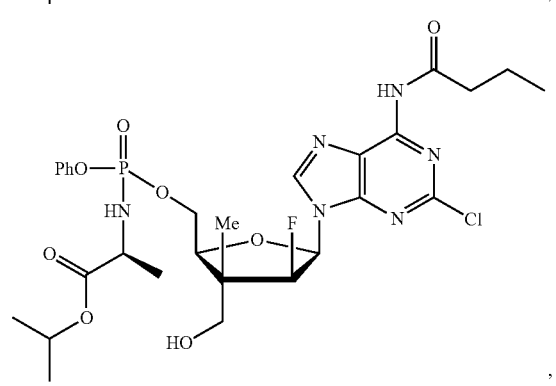
,
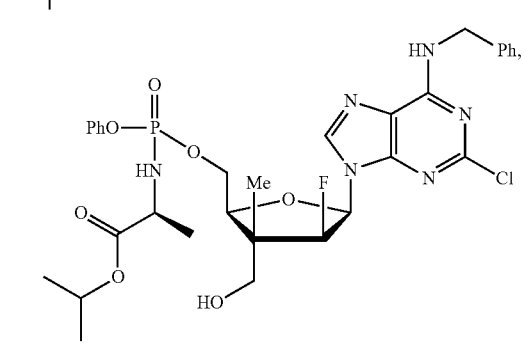
,
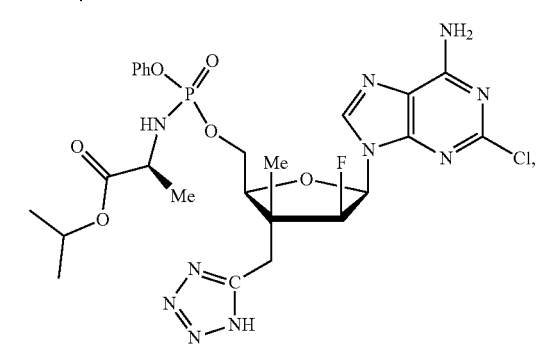
,
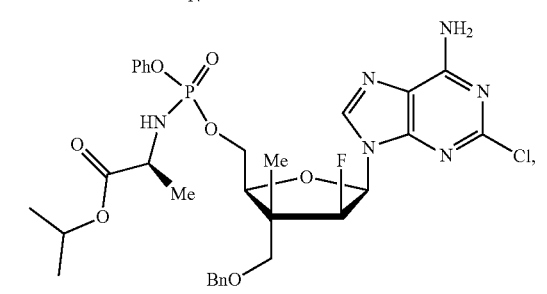
214
-continued
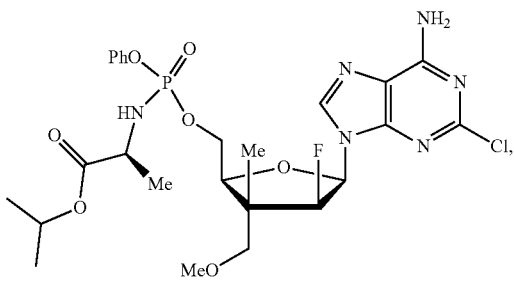
,
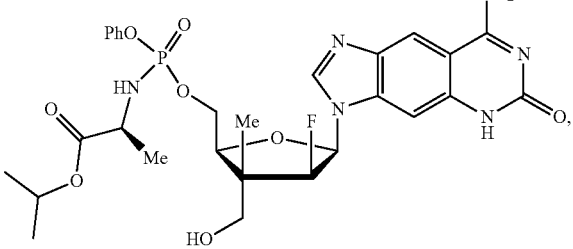
,
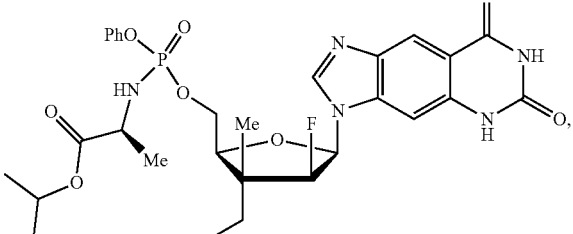
,
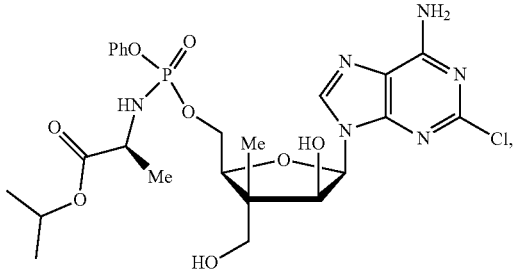
,
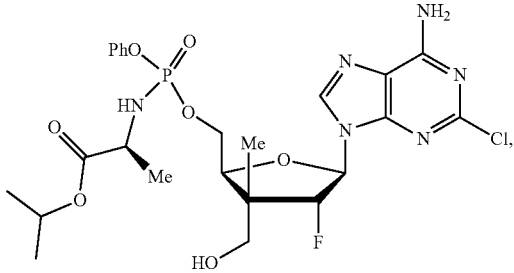
,
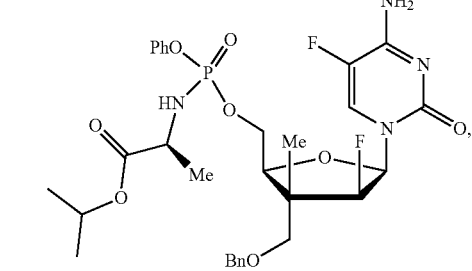

-continued
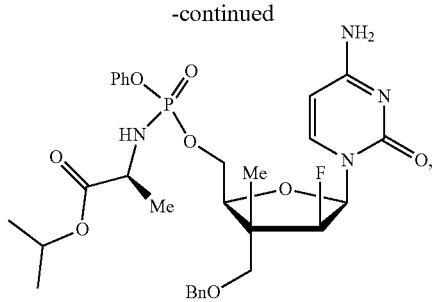
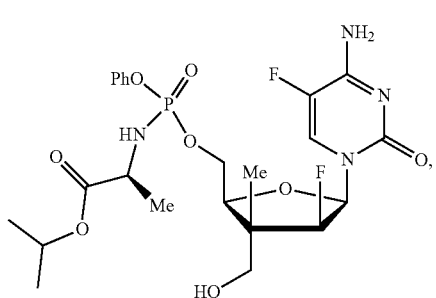
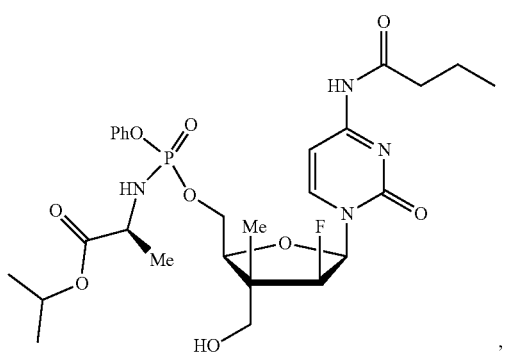
, or
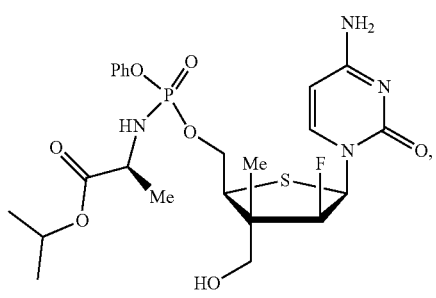
wherein Bn is benzyl, or a pharmaceutically acceptable salt thereof.
12. The compound of claim 1, comprising two phosphoryl groups of formula (XX), $R_1$ representing one said phosphoryl groups and one of A and B being —$(CH_2)_nM$, M being $OR_2$, and $R_2$ representing another of said phosphoryl group of formula (XX).
13. A compound selected from:
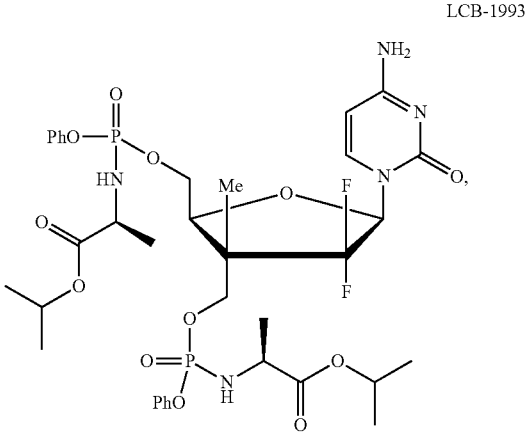
LCB-1993
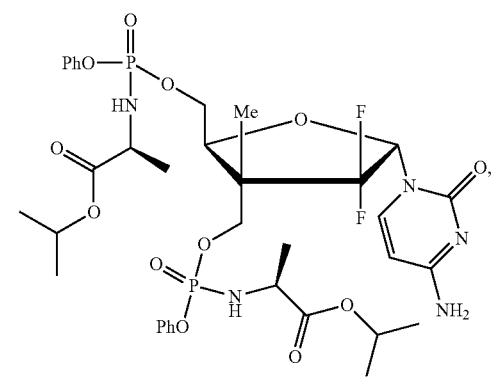
LCB-1995
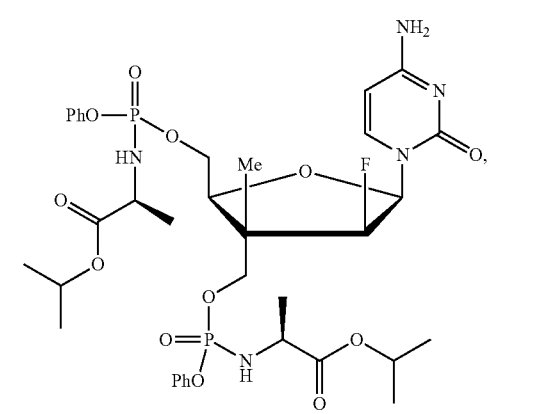
LCB-1996

LCB-1997
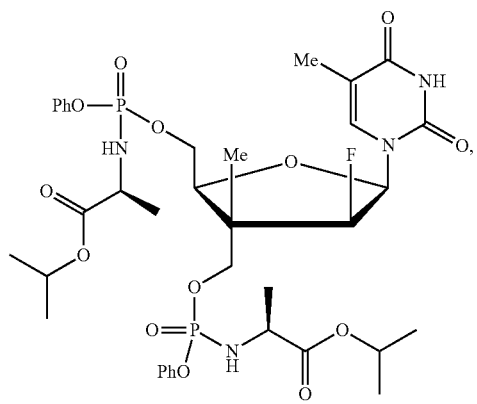
LCB-1999
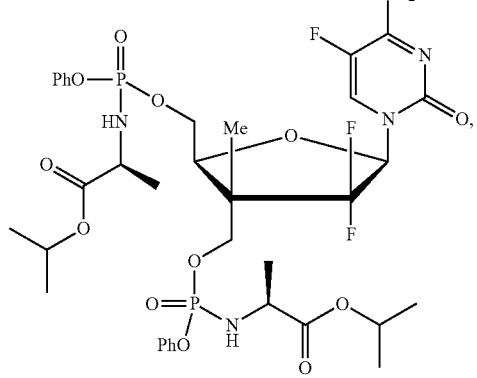
LCB-2002
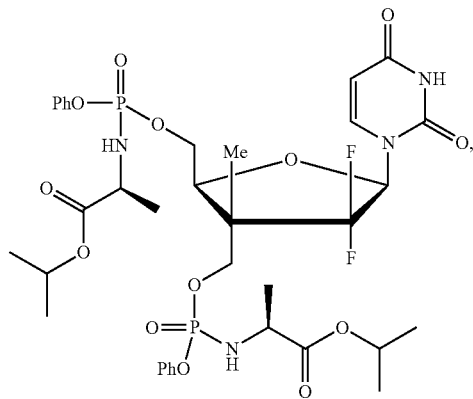
LCB-2009
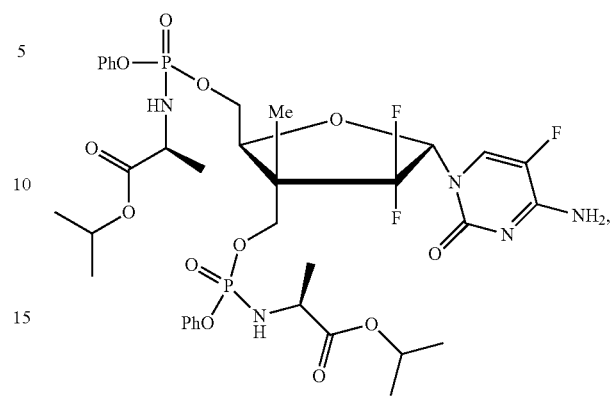
LCB-2015
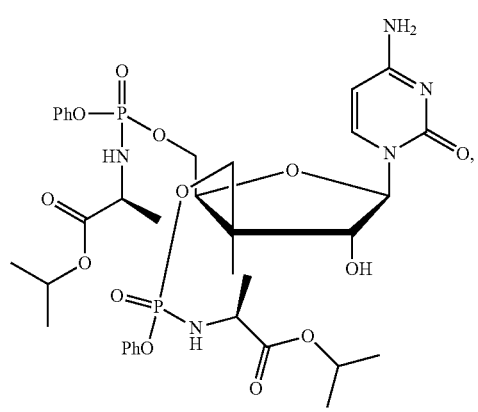
LCB-2016
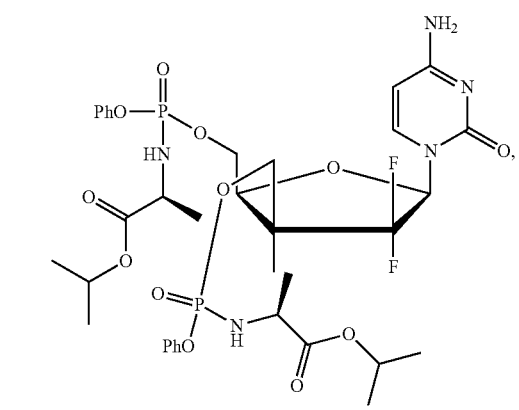
LCB-2017

219
-continued
LCB-2029
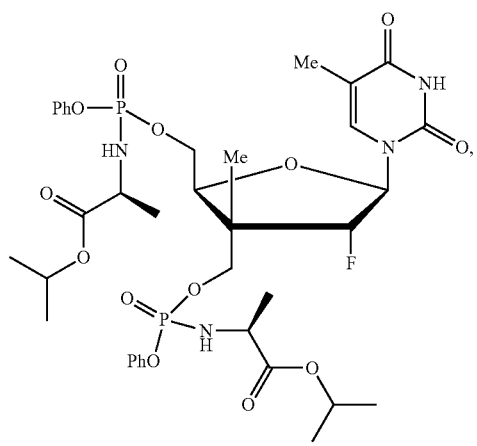
LCB-2035
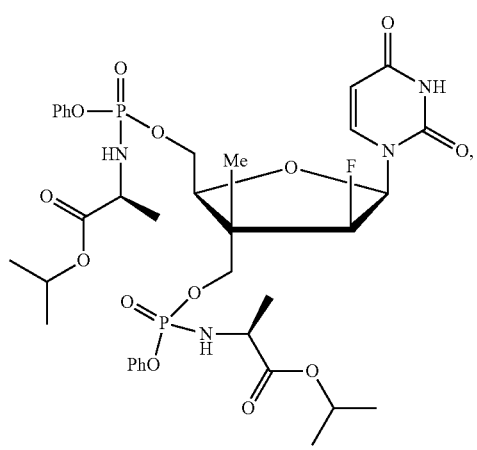
LCB-2036
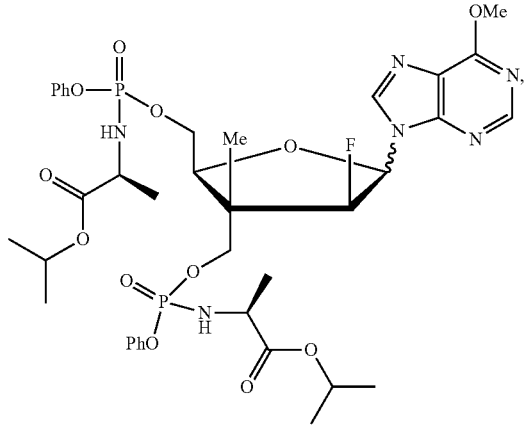
220
-continued
LCB-2045
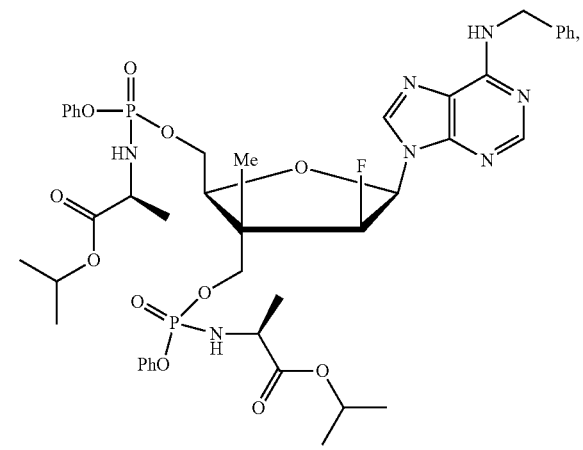
LCB-2076
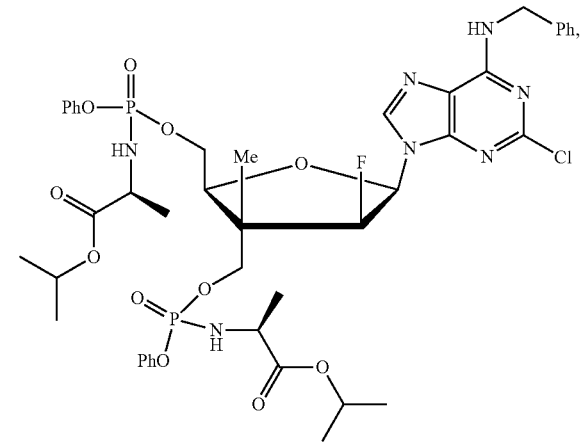
LCB-2079
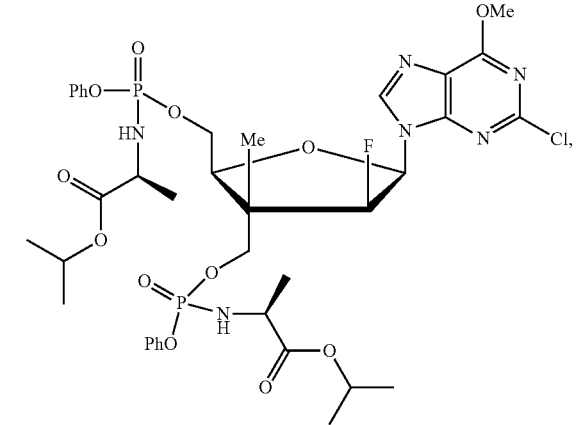

221
-continued
LCB-2080
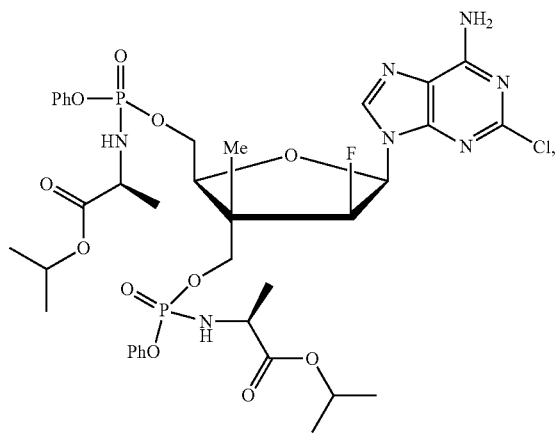
LCB-2088
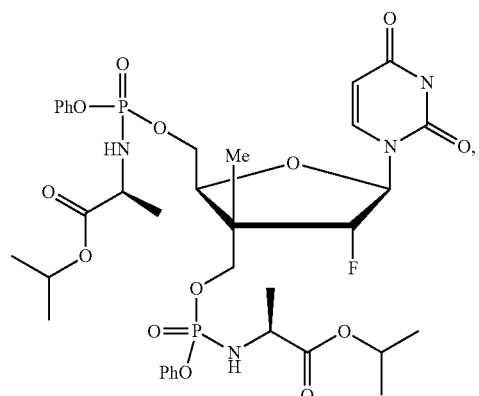
LCB-2092
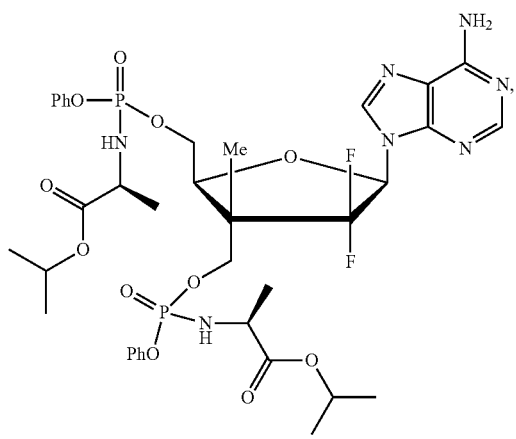
222
-continued
LCB-2095
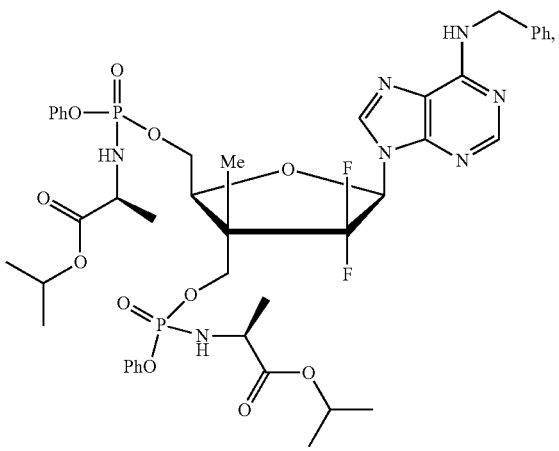
LCB-2105
LCB-2127
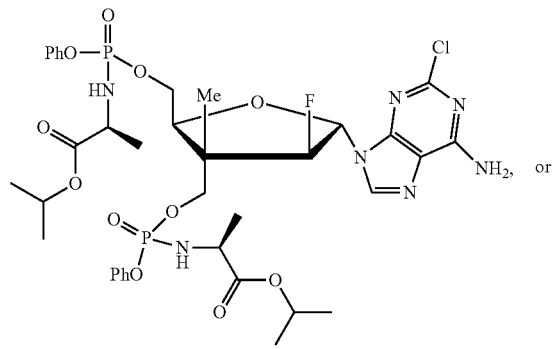

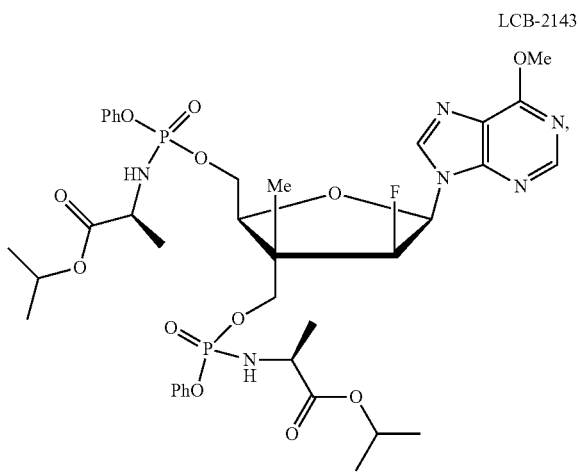
LCB-2143
or a pharmaceutically acceptable salt thereof.
14. The compound of claim 1, comprising one lipoate group of formula (XXI), said compound either being free of a phosphoryl group of formula (XX) or comprising a phosphoryl group of formula (XX) in $R_1$.
15. The compound of claim 14, being free of phosphoryl group.
16. A compound selected from:
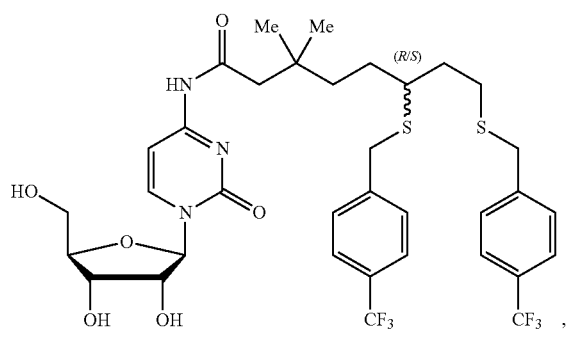
LCB-2125
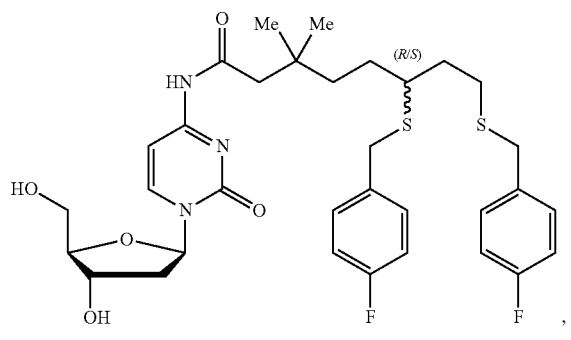
LCB-2131
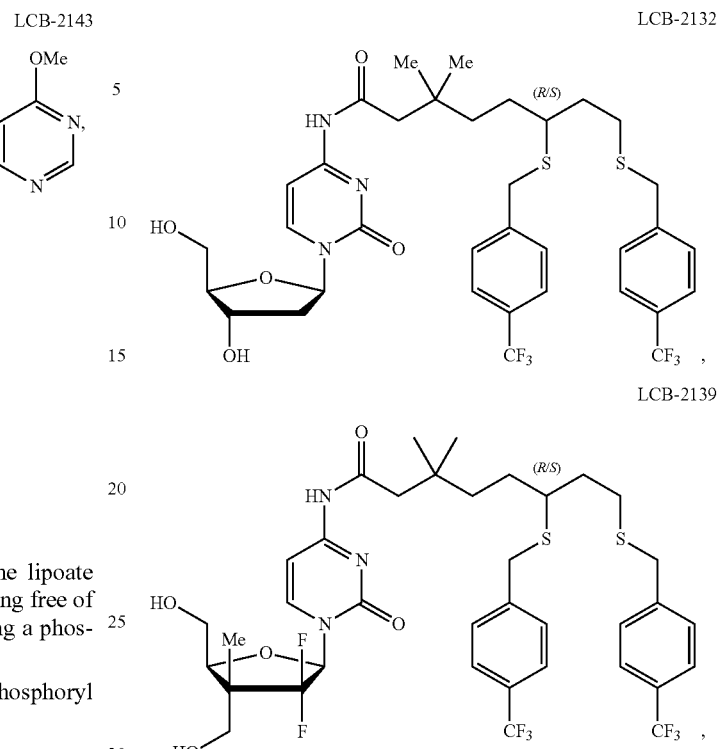
LCB-2132
LCB-2139
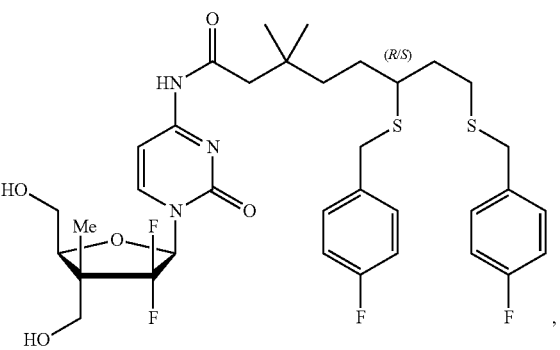
LCB-2140
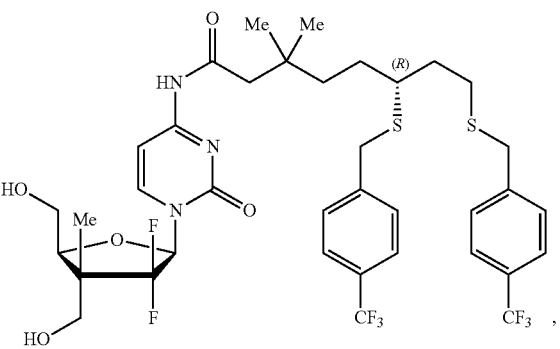
LCB-2151

LCB-2216
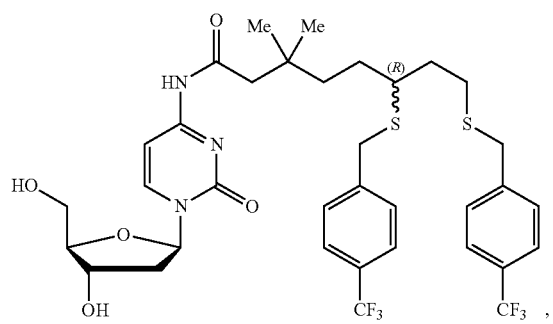
LCB-2227
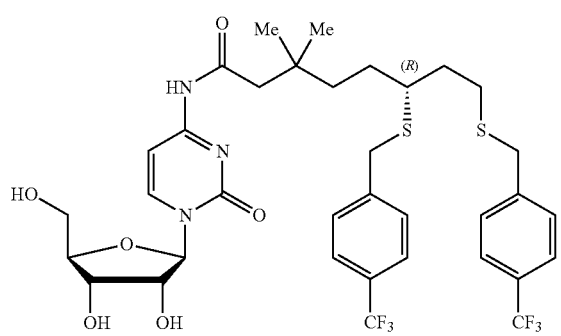
or a pharmaceutically acceptable salt thereof.
17. The compound of claim 14, comprising said phosphoryl group of Formula (XX) in $R_1$.
18. The compound of claim 17, being:
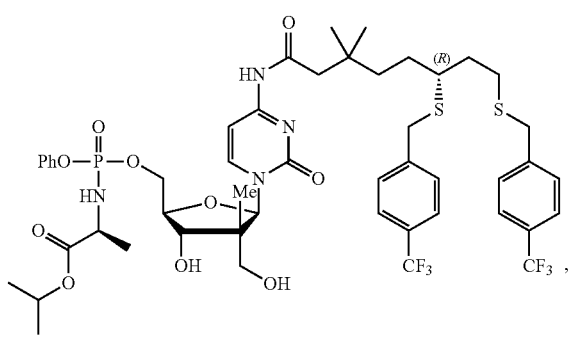
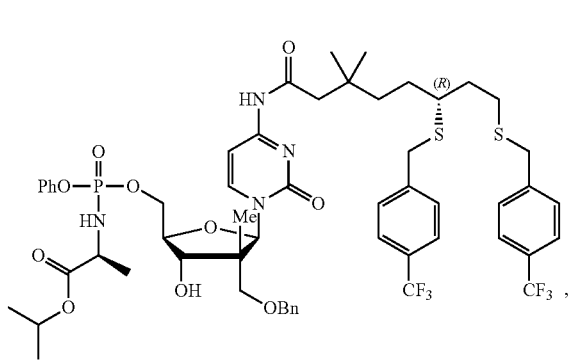
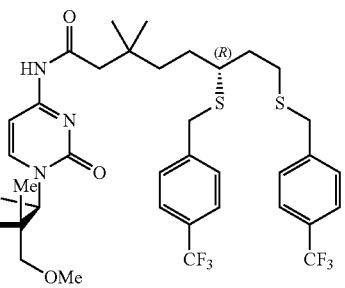
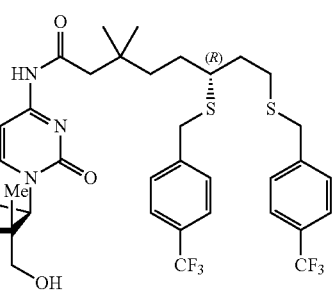
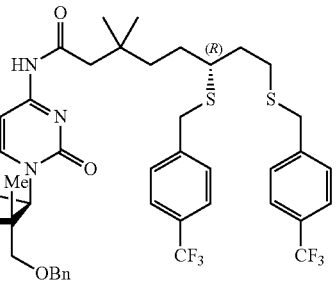

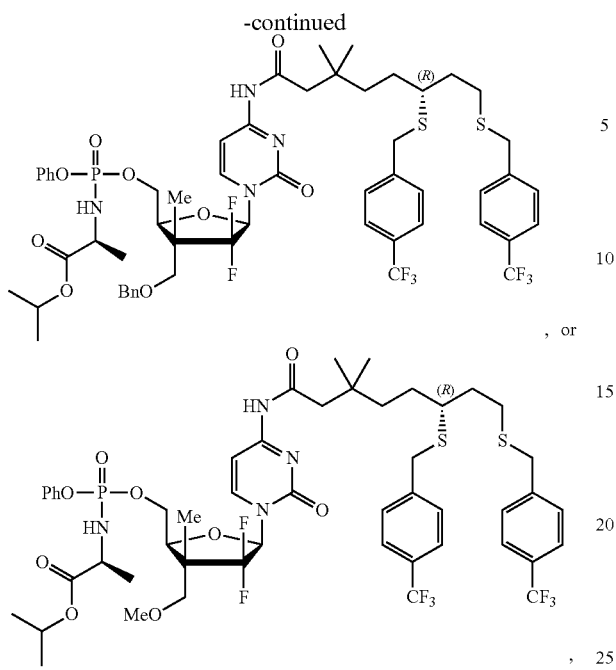
, or a pharmaceutically acceptable salt thereof.
* * * * *